United States Patent [19]
Onda et al.

[11] Patent Number: 5,858,787
[45] Date of Patent: Jan. 12, 1999

[54] DNA ENCODING PACAP RECEPTOR PROTEIN AND METHOD FOR PREPARING SAID PROTEIN

[75] Inventors: Haruo Onda, Tsuchiura; Masaki Hosoya, Tsukuba; Kazuhiro Ogi, Tsukuba; Yasunori Miyamoto, Tsukuba; Yugo Habata, Tsukuba, all of Japan

[73] Assignee: Takeda Chemical Industries, Ltd., Osaka, Japan

[21] Appl. No.: 811,897

[22] Filed: Mar. 5, 1997

Related U.S. Application Data

[62] Division of Ser. No. 202,986, Feb. 25, 1994, abandoned.

[30] Foreign Application Priority Data

| Feb. 26, 1993 | [JP] | Japan | 5-038755 |
|---|---|---|---|
| Apr. 5, 1993 | [JP] | Japan | 5-078290 |
| Apr. 27, 1993 | [JP] | Japan | 5-100669 |
| May 17, 1993 | [JP] | Japan | 5-114446 |
| Jun. 24, 1993 | [JP] | Japan | 5-153963 |
| Nov. 10, 1993 | [JP] | Japan | 5-281413 |
| Dec. 27, 1993 | [JP] | Japan | 5-333175 |

[51] Int. Cl.$^6$ .............................. C12N 1/21; C12N 5/10; C12N 15/12; C12N 15/63
[52] U.S. Cl. .......................... 435/471; 435/455; 435/476; 435/320.1; 435/325; 435/252.3; 435/69.1; 536/23.5
[58] Field of Search ....................... 536/23.5; 435/320.1, 435/325, 252.3, 69.1, 172.3, 455, 471, 476

[56] References Cited

U.S. PATENT DOCUMENTS 5,128,242   7/1992   Arimura et al. .

OTHER PUBLICATIONS

Wells. Biochemistry 29:8509–8517, 1990.
Bowie et al. Science 247:1306–1310, 1990.
Ohtaki, et al., Biochem. Biophy. Res. Comm. 171:838–844 (1990).
Finn and Hofman, Methods in Enzymology, [27] 184:245 (1990).
Hosoya, et al., Biochem. Biophy. Res. Comm. 194(1):133–143 (1993).
Pisegna, et al., Proc. Natl. Acad. Sci. USA 90:6345–6349 (1993).
Morrow, et al. Federation of European Biochemical Societies 329(1,2):99–105 (1993).
Spengler, et al., Nature, 365:170 (1993).
Hashimoto, et al., Neuron, 11:333–342 (1993).
Schafer, et al., Eur. J. Biochem., 217:823–830 (1993).
Schaefer, et al., Eur. J. Biochem., 202:951–8 (1991).
Bowie, et al., Science 247:1306–1310 (1990).
Reeck, et al., Cell 50:667 (1987).
Lewin, Science 237:1570 (1987).
Larsson, Histology & Histopathology 9:615–629 (1994).
Ishihara, et al., Neuron, 8:811–819 (1992).

*Primary Examiner*—Elizabeth Kemmerer
*Attorney, Agent, or Firm*—David G. Conlin; David S. Resnick; Dike, Bronstein, Roberts & Cushman, LLP

[57] ABSTRACT

This invention discloses a PACAP receptor protein or a salt thereof, a DNA comprising a DNA fragment coding for the protein, a method for preparing the protein, antibody against the protein and use of the protein, DNA and antibodies. A PACAP receptor protein was purified from the bovine cerebrum. DNAs coding for PACAP receptor proteins were isolated from bovine, rat and human cDNA libraries, and their nucleotide sequences were determined. The PACAP receptor proteins and the DNAs coding for the proteins of the present invention can be used for (1) acquisition of antibodies and antisera, (2) construction of expression systems of recombinant receptor proteins, (3) development of receptor binding assay systems using said expression systems and screening of potential compounds for drugs, (4) execution of drug design based on the comparison of ligands and receptors which are structurally similar to each other, (5) preparation of probes and PCR primers in gene diagnosis, and the like.

ms, 62 Drawing Sheets

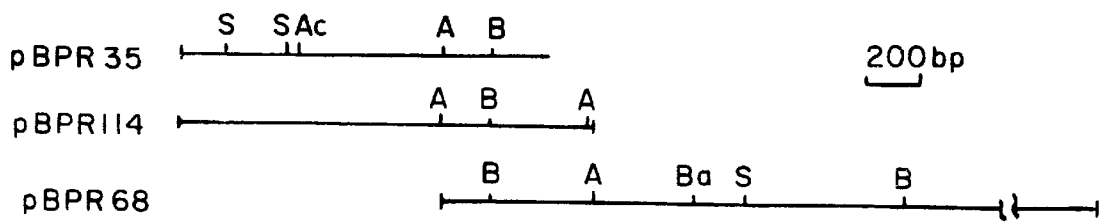
FIG. 1
```
                         1              5                10
Bovine cDNA           Met His Ser Asp Cys Ile Phe Lys Lys Glu Gln
                       *   *   *   *   *   *   *   *   *   *   *
Purfined bovine Sample Met His Ser Asp Cys Ile Phe Lys Lys Glu Gln
            15                  20              25
Ala Met Cys Leu Glu Lys Ile Gln Arg Val Asn Asp Leu Met
 *   *   *   *   *   *   *   *   *   *   *   *   *   *
Ala Met Cys Leu Glu Lys Ile Gln Arg Val Asn Asp Leu Met
Gly Leu Asn Asp
 *   *   *   *
Gly Leu Asn Asp
```
FIG. 4
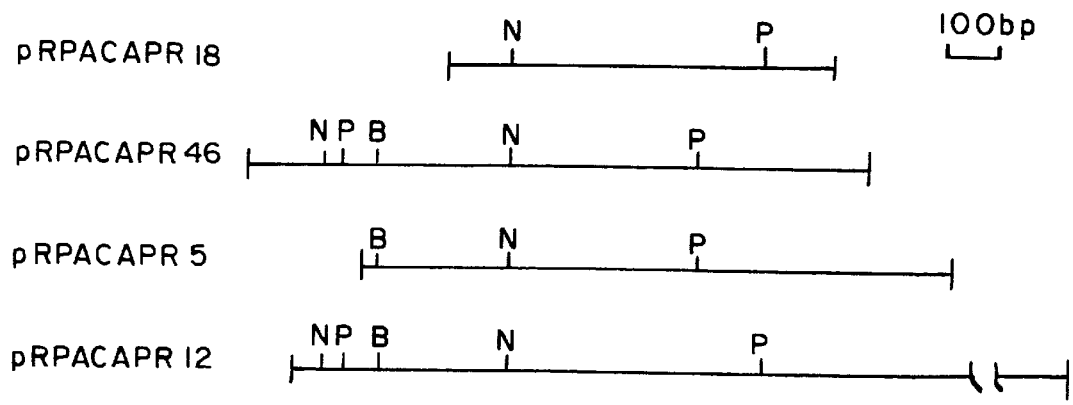
FIG. 6

```
TGGCCTGCAC CCCACCCCCC AGCCTGCGAA GACGGGGGGA GGCGGTGGTC GGTCGCCTCC    60
CTCCTGCCCC CGGCCTGGCT TCGCGGTGGA GGCGGTGCCT CTCCGGCAAG GCAGACCAGG   120
CTGGGCGGAC GCGCGGCGCG GGGCGGGCTA GGGAAGGCCG GGGGCCTCGC GCTCGGGCCC   180
CGGGCGGCGA CTGACAGCGG CGGCGGCGGC GGCAGCGGCT CCAAGGCGAG CGTGGTCCCC   240
GCGTGCGCAC AAGCTCGCCG CCGCGCAGGG ACCCACGGAC ACCGGCGCCG GGCGGACACA   300
CAGACGCGGA GATCGGGCTC TACGCGCGCT ACTCAGCGCA CGAGCTCCCC ATCCCTGGGC   360
GGAGCGGGGC GCGGACTCGC CGCTGCGCGC CCTCCCCGCG GAGTCTGCCC CGGGCAGACC   420
CGCAGCCCGC GGCCCCGCCG CGAGGCCCCT GGGTGAGCAG CCTGTAGACA CCTGGGGTTG   480
AGCAGTGGCG GCTGTGA ATG AGA GGC GGG CGG CAC TGG CCC GAG CCG CCT     530
                    Met Arg Gly Gly Arg His Trp Pro Glu Pro Pro
                     1           5                       10
```

```
TGC AGG CTG AGA AGC GTC ATG GCC AGC ATC GCG CAG GTC TCC CTG GCT    578
Cys Arg Leu Arg Ser Val Met Ala Ser Ile Ala Gln Val Ser Leu Ala
             15                  20                  25
```

```
GCT CTC CTC CTG CTG CCT ATG GCC ACC GCC ATG CAT TCC GAC TGC ATC    626
Ala Leu Leu Leu Leu Pro Met Ala Thr Ala Met His Ser Asp Cys Ile
             30                  35                  40
```

```
TTC AAG AAG GAG CAA GCC ATG TGC CTG GAG AAG ATC CAG AGG GTG AAT    674
Phe Lys Lys Glu Gln Ala Met Cys Leu Glu Lys Ile Gln Arg Val Asn
         45                  50                  55
```

```
GAC CTG ATG GGC TTG AAT GAC TCC TCC CCA GGG TGC CCT GGG ATG TGG    722
Asp Leu Met Gly Leu Asn Asp Ser Ser Pro Gly Cys Pro Gly Met Trp
60                  65                  70                  75
```

```
GAC AAC ATC ACG TGT TGG AAG CCC GCC CAC GTG GGT GAG ATG GTC CTG    770
Asp Asn Ile Thr Cys Trp Lys Pro Ala His Val Gly Glu Met Val Leu
                 80                  85                  90
```

```
GTC AGT TGC CCT GAA CTC TTC CGA ATC TTC AAC CCA GAC CAA GTC TGG    818
Val Ser Cys Pro Glu Leu Phe Arg Ile Phe Asn Pro Asp Gln Val Trp
             95                 100                 105
```

```
GAG ACG GAA ACC ATC GGA GAG TTC GGT TTT GCA GAC AGT AAA TCC TTG    866
Glu Thr Glu Thr Ile Gly Glu Phe Gly Phe Ala Asp Ser Lys Ser Leu
            110                 115                 120
```

```
GAT CTC TCA GAC ATG AGG GTG GTG AGC CGG AAT TGC ACG GAG GAT GGA    914
Asp Leu Ser Asp Met Arg Val Val Ser Arg Asn Cys Thr Glu Asp Gly
    125                 130                 135
```

```
TGG TCA GAG CCA TTC CCT CAT TAT TTC GAT GCC TGT GGG TTT GAG GAG    962
Trp Ser Glu Pro Phe Pro His Tyr Phe Asp Ala Cys Gly Phe Glu Glu
140                 145                 150                 155
```

```
TAC GAA TCT GAG ACT GGG GAC CAG GAT TAC TAC TAC CTG TCA GTG AAG   1010
Tyr Glu Ser Glu Thr Gly Asp Gln Asp Tyr Tyr Tyr Leu Ser Val Lys
            160                 165                 170
```

FIG. 2A

```
GCC CTG TAC ACA GTT GGC TAC AGC ACG TCC CTC GTC ACC CTC ACC ACT    1058
Ala Leu Tyr Thr Val Gly Tyr Ser Thr Ser Leu Val Thr Leu Thr Thr
            175                 180                 185

GCC ATG GTC ATC CTG TGT CGT TTC CGG AAG CTG CAC TGC ACC CGC AAC    1106
Ala Met Val Ile Leu Cys Arg Phe Arg Lys Leu His Cys Thr Arg Asn
        190                 195                 200

TTC ATC CAC ATG AAC CTC TTC GTG TCG TTT ATG CTG AGG GCC ATC TCC    1154
Phe Ile His Met Asn Leu Phe Val Ser Phe Met Leu Arg Ala Ile Ser
        205                 210                 215

GTC TTC ATC AAA GAC TGG ATC CTC TAT GCT GAG CAG GAC AGC AAT CAC    1202
Val Phe Ile Lys Asp Trp Ile Leu Tyr Ala Glu Gln Asp Ser Asn His
220             225                 230                 235

TGC TTT GTC TCC ACT GTG GAA TGC AAG GCT GTG ATG GTT TTC TTC CAC    1250
Cys Phe Val Ser Thr Val Glu Cys Lys Ala Val Met Val Phe Phe His
                240                 245                 250

TAC TGT GTT GTA TCC AAC TAC TTC TGG CTG TTC ATC GAG GGC CTG TAT    1298
Tyr Cys Val Val Ser Asn Tyr Phe Trp Leu Phe Ile Glu Gly Leu Tyr
            255                 260                 265

CTC TTC ACC CTG CTG GTG GAG ACC TTC TTC CCC GAG AGG AGA TAT TTC    1346
Leu Phe Thr Leu Leu Val Glu Thr Phe Phe Pro Glu Arg Arg Tyr Phe
        270                 275                 280

TAC TGG TAC ATC ATC ATT GGC TGG GGG ACA CCA ACT GTG TGT GTG TCT    1394
Tyr Trp Tyr Ile Ile Ile Gly Trp Gly Thr Pro Thr Val Cys Val Ser
        285                 290                 295

GTG TGG GCT ATG CTG AGG CTC TAC TTC GAT GAC ACA GGC TGC TGG GAT    1442
Val Trp Ala Met Leu Arg Leu Tyr Phe Asp Asp Thr Gly Cys Trp Asp
300             305                 310                 315

ATG AAT GAC AAC ACG GCT CTG TGG TGG GTG ATC AAA GGC CCT GTA GTT    1490
Met Asn Asp Asn Thr Ala Leu Trp Trp Val Ile Lys Gly Pro Val Val
                320                 325                 330

GGC TCC ATA ATG GTT AAT TTT GTG CTC TTC ATC GGC ATC ATT GTC ATC    1538
Gly Ser Ile Met Val Asn Phe Val Leu Phe Ile Gly Ile Ile Val Ile
            335                 340                 345

CTT GTG CAG AAA CTT CAG TCT CCA GAC ATG GGA GGC AAC GAG TCC AGC    1586
Leu Val Gln Lys Leu Gln Ser Pro Asp Met Gly Gly Asn Glu Ser Ser
        350                 355                 360

ATC TAC TTC AGC TGC GTG CAG AAA TGC TAC TGC AAG CCA CAG CGG GCT    1634
Ile Tyr Phe Ser Cys Val Gln Lys Cys Tyr Cys Lys Pro Gln Arg Ala
        365                 370                 375

CAG CAG CAC TCT TGC AAG ATG TCA GAA CTG TCC ACC ATT ACT CTA CGG    1682
Gln Gln His Ser Cys Lys Met Ser Glu Leu Ser Thr Ile Thr Leu Arg
```

FIG. 2B

```
         380                      385                      390                      395
CTC GCC AGG TCC ACC TTG CTG CTC ATC CCA CTC TTT GGA ATC CAC TAC         1730
Leu Ala Arg Ser Thr Leu Leu Leu Ile Pro Leu Phe Gly Ile His Tyr
                    400                      405                      410

ACT GTC TTT GCT TTC TCC CCG GAG AAC GTC AGC AAG AGG GAG AGA CTG         1778
Thr Val Phe Ala Phe Ser Pro Glu Asn Val Ser Lys Arg Glu Arg Leu
                415                      420                      425

GTG TTT GAG CTG GGT CTG GGC TCC TTC CAG GGC TTT GTG GTG GCT GTT         1826
Val Phe Glu Leu Gly Leu Gly Ser Phe Gln Gly Phe Val Val Ala Val
            430                      435                      440

CTC TAT TGC TTT CTG AAT GGA GAG GTG CAG GCG GAG ATC AAG AGG AAG         1874
Leu Tyr Cys Phe Leu Asn Gly Glu Val Gln Ala Glu Ile Lys Arg Lys
        445                      450                      455

TGG CGG AGC TGG AAG GTG AAC CGC TAC TTC ACC ATG GAC TTC AAG CAC         1922
Trp Arg Ser Trp Lys Val Asn Arg Tyr Phe Thr Met Asp Phe Lys His
460                      465                      470                      475

CGG CAC CCA TCC CTG GCC AGC AGC GGG GTG AAC GGG GGC ACC CAG CTC         1970
Arg His Pro Ser Leu Ala Ser Ser Gly Val Asn Gly Gly Thr Gln Leu
                    480                      485                      490

TCC ATC CTG AGC AAG AGC AGC TCC CAG ATC CGC ATG TCT GGG CTT CCG         2018
Ser Ile Leu Ser Lys Ser Ser Ser Gln Ile Arg Met Ser Gly Leu Pro
                495                      500                      505

GCC GAC AAC CTG GCC ACC TGAGCCCACC CTGCCCCCTC CTCTCCTCTG TACGCAGGC      2075
Ala Asp Asn Leu Ala Thr
            510

TGGGGCTGTG GTGGGGCGCC GGCCCACGCA TGTTGTGCCT CTTCTCGCCT TCGGGCAGGC       2135
CCCGGGCTGG GCGCCTGGCC CCCGAGGTTG GAGAAGGATG CGGGACAGGC AGCTGTTTAG       2195
CCTTCCTGTT TTGGCGCTGG CCCAACCACC GTGGGTCCCT GGGCCTGCAC CCAGACATGT       2255
AATACTCCTT AATTGGGAAG TCATCCATTC TTTCCCTTTC CCAAGTCCTT GCTTATTAAG       2315
AGGTTCAAGT CACCTACCCA ATTCAGAAGC TTAAGTAACC ACTAACCACC GTGACTGCGT       2375
GGGAGGCCTC CCATGGGCTG AGCTACTGAC TTGGCTTTGG GGGCCTTGGG CTGGGGCCCT       2435
CCTTAAAGCC CCCCCTGAAA TTGTCGGACC TCAAAGTGTG ACTCCTTTGA GTCTACTCGC       2495
CACCCCCGTG GCCCTTTGCA GCCCTGGTCC AGTCACCGAG GTTACTGGAA GTCCAGCTTG       2555
GATGGCCAGA CAGCTTTTTG GCACAGGCAG ACCCATGCTC ACCCAACATT TTAGTGTCCA       2615
GGTGCCCAGG TGCCCAGGTG CCCAGCTCCT GGGCATCAGA CAGTGGGAAA GCTCCAGGGA       2675
TCTACCATTC AGAGACTTCA GTTTGGATGT AGGGCTAAGG CCAGAGAAAA GTTCTGGAGC       2735
TTTTCATTTG GCCCAAGAAA AAACTGCCAA GATCCAGAAA AGTGGATCTG AGTGGAATTT       2795
AGATGCAAAG AGCTTGGAG                                                    2814
```

FIG. 2C

| | |
|---|---|
| TGGCCTGCAC CCCACCCCCC AGCCTGCGAA GACGGGGGGA GGCGGTGGTC GGTCGCCTCC | 60 |
| CTCCTGCCCC CGGCCTGGCT TCGCGGTGGA GGCGGTGCCT CTCCGGCAAG GCAGACCAGG | 120 |
| CTGGGCGGAC GCGCGGCGCG GGGCGGGCTA GGGAAGGCCG GGGGCCTCGC GCTCGGGCCC | 180 |
| CGGGCGGCGA CTGACAGCGG CGGCGGCGGC GGCAGCGGCT CCAAGGCGAG CGTGGTCCCC | 240 |
| GCGTGCGCAC AAGCTCGCCG CCGCGCAGGG ACCCACGGAC ACCGGCGCCG GCGGACACA | 300 |
| CAGACGCGGA GATCGGGCTC TACGCGCGCT ACTCAGCGCA CGAGCTCCCC ATCCCTGGGC | 360 |
| GGAGCGGGGC GCGGACTCGC CGCTGCGCGC CCTCCCCGCG GAGTCTGCCC CGGGCAGACC | 420 |
| CGCAGCCCGC GGCCCCGCCG CGAGGCCCCT GGGTGAGCAG CCTGTAGACA CCTGGGGTTG | 480 |
| AGCAGTGGCG GCTGTGA ATG AGA GGC GGG CGG CAC TGG CCC GAG CCG CCT | 530 |
|                  Met Arg Gly Gly Arg His Trp Pro Glu Pro Pro | |
|                    1             5                 10 | |
| TGC AGG CTG AGA AGC GTC ATG GCC AGC ATC GCG CAG GTC TCC CTG GCT<br>Cys Arg Leu Arg Ser Val Met Ala Ser Ile Ala Gln Val Ser Leu Ala<br>             15                   20                25 | 578 |
| GCT CTC CTC CTG CTG CCT ATG GCC ACC GCC ATG CAT TCC GAC TGC ATC<br>Ala Leu Leu Leu Leu Pro Met Ala Thr Ala Met His Ser Asp Cys Ile<br>        30                   35                40 | 626 |
| TTC AAG AAG GAG CAA GCC ATG TGC CTG GAG AAG ATC CAG AGG GTG AAT<br>Phe Lys Lys Glu Gln Ala Met Cys Leu Glu Lys Ile Gln Arg Val Asn<br>    45                   50                55 | 674 |
| GAC CTG ATG GGC TTG AAT GAC TCC TCC CCA GGG TGC CCT GGG ATG TGG<br>Asp Leu Met Gly Leu Asn Asp Ser Ser Pro Gly Cys Pro Gly Met Trp<br>60                  65                70                75 | 722 |
| GAC AAC ATC ACG TGT TGG AAG CCC GCC CAC GTG GGT GAG ATG GTC CTG<br>Asp Asn Ile Thr Cys Trp Lys Pro Ala His Val Gly Glu Met Val Leu<br>             80                   85                90 | 770 |
| GTC AGT TGC CCT GAA CTC TTC CGA ATC TTC AAC CCA GAC CAA GTC TGG<br>Val Ser Cys Pro Glu Leu Phe Arg Ile Phe Asn Pro Asp Gln Val Trp<br>               95                  100             105 | 818 |
| GAG ACG GAA ACC ATC GGA GAG TTC GGT TTT GCA GAC AGT AAA TCC TTG<br>Glu Thr Glu Thr Ile Gly Glu Phe Gly Phe Ala Asp Ser Lys Ser Leu<br>          110                  115                120 | 866 |
| GAT CTC TCA GAC ATG AGG GTG GTG AGC CGG AAT TGC ACG GAG GAT GGA<br>Asp Leu Ser Asp Met Arg Val Val Ser Arg Asn Cys Thr Glu Asp Gly<br>        125                  130                135 | 914 |
| TGG TCA GAG CCA TTC CCT CAT TAT TTC GAT GCC TGT GGG TTT GAG GAG<br>Trp Ser Glu Pro Phe Pro His Tyr Phe Asp Ala Cys Gly Phe Glu Glu<br>140                145                  150             155 | 962 |
| TAC GAA TCT GAG ACT GGG GAC CAG GAT TAC TAC TAC CTG TCA GTG AAG | 1010 |

FIG. 3A

```
Tyr Glu Ser Glu Thr Gly Asp Gln Asp Tyr Tyr Tyr Leu Ser Val Lys
            160             165             170

GCC CTG TAC ACA GTT GGC TAC AGC ACG TCC CTC GTC ACC CTC ACC ACT    1058
Ala Leu Tyr Thr Val Gly Tyr Ser Thr Ser Leu Val Thr Leu Thr Thr
            175             180             185

GCC ATG GTC ATC CTG TGT CGT TTC CGG AAG CTG CAC TGC ACC CGC AAC    1106
Ala Met Val Ile Leu Cys Arg Phe Arg Lys Leu His Cys Thr Arg Asn
            190             195             200

TTC ATC CAC ATG AAC CTC TTC GTG TCG TTT ATG CTG AGG GCC ATC TCC    1154
Phe Ile His Met Asn Leu Phe Val Ser Phe Met Leu Arg Ala Ile Ser
            205             210             215

GTC TTC ATC AAA GAC TGG ATC CTC TAT GCT GAG CAG GAC AGC AAT CAC    1202
Val Phe Ile Lys Asp Trp Ile Leu Tyr Ala Glu Gln Asp Ser Asn His
220             225             230             235

TGC TTT GTC TCC ACT GTG GAA TGC AAG GCT GTG ATG GTT TTC TTC CAC    1250
Cys Phe Val Ser Thr Val Glu Cys Lys Ala Val Met Val Phe Phe His
            240             245             250

TAC TGT GTT GTA TCC AAC TAC TTC TGG CTG TTC ATC GAG GGC CTG TAT    1298
Tyr Cys Val Val Ser Asn Tyr Phe Trp Leu Phe Ile Glu Gly Leu Tyr
            255             260             265

CTC TTC ACC CTG CTG GTG GAG ACC TTC TTC CCC GAG AGG AGA TAT TTC    1346
Leu Phe Thr Leu Leu Val Glu Thr Phe Phe Pro Glu Arg Arg Tyr Phe
            270             275             280

TAC TGG TAC ATC ATC ATT GGC TGG GGG ACA CCA ACT GTG TGT GTG TCT    1394
Tyr Trp Tyr Ile Ile Ile Gly Trp Gly Thr Pro Thr Val Cys Val Ser
            285             290             295

GTG TGG GCT ATG CTG AGG CTC TAC TTC GAT GAC ACA GGC TGC TGG GAT    1442
Val Trp Ala Met Leu Arg Leu Tyr Phe Asp Asp Thr Gly Cys Trp Asp
300             305             310             315

ATG AAT GAC AAC ACG GCT CTG TGG TGG GTG ATC AAA GGC CCT GTA GTT    1490
Met Asn Asp Asn Thr Ala Leu Trp Trp Val Ile Lys Gly Pro Val Val
            320             325             330

GGC TCC ATA ATG GTT AAT TTT GTG CTC TTC ATC GGC ATC ATT GTC ATC    1538
Gly Ser Ile Met Val Asn Phe Val Leu Phe Ile Gly Ile Ile Val Ile
            335             340             345

CTT GTG CAG AAA CTT CAG TCT CCA GAC ATG GGA GGC AAC GAG TCC AGC    1586
Leu Val Gln Lys Leu Gln Ser Pro Asp Met Gly Gly Asn Glu Ser Ser
            350             355             360

ATC TAC TTA CGG CTC GCC AGG TCC ACC TTG CTG CTC ATC CCA CTC TTT    1634
Ile Tyr Leu Arg Leu Ala Arg Ser Thr Leu Leu Leu Ile Pro Leu Phe
            365             370             375
```

FIG. 3B

```
GGA ATC CAC TAC ACT GTC TTT GCT TTC TCC CCG GAG AAC GTC AGC AAG    1682
Gly Ile His Tyr Thr Val Phe Ala Phe Ser Pro Glu Asn Val Ser Lys
380             385                 390                 395

AGG GAG AGA CTG GTG TTT GAG CTG GGT CTG GGC TCC TTC CAG GGC TTT    1730
Arg Glu Arg Leu Val Phe Glu Leu Gly Leu Gly Ser Phe Gln Gly Phe
                400                 405                 410

GTG GTG GCT GTT CTC TAT TGC TTT CTG AAT GGA GAG GTG CAG GCG GAG    1778
Val Val Ala Val Leu Tyr Cys Phe Leu Asn Gly Glu Val Gln Ala Glu
            415                 420                 425

ATC AAG AGG AAG TGG CGG AGC TGG AAG GTG AAC CGC TAC TTC ACC ATG    1826
Ile Lys Arg Lys Trp Arg Ser Trp Lys Val Asn Arg Tyr Phe Thr Met
        430                 435                 440

GAC TTC AAG CAC CGG CAC CCA TCC CTG GCC AGC AGC GGG GTG AAC GGG    1874
Asp Phe Lys His Arg His Pro Ser Leu Ala Ser Ser Gly Val Asn Gly
    445                 450                 455

GGC ACC CAG CTC TCC ATC CTG AGC AAG AGC AGC TCC CAG ATC CGC ATG    1922
Gly Thr Gln Leu Ser Ile Leu Ser Lys Ser Ser Ser Gln Ile Arg Met
460                 465                 470                 475

TCT GGG CTT CCG GCC GAC AAC CTG GCC ACC TGAGCCCACC CTGCCCCCTC CTCT 1976
Ser Gly Leu Pro Ala Asp Asn Leu Ala Thr
                480                 485

CCTCTGTACG CAGGCTGGGG CTGTGGTGGG GCGCCGGCCC ACGCATGTTG TGCCTCTTCT    2036
CGCCTTCGGG CAGGCCCCGG GCTGGGCGCC TGGCCCCCGA GGTTGGAGAA GGATGCGGGA    2096
CAGGCAGCTG TTTAGCCTTC CTGTTTTGGC GCTGGCCCAA CCACCGTGGG TCCCTGGGCC    2156
TGCACCCAGA CATGTAATAC TCCTTAATTG GGAAGTCATC CATTCTTTCC CTTTCCCAAG    2216
TCCTTGCTTA TTAAGAGGTT CAAGTCACCT ACCCAATTCA GAAGCTTAAG TAACCACTAA    2276
CCACCGTGAC TGCGTGGGAG GCCTCCCATG GGCTGAGCTA CTGACTTGGC TTTGGGGGCC    2336
TTGGGCTGGG GCCCTCCTTA AAGCCCCCCC TGAAATTGTC GGACCTCAAA GTGTGACTCC    2396
TTTGAGTCTA CTCGCCACCC CCGTGGCCCT TTGCAGCCCT GGTCCAGTCA CCGAGGTTAC    2456
TGGAAGTCCA GCTTGGATGG CCAGACAGCT TTTTGGCACA GGCAGACCCA TGCTCACCCA    2516
ACATTTTAGT GTCCAGGTGC CCAGGTGCCC AGGTGCCCAG CTCCTGGGCA TCAGACAGTG    2576
GGAAAGCTCC AGGGATCTAC CATTCAGAGA CTTCAGTTTG GATGTAGGGC TAAGGCCAGA    2636
GAAAAGTTCT GGAGCTTTTC ATTTGGCCCA AGAAAAAACT GCCAAGATCC AGAAAAGTGG    2696
ATCTGAGTGG AATTTAGATG CAAAGAGCTT GGAG                                2730
```

FIG. 3C

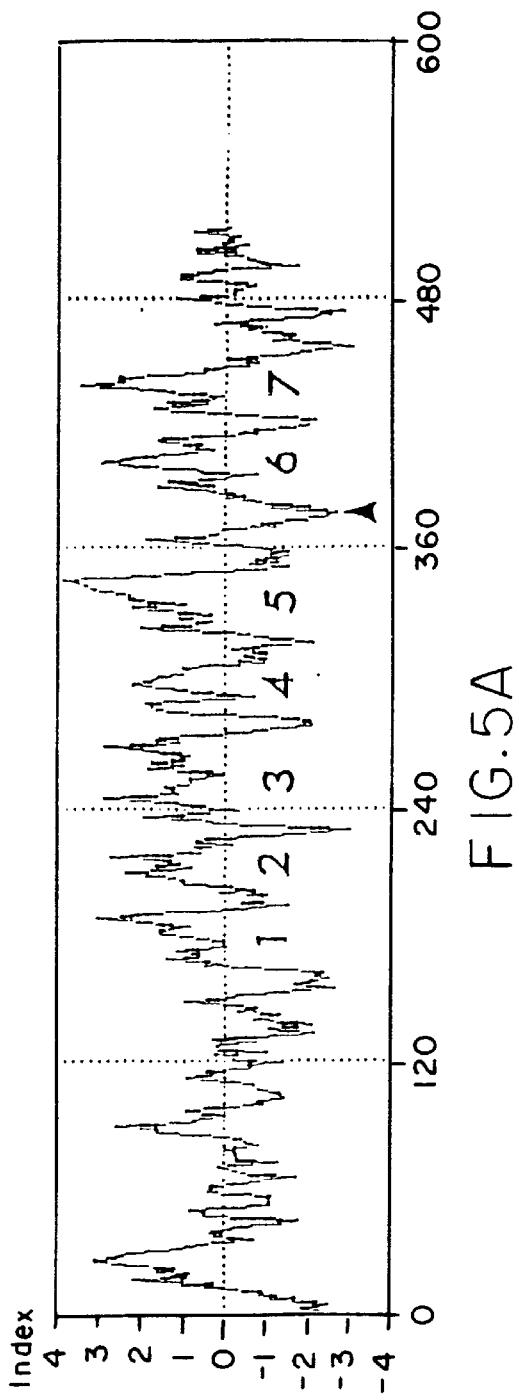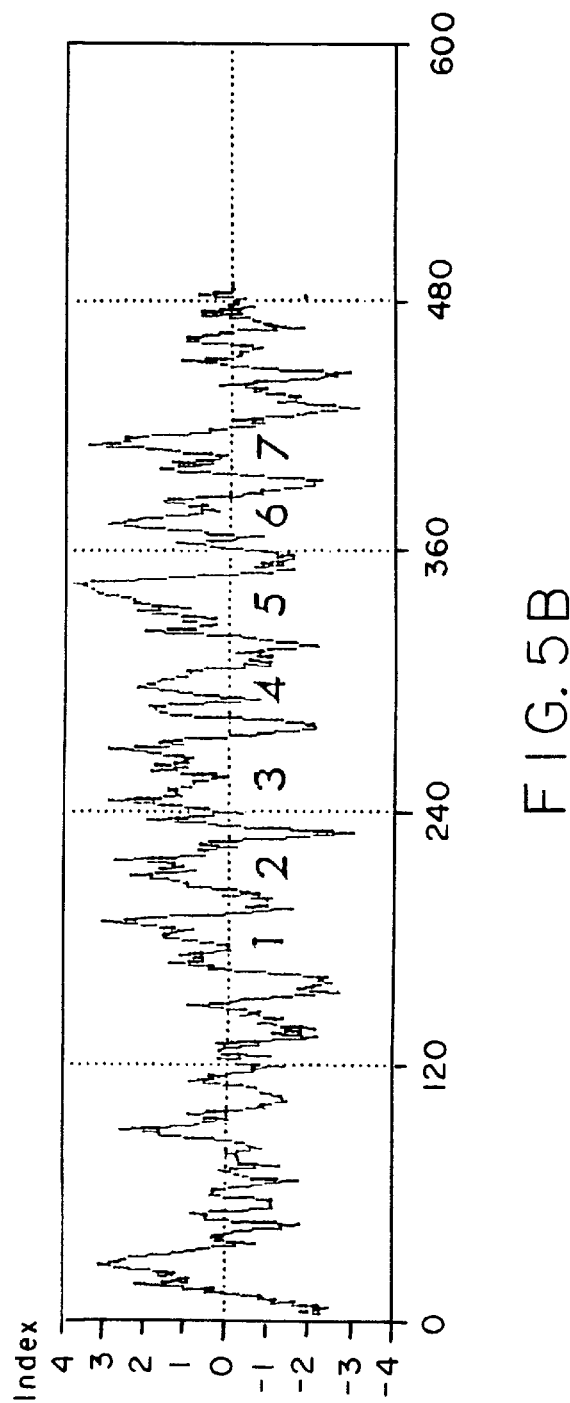
FIG.5A
FIG.5B

```
CGAGTGGACA GTGGCAGGCG GTGACTGAAT CTCCAAGTCT GGAAACAATA GCCAGAGATA      60
GTGGCTGGGA AGCACC ATG GCC AGA GTC CTG CAG CTC TCC CTG ACT GCT CTC    112
               Met Ala Arg Val Leu Gln Leu Ser Leu Thr Ala Leu
                1               5                   10

CTG CTG CCT GTG GCT ATT GCT ATG CAC TCT GAC TGC ATC TTC AAG AAG      160
Leu Leu Pro Val Ala Ile Ala Met His Ser Asp Cys Ile Phe Lys Lys
            15                  20                  25

GAG CAA GCC ATG TGC CTG GAG AGG ATC CAG AGG GCC AAC GAC CTG ATG      208
Glu Gln Ala Met Cys Leu Glu Arg Ile Gln Arg Ala Asn Asp Leu Met
        30                  35                  40

GGA CTA AAC GAG TCT TCC CCA GGT TGC CCT GGC ATG TGG GAC AAT ATC      256
Gly Leu Asn Glu Ser Ser Pro Gly Cys Pro Gly Met Trp Asp Asn Ile
45                  50                  55                  60

ACA TGT TGG AAG CCA GCT CAA GTA GGT GAG ATG GTC CTT GTA AGC TGC      304
Thr Cys Trp Lys Pro Ala Gln Val Gly Glu Met Val Leu Val Ser Cys
                65                  70                  75

CCT GAG GTC TTC CGG ATC TTC AAC CCG GAC CAA GTC TGG ATG ACA GAA      352
Pro Glu Val Phe Arg Ile Phe Asn Pro Asp Gln Val Trp Met Thr Glu
            80                  85                  90

ACC ATA GGA GAT TCT GGT TTT GCC GAT AGT AAT TCC TTG GAG ATC ACA      400
Thr Ile Gly Asp Ser Gly Phe Ala Asp Ser Asn Ser Leu Glu Ile Thr
        95                  100                 105

GAC ATG GGG GTC GTG GGC CGG AAC TGC ACA GAG GAC GGC TGG TCG GAG      448
Asp Met Gly Val Val Gly Arg Asn Cys Thr Glu Asp Gly Trp Ser Glu
    110                 115                 120

CCC TTC CCC CAC TAC TTC GAT GCT TGT GGG TTT GAT GAT TAT GAG CCT      496
Pro Phe Pro His Tyr Phe Asp Ala Cys Gly Phe Asp Asp Tyr Glu Pro
125                 130                 135                 140

GAG TCT GGA GAT CAG GAT TAT TAC TAC CTG TCG GTG AAG GCT CTC TAC      544
Glu Ser Gly Asp Gln Asp Tyr Tyr Tyr Leu Ser Val Lys Ala Leu Tyr
                145                 150                 155

ACA GTC GGC TAC AGC ACT TCC CTC GCC ACC CTC ACT ACT GCC ATG GTC      592
Thr Val Gly Tyr Ser Thr Ser Leu Ala Thr Leu Thr Thr Ala Met Val
            160                 165                 170

ATC TTG TGC CGC TTC CGG AAG CTG CAT TGC ACT CGC AAC TTC ATC CAC      640
Ile Leu Cys Arg Phe Arg Lys Leu His Cys Thr Arg Asn Phe Ile His
        175                 180                 185

ATG AAC CTG TTT GTA TCC TTC ATG CTG AGG GCT ATC TCC GTC TTC ATC      688
Met Asn Leu Phe Val Ser Phe Met Leu Arg Ala Ile Ser Val Phe Ile
```

FIG. 7A

|     |     |     | 190 |     |     |     |     | 195 |     |     |     |     | 200 |     |     |      |
|-----|-----|-----|-----|-----|-----|-----|-----|-----|-----|-----|-----|-----|-----|-----|-----|------|
| AAG | GAC | TGG | ATC | TTG | TAC | GCC | GAG | CAG | GAC | AGC | AGT | CAC | TGC | TTC | GTT | 736  |
| Lys | Asp | Trp | Ile | Leu | Tyr | Ala | Glu | Gln | Asp | Ser | Ser | His | Cys | Phe | Val |      |
| 205 |     |     |     |     | 210 |     |     |     |     | 215 |     |     |     |     | 220 |      |

| TCC | ACC | GTG | GAG | TGC | AAA | GCT | GTC | ATG | GTT | TTC | TTC | CAC | TAC | TGC | GTG | 784  |
|-----|-----|-----|-----|-----|-----|-----|-----|-----|-----|-----|-----|-----|-----|-----|-----|------|
| Ser | Thr | Val | Glu | Cys | Lys | Ala | Val | Met | Val | Phe | Phe | His | Tyr | Cys | Val |      |
|     |     |     |     | 225 |     |     |     |     | 230 |     |     |     |     | 235 |     |      |

| GTG | TCC | AAC | TAC | TTC | TGG | CTG | TTC | ATT | GAA | GGC | CTG | TAC | CTC | TTT | ACA | 832  |
| Val | Ser | Asn | Tyr | Phe | Trp | Leu | Phe | Ile | Glu | Gly | Leu | Tyr | Leu | Phe | Thr |      |
|     |     |     | 240 |     |     |     |     | 245 |     |     |     |     | 250 |     |     |      |

| CTG | CTG | GTG | GAG | ACC | TTC | TTC | CCT | GAG | AGG | AGA | TAT | TTC | TAC | TGG | TAC | 880  |
| Leu | Leu | Val | Glu | Thr | Phe | Phe | Pro | Glu | Arg | Arg | Tyr | Phe | Tyr | Trp | Tyr |      |
|     |     | 255 |     |     |     |     | 260 |     |     |     |     | 265 |     |     |     |      |

| ACC | ATC | ATC | GGC | TGG | GGG | ACA | CCT | ACT | GTG | TGT | GTA | ACA | GTG | TGG | GCT | 928  |
| Thr | Ile | Ile | Gly | Trp | Gly | Thr | Pro | Thr | Val | Cys | Val | Thr | Val | Trp | Ala |      |
|     | 270 |     |     |     |     | 275 |     |     |     |     | 280 |     |     |     |     |      |

| GTG | CTG | AGG | CTC | TAT | TTT | GAT | GAT | GCA | GGA | TGC | TGG | GAT | ATG | AAT | GAC | 976  |
| Val | Leu | Arg | Leu | Tyr | Phe | Asp | Asp | Ala | Gly | Cys | Trp | Asp | Met | Asn | Asp |      |
| 285 |     |     |     |     | 290 |     |     |     |     | 295 |     |     |     |     | 300 |      |

| AGC | ACA | GCT | CTG | TGG | TGG | GTG | ATC | AAA | GGC | CCC | GTG | GTT | GGC | TCT | ATA | 1024 |
| Ser | Thr | Ala | Leu | Trp | Trp | Val | Ile | Lys | Gly | Pro | Val | Val | Gly | Ser | Ile |      |
|     |     |     |     | 305 |     |     |     |     | 310 |     |     |     |     | 315 |     |      |

| ATG | GTT | AAC | TTT | GTG | CTT | TTC | ATC | GGC | ATC | ATC | ATC | CTT | GTA | CAG |     | 1072 |
| Met | Val | Asn | Phe | Val | Leu | Phe | Ile | Gly | Ile | Ile | Ile | Leu | Val | Gln |     |      |
|     |     |     | 320 |     |     |     |     | 325 |     |     |     |     | 330 |     |     |      |

| AAG | CTG | CAG | TCC | CCA | GAC | ATG | GGA | GGC | AAC | GAG | TCC | AGC | ATC | TAC | TTA | 1120 |
| Lys | Leu | Gln | Ser | Pro | Asp | Met | Gly | Gly | Asn | Glu | Ser | Ser | Ile | Tyr | Leu |      |
|     |     | 335 |     |     |     |     | 340 |     |     |     |     | 345 |     |     |     |      |

| CGG | CTG | GCC | CGC | TCC | ACC | CTA | CTG | CTC | ATC | CCA | CTC | TTC | GGA | ATC | CAC | 1168 |
| Arg | Leu | Ala | Arg | Ser | Thr | Leu | Leu | Leu | Ile | Pro | Leu | Phe | Gly | Ile | His |      |
|     | 350 |     |     |     |     | 355 |     |     |     |     | 360 |     |     |     |     |      |

| TAC | ACA | GTA | TTC | GCC | TTC | TCT | CCA | GAG | AAC | GTC | AGC | AAG | AGG | GAA | AGA | 1216 |
| Tyr | Thr | Val | Phe | Ala | Phe | Ser | Pro | Glu | Asn | Val | Ser | Lys | Arg | Glu | Arg |      |
| 365 |     |     |     |     | 370 |     |     |     |     | 375 |     |     |     |     | 380 |      |

| CTT | GTG | TTT | GAG | CTT | GGG | CTG | GGC | TCC | TTC | CAG | GGC | TTT | GTG | GTG | GCT | 1264 |
| Leu | Val | Phe | Glu | Leu | Gly | Leu | Gly | Ser | Phe | Gln | Gly | Phe | Val | Val | Ala |      |
|     |     |     |     | 385 |     |     |     |     | 390 |     |     |     |     | 395 |     |      |

| GTA | CTC | TAC | TGC | TTC | CTG | AAT | GGG | GAG | GTA | CAG | GCA | GAG | ATT | AAG | AGG | 1312 |
| Val | Leu | Tyr | Cys | Phe | Leu | Asn | Gly | Glu | Val | Gln | Ala | Glu | Ile | Lys | Arg |      |
|     |     |     | 400 |     |     |     |     | 405 |     |     |     |     | 410 |     |     |      |

FIG. 7B

```
AAA TGG AGG AGC TGG AAG GTG AAC CGT TAC TTC ACT ATG GAC TTC AAG    1360
Lys Trp Arg Ser Trp Lys Val Asn Arg Tyr Phe Thr Met Asp Phe Lys
        415                 420                 425

CAC CGG CAC CCG TCC CTG GCC AGC AGT GGA GTA AAT GGG GGA ACC CAG    1408
His Arg His Pro Ser Leu Ala Ser Ser Gly Val Asn Gly Gly Thr Gln
        430                 435                 440

CTG TCC ATC CTG AGC AAG AGC AGC TCC CAG CTC CGC ATG TCC AGC CTC    1456
Leu Ser Ile Leu Ser Lys Ser Ser Ser Gln Leu Arg Met Ser Ser Leu
445                 450                 455                 460

CCG GCC GAC AAC TTG GCC ACC TGAGGCCTGT CTCCCTCCTC CTTCTGCACA GGCTG 1512
Pro Ala Asp Asn Leu Ala Thr
                465

GGGCTGCGGG CCAGTGCCTG AGCATGTTTG TGCCTCTCCC CTCTCCTTGG GCAGGCCCTG  1572
GGTAGGAAGC TGGGCTCCTC CCCAAAGGGG AAGAGAGAGA TAGGGTATAG GCTGATATTG  1632
CTCCTCCTGT TTGGGTCCCA CCTACTGTGA TTCATTGAGC CTGATTTGAC ATGTAAATAC  1692
ACCTCAAATT TGGAAAGTTG CCCCATCTCT GCCCCAACC CATGCCCCTG CTCACCTCTG   1752
CCAGGCCCCA GCTCAACCTA CTGTGTCAAG GCCAGCCTCA GTGATAGTCT GATCCCAGGT  1812
ACAAGGCCTT GTGAGCTGAG GCTGAAAGGC CTGTTTTGGA GAGGCTGGGG TAGTGCC     1869
```

FIG. 8

```
CGAGTGGACA GTGGCAGGCG GTGACTGAAT CTCCAAGTCT GGAAACAATA GCCAGAGATA      60
GTGGCTGGGA AGCACC ATG GCC AGA GTC CTG CAG CTC TCC CTG ACT GCT CTC    112
               Met Ala Arg Val Leu Gln Leu Ser Leu Thr Ala Leu
                 1               5                  10

CTG CTG CCT GTG GCT ATT GCT ATG CAC TCT GAC TGC ATC TTC AAG AAG      160
Leu Leu Pro Val Ala Ile Ala Met His Ser Asp Cys Ile Phe Lys Lys
            15              20                  25

GAG CAA GCC ATG TGC CTG GAG AGG ATC CAG AGG GCC AAC GAC CTG ATG      208
Glu Gln Ala Met Cys Leu Glu Arg Ile Gln Arg Ala Asn Asp Leu Met
    30                  35                  40

GGA CTA AAC GAG TCT TCC CCA GGT TGC CCT GGC ATG TGG GAC AAT ATC      256
Gly Leu Asn Glu Ser Ser Pro Gly Cys Pro Gly Met Trp Asp Asn Ile
45              50                  55                  60

ACA TGT TGG AAG CCA GCT CAA GTA GGT GAG ATG GTC CTT GTA AGC TGC      304
Thr Cys Trp Lys Pro Ala Gln Val Gly Glu Met Val Leu Val Ser Cys
                65                  70                  75

CCT GAG GTC TTC CGG ATC TTC AAC CCG GAC CAA GTC TGG ATG ACA GAA      352
Pro Glu Val Phe Arg Ile Phe Asn Pro Asp Gln Val Trp Met Thr Glu
            80                  85                  90

ACC ATA GGA GAT TCT GGT TTT GCC GAT AGT AAT TCC TTG GAG ATC ACA      400
Thr Ile Gly Asp Ser Gly Phe Ala Asp Ser Asn Ser Leu Glu Ile Thr
        95                  100                 105

GAC ATG GGG GTC GTG GGC CGG AAC TGC ACA GAG GAC GGC TGG TCG GAG      448
Asp Met Gly Val Val Gly Arg Asn Cys Thr Glu Asp Gly Trp Ser Glu
    110                 115                 120

CCC TTC CCC CAC TAC TTC GAT GCT TGT GGG TTT GAT GAT TAT GAG CCT      496
Pro Phe Pro His Tyr Phe Asp Ala Cys Gly Phe Asp Asp Tyr Glu Pro
125             130                 135                 140

GAG TCT GGA GAT CAG GAT TAT TAC TAC CTG TCG GTG AAG GCT CTC TAC      544
Glu Ser Gly Asp Gln Asp Tyr Tyr Tyr Leu Ser Val Lys Ala Leu Tyr
            145                 150                 155

ACA GTC GGC TAC AGC ACT TCC CTC GCC ACC CTC ACT ACT GCC ATG GTC      592
Thr Val Gly Tyr Ser Thr Ser Leu Ala Thr Leu Thr Thr Ala Met Val
        160                 165                 170

ATC TTG TGC CGC TTC CGG AAG CTG CAT TGC ACT CGC AAC TTC ATC CAC      640
Ile Leu Cys Arg Phe Arg Lys Leu His Cys Thr Arg Asn Phe Ile His
    175                 180                 185

ATG AAC CTG TTT GTA TCC TTC ATG CTG AGG GCT ATC TCC GTC TTC ATC      688
Met Asn Leu Phe Val Ser Phe Met Leu Arg Ala Ile Ser Val Phe Ile
190                 195                 200
```

FIG. 9A

| | |
|---|---|
| AAG GAC TGG ATC TTG TAC GCC GAG CAG GAC AGC AGT CAC TGC TTC GTT<br>Lys Asp Trp Ile Leu Tyr Ala Glu Gln Asp Ser Ser His Cys Phe Val<br>205              210              215              220 | 736 |
| TCC ACC GTG GAG TGC AAA GCT GTC ATG GTT TTC TTC CAC TAC TGC GTG<br>Ser Thr Val Glu Cys Lys Ala Val Met Val Phe Phe His Tyr Cys Val<br>              225              230              235 | 784 |
| GTG TCC AAC TAC TTC TGG CTG TTC ATT GAA GGC CTG TAC CTC TTT ACA<br>Val Ser Asn Tyr Phe Trp Leu Phe Ile Glu Gly Leu Tyr Leu Phe Thr<br>        240              245              250 | 832 |
| CTG CTG GTG GAG ACC TTC TTC CCT GAG AGG AGA TAT TTC TAC TGG TAC<br>Leu Leu Val Glu Thr Phe Phe Pro Glu Arg Arg Tyr Phe Tyr Trp Tyr<br>        255              260              265 | 880 |
| ACC ATC ATC GGC TGG GGG ACA CCT ACT GTG TGT GTA ACA GTG TGG GCT<br>Thr Ile Ile Gly Trp Gly Thr Pro Thr Val Cys Val Thr Val Trp Ala<br>        270              275              280 | 928 |
| GTG CTG AGG CTC TAT TTT GAT GAT GCA GGA TGC TGG GAT ATG AAT GAC<br>Val Leu Arg Leu Tyr Phe Asp Asp Ala Gly Cys Trp Asp Met Asn Asp<br>285              290              295              300 | 976 |
| AGC ACA GCT CTG TGG TGG GTG ATC AAA GGC CCC GTG GTT GGC TCT ATA<br>Ser Thr Ala Leu Trp Trp Val Ile Lys Gly Pro Val Val Gly Ser Ile<br>              305              310              315 | 1024 |
| ATG GTT AAC TTT GTG CTT TTC ATC GGC ATC ATC ATC CTT GTA CAG<br>Met Val Asn Phe Val Leu Phe Ile Gly Ile Ile Ile Ile Leu Val Gln<br>        320              325              330 | 1072 |
| AAG CTG CAG TCC CCA GAC ATG GGA GGC AAC GAG TCC AGC ATC TAC TTC<br>Lys Leu Gln Ser Pro Asp Met Gly Gly Asn Glu Ser Ser Ile Tyr Phe<br>        335              340              345 | 1120 |
| AGC TGC GTG CAG AAA TGC TAC TGC AAG CCA CAG CGG GCT CAG CAG CAC<br>Ser Cys Val Gln Lys Cys Tyr Cys Lys Pro Gln Arg Ala Gln Gln His<br>        350              355              360 | 1168 |
| TCT TGC AAG ATG TCA GAA CTA TCC ACC ATT ACT CTA CGG CTG GCC CGC<br>Ser Cys Lys Met Ser Glu Leu Ser Thr Ile Thr Leu Arg Leu Ala Arg<br>365              370              375              380 | 1216 |
| TCC ACC CTA CTG CTC ATC CCA CTC TTC GGA ATC CAC TAC ACA GTA TTC<br>Ser Thr Leu Leu Leu Ile Pro Leu Phe Gly Ile His Tyr Thr Val Phe<br>              385              390              395 | 1264 |
| GCC TTC TCT CCA GAG AAC GTC AGC AAG AGG GAA AGA CTT GTG TTT GAG<br>Ala Phe Ser Pro Glu Asn Val Ser Lys Arg Glu Arg Leu Val Phe Glu<br>        400              405              410 | 1312 |
| CTT GGG CTG GGC TCC TTC CAG GGC TTT GTG GTG GCT GTA CTC TAC TGC<br>Leu Gly Leu Gly Ser Phe Gln Gly Phe Val Val Ala Val Leu Tyr Cys | 1360 |

FIG. 9B

```
              415                    420                    425
TTC CTG AAT GGG GAG GTA CAG GCA GAG ATT AAG AGG AAA TGG AGG AGC        1408
Phe Leu Asn Gly Glu Val Gln Ala Glu Ile Lys Arg Lys Trp Arg Ser
        430                    435                    440

TGG AAG GTG AAC CGT TAC TTC ACT ATG GAC TTC AAG CAC CGG CAC CCG        1456
Trp Lys Val Asn Arg Tyr Phe Thr Met Asp Phe Lys His Arg His Pro
445                    450                    455                 460

TCC CTG GCC AGC AGT GGA GTA AAT GGG GGA ACC CAG CTG TCC ATC CTG        1504
Ser Leu Ala Ser Ser Gly Val Asn Gly Gly Thr Gln Leu Ser Ile Leu
                    465                    470                475

AGC AAG AGC AGC TCC CAG CTC CGC ATG TCC AGC CTC CCG GCC GAC AAC        1552
Ser Lys Ser Ser Ser Gln Leu Arg Met Ser Ser Leu Pro Ala Asp Asn
                480                    485                    490

TTG GCC ACC TGAGGCCTGT CTCCCTCCTC CTTCTGCACA GGCTGGGGCT GCGGGCCAGT    1611
Leu Ala Thr
        495

GCCTGAGCAT GTTTGTGCCT CTCCCCTCTC CTTGGGCAGG CCCTGGGTAG GAAGCTGGGC     1671
TCCTCCCCAA AGGGGAAGAG AGAGATAGGG TATAGGCTGA TATTGCTCCT CCTGTTTGGG     1731
TCCCACCTAC TGTGATTCAT TGAGCCTGAT TTGACATGTA AATACACCTC AAATTTGGAA     1791
AGTTGCCCCA TCTCTGCCCC CAACCCATGC CCCTGCTCAC CTCTGCCAGG CCCCAGCTCA     1851
ACCTACTGTG TCAAGGCCAG CCTCAGTGAT AGTCTGATCC CAGGTACAAG GCCTTGTGAG     1911
CTGAGGCTGA AAGGCCTGTT TTGGAGAGGC TGGGGTAGTG CCCACCCCAG CAGCCTTTCA     1971
GCAAATTGAC TTTGGATGTG GACCCTTCTC AGCCTGTACC AAGTACTGCA GTTGGCTAGG     2031
GATGCAGCTC AGTTTCCTGA GCATCCTTTG GAGCAGGTCA ACCTGAGGCT CCTTTTGCTT     2091
ACCCGACATC TAAGTTGTCC AGGTGCTCGG CTCCTGTGTG CCTGGATGAC GGGAGGGCTC     2151
CGGGGTCTTT CAGTCAAAGA CTTACATTGA GGTGGGGTGA GAGTCAGAGA AAAGTTCTGG     2211
TGCTTTTCAT TTGTTCTAAG AGCTGAGAGC CAGGAATGCA GAGTCAATTG GGAAGGAGAT     2271
GGGATAGCTG ATGATCTTAC CATGTCCATG ACTGTGCCCC TGATTCAAGA CCGGATCATG     2331
TGGTGGCTTT ATTTCTACAC TTCTTGTCCA CAATGGACAG TCTGAGGAAG CTCTTCTTTC     2391
AGCCACAACA ACCACAGAAA GCCCTTTCTT CTCCCCTCTT GTTTCTCCAT AAGTCAAAGC     2451
CATGTTTAGA ACGGACCAGC CACCTTGCGA TGAAATCACT GAGTTCTGAA GCAACTTTCA     2511
ATTTCCACGA GCCAAGTCCT GGGTCCAGGG ACGCCCC                              2548
```

FIG. 10

Rat     Met His Ser Asp Cys Ile Phe Lys Lys Glu Gln Ala Met Cys Leu Glu
         *   *   *   *   *   *   *   *   *   *   *   *   *   *   *   *
Bovine  Met His Ser Asp Cys Ile Phe Lys Lys Glu Gln Ala Met Cys Leu Glu
         1           5                   10                      15

Rat     Arg Ile Gln Arg Ala Asn Asp Leu Met Gly Leu Asn Glu
         *   *   *       *   *   *   *   *   *   *   *
Bovine  Lys Ile Gln Arg Val Asn Asp Leu Met Gly Leu Asn Asp
                     20              25

FIG. 11

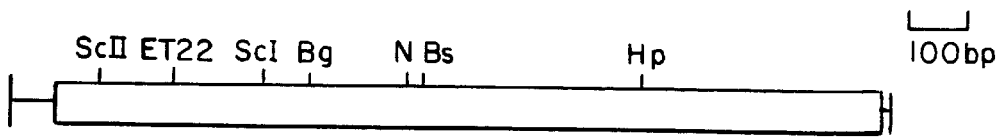

FIG. 12

5                    10                   15
Human   Met His Ser Asp Cys Ile Phe Lys Lys Glu Gln Ala Met Cys Leu
         *   *   *   *   *   *   *   *   *   *   *   *   *   *   *
Bovine  Met His Ser Asp Cys Ile Phe Lys Lys Glu Gln Ala Met Cys Leu 20              25
Human   Gly Lys Ile Gln Arg Ala Asn Glu Leu Met Gly Phe Asn Asp
         *   *   *   *   *       *       *   *   *       *   *
Bovine  Glu Lys Ile Gln Arg Val Asn Asp Leu Met Gly Leu Asn Asp

FIG. 14

```
AGCCCAGAGA CACATTGGGG CTGACCTGCC GCTGCTGTCA GTGGGAGGCC AGTGGTGCTG        60
GCCAAGAAGT GTC ATG GCT GGT GTC GTG CAC GTT TCC CTG GCT GCT CAC         109
            Met Ala Gly Val Val His Val Ser Leu Ala Ala His
             1               5                      10

TGC GGG GCC TGT CCG TGG GGC CGG GGC AGA CTC CGC AAA GGA CGC GCA        157
Cys Gly Ala Cys Pro Trp Gly Arg Gly Arg Leu Arg Lys Gly Arg Ala
            15                  20                  25

GCC TGC AAG TCC GCG GCC CAG AGA CAC ATT GGG GCT GAC CTG CCG CTG        205
Ala Cys Lys Ser Ala Ala Gln Arg His Ile Gly Ala Asp Leu Pro Leu
        30                  35                  40

CTG TCA GTG GGA GGC CAG TGG TGC TGG CCA AGA AGT GTC ATG GCT GGT        253
Leu Ser Val Gly Gly Gln Trp Cys Trp Pro Arg Ser Val Met Ala Gly
45                  50                  55                  60

GTC GTG CAC GTT TCC CTG GCT GCT CTC CTC CTG CCT ATG GCC CCT            301
Val Val His Val Ser Leu Ala Ala Leu Leu Leu Leu Pro Met Ala Pro
                65                  70                  75

GCC ATG CAT TCT GAC TGC ATC TTC AAG AAG GAG CAA GCC ATG TGC CTG        349
Ala Met His Ser Asp Cys Ile Phe Lys Lys Glu Gln Ala Met Cys Leu
                80                  85                  90

GAG AAG ATC CAG AGG GCC AAT GAG CTG ATG GGC TTC AAT GAT TCC TCT        397
Glu Lys Ile Gln Arg Ala Asn Glu Leu Met Gly Phe Asn Asp Ser Ser
            95                  100                 105

CCA GGC TGT CCT GGG ATG TGG GAC AAC ATC ACG TGT TGG AAG CCC GCC        445
Pro Gly Cys Pro Gly Met Trp Asp Asn Ile Thr Cys Trp Lys Pro Ala
        110                 115                 120

CAT GTG GGT GAG ATG GTC CTG GTC AGC TGC CCT GAG CTC TTC CGA ATC        493
His Val Gly Glu Met Val Leu Val Ser Cys Pro Glu Leu Phe Arg Ile
125                 130                 135                 140

TTC AAC CCA GAC CAA GTC TGG GAG ACC GAA ACC ATT GGA GAG TCT GAT        541
Phe Asn Pro Asp Gln Val Trp Glu Thr Glu Thr Ile Gly Glu Ser Asp
                145                 150                 155

TTT GGT GAC AGT AAC TCC TTA GAT CTC TCA GAC ATG GGA GTG GTG AGC        589
Phe Gly Asp Ser Asn Ser Leu Asp Leu Ser Asp Met Gly Val Val Ser
                160                 165                 170

CGG AAC TGC ACG GAG GAT GGC TGG TCG GAA CCC TTC CCT CAT TAC TTT        637
Arg Asn Cys Thr Glu Asp Gly Trp Ser Glu Pro Phe Pro His Tyr Phe
            175                 180                 185

GAT GCC TGT GGG TTT GAT GAA TAT GAA TCT GAG ACT GGG GAC CAG GAT        685
Asp Ala Cys Gly Phe Asp Glu Tyr Glu Ser Glu Thr Gly Asp Gln Asp
```

FIG. 13A

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     | 190 |     |     |     |     | 195 |     |     |     |     | 200 |     |     |     |       |
| TAT | TAC | TAC | CTG | TCA | GTG | AAG | GCC | CTC | TAC | ACG | GTT | GGC | TAC | AGC | ACA | 733   |
| Tyr | Tyr | Tyr | Leu | Ser | Val | Lys | Ala | Leu | Tyr | Thr | Val | Gly | Tyr | Ser | Thr |       |
| 205 |     |     |     |     | 210 |     |     |     |     | 215 |     |     |     |     | 220 |       |
| TCC | CTC | GTC | ACC | CTC | ACC | ACT | GCC | ATG | GTC | ATC | CTT | TGT | CGC | TTC | CGG | 781   |
| Ser | Leu | Val | Thr | Leu | Thr | Thr | Ala | Met | Val | Ile | Leu | Cys | Arg | Phe | Arg |       |
|     |     |     |     | 225 |     |     |     |     | 230 |     |     |     |     | 235 |     |       |
| AAG | CTG | CAC | TGC | ACA | CGC | AAC | TTC | ATC | CAC | ATG | AAC | CTG | TTT | GTG | TCG | 829   |
| Lys | Leu | His | Cys | Thr | Arg | Asn | Phe | Ile | His | Met | Asn | Leu | Phe | Val | Ser |       |
|     |     |     | 240 |     |     |     |     | 245 |     |     |     |     | 250 |     |     |       |
| TTC | ATG | CTG | AGG | GCG | ATC | TCC | GTC | TTC | ATC | AAA | GAC | TGG | ATT | CTG | TAT | 877   |
| Phe | Met | Leu | Arg | Ala | Ile | Ser | Val | Phe | Ile | Lys | Asp | Trp | Ile | Leu | Tyr |       |
|     |     | 255 |     |     |     |     | 260 |     |     |     |     | 265 |     |     |     |       |
| GCG | GAG | CAG | GAC | AGC | AAC | CAC | TGC | TTC | ATC | TCC | ACT | GTG | GAA | TGT | AAG | 925   |
| Ala | Glu | Gln | Asp | Ser | Asn | His | Cys | Phe | Ile | Ser | Thr | Val | Glu | Cys | Lys |       |
|     | 270 |     |     |     |     | 275 |     |     |     |     | 280 |     |     |     |     |       |
| GCC | GTC | ATG | GTT | TTC | TTC | CAC | TAC | TGT | GTT | GTG | TCC | AAC | TAC | TTC | TGG | 973   |
| Ala | Val | Met | Val | Phe | Phe | His | Tyr | Cys | Val | Val | Ser | Asn | Tyr | Phe | Trp |       |
| 285 |     |     |     |     | 290 |     |     |     |     | 295 |     |     |     |     | 300 |       |
| CTG | TTC | ATC | GAG | GGC | CTG | TAC | CTC | TTC | ACT | CTG | CTG | GTG | GAG | ACC | TTC | 1021  |
| Leu | Phe | Ile | Glu | Gly | Leu | Tyr | Leu | Phe | Thr | Leu | Leu | Val | Glu | Thr | Phe |       |
|     |     |     |     | 305 |     |     |     |     | 310 |     |     |     |     | 315 |     |       |
| TTC | CCT | GAA | AGG | AGA | TAC | TTC | TAC | TGG | TAC | ACC | ATC | ATT | GGC | TGG | GGG | 1069  |
| Phe | Pro | Glu | Arg | Arg | Tyr | Phe | Tyr | Trp | Tyr | Thr | Ile | Ile | Gly | Trp | Gly |       |
|     |     |     | 320 |     |     |     |     | 325 |     |     |     |     | 330 |     |     |       |
| TCC | CCA | ACT | GTG | TGT | GTG | ACA | GTG | TGG | GCT | ACG | CTG | AGA | CTC | TAC | TTT | 1117  |
| Ser | Pro | Thr | Val | Cys | Val | Thr | Val | Trp | Ala | Thr | Leu | Arg | Leu | Tyr | Phe |       |
|     |     | 335 |     |     |     |     | 340 |     |     |     |     | 345 |     |     |     |       |
| GAT | GAC | ACA | GGC | TGC | TGG | GAT | ATG | AAT | GAC | AGC | ACA | GCT | CTG | TGG | TGG | 1165  |
| Asp | Asp | Thr | Gly | Cys | Trp | Asp | Met | Asn | Asp | Ser | Thr | Ala | Leu | Trp | Trp |       |
|     |     | 350 |     |     |     |     | 355 |     |     |     |     | 360 |     |     |     |       |
| GTG | ATC | AAA | GGC | CCT | GTG | GTT | GGC | TCT | ATC | ATG | GTT | AAC | TTT | GTG | CTT | 1213  |
| Val | Ile | Lys | Gly | Pro | Val | Val | Gly | Ser | Ile | Met | Val | Asn | Phe | Val | Leu |       |
| 365 |     |     |     |     | 370 |     |     |     |     | 375 |     |     |     |     | 380 |       |
| TTT | ATT | GGC | ATT | ATC | GTC | ATC | CTT | GTG | CAG | AAA | CTT | CAG | TCT | CCA | GAC | 1261  |
| Phe | Ile | Gly | Ile | Ile | Val | Ile | Leu | Val | Gln | Lys | Leu | Gln | Ser | Pro | Asp |       |
|     |     |     |     | 385 |     |     |     |     | 390 |     |     |     |     | 395 |     |       |
| ATG | GGA | GGC | AAT | GAG | TCC | AGC | ATC | TAC | TTG | CGA | CTG | GCC | CGG | TCC | ACC | 1309  |
| Met | Gly | Gly | Asn | Glu | Ser | Ser | Ile | Tyr | Leu | Arg | Leu | Ala | Arg | Ser | Thr |       |
|     |     |     | 400 |     |     |     |     | 405 |     |     |     |     | 410 |     |     |       |

FIG. 13B

```
CTG CTG CTC ATC CCA CTA TTC GGA ATC CAC TAC ACA GTA TTT GCC TTC      1357
Leu Leu Leu Ile Pro Leu Phe Gly Ile His Tyr Thr Val Phe Ala Phe
        415                     420                 425

TCC CCA GAG AAT GTC AGC AAA AGG GAA AGA CTC GTG TTT GAG CTG GGG      1405
Ser Pro Glu Asn Val Ser Lys Arg Glu Arg Leu Val Phe Glu Leu Gly
        430                     435                 440

CTG GGC TCC TTC CAG GGC TTT GTG GTG GCT GTT CTC TAC TGT TTT CTG      1453
Leu Gly Ser Phe Gln Gly Phe Val Val Ala Val Leu Tyr Cys Phe Leu
445                     450                 455                 460

AAT GGT GAG GTA CAA GCG GAG ATC AAG CGA AAA TGG CGA AGC TGG AAG      1501
Asn Gly Glu Val Gln Ala Glu Ile Lys Arg Lys Trp Arg Ser Trp Lys
                465                 470                 475

GTG AAC CGT TAC TTC GCT GTG GAC TTC AAG CAC CGA CAC CCG TCT CTG      1549
Val Asn Arg Tyr Phe Ala Val Asp Phe Lys His Arg His Pro Ser Leu
            480                 485                 490

GCC AGC AGT GGG GTG AAT GGG GGC ACC CAG CTC TCC ATC CTG AGC AAG      1597
Ala Ser Ser Gly Val Asn Gly Gly Thr Gln Leu Ser Ile Leu Ser Lys
            495                 500                 505

AGC AGC TCC CAA ATC CGC ATG TCT GGC CTC CCT GCT GAC AAT CTG GCC      1645
Ser Ser Ser Gln Ile Arg Met Ser Gly Leu Pro Ala Asp Asn Leu Ala
        510                 515                 520

ACC TGAGCCATGC TCCCCT                                                1664
Thr
525
```

FIG. 13C

```
Rat              Asn Glu Ser Ser Ile Tyr Phe Ser Cys Val Gln Lys Cys Tyr Cys Lys
Type I-B         AAC GAG TCC AGC ATC TAC TTC AGC TGC GTG CAG AAA TGC TAC TGC AAA
                                         ▲ pHRP15A          Asn Glu Ser Ser Ile Tyr Phe Ser Cys Val Gln Lys Cys Tyr Cys Lys
human Type I-B   AAT GAG TCC AGC ATC TAC TTC AGC TGC GTG CAG AAA TGC TAC TGC AAG
                                         ▲ pHPR55A          Asn Glu Ser Ser Ile Tyr Phe ___ Cys Val Gln Lys Cys Tyr Cys Lys
Type I-B2        AAT GAG TCC AGC ATC TAC TTC     TGC GTG CAG AAA TGC TAC TGC AAG
                                         ▲ pHRP66P          Asn Glu Ser Ser Ile Tyr Leu Thr Asn Leu Ser Pro Arg Val Pro Lys
Type I-C         AAT GAG TCC AGC ATC TAC TTA ACA AAT TTA AGC CCG CGA GTC CCC AAG
                                         ▲
```

```
           Pro Gln Arg Ala Gln Gln His Ser Cys Lys Met Ser Glu Leu Ser Thr
           CCA CAG CGG CGT CAG CAG CAC TCT TGC AAG ATC TCA GAA CTA TCC ACC

Pro Gln Arg Ala Gln Gln His Ser Cys Lys Met Ser Glu Leu Ser Thr
           CCA CAG CGG GCT CAG CAG CAC TCT TGC AAG ATG TCA GAA CTG TCC ACC

Pro Gln Arg Ala Gln Gln His Ser Cys Lys Met Ser Glu Leu Ser Thr
           CCA CAG CGG GCT CAG CAG CAC TCT TGC AAG ATG TCA GAA CTG TCC ACC

Lys Ala Arg Glu Asp Pro Leu Pro Val Pro Ser Asp Gln His Ser Leu
           AAA GCC CGA GAG GAC CCC CTG CCT GTG CCC TCA GAC CAG CAT TCA CTC
```

```
                  Ile Thr Leu Arg Leu Ala Arg Ser Thr Leu
                  ATT ACT CTA CGG CTG GCC CGC TCC ACC CTA
                              ▲

Ile Thr Leu Arg Leu Ala Arg Ser Thr Leu
                  ATT ACT CTG CGA CTG GCC CGG TCC ACC CTG
                              ▲

Ile Thr Leu Arg Leu Ala Arg Ser Thr Leu
                  ATT ACT CTG CGA CTG GCC CGG TCC ACC CTG
                              ▲

Pro Phe Leu Arg Leu Ala Arg Ser Thr Leu
                  CCT TTC CTG CGA CTG GCC CGG TCC ACC CTG
                              ▲
```

FIG. 15

```
AGCCCAGAGA CACATTGGGG CTGACCTGCC GCTGCTGTCA GTGGGAGGCC AGTGGTGCTG    60
GCCAAGAAGT GTC ATG GCT GGT GTC GTG CAC GTT TCC CTG GCT GCT CAC      109
            Met Ala Gly Val Val His Val Ser Leu Ala Ala His
             1           5                           10

TGC GGG GCC TGT CCG TGG GGC CGG GGC AGA CTC CGC AAA GGA CGC GCA     157
Cys Gly Ala Cys Pro Trp Gly Arg Gly Arg Leu Arg Lys Gly Arg Ala
         15              20                  25

GCC TGC AAG TCC GCG GCC CAG AGA CAC ATT GGG GCT GAC CTG CCG CTG     205
Ala Cys Lys Ser Ala Ala Gln Arg His Ile Gly Ala Asp Leu Pro Leu
     30                  35                  40

CTG TCA GTG GGA GGC CAG TGG TGC TGG CCA AGA AGT GTC ATG GCT GGT     253
Leu Ser Val Gly Gly Gln Trp Cys Trp Pro Arg Ser Val Met Ala Gly
45                  50                  55                  60

GTC GTG CAC GTT TCC CTG GCT GCT CTC CTC CTG CTG CCT ATG GCC CCT     301
Val Val His Val Ser Leu Ala Ala Leu Leu Leu Leu Pro Met Ala Pro
             65                  70                  75

GCC ATG CAT TCT GAC TGC ATC TTC AAG AAG GAG CAA GCC ATG TGC CTG     349
Ala Met His Ser Asp Cys Ile Phe Lys Lys Glu Gln Ala Met Cys Leu
                 80                  85                  90

GAG AAG ATC CAG AGG GCC AAT GAG CTG ATG GGC TTC AAT GAT TCC TCT     397
Glu Lys Ile Gln Arg Ala Asn Glu Leu Met Gly Phe Asn Asp Ser Ser
             95                 100                 105

CCA GGC TGT CCT GGG ATG TGG GAC AAC ATC ACG TGT TGG AAG CCC GCC     445
Pro Gly Cys Pro Gly Met Trp Asp Asn Ile Thr Cys Trp Lys Pro Ala
         110                 115                 120

CAT GTG GGT GAG ATG GTC CTG GTC AGC TGC CCT GAG CTC TTC CGA ATC     493
His Val Gly Glu Met Val Leu Val Ser Cys Pro Glu Leu Phe Arg Ile
125                 130                 135                 140

TTC AAC CCA GAC CAA GTC TGG GAG ACC GAA ACC ATT GGA GAG TCT GAT     541
Phe Asn Pro Asp Gln Val Trp Glu Thr Glu Thr Ile Gly Glu Ser Asp
                 145                 150                 155

TTT GGT GAC AGT AAC TCC TTA GAT CTC TCA GAC ATG GGA GTG GTG AGC     589
Phe Gly Asp Ser Asn Ser Leu Asp Leu Ser Asp Met Gly Val Val Ser
             160                 165                 170

CGG AAC TGC ACG GAG GAT GGC TGG TCG GAA CCC TTC CCT CAT TAC TTT     637
Arg Asn Cys Thr Glu Asp Gly Trp Ser Glu Pro Phe Pro His Tyr Phe
         175                 180                 185

GAT GCC TGT GGG TTT GAT GAA TAT GAA TCT GAG ACT GGG GAC CAG GAT     685
Asp Ala Cys Gly Phe Asp Glu Tyr Glu Ser Glu Thr Gly Asp Gln Asp
```

FIG. 16A

```
              190                    195                    200
    TAT TAC TAC CTG TCA GTG AAG GCC CTC TAC ACG GTT GGC TAC AGC ACA     733
    Tyr Tyr Tyr Leu Ser Val Lys Ala Leu Tyr Thr Val Gly Tyr Ser Thr
    205                 210                 215                 220

TCC CTC GTC ACC CTC ACC ACT GCC ATG GTC ATC CTT TGT CGC TTC CGG     781
    Ser Leu Val Thr Leu Thr Thr Ala Met Val Ile Leu Cys Arg Phe Arg
                        225                 230                 235

AAG CTG CAC TGC ACA CGC AAC TTC ATC CAC ATG AAC CTG TTT GTG TCG     829
    Lys Leu His Cys Thr Arg Asn Phe Ile His Met Asn Leu Phe Val Ser
                240                 245                 250

TTC ATG CTG AGG GCG ATC TCC GTC TTC ATC AAA GAC TGG ATT CTG TAT     877
    Phe Met Leu Arg Ala Ile Ser Val Phe Ile Lys Asp Trp Ile Leu Tyr
                255                 260                 265

GCG GAG CAG GAC AGC AAC CAC TGC TTC ATC TCC ACT GTG GAA TGT AAG     925
    Ala Glu Gln Asp Ser Asn His Cys Phe Ile Ser Thr Val Glu Cys Lys
                270                 275                 280

GCC GTC ATG GTT TTC TTC CAC TAC TGT GTT GTG TCC AAC TAC TTC TGG     973
    Ala Val Met Val Phe Phe His Tyr Cys Val Val Ser Asn Tyr Phe Trp
    285                 290                 295                 300

CTG TTC ATC GAG GGC CTG TAC CTC TTC ACT CTG CTG GTG GAG ACC TTC    1021
    Leu Phe Ile Glu Gly Leu Tyr Leu Phe Thr Leu Leu Val Glu Thr Phe
                        305                 310                 315

TTC CCT GAA AGG AGA TAC TTC TAC TGG TAC ACC ATC ATT GGC TGG GGG    1069
    Phe Pro Glu Arg Arg Tyr Phe Tyr Trp Tyr Thr Ile Ile Gly Trp Gly
                    320                 325                 330

ACC CCA ACT GTG TGT GTG ACA GTG TGG GCT ACG CTG AGA CTC TAC TTT    1117
    Thr Pro Thr Val Cys Val Thr Val Trp Ala Thr Leu Arg Leu Tyr Phe
                    335                 340                 345

GAT GAC ACA GGC TGC TGG GAT ATG AAT GAC AGC ACA GCT CTG TGG TGG    1165
    Asp Asp Thr Gly Cys Trp Asp Met Asn Asp Ser Thr Ala Leu Trp Trp
                350                 355                 360

GTG ATC AAA GGC CCT GTG GTT GGC TCT ATC ATG GTT AAC TTT GTG CTT    1213
    Val Ile Lys Gly Pro Val Val Gly Ser Ile Met Val Asn Phe Val Leu
    365                 370                 375                 380

TTT ATT GGC ATT ATC GTC ATC CTT GTG CAG AAA CTT CAG TCT CCA GAC    1261
    Phe Ile Gly Ile Ile Val Ile Leu Val Gln Lys Leu Gln Ser Pro Asp
                        385                 390                 395

ATG GGA GGC AAT GAG TCC AGC ATC TAC TTC AGC TGC GTG CAG AAA TGC    1309
    Met Gly Gly Asn Glu Ser Ser Ile Tyr Phe Ser Cys Val Gln Lys Cys
                    400                 405                 410
```

FIG. 16B

```
TAC TGC AAG CCA CAG CGG GCT CAG CAG CAC TCT TGC AAG ATG TCA GAA    1357
Tyr Cys Lys Pro Gln Arg Ala Gln Gln His Ser Cys Lys Met Ser Glu
        415             420             425

CTG TCC ACC ATT ACT CTG CGA CTG GCC CGG TCC ACC CTG CTG CTC ATC    1405
Leu Ser Thr Ile Thr Leu Arg Leu Ala Arg Ser Thr Leu Leu Leu Ile
        430             435             440

CCA CTA TTC GGA ATC CAC TAC ACA GTA TTT GCC TTC TCC CCA GAG AAT    1453
Pro Leu Phe Gly Ile His Tyr Thr Val Phe Ala Phe Ser Pro Glu Asn
445             450             455             460

GTC AGC AAA AGG GAA AGA CTC GTG TTT GAG CTG GGG CTG GGC TCC TTC    1501
Val Ser Lys Arg Glu Arg Leu Val Phe Glu Leu Gly Leu Gly Ser Phe
        465             470             475

CAG GGC TTT GTG GTG GCT GTT CTC TAC TGT TTT CTG AAT GGT GAG GTA    1549
Gln Gly Phe Val Val Ala Val Leu Tyr Cys Phe Leu Asn Gly Glu Val
        480             485             490

CAA GCG GAG ATC AAG CGA AAA TGG CGA AGC TGG AAG GTG AAC CGT TAC    1597
Gln Ala Glu Ile Lys Arg Lys Trp Arg Ser Trp Lys Val Asn Arg Tyr
        495             500             505

TTC GCT GTG GAC TTC AAG CAC CGA CAC CCG TCT CTG GCC AGC AGT GGG    1645
Phe Ala Val Asp Phe Lys His Arg His Pro Ser Leu Ala Ser Ser Gly
        510             515             520

GTG AAT GGG GGC ACC CAG CTC TCC ATC CTG AGC AAG AGC AGC TCC CAA    1693
Val Asn Gly Gly Thr Gln Leu Ser Ile Leu Ser Lys Ser Ser Ser Gln
525             530             535             540

ATC CGC ATG TCT GGC CTC CCT GCT GAC AAT CTG GCC ACC TGAGCCATGC TCC  1745
Ile Arg Met Ser Gly Leu Pro Ala Asp Asn Leu Ala Thr
                545             550

CCT                                                                1748
```

FIG. 16C

```
AGCCCAGAGA CACATTGGGG CTGACCTGCC GCTGCTGTCA GTGGGAGGCC AGTGGTGCTG        60
GCCAAGAAGT GTC ATG GCT GGT GTC GTG CAC GTT TCC CTG GCT GCT CAC         109
            Met Ala Gly Val Val His Val Ser Leu Ala Ala His
             1           5                      10

TGC GGG GCC TGT CCG TGG GGC CGG GGC AGA CTC CGC AAA GGA CGC GCA        157
Cys Gly Ala Cys Pro Trp Gly Arg Gly Arg Leu Arg Lys Gly Arg Ala
        15                  20                  25

GCC TGC AAG TCC GCG GCC CAG AGA CAC ATT GGG GCT GAC CTG CCG CTG        205
Ala Cys Lys Ser Ala Ala Gln Arg His Ile Gly Ala Asp Leu Pro Leu
        30                  35                  40

CTG TCA GTG GGA GGC CAG TGG TGC TGG CCA AGA AGT GTC ATG GCT GGT        253
Leu Ser Val Gly Gly Gln Trp Cys Trp Pro Arg Ser Val Met Ala Gly
45              50                  55                      60

GTC GTG CAC GTT TCC CTG GCT GCT CTC CTC CTG CTG CCT ATG GCC CCT        301
Val Val His Val Ser Leu Ala Ala Leu Leu Leu Leu Pro Met Ala Pro
                65                  70                  75

GCC ATG CAT TCT GAC TGC ATC TTC AAG AAG GAG CAA GCC ATG TGC CTG        349
Ala Met His Ser Asp Cys Ile Phe Lys Lys Glu Gln Ala Met Cys Leu
            80                  85                  90

GAG AAG ATC CAG AGG GCC AAT GAG CTG ATG GGC TTC AAT GAT TCC TCT        397
Glu Lys Ile Gln Arg Ala Asn Glu Leu Met Gly Phe Asn Asp Ser Ser
        95                  100                 105

CCA GGC TGT CCT GGG ATG TGG GAC AAC ATC ACG TGT TGG AAG CCC GCC        445
Pro Gly Cys Pro Gly Met Trp Asp Asn Ile Thr Cys Trp Lys Pro Ala
        110                 115                 120

CAT GTG GGT GAG ATG GTC CTG GTC AGC TGC CCT GAG CTC TTC CGA ATC        493
His Val Gly Glu Met Val Leu Val Ser Cys Pro Glu Leu Phe Arg Ile
125                 130                 135                 140

TTC AAC CCA GAC CAA GTC TGG GAG ACC GAA ACC ATT GGA GAG TCT GAT        541
Phe Asn Pro Asp Gln Val Trp Glu Thr Glu Thr Ile Gly Glu Ser Asp
                145                 150                 155

TTT GGT GAC AGT AAC TCC TTA GAT CTC TCA GAC ATG GGA GTG GTG AGC        589
Phe Gly Asp Ser Asn Ser Leu Asp Leu Ser Asp Met Gly Val Val Ser
            160                 165                 170

CGG AAC TGC ACG GAG GAT GGC TGG TCG GAA CCC TTC CCT CAT TAC TTT        637
Arg Asn Cys Thr Glu Asp Gly Trp Ser Glu Pro Phe Pro His Tyr Phe
        175                 180                 185

GAT GCC TGT GGG TTT GAT GAA TAT GAA TCT GAG ACT GGG GAC CAG GAT        685
Asp Ala Cys Gly Phe Asp Glu Tyr Glu Ser Glu Thr Gly Asp Gln Asp
        190                 195                 200
```

FIG. 17A

```
TAT TAC TAC CTG TCA GTG AAG GCC CTC TAC ACG GTT GGC TAC AGC ACA    733
Tyr Tyr Tyr Leu Ser Val Lys Ala Leu Tyr Thr Val Gly Tyr Ser Thr
205             210             215             220

TCC CTC GTC ACC CTC ACC ACT GCC ATG GTC ATC CTT TGT CGC TTC CGG    781
Ser Leu Val Thr Leu Thr Thr Ala Met Val Ile Leu Cys Arg Phe Arg
                225             230             235

AAG CTG CAC TGC ACA CGC AAC TTC ATC CAC ATG AAC CTG TTT GTG TCG    829
Lys Leu His Cys Thr Arg Asn Phe Ile His Met Asn Leu Phe Val Ser
            240             245             250

TTC ATG CTG AGG GCG ATC TCC GTC TTC ATC AAA GAC TGG ATT CTG TAT    877
Phe Met Leu Arg Ala Ile Ser Val Phe Ile Lys Asp Trp Ile Leu Tyr
        255             260             265

GCG GAG CAG GAC AGC AAC CAC TGC TTC ATC TCC ACT GTG GAA TGT AAG    925
Ala Glu Gln Asp Ser Asn His Cys Phe Ile Ser Thr Val Glu Cys Lys
    270             275             280

GCC GTC ATG GTT TTC TTC CAC TAC TGT GTT GTG TCC AAC TAC TTC TGG    973
Ala Val Met Val Phe Phe His Tyr Cys Val Val Ser Asn Tyr Phe Trp
285             290             295             300

CTG TTC ATC GAG GGC CTG TAC CTC TTC ACT CTG CTG GTG GAG ACC TTC   1021
Leu Phe Ile Glu Gly Leu Tyr Leu Phe Thr Leu Leu Val Glu Thr Phe
                305             310             315

TTC CCT GAA AGG AGA TAC TTC TAC TGG TAC ACC ATC ATT GGC TGG GGG   1069
Phe Pro Glu Arg Arg Tyr Phe Tyr Trp Tyr Thr Ile Ile Gly Trp Gly
            320             325             330

ACC CCA ACT GTG TGT GTG ACA GTG TGG GCT ACG CTG AGA CTC TAC TTT   1117
Thr Pro Thr Val Cys Val Thr Val Trp Ala Thr Leu Arg Leu Tyr Phe
        335             340             345

GAT GAC ACA GGC TGC TGG GAT ATG AAT GAC AGC ACA GCT CTG TGG TGG   1165
Asp Asp Thr Gly Cys Trp Asp Met Asn Asp Ser Thr Ala Leu Trp Trp
    350             355             360

GTG ATC AAA GGC CCT GTG GTT GGC TCT ATC ATG GTT AAC TTT GTG CTT   1213
Val Ile Lys Gly Pro Val Val Gly Ser Ile Met Val Asn Phe Val Leu
365             370             375             380

TTT ATT GGC ATT ATC GTC ATC CTT GTG CAG AAA CTT CAG TCT CCA GAC   1261
Phe Ile Gly Ile Ile Val Ile Leu Val Gln Lys Leu Gln Ser Pro Asp
                385             390             395

ATG GGA GGC AAT GAG TCC AGC ATC TAC TTC TGC GTG CAG AAA TGC TAC   1309
Met Gly Gly Asn Glu Ser Ser Ile Tyr Phe Cys Val Gln Lys Cys Tyr
            400             405             410

TGC AAG CCA CAG CGG GCT CAG CAG CAC TCT TGC AAG ATG TCA GAA CTG   1357
Cys Lys Pro Gln Arg Ala Gln Gln His Ser Cys Lys Met Ser Glu Leu
```

FIG. 17B

```
                415                    420                   425
TCC ACC ATT ACT CTG CGA CTG GCC CGG TCC ACC CTG CTG CTC ATC CCA    1405
Ser Thr Ile Thr Leu Arg Leu Ala Arg Ser Thr Leu Leu Leu Ile Pro
        430                 435                 440

CTA TTC GGA ATC CAC TAC ACA GTA TTT GCC TTC TCC CCA GAG AAT GTC    1453
Leu Phe Gly Ile His Tyr Thr Val Phe Ala Phe Ser Pro Glu Asn Val
445                 450                 455                 460

AGC AAA AGG GAA AGA CTC GTG TTT GAG CTG GGG CTG GGC TCC TTC CAG    1501
Ser Lys Arg Glu Arg Leu Val Phe Glu Leu Gly Leu Gly Ser Phe Gln
                465                 470                 475

GGC TTT GTG GTG GCT GTT CTC TAC TGT TTT CTG AAT GGT GAG GTA CAA    1549
Gly Phe Val Val Ala Val Leu Tyr Cys Phe Leu Asn Gly Glu Val Gln
            480                 485                 490

GCG GAG ATC AAG CGA AAA TGG CGA AGC TGG AAG GTG AAC CGT TAC TTC    1597
Ala Glu Ile Lys Arg Lys Trp Arg Ser Trp Lys Val Asn Arg Tyr Phe
        495                 500                 505

GCT GTG GAC TTC AAG CAC CGA CAC CCG TCT CTG GCC AGC AGT GGG GTG    1645
Ala Val Asp Phe Lys His Arg His Pro Ser Leu Ala Ser Ser Gly Val
    510                 515                 520

AAT GGG GGC ACC CAG CTC TCC ATC CTG AGC AAG AGC AGC TCC CAA ATC    1693
Asn Gly Gly Thr Gln Leu Ser Ile Leu Ser Lys Ser Ser Ser Gln Ile
525                 530                 535                 540

CGC ATG TCT GGC CTC CCT GCT GAC AAT CTG GCC ACC TGAGCCATGC TCCCCT  1745
Arg Met Ser Gly Leu Pro Ala Asp Asn Leu Ala Thr
                545                 550
```

FIG. 17C

```
AGCCCAGAGA CACATTGGGG CTGACCTGCC GCTGCTGTCA GTGGGAGGCC AGTGGTGCTG    60
GCCAAGAAGT GTC ATG GCT GGT GTC GTG CAC GTT TCC CTG GCT GCT CAC     109
        Met Ala Gly Val Val His Val Ser Leu Ala Ala His
         1           5                       10

TGC GGG GCC TGT CCG TGG GGC CGG GGC AGA CTC CGC AAA GGA CGC GCA    157
Cys Gly Ala Cys Pro Trp Gly Arg Gly Arg Leu Arg Lys Gly Arg Ala
         15              20                  25

GCC TGC AAG TCC GCG GCC CAG AGA CAC ATT GGG GCT GAC CTG CCG CTG    205
Ala Cys Lys Ser Ala Ala Gln Arg His Ile Gly Ala Asp Leu Pro Leu
     30              35                  40

CTG TCA GTG GGA GGC CAG TGG TGC TGG CCA AGA AGT GTC ATG GCT GGT    253
Leu Ser Val Gly Gly Gln Trp Cys Trp Pro Arg Ser Val Met Ala Gly
45              50                  55                      60

GTC GTG CAC GTT TCC CTG GCT GCT CTC CTC CTG CTG CCT ATG GCC CCT    301
Val Val His Val Ser Leu Ala Ala Leu Leu Leu Leu Pro Met Ala Pro
                 65                  70                  75

GCC ATG CAT TCT GAC TGC ATC TTC AAG AAG GAG CAA GCC ATG TGC CTG    349
Ala Met His Ser Asp Cys Ile Phe Lys Lys Glu Gln Ala Met Cys Leu
             80                  85                  90

GAG AAG ATC CAG AGG GCC AAT GAG CTG ATG GGC TTC AAT GAT TCC TCT    397
Glu Lys Ile Gln Arg Ala Asn Glu Leu Met Gly Phe Asn Asp Ser Ser
         95                  100                 105

CCA GGC TGT CCT GGG ATG TGG GAC AAC ATC ACG TGT TGG AAG CCC GCC    445
Pro Gly Cys Pro Gly Met Trp Asp Asn Ile Thr Cys Trp Lys Pro Ala
     110                 115                 120

CAT GTG GGT GAG ATG GTC CTG GTC AGC TGC CCT GAG CTC TTC CGA ATC    493
His Val Gly Glu Met Val Leu Val Ser Cys Pro Glu Leu Phe Arg Ile
125                 130                 135                 140

TTC AAC CCA GAC CAA GTC TGG GAG ACC GAA ACC ATT GGA GAG TCT GAT    541
Phe Asn Pro Asp Gln Val Trp Glu Thr Glu Thr Ile Gly Glu Ser Asp
                 145                 150                 155

TTT GGT GAC AGT AAC TCC TTA GAT CTC TCA GAC ATG GGA GTG GTG AGC    589
Phe Gly Asp Ser Asn Ser Leu Asp Leu Ser Asp Met Gly Val Val Ser
             160                 165                 170

CGG AAC TGC ACG GAG GAT GGC TGG TCG GAA CCC TTC CCT CAT TAC TTT    637
Arg Asn Cys Thr Glu Asp Gly Trp Ser Glu Pro Phe Pro His Tyr Phe
         175                 180                 185

GAT GCC TGT GGG TTT GAT GAA TAT GAA TCT GAG ACT GGG GAC CAG GAT    685
Asp Ala Cys Gly Phe Asp Glu Tyr Glu Ser Glu Thr Gly Asp Gln Asp
```

FIG. 18A

|     | 190 |     |     |     |     | 195 |     |     |     |     | 200 |     |     |     |     |
| --- | --- | --- | --- | --- | --- | --- | --- | --- | --- | --- | --- | --- | --- | --- | --- |

```
TAT TAC TAC CTG TCA GTG AAG GCC CTC TAC ACG GTT GGC TAC AGC ACA    733
Tyr Tyr Tyr Leu Ser Val Lys Ala Leu Tyr Thr Val Gly Tyr Ser Thr
205             210                 215                 220

TCC CTC GTC ACC CTC ACC ACT GCC ATG GTC ATC CTT TGT CGC TTC CGG    781
Ser Leu Val Thr Leu Thr Thr Ala Met Val Ile Leu Cys Arg Phe Arg
                225                 230                 235

AAG CTG CAC TGC ACA CGC AAC TTC ATC CAC ATG AAC CTG TTT GTG TCG    829
Lys Leu His Cys Thr Arg Asn Phe Ile His Met Asn Leu Phe Val Ser
            240                 245                 250

TTC ATG CTG AGG GCG ATC TCC GTC TTC ATC AAA GAC TGG ATT CTG TAT    877
Phe Met Leu Arg Ala Ile Ser Val Phe Ile Lys Asp Trp Ile Leu Tyr
        255                 260                 265

GCG GAG CAG GAC AGC AAC CAC TGC TTC ATC TCC ACT GTG GAA TGT AAG    925
Ala Glu Gln Asp Ser Asn His Cys Phe Ile Ser Thr Val Glu Cys Lys
    270                 275                 280

GCC GTC ATG GTT TTC TTC CAC TAC TGT GTT GTG TCC AAC TAC TTC TGG    973
Ala Val Met Val Phe Phe His Tyr Cys Val Val Ser Asn Tyr Phe Trp
285                 290                 295                 300

CTG TTC ATC GAG GGC CTG TAC CTC TTC ACT CTG CTG GTG GAG ACC TTC    1021
Leu Phe Ile Glu Gly Leu Tyr Leu Phe Thr Leu Leu Val Glu Thr Phe
                305                 310                 315

TTC CCT GAA AGG AGA TAC TTC TAC TGG TAC ACC ATC ATT GGC TGG GGG    1069
Phe Pro Glu Arg Arg Tyr Phe Tyr Trp Tyr Thr Ile Ile Gly Trp Gly
                320                 325                 330

ACC CCA ACT GTG TGT GTG ACA GTG TGG GCT ACG CTG AGA CTC TAC TTT    1117
Thr Pro Thr Val Cys Val Thr Val Trp Ala Thr Leu Arg Leu Tyr Phe
            335                 340                 345

GAT GAC ACA GGC TGC TGG GAT ATG AAT GAC AGC ACA GCT CTG TGG TGG    1165
Asp Asp Thr Gly Cys Trp Asp Met Asn Asp Ser Thr Ala Leu Trp Trp
        350                 355                 360

GTG ATC AAA GGC CCT GTG GTT GGC TCT ATC ATG GTT AAC TTT GTG CTT    1213
Val Ile Lys Gly Pro Val Val Gly Ser Ile Met Val Asn Phe Val Leu
365                 370                 375                 380

TTT ATT GGC ATT ATC GTC ATC CTT GTG CAG AAA CTT CAG TCT CCA GAC    1261
Phe Ile Gly Ile Ile Val Ile Leu Val Gln Lys Leu Gln Ser Pro Asp
                385                 390                 395

ATG GGA GGC AAT GAG TCC AGC ATC TAC TTA ACA AAT TTA AGC CCG CGA    1309
Met Gly Gly Asn Glu Ser Ser Ile Tyr Leu Thr Asn Leu Ser Pro Arg
            400                 405                 410
```

FIG. 18B

```
GTC CCC AAG AAA GCC CGA GAG GAC CCC CTG CCT GTG CCC TCA GAC CAG    1357
Val Pro Lys Lys Ala Arg Glu Asp Pro Leu Pro Val Pro Ser Asp Gln
        415             420             425

CAT TCA CTC CCT TTC CTG CGA CTG GCC CGG TCC ACC CTG CTG CTC ATC    1405
His Ser Leu Pro Phe Leu Arg Leu Ala Arg Ser Thr Leu Leu Leu Ile
        430             435             440

CCA CTA TTC GGA ATC CAC TAC ACA GTA TTT GCC TTC TCC CCA GAG AAT    1453
Pro Leu Phe Gly Ile His Tyr Thr Val Phe Ala Phe Ser Pro Glu Asn
445             450             455             460

GTC AGC AAA AGG GAA AGA CTC GTG TTT GAG CTG GGG CTG GGC TCC TTC    1501
Val Ser Lys Arg Glu Arg Leu Val Phe Glu Leu Gly Leu Gly Ser Phe
        465             470             475

CAG GGC TTT GTG GTG GCT GTT CTC TAC TGT TTT CTG AAT GGT GAG GTA    1549
Gln Gly Phe Val Val Ala Val Leu Tyr Cys Phe Leu Asn Gly Glu Val
        480             485             490

CAA GCG GAG ATC AAG CGA AAA TGG CGA AGC TGG AAG GTG AAC CGT TAC    1597
Gln Ala Glu Ile Lys Arg Lys Trp Arg Ser Trp Lys Val Asn Arg Tyr
        495             500             505

TTC GCT GTG GAC TTC AAG CAC CGA CAC CCG TCT CTG GCC AGC AGT GGG    1645
Phe Ala Val Asp Phe Lys His Arg His Pro Ser Leu Ala Ser Ser Gly
        510             515             520

GTG AAT GGG GGC ACC CAG CTC TCC ATC CTG AGC AAG AGC AGC TCC CAA    1693
Val Asn Gly Gly Thr Gln Leu Ser Ile Leu Ser Lys Ser Ser Ser Gln
525             530             535             540

ATC CGC ATG TCT GGC CTC CCT GCT GAC AAT CTG GCC ACC TGAGCCATGC TCC 1745
Ile Arg Met Ser Gly Leu Pro Ala Asp Asn Leu Ala Thr
                545             550

CCT                                                                1748
```

FIG. 18C

```
                19        29        39        49        59        69        79
          TALLLPVAIAMHSDCIFKKEQAMCLERIQRANDLMGLNESSPGCPGMWDNITCWKPAQVGEMVLVSCPEV
           * *              **      * *        *         * *       * *         **
          MRPPSPPHVRWLCVLAGALACALRPAGSQAASPQHECEYLQLIEIQRQQCLEEAQLENETTGCSKMWDNL
                    10        20        30        40        50        60        70

89        99        109       119       129       139       149
          FRIFNPDQVWMTETIGDSGFADSNSLEITDMGVVGRNCTEDGWSEPFPHYFDACGFDDYEPESGDQDYYY
             *              *        **    ***      * *      * *   *        *  *** **
          TCWPTTPRGQAVVLDCPLIFQLFAPIHGYNISRSCTEEGWSQLEPGPYHIACGLNDRASSLDEQQQTKFY
                    80        90        100       110       120       130       140

159       169       179       189       199       209       219
          LSVKALYTVGYSTSLATLTTAMVILCRFRKLHCTRNFIHMNLFVSFMLRAISVFIKDWILYAEQDSSHCF
           ****  ******  *****   ** **   ************* *********  ******  **   *  **
          NTVKTGYTIGYSLSLASLLVAMAILSLFRKLHCTRNYIHMHLFMSFILRATAVFIKDMALFNSGEIDHCS
                    150       160       170       180       190       200       210

229       239       249       259       269       279       289
          VSTVECKAVMVFFHYCVVSNYFWLFIEGLYLFTLLVETFFPERRYFYWYTIIGWGTPTVCVTVWAVLRLY
           ***  ***  ****  **********  **********    ********** * *****  *** **********
          EASVGCKAAVVFFQYCVMANFFWLLVEGLYLYTLLAVSFFSERKYFWGYILIGWGVPSVFITIWTVVRIY
                    220       230       240       250       260       270       280

299       309       319       329       339       349       359
          FDDAGCWDMNDSTALWWVIKGPVVGSIMVNFVLFIGIIIILVQKLQSPDMGGNESSIYLRLARSTLLLIP
           ***  ****           ************  **********  ** ****** *****  ****  *  **********
          FEDFGCWDTIINSSLWWIIKAPILLSILVNFVLFICIIRILVQKLRPPDIGKNDSSPYSRLAKSTLLLIP
                    290       300       310       320       330       340       350

369       379       389       399       409       419       429
          LFGIHYTVFAFSPENVSKRERLVFELGLGSFQGFVVAVLYCFLNGEVQAEIKRKWRSWKVNRYFTMDFKH
          ******  ****  ***          ******  *****************************    ****   *        *
          LFGIHYVMFAFFPDNFKAQVKMVFELVVGSFQGFVVAILYCFLNGEVQAELRRKWRRWHLQGVLGWSSKS
                    360       370       380       390       400       410       420

439       449       459
          RHPSLASSGVNGGTQLSILSKSSSQLRMSSLPADNLAT*
           **  ** *   *********  **  * **     ***
          QHPWGGSNGATCSTQVSMLTRVSPSARRSSSFQAEVSLV
                    430       440       450
```

HYDROPHOBIC    MARVLQLSLTALLLPVAIA                                              I
HYDROPHILIC                       MHSDCIFKKEQANCLERIQRANDLMGLNESSPGCPMWDN

HYDROPHOBIC    PAQVGENVLVSC      I   QV          F    SLEI DN
HYDROPHILIC  TCWK          FEVFR FNPD  WMTETIGDSG  ADSN    T  GVVGRNCTED

HYDROPHOBIC                          YYYLSVKALYTVGYSTSLATLTTANVI
HYDROPHILIC  GWSEPFPHYFDACGFDDYEPESGDQD                          LCRFRKL

HYDROPHOBIC   ALWWVIKGPVVGSIMVNFVLFIGIIVI           ESSIYLRLARSTLLLIPLFG
HYDROPHILIC                              LVQKLQSPDMGGN

HYDROPHOBIC   IHYTVF        ERLVFELGLGSFQGFVVAVLYC                    V
HYDROPHILIC         AFSPENVSKR                      FLNGEVQAEIKRKWRSWK   NRY

HYDROPHOBIC           HPSL   VNGGTQL  I   QI  MSGL   NLA
HYDROPHILIC   FAVDFKHR    ASSG      S LSKSSS   R   PAD   T

DNA ENCODING PACAP RECEPTOR PROTEIN AND METHOD FOR PREPARING SAID PROTEIN

This is a divisional of application(s) Ser. No. 08/202,986 filed on Feb. 25, 1994 now abandoned.

FIELD OF THE INVENTION

The present invention relates to a pituitary adenylate cyclase activating polypeptide (hereinafter referred to "PACAP") receptor protein (hereinafter may be referred to "PACAP receptor protein") or a salt thereof which is capable of binding a PACAP, a DNA comprising a DNA fragment coding for said protein, a method for preparing said protin or the salt thereof, and use of said protein and said DNA.

BACKGROUND OF THE INVENTION

PACAP was first isolated from the hypothalami of sheep as a peptide promoting adenylate cyclase activity of the pituitary glands [*Biochemical Biophysical Research Communications*, 164, 567–574 (1989)]. PACAP first isolated was one consisting of 38 amino acid residues. However, the presence of PACAP consisting of 27 residues on the N-terminal side was also revealed. Both are nearly equal in adenylate cyclase activating ability to each other. The former is referred to as PACAP38, and the latter is referred to as PACAP27. The expression of a PACAP having the same structure as that of sheep was also proved in humans, which suggested that PACAPs are important peptides conserved beyond species [*Biochem. Biophys. Res. Commun.*, 166, 81–89 (1990)]. For the distribution thereof in organs, they are observed not only in the brain hypothalami, but also in the pituitary glands, the testes and the adrenals (*Endocrinology*, 129, 2787–2789). At present, PACAPs such as PACAP27 to PACAP38 (U.S. Pat. No. 5,128,242) and PACAP23 to PACAP26 (European Patent Publication No. 0467279A3) have been reported.

Physiological actions of PACAPs diversely varies according to their occurrence sites. Various actions of the PACAPs as described below have hitherto been reported:

(1) Promotion of cAMP production in primary culture cells of the rat pituitary glands [A. Miyata et al., *Biochem. Biophys. Res. Commun.*, 164, 567–574 (1989)];

(2) Promotion of secretion of GH, ACTH, PRL and LH in the rat pituitary gland superfusion process [A. Miyata et al., *Biochem. Biophys. Res. Commun.*, 164, 567–574 (1989)];

(3) Production of cAMP in adrenomedullary chromaffinoma-derived cells PC12h and promotion of neurite outgrowth [T. Watanabe et al., *Biochem. Biophys. Res. Commun.*, 173, 252–258 (1990), and K. Okazaki et al., *FEBS Letters*, 298, 49–56 (1992)];

(4) Promotion of interleukin-6 production in pituitary gland culture cells [I. Tatsuno et al., *Endocrinology*, 129, 1797–1804 (1991)]; and (5) Promotion of cAMP production in primary culture of rat astrocytes and promotion of action preventing nerve cell death [*Biochem. Biophys. Res. Commun.*, 168, 1027–1033 (1990)].

In order for PACAP to exhibit its action, the presence of a receptor specific for PACAP in target organs and cells is indispensable.

Receptor binding experiments using radioactive iodine-labeled PACAP27 (($^{125}$I] PACAP27) have proved the presence of a PACAP receptor. Namely, when a membrane fraction prepared from a tissue is mixed with [$^{125}$I] PACAP27 and reacted for an appropriate period of time, binding of [$^{125}$I] PACAP27 to the membrane fraction is observed. This binding is inhibited by unlabeled PACAP27 or PACAP38, but not inhibited by VIP, an analogous peptide of the PACAPs. This result suggests that a substance specifically binding to the PACAPs occurs in the tissue. Such binding activity is highest in membrane fractions of the brain hypothalamic and also observed in the pituitary glands, the adrenals and the like [*Endocrinology*, 127, 272–277 (1990)]. Further, a body of PACAP binding activity observed in membrana cerebri fractions, namely a receptor, is deduced to be a protein having a molecular weight of 57,000 from a technique (so-called affinity-label experiment) comprising binding [$^{125}$I] PACAP27 to the membrana cerebri fraction, crosslinking [$^{125}$I] PACAP27 and the body of its binding activity with a crosslinking reagent, then subjecting the product to polyacrylamide gel electrophoresis in the presence of sodium dodecylsulfate, and analyzing by autoradiography [*Biochem. Biophys. Res. Commun.*, 171, 838–844 (1990)].

It is expected that clarification of some fundamental properties of this specific receptor allows elucidation of additional various properties of the PACAP receptor to proceed more than before. In particular, cloning of cDNA coding for the receptor protein and structure analysis thereof enable elucidation of the mechanism of its mutual interaction with a ligand, production of receptor-agonists and antagonists and detailed analysis of sites of action by in situ hybridization using said cDNA. Although cloning of the VIP, secretin and growth hormone releasing factor receptor proteins cDNA has been reported, the cloning of the PACAP receptor has not. These three kinds of bioactive peptides have also showed a capital similarity in the structures of their receptor proteins. For the PACAP receptors, however, cloning of cDNA has hitherto not been carried out.

Recently, the following five documents reported amino acid sequences for a rat PACAP receptor protein and nucleotide sequences of DNAs coding for the protein [Document 1: Biochemical and Biophysical Research Communications, 194, 1, pp.133–143, 1993; Document 2: Federation of European Biochemical Societies (FEBS), 329, 1 and 2, pp. 99–105; Document 3: Proceedings of the National Academy of Science, U.S.A., 90, pp. 6345–6349, 1993; Document 4: Nature, 365, pp. 170–175, 1993 and Document 5: Neuron, 11, pp.333–342, 1993). Among them, the amino acid sequences and the nucleotide sequences described in the Documents 1, 2, 4 and 5 are identified with the amino acid sequence for a rat PACAP receptor protein and with the nucleotide sequence for a DNA coding for the protein. The amino acid sequence described in Document 3 is different from the amino acid sequence of the present invention for a rat PACAP receptor protein in one amino acid, and the nucleotide sequence of Document 3 is also different from the nucleotide sequence of the present invention in one nucleotide. All of the five documents were published after Jun. 24, 1993 which is one of the priority dates of the present invention.

In general, when specific binding substances such as receptors are purified, affinity column chromatography applying its mutual interaction with the specific binding substance (for example, ligands for receptors) are frequently used. A process using an affinity column in which a ligand is fixed on a carrier is simplest. However, many successful examples of complicated affinity chromatography are known in which the specific mutual interaction between avidin and biotin is utilized for purification of receptors. This process comprises synthesizing a biotinylated ligand in which biotin is bound to an appropriate site, and specifically capturing a receptor on a carrier on which avidin is fixed through the biotinylated ligand [*Methods in Enzymology*, 184, 244–274 (1990)]. This process suffers from the problem of designing the biotinylated ligand having affinity for both the receptor and avidin, and examination is required in purifying PACAP receptor.

PACAP38 and PACAP27 are peptides represented by the following amino acid sequences, respectively:

PACAP38
His Ser Asp Gly Ile Phe Thr Asp Ser Tyr Ser Arg Tyr
1               5                   10
Arg Lys Gln Met Ala Val Lys Lys Tyr Leu Ala Ala Val
    15              20                  25
Leu Gly Lys Arg Tyr Lys Gln Arg Val Lys Asn Lys-NH₂
            30                  35

(SEQ ID NO: 46-NH₂)

PACAP27
His Ser Asp Gly Ile Phe Thr Asp Ser Tyr Ser Arg Tyr
1               5                   10
Arg Lys Gln Met Ala Val Lys Lys Tyr Leu Ala Ala Val
    15              20                  25
Leu-NH₂

(SEQ ID NO: 47-NH₂)

SUMMARY OF THE INVENTION

In order to further elucidate the properties of the PACAP receptor protein which is a giant protein molecule and to collect useful information for development of drugs, purification of said protein, structure analysis by cDNA cloning and construction of its expression system are indispensable. As described above, the presence of a protein showing high affinity for the PACAP, namely the PACAP receptor protein, has been known in the animal tissues. However, no report has so far been made that the PACAP receptor protein has yet to be obtained.

An object of the present invention is to purify the PACAP receptor protein and to clone a DNA coding for the PACAP receptor protein. If detailed information about the facts of the structure and functions of said protein is obtained, not only development of diagnostic methods for neuropathy such as Alzheimer's disease induced by a decrease in PACAP concentration is enabled by detecting the PACAP concentration in vivo, but also compounds activating PACAP receptor other than the known PACAP proteins or compounds antagonizing binding of a PACAP to a PACAP receptor can be enabled by using the PACAP receptor protein and the DNA cording for said protein. In addition, gene therapeutic composition for neuropathy such as Alzheimer's disease can be enabled by using said DNA.

The present inventors conducted intensive investigations, in view of the above-mentioned situation. As a result, bovine PACAP receptor protein was prepared unexpectedly efficiently by affinity chromatography using biotinylated PACAPs (particularly, biotinylated PACAP27). Further, synthetic DNA was prepared as a probe, based on the N-terminal amino acid sequence of the purified bovine PACAP receptor protein, and a bovine brain cDNA library was screened to clone cDNA of bovine PACAP receptor. As a result, the present inventors first succeeded in cloning a bovine cDNA encoding the receptor protein for PACAP from the bovine brain cDNA library and in determining a nucleotide sequence of a translation region thereof. Further, the present inventors elucidated the amino acid sequence of bovine PACAP receptor protein from this cDNA, and succeeded in pioneering the mass production thereof by recombinant technology.

Furthermore, the present inventors based on the similarity of the structure of PACAPs to that of VIP, secretin and growth hormone releasing factor, and deduced that receptors for the PACAPs would also show a similar structure to these, from the fact that the receptors already elucidated extremely resemble in structure among VIP, secretin and growth hormone releasing factor. Then, using as a probe cDNA of the VIP receptor having a higher similarity in structure as a ligand, cDNA of PACAP receptors was screened by homology screening. As a result, the present inventors first succeeded in cloning cDNA coding for rat PACAP receptor protein from a rat brain cDNA library, and in determining a nucleotide sequence of a translation region thereof. Further, the present inventors elucidated the amino acid sequence of rat PACAP receptor protein from this cDNA, and succeeded in pioneering the mass production thereof by recombinant technology.

In addition, the present inventors succeeded in cloning cDNA coding for human PACAP receptor protein from a human pituitary cDNA library, using as a probe synthetic DNA prepared based on the amino acid sequence (sequence consisting of 16 amino acids) on the N-terminal side of the purified bovine PACAP receptor protein, and in determining a nucleotide sequence of a translation region thereof. Then, the present inventors elucidated the amino acid sequence of human PACAP receptor protein from this cDNA, produced this in large amounts by recombinant technology, and succeeded in pioneering the screening of compounds activating PACAP receptors or compounds antagonizing PACAP receptors by use of human PACAP receptor protein thus produced.

Namely, the present invention provides:

(1) A receptor protein capable of binding a PACAP or a salt thereof;

(2) The receptor protein of (1), wherein the receptor is endogenous to rat, bovine or human;

(3) The receptor protein of (1) which comprises an amino acid sequence containing at least one member selected from the group consisting of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12 or a salt thereof;

(4) The receptor protein of (1) which comprises an amino acid sequence containing the amino acid sequence of SEQ ID NO: 13 or a salt thereof;

(5) The receptor protein of (1) which comprises an amino acid sequence having 90 to 100% homology as determined by sequence analysis with at least one member selected from the group consisting of the amino acid sequences of SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28 or a salt thereof;

(6) The receptor protein of (1) which comprises an amino acid sequence selected from the group consisting of the amino acid sequences of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29 or a salt thereof;

(7) A receptor fragment containing a sufficient portion of the receptor of (1) to bind PACAP or a salt thereof;

(8) The receptor fragment of (7) selected from the group consisting of
  (i) peptides having the amino acid sequence consisting of the 38th to 164th, 223rd to 232nd, 303rd to 317th or 416th to 424th amino acid residues of SEQ ID NO: 15,
  (ii) peptides having the amino acid sequence consisting of the 38th to 164th, 223rd to 232nd, 303rd to 317th or 388th to 397th amino acid residues of SEQ ID NO: 17,
  (iii) peptides having the amino acid sequence consisting of the 20th to 146th, 205th to 214th, 286th to 299th or 369th to 378th amino acid residues of SEQ ID NO: 19,
  (iv) peptides having the amino acid sequence consisting of the 20th to 146th, 205th to 214th, 286th to 299th or 397th to 406th amino acid residues of SEQ ID NO: 21, and
  (v) peptides having the amino acid sequence consisting of the 78th to 204th, 263rd to 272nd, 342nd to 357th or 427th to 436th amino acid residues of SEQ ID NO: 23; or a salt thereof;
(9) An isolated DNA coding for a receptor protein capable of binding a PACAP;
(10) The DNA of (9) wherein the receptor protein comprises the amino acid sequence of SEQ ID NO: 14, SEQ ID NO 15, SEQ ID NO: 16, SEQ ID NO: 17, SEQ ID NO 18, SEQ ID NO: 19, SEQ ID NO 20, SEQ ID NO: 21, SEQ ID NO 22, SEQ ID NO: 23, SEQ ID NO: 24, SEQ ID NO 25, SEQ ID NO: 26, SEQ ID NO 27, SEQ ID NO: 28 or SEQ ID NO 29;
(11) The DNA of (9) comprising the nucleotide sequence of SEQ ID NO: 30, SEQ ID NO: 31, SEQ ID NO 32,
(13) A vector containing the DNA of (9);
(14) A transformant containing the DNA of (9);
(15) A method for preparing the receptor protein or the salt thereof of (1) comprising cultivating a transformant containing a DNA encoding said protein under conditions suitable for expression of said protein and recovering said protein;
(16) A method for purifying the receptor protein or the salt thereof of (1) comprising subjecting a sample containing unpurified receptor protein to affinity chromatography using a biotinylated PACAP;
(17) The method of (16) comprising the steps of:
  (a) preparing a membrane protein fraction from an animal tissue or cell,
  (b) solubilizing the membrane protein fraction obtained in step (a),
  (c) subjecting the solubilized membrane protein fraction obtained in step (b) to anion exchange chromatography and/or hydroxyapatite chromatography, and
  (d) subjecting the active fraction obtained in step (c) to affinity chromatography using a biotinylated PACAP;
(18) The method of (17), in which the animal tissue is a bovine cerebrum;
(19) A method for preparing the receptor protein or the salt thereof of (1) comprising condensing a partial peptide fragment or a single amino acid corresponding to a portion of the protein as claimed in claim 1 with a residual moiety, and removing a protective group as so desired when the product has the protective group, until said protein is obtained;

(20) A diagnostic composition for neuropathy comprising the PACAP receptor protein or the salt thereof of (1), or the receptor fragment or the salt thereof of (7);
(21) The diagnostic composition of (20) which is a diagnostic composition for Alzheimer's disease;
(22) A gene therapeutic composition comprising the DNA of (9);
(23) The gene therapeutic composition of (22) to be administered to a patient whose an amount of PACAP receptor protein is decreased, to increase the amount of PACAP receptor protein;
(24) A method of diagnosis for neuropathy comprising contacting a sample to be tested with a receptor protein capable of binding a PACAP protein and measuring the amount of PACAP binding to the receptor protein;
(25) The method of diagnosis of (24), wherein the receptor protein is a receptor fragment of (7);
(26) The method of (24) wherein a decrease in PACAP concentration is an indication of the presence of Alzheimer's disease;
(27) A method of using the DNA of (9) to transform a cell;
(28) The method of (27) wherein the cell is transformed in vitro;
(29) The method of (27) wherein the cell is transformed in vivo;
(30) The method of (27), in which the expression of the DNA increases the amount of PACAP receptor protein;
(31) A method for determining
  (i) an effect of a test compound on PACAP receptor activity comprising comparing PACAP receptor activities in cases of (a) and (b);
    (a) contacting PACAP receptor with a PACAP;
    (b) contacting PACAP receptor with a PACAP and a test compound, or
  (ii) an effect of a test compound on binding of PACAP to PACAP receptor comprising comparing an amount of binding of PACAP to PACAP receptor in cases of (a) and (b);
    (a) contacting PACAP receptor with a PACAP;
    (b) contacting PACAP receptor with a PACAP and a test compound;
(32) The method of (31) wherein the PACAP receptor is a protein of (1);
(33) The method of (31) wherein the PACAP receptor is a receptor fragment of (7);
(34) The method of (31) wherein the PACAP receptor is a protein produced by cultivating a transformant containing the DNA of (9);
(35) The method of (31) which is a method for screening a compound activating PACAP receptor or a compound antagonizing binding of a PACAP to a PACAP receptor;
(36) An assay for quantifying a test compound's effect
  (i) on PACAP receptor activity comprising comparing an amount of PACAP receptor activation in cases of (a) and (b);
    (a) contacting PACAP receptor with a PACAP;
    (b) contacting PACAP receptor with a PACAP and a test compound, or
  (ii) on binding of PACAP to PACAP receptor comprising comparing an amount of binding of PACAP to PACAP receptor in cases of (a) and (b);
    (a) contacting PACAP receptor with a PACAP;
    (b) contacting PACAP receptor with a PACAP and a test compound;

(37) A compound or a salt thereof obtained by the method of (31);

(38) The compound or a salt thereof of (37) which is a compound activating PACAP receptor or a compound antagonizing binding of a PACAP to a PACAP receptor;

(39) A pharmaceutical composition for neuropathy comprising an effective amount of the compound or the salt thereof of (37);

(40) The pharmaceutical composition of (39), wherein the neuropathy is Alzheimer's disease;

(41) An antibody to a receptor protein capable of binding a PACAP, a partial peptide thereof or a salt thereof;

(42) The antibody of (41) which is a monoclonal antibody selected from the group consisting of PRN1-25a, PRN1-109a and PRN1-159a;

(43) Hybridoma which produces a monoclonal antibody of (42);

(44) A signal peptide selected from the group of peptides consisting of a peptide which has 1st to 37th amino acid sequence of SEQ ID NO:15, a peptide which has 1st to 37th amino acid sequence of SEQ ID NO:17, a peptide which has 1st to 19th amino acid sequence of SEQ ID NO:19, a peptide which has 1st to 19th amino acid sequence of SEQ ID NO:21, a peptide which has 1st to 77th amino acid sequence of SEQ ID NO:23, a peptide which has 1st to 77th amino acid sequence of SEQ ID NO:25, a peptide which has 1st to 77th amino acid sequence of SEQ ID NO:27, a peptide which has 1st to 77th amino acid sequence of SEQ ID NO:29, a peptide which has 58th to 77th amino acid sequence of SEQ ID NO:23, a peptide which has 58th to 77th amino acid sequence of SEQ ID NO:25, a peptide which has 58th to 77th amino acid sequence of SEQ ID NO:27 and a peptide which has 58th to 77th amino acid sequence of SEQ ID NO:29; or a salt thereof;

(45) A DNA which codes for a peptide of (44);

(46) A DNA of (45) which is selected from the group consisting of a DNA which has 1st to 111th nucleotide sequence of SEQ ID NO:30, a DNA which has 1st to 111th nucleotide sequence of SEQ ID NO:31, a DNA which has 1st to 57th nucleotide sequence of SEQ ID NO:32, a DNA which has 1st to 57th nucleotide sequence of SEQ ID NO:33, a DNA which has 1st to 231st nucleotide sequence of SEQ ID NO:34, a DNA which has 1st to 231st nucleotide sequence of SEQ ID NO:35, a DNA which has 1st to 231st nucleotide sequence of SEQ ID NO:36, a DNA which has 1st to 231st nucleotide sequence of SEQ ID NO:37, a DNA which has 172nd to 231st nucleotide sequence of SEQ ID NO:34, a DNA which has 172nd to 231st nucleotide sequence of SEQ ID NO:35, a DNA which has 172nd to 231st nucleotide sequence of SEQ ID NO:36 and a DNA which has 172nd to 231st nucleotide sequence of SEQ ID NO:37;

(47) A biotinylated PACAP;

(48) The biotinylated PACAP of (47) which is represented by the following formula:

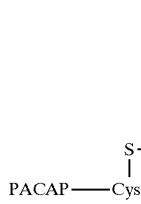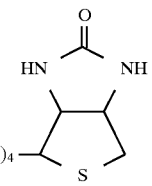

(49) The biotinylated PACAP of (47) or (48), in which the PACAP is PACAP27; and

(50) A method for preparing the biotinylated PACAP of (47) comprising reacting a PACAP derivative in which a cysteine residue is introduced into the carboxyl terminus of a PACAP with a biotinylating reagent.

BRIEF DESCRIPTION OF THE DRAWINGS

FIG. 1 shows a restriction enzyme cleavage map of a bovine PACAP receptor cDNA clone, wherein A indicates AvaII, Ac indicates AccI, B indicates BamHI, Ba indicates BalI, and S indicates SmaI;

FIG. 2 shows a nucleotide sequence (SEQ ID NO:38) of a bovine cDNA clone, pBPR-T, encoding receptor protein for PACAP and the predicted amino acid sequence (SEQ ID NO:15). A signal sequence is deduced to be cleaved at that position indicated by the upward arrow ▲. Disappearance of the region between the open triangles Δ is observed for pBPR-TD;

FIG. 3 shows a nucleotide sequence (SEQ ID NO:39) of a bovine cDNA clone, pBPR-T, encoding receptor protein for PACAP and the predicted amino acid sequence (SEQ ID NO:17). A signal sequence is deduced to be cleaved at the position indicated by the upward arrow ▲. Insertion was observed at the position indicated by the open triangle Δ for pBPR-TD;

FIG. 4 shows the N-terminal amino acid sequence of bovine PACAP receptor protein and an amino acid sequence deduced from pBPR-T and pBPR-TD for comparison;

FIG. 5 shows graphs in which the degree of hydrophobicity of bovine PACAP receptor protein, encoded by pBPR-T and pBPR-TD, is shown as an index. A and B corresponds to pBPR-T and pBPR-TD, respectively. The numerals 1 to 7 indicate transmembrane domains presumed from the degree of hydrophobicity. The upward arrow ▲ indicates the position of a sequence which does not exist in pBPR-TD, but exists in pBPR-T;

FIG. 6 shows a restriction enzyme cleavage map of a rat PACAP receptor cDNA clone, wherein N indicates NcoI, P indicates PstI, and B indicates BamHI;

FIG. 7 shows a nucleotide sequence (SEQ ID NO:40) of rat PACAP receptor cDNA contained in pRPACAPR46-5 and an amino acid sequence (SEQ ID NO:19) of a translation frame derived therefrom. A signal sequence is deduced to be cleaved at the position indicated by the upward arrow ▲. Insertion is observed at the position indicated by the open triangle Δ for pRPACAPR12;

FIG. 8 is a continuation of FIG. 7;

FIG. 9 shows a nucleotide sequence (SEQ ID NO:41) of rat PACAP receptor cDNA contained in pRPACAPR12 and an amino acid sequence (SEQ ID NO:21) of a translation frame derived therefrom. A signal sequence is deduced to be cleaved at the position indicated by the upward arrow A. The sequence between the open triangles Δ is a sequence not existing in pRPACAPR46-5 and characteristic of pRPACAPR12;

FIG. 10 is a continuation of FIG. 9;

FIG. 11 shows the N-terminal amino acid sequence of bovine PACAP receptor protein and the N-terminal amino acid sequence of rat PACAP receptor protein for comparison;

FIG. 12 shows a restriction enzyme cleavage map of a human PACAP receptor cDNA clone, wherein N indicates NcoI, ScI indicates SacI, Bg indicates BglII, Hp indicates HpaI, ScII indicates SacII, ET22 indicates EcoT22I, and Bs indicates BspEI;

FIG. 13 shows a nucleotide sequence (SEQ ID NO:42) of human PACAP receptor Type I-A cDNA coded with pTS847-1 and an amino acid sequence (SEQ ID NO:23) of a translation frame derived therefrom;

FIG. 14 shows the N-terminal amino acid sequence of bovine PACAP receptor protein and the N-terminal amino acid sequence deduced from human PACAP receptor protein cDNA for comparison;

FIG. 15 shows nucleotide sequences of pHPR15A, pHPR55A and pHPR66P encoding a portion of human PACAP receptor Type I-B (nucleotide 400–441 of SEQ ID NO:25), Type I-B2 (nucleotide 400–440 of SEQ ID NO:27) and Type I-C (nucleotide 400–441 of SEQ ID NO:29) respectively and predicted amino acid sequences of a translation frame. The region between two arrows shows an insertion sequence into human PACAP receptor Type I-A Rat Types I-B (342–383 of SEQ ID NO:2);

FIG. 16 shows a nucleotide sequence (SEQ ID NO:45) of cDNA of human PACAP receptor Type I-B and a predicted amino acid sequence (SEQ ID NO:29) of a translation frame. An underlined region is a sequence inserted by an alternative splicing;

FIG. 17 shows a nucleotide sequence (SEQ ID NO:44) of cDNA of human PACAP receptor Type I-B2 and a predicted amino acid sequence (SEQ ID NO:27) of a translation frame. An underlined region is a sequence inserted by an alternative splicing;

FIG. 18 shows a nucleotide sequence (SEQ ID NO:43) of cDNA of human PACAP receptor Type I-C and a predicted amino acid sequence (SEQ ID NO:29) of a translation frame. An underlined region is a sequence inserted by an alternative splicing;

FIG. 20 shows an amino acid sequence (amino acids 10–467 of SEQ ID NO:19) of rat PACAP receptor protein encoded by pRPACAPR46-5, and an amino acid sequence (SEQ ID NO:56) of rat VIP receptor protein for comparison. A group of amino acids 1 to 5 shown in the upper portion of the figure are regarded as equivalent to one another. Residues in which agreement is observed, including these amino acids, are given asterisks (*). The upper lines indicate the amino acid sequence of the PACAP receptor protein encoded by pRPACAPR46-5, and the lower lines indicate the sequence of rat VIP receptor. The numerals given above and under the respective sequences indicate the positions from the N-termini;

FIG. 22 shows amino acid sequences of human PACAP receptor protein (amino acids 1–525 of SEQ ID NO:23), bovine PACAP receptor protein (amino acids 1–513 of SEQ ID NO:15) and rat PACAP receptor protein (amino acids 1–495 of SEQ ID NO:21) for comparison. The arrow indicates a cleavage site of a signal peptide;

Column 1: untreated CHO cells+[$^{125}$I]-PACAP27

Column 2: untreated CHO cells+[$^{125}$I]-PACAP27+cold PACAP27

Column 3: untreated CHO cells+[$^{125}$I]-PACAP27+cold VIP

Column 4: pRPR3-A-introduced CHO cells+[$^{125}$I]-PACAP27

Column 5: pRPR3-A-introduced CHO cells+[$^{125}$I]-PACAP27+cold PACAP27

Column 6: pRPR3-A-introduced CHO cells+[$^{125}$I]-PACAP$_{27}$+cold VIP

Column 7: pRPR4-B-introduced CHO cells+[$^{125}$I]-PACAP27

Column 8: pRPR4-B-introduced CHO cells+[$^{125}$I]-PACAP27+cold PACAP27

Column 9: pRPR4-B-introduced CHO cells+[$^{125}$I]-PACAP27+cold VIP

Column 10: rat VIP receptor cDNA-introduced CHO cells+[$^{125}$I]-PACAP27

Column 11: rat VIP receptor cDNA-introduced CHO cells+[$^{125}$I]-PACAP27+cold PACAP27

Figure 37:
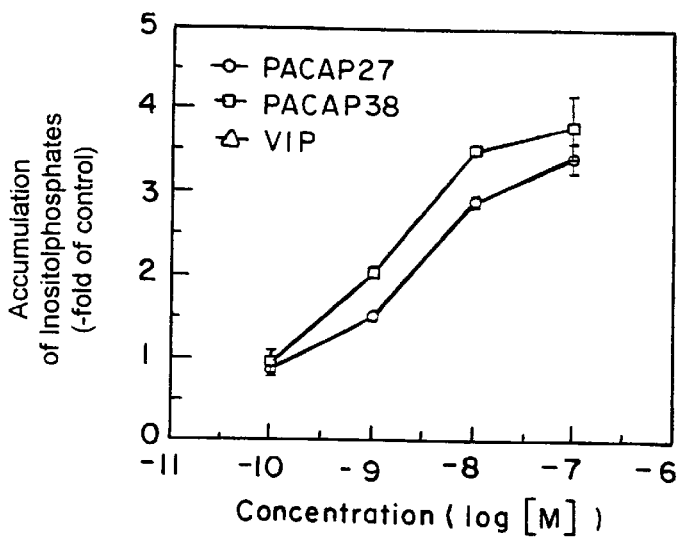
FIG. 37 is a graph showing changes in the amounts of intracellular inositol phosphate of CHO cells transfected with the bovine PACAP receptor protein cDNA (pBPR-T) produced by PACAP27, PACAP38 and VIP. The numerals on the abscissa indicate the concentrations (log M) of PACAP27, PACAP38 and VIP, and the numerals on the ordinate indicate the relative concentrations of inositol phosphate in transformant CHO cells treated with peptides having respective concentrations, taking the concentration of inositol phosphate in untreated transformant CHO cells as 1.
Figure 42:
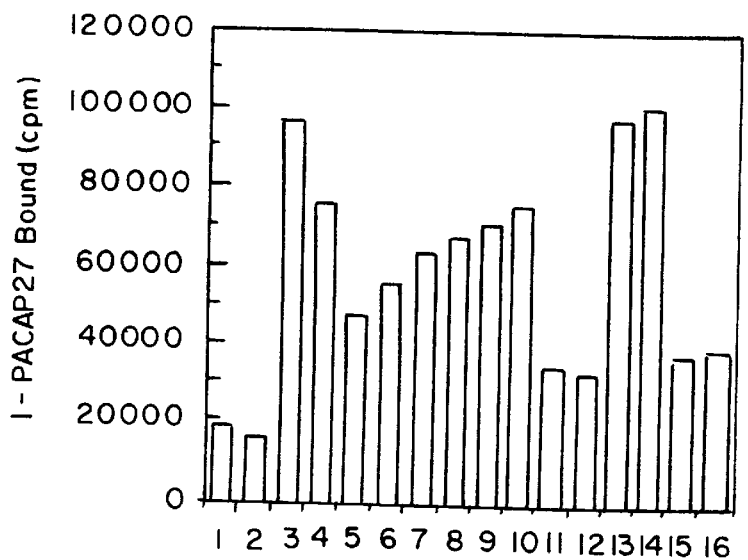
Figure 40A:
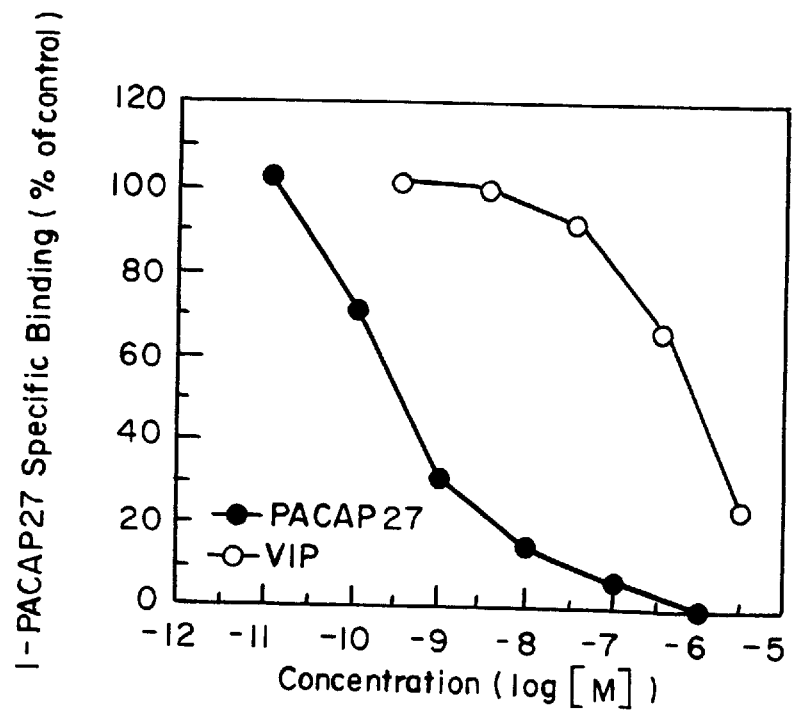
Figure 40B:
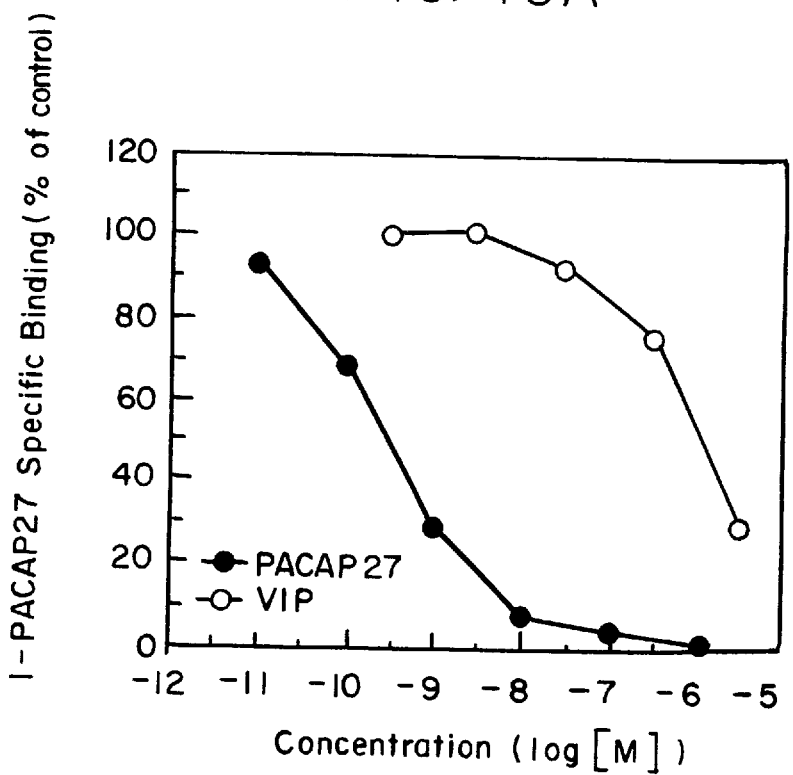
Figure 41:
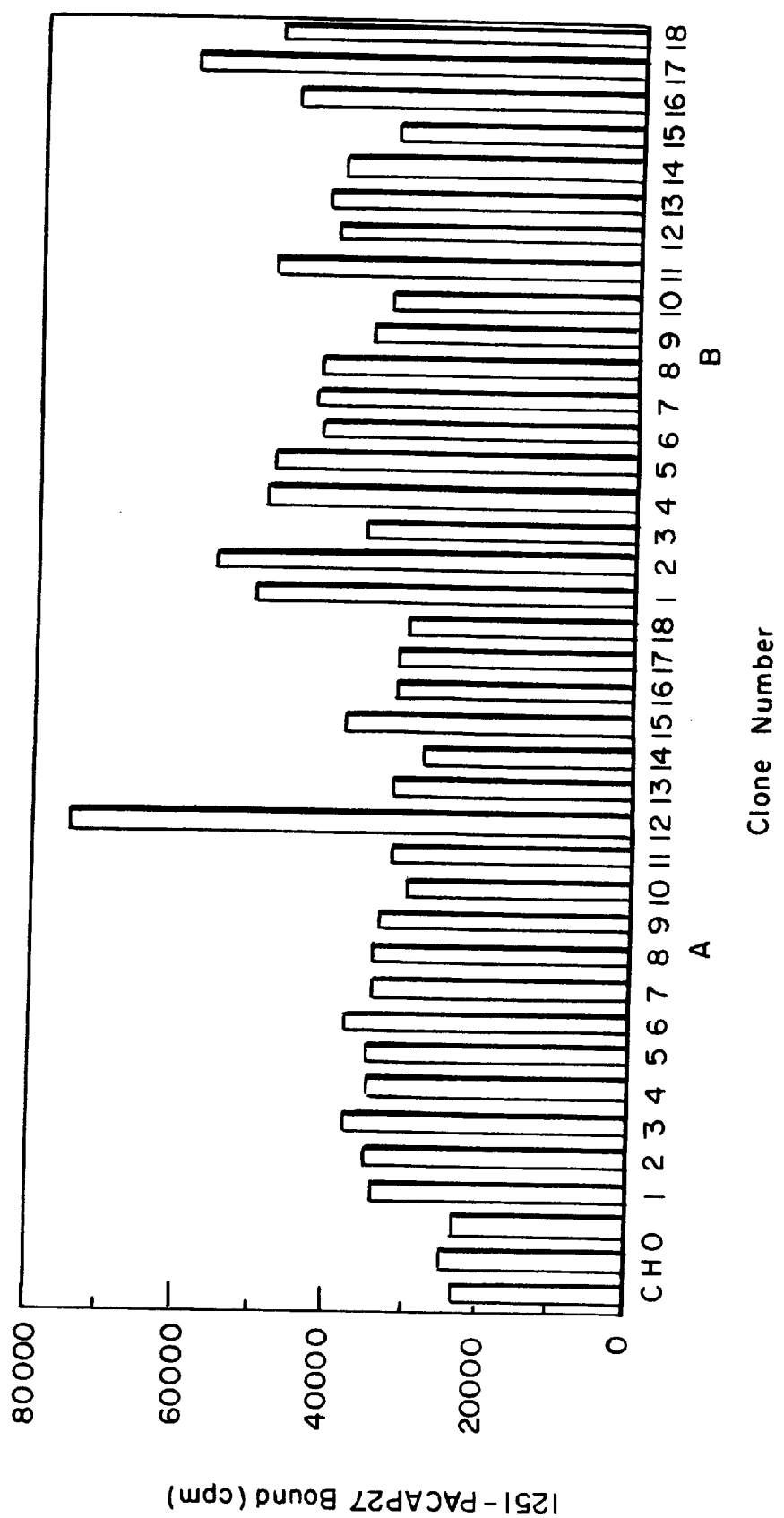
Figure 43A:
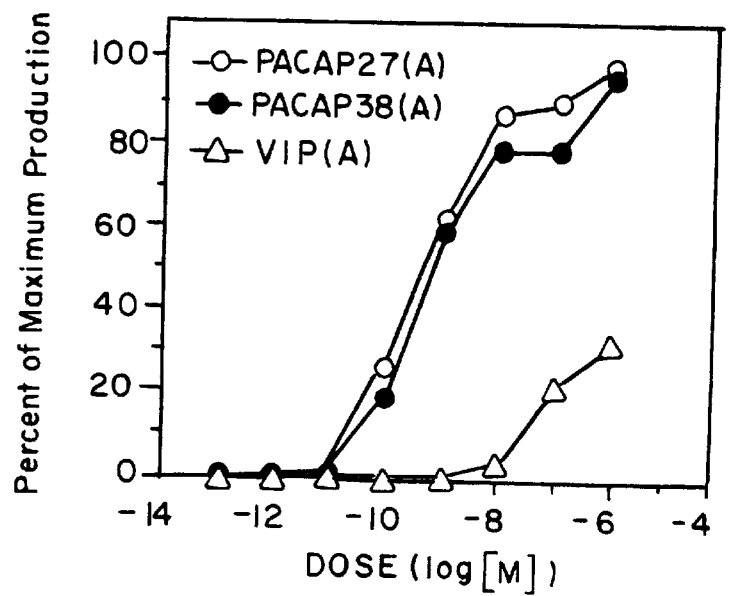
Figure 43B:
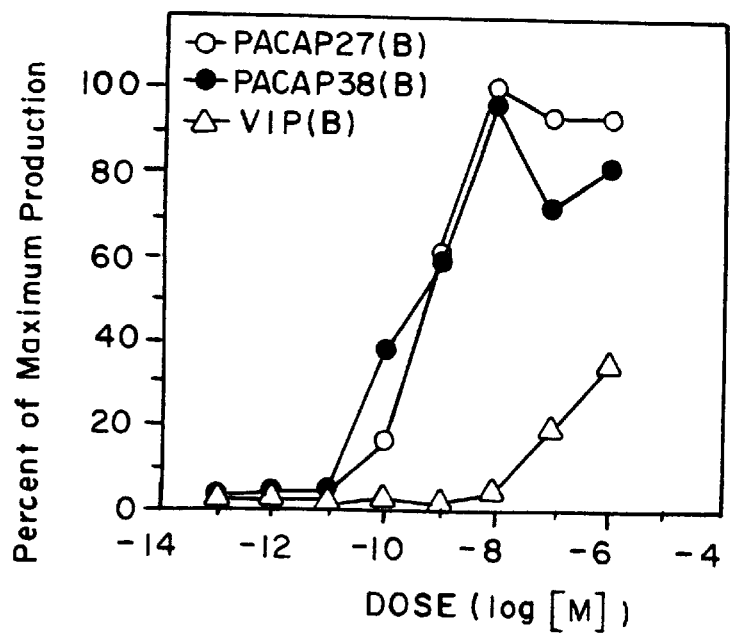

Column 12: rat VIP receptor cDNA-introduced CHO cells+[$^{125}$I]-PACAP27+cold VIP;

FIG. 40 are graphs showing results of competitive binding experiments. (A) is a graph showing results of the competitive binding experiments of PACAP27 and VIP to [$^{125}$I]-PACAP27 in a membrane fraction of CHO cells transfected with rat PACAP receptor protein cDNA (pRPR3-A). (B) is a graph showing results of the competitive binding experiments of PACAP27 and VIP to [$^{125}$I]-PACAP27 in a membrane fraction of CHO cells transfected with rat PACAP receptor protein cDNA (pRPR4-B). The numerals on the abscissa indicate the concentrations (log M) of PACAP27 and VIP, and the numerals on the ordinate indicate the binding (%) of [$^{125}$I]-PACAP27, taking the specific binding as 100, when each peptide is added so as to give the final concentrations on the abscissa;

FIG. 41 shows the binding of [$^{125}$I]-PACAP27 in the membrane fraction of CHO cells transfected with the rat PACAP receptor protein cDNA (pRPR3-A). A indicates CHO cells transfected with a rat PACAP receptor protein cDNA (pRPR3-A), and B indicates CHO cells transfected with a rat PACAP receptor protein cDNA (pRPR4-B). The numerals on the abscissa indicate sample Nos. of transformant CHO cells obtained by separating single clone-derived colonies, and the numerals on the ordinate indicate the binding (cpm) of [$^{125}$I]-PACAP27;

FIG. 42 shows results of examination of reproducibility of clones having much [$^{125}$I] binding in FIG. 37. The numerals 1 and 2 on the abscissa indicate untreated CHO cells, the numerals 3 and 4 VIP cDNA-introduced CHO cells, the numerals 5 and 6 clone B1, the numerals 7 and 8 clone B2, the numerals 9 and 10 clone B17, the numerals 11 and 12 clone A6, the numerals 13 and 14 clone A12, and the numerals 15 and 16 clone A15. The numerals on the ordinate indicate the binding (cpm) of [$^{125}$I]-PACAP27;

FIG. 43 are graphs showing the changes in the amounts of intracellular cyclic AMP. The upper graph (type I-A) indicates changes in the amounts of intracellular cyclic AMP of CHO cells transfected with the rat PACAP receptor protein cDNA (pBPR-T) produced by PACAP27, PACAP38 and VIP. The numerals on the abscissa indicate the concentrations (log M) of PACAP27, PACAP38 and VIP, and the numerals on the ordinate indicate the concentration (ratio (%) to the maximum production amount) of intracellular cyclic AMP.

Figure 44:
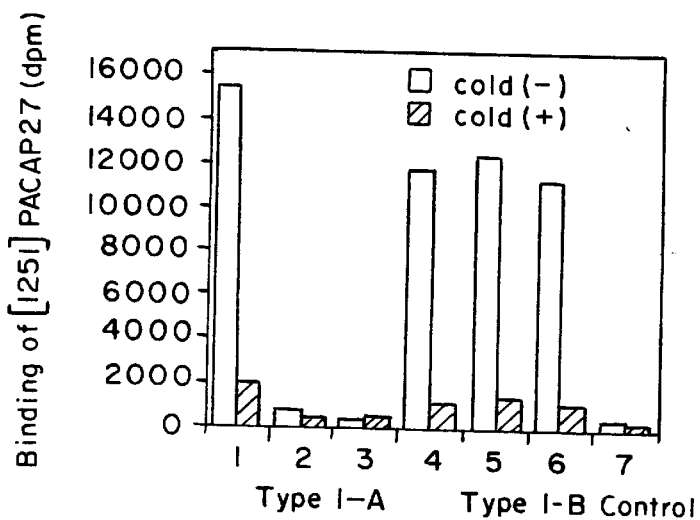
Figure 45:
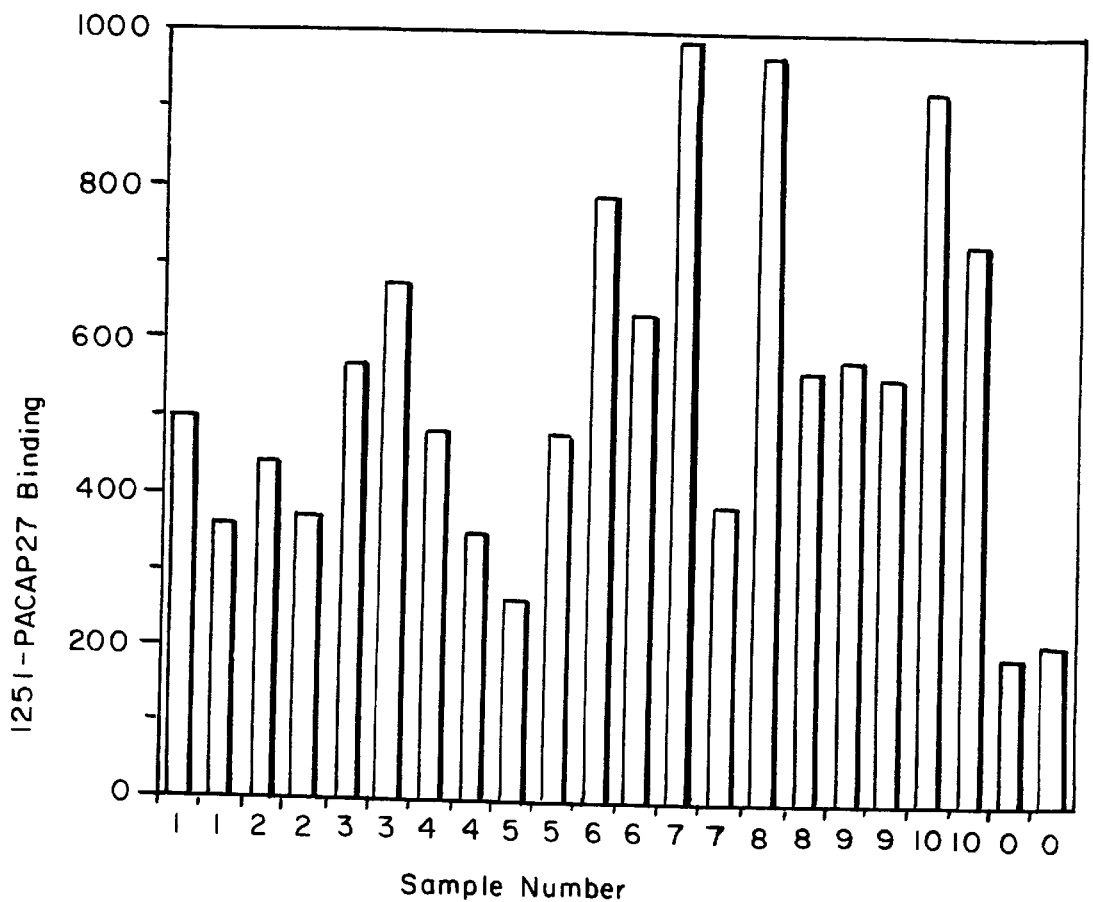
Figure 46:
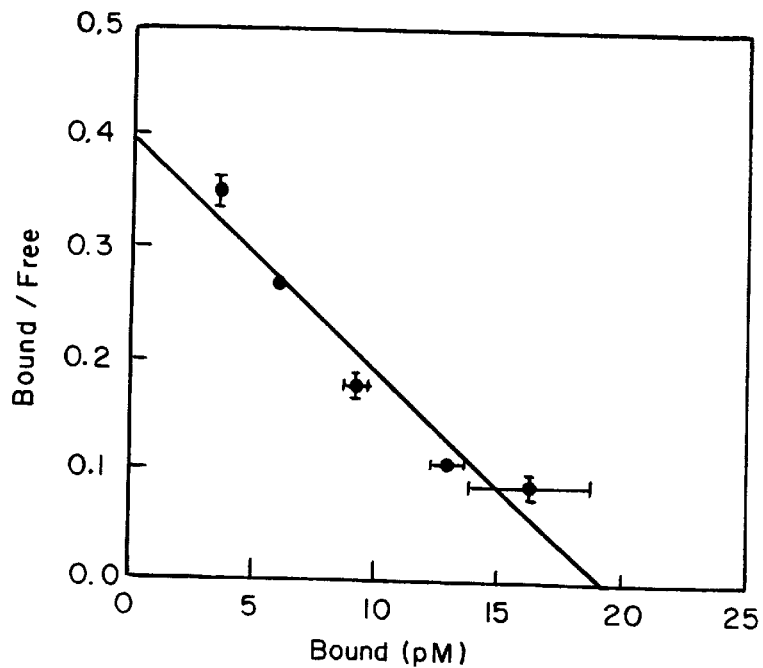

The lower graph (type I-B) indicates changes in the amounts of intracellular cyclic AMP of CHO cells transfected with the rat PACAP receptor protein cDNA (pBPR-TD) produced by PACAP27, PACAP38 and VIP. The numerals on the abscissa indicate the concentrations (log M) of PACAP27, PACAP38 and VIP, and the numerals on the ordinate indicate the concentration (ratio (%) to the maximum production amount) of intracellular cyclic AMP;

FIG. 44 shows the amount of rat PACAP receptor protein expressed in transformant Sf9 cells with baculoviruses. Sf9 was infected with 10 clones of recombinant viruses at the stage of primary plaque measurement, and 4 days after culture, the binding of the cells to [$^{125}$I]-PACAP27 was assayed. The numerals on the abscissa indicate sample Nos. of the transformant Sf9 cells. Sample Nos. 1 to 3 indicate transformant Sf9 cells containing rat PACAP receptor protein cDNA introduced by a vector modified from pRPR3-A, sample Nos. 4 to 6 indicate transformant Sf9 cells containing rat PACAP receptor protein cDNA introduced by a vector modified from pRPR4-B, and sample No. 7 indicates uninfected Sf9 cells (control). Cold (−) on the ordinate indicates the binding of each sample to [$^{125}$I]-PACAP27 when only 100 pM [$^{125}$I]-PACAP27 is added, and cold (+) indicates the binding of each sample to [$^{125}$I]-PACAP27 when 100 pM [$^{125}$I]-PACAP27 and 1 μm unlabeled PACAP27 are added;

FIG. 45 shows the amount of human PACAP receptor protein expressed in transformant Sf9 cells with baculoviruses. Sf9 was infected with 10 clones of recombinant viruses at the stage of primary purification, and cultured for 4 days after infection. The binding of [$^{125}$I]-PACAP27 on the cells was assayed. The numerals on the abscissa indicate sample Nos., and the numerals on the ordinate indicate the amount of [$^{125}$I]-PACAP27 binding. Sample No. 0 indicates uninfected Sf9 cells (control);

FIG. 46 is a graph showing Scatchard plot in a membrane fraction of CHO-K1 cells transfected with pTS849 which expresses human PACAP receptor protein.

Figure 47:
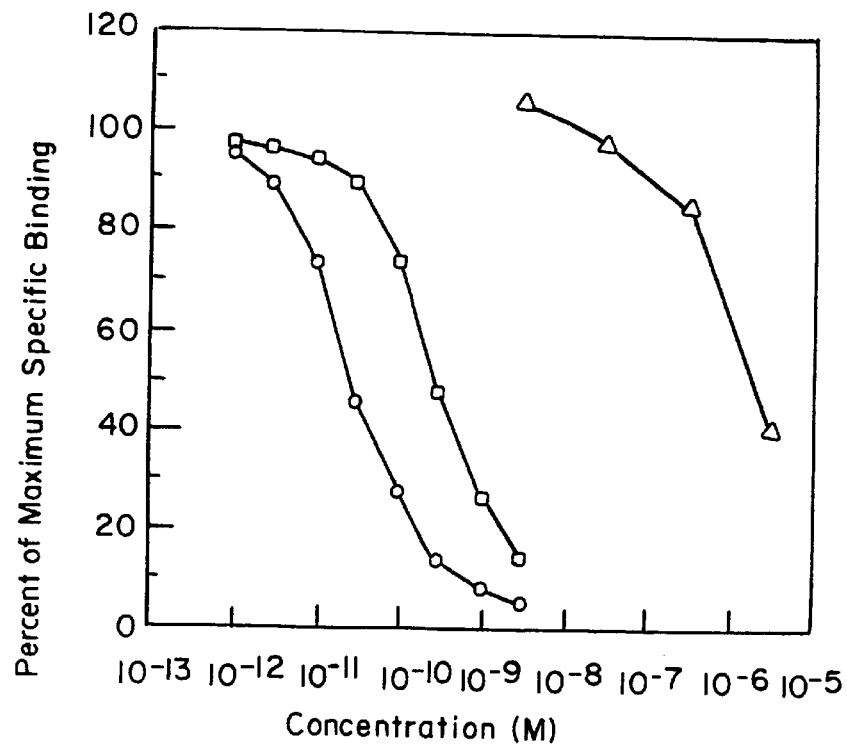
Figure 48:
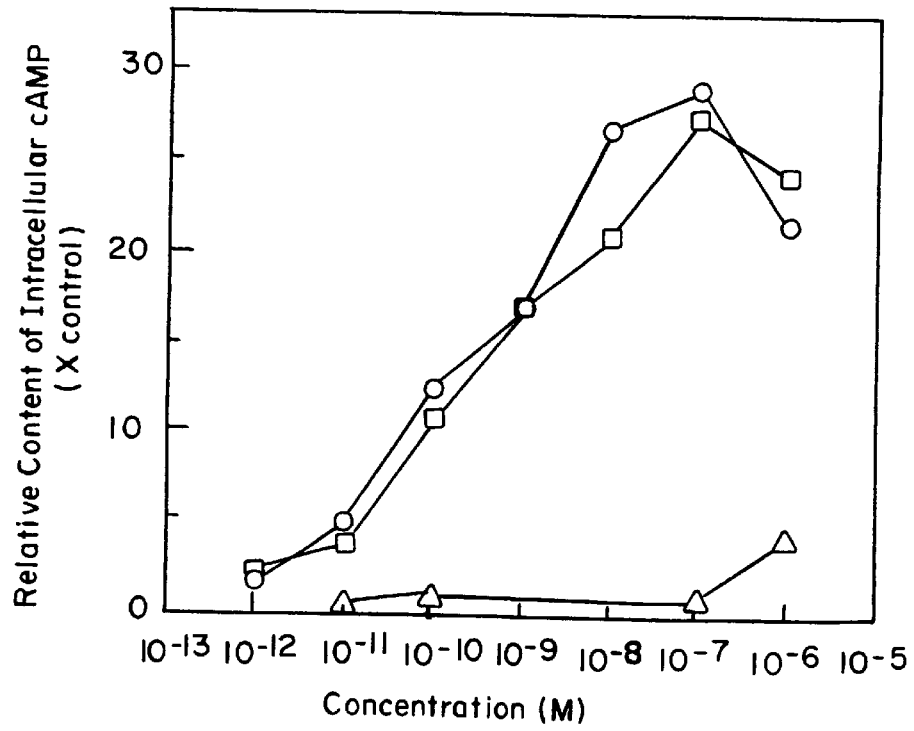
Figure 49:
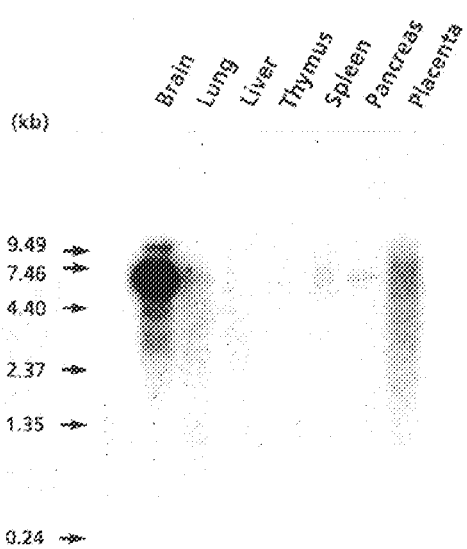
Figure 50:
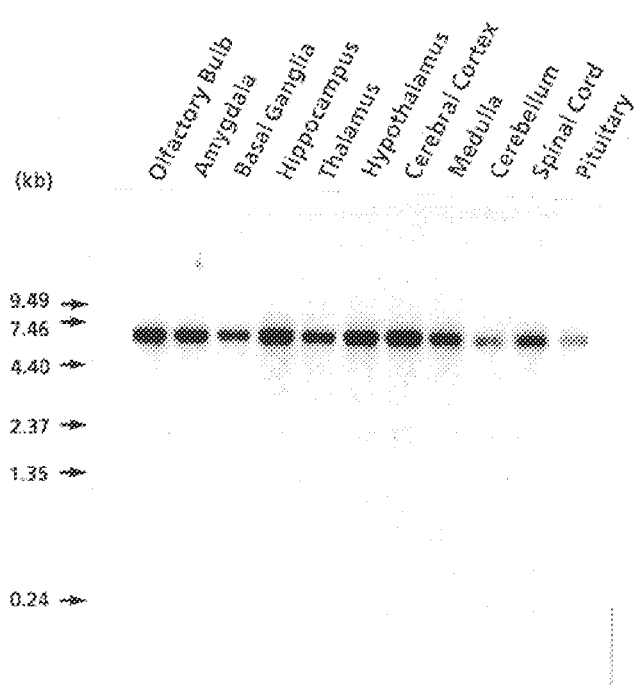
Figure 51A:
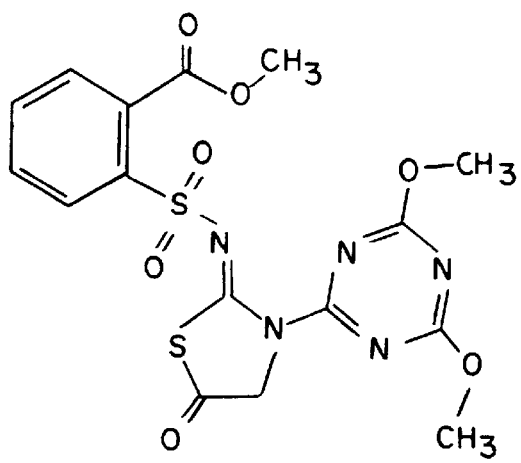
Figure 51B:
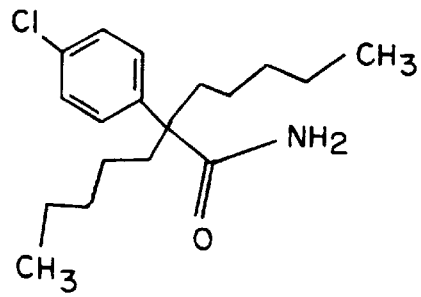
Figure 51C:
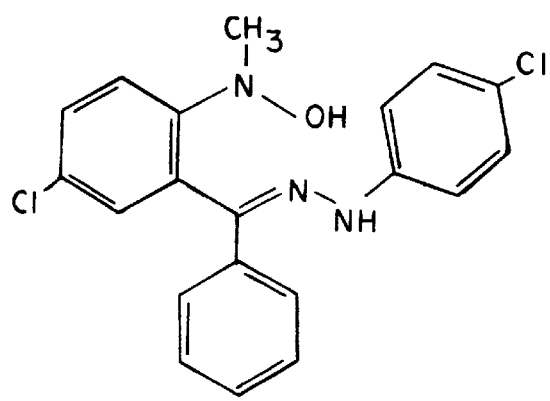
Figure 51D:
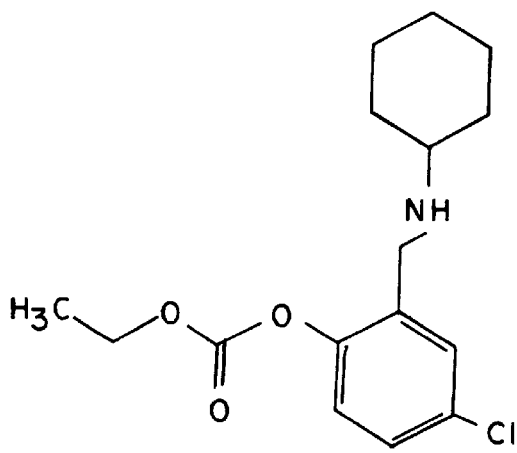
Figure 51E:
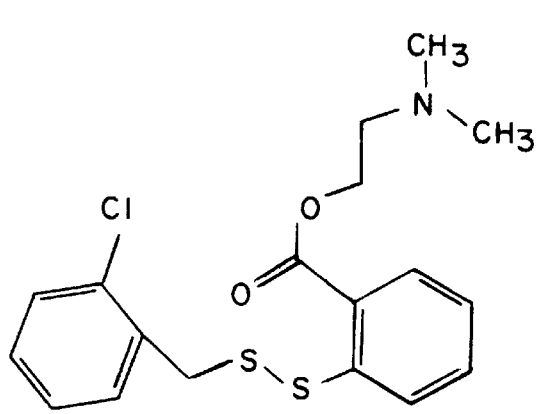
Figure 51F:
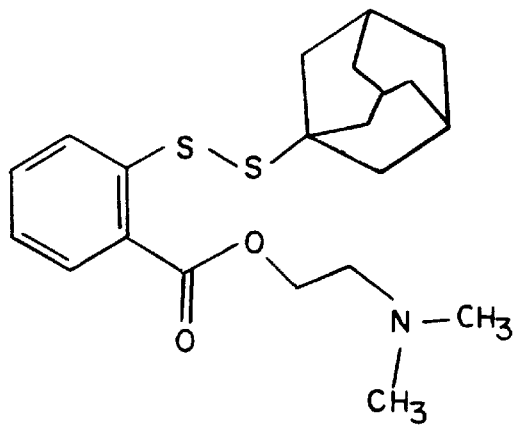
Figure 51G:
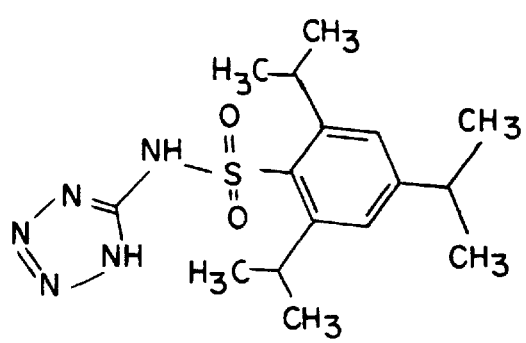
Figure 51H:
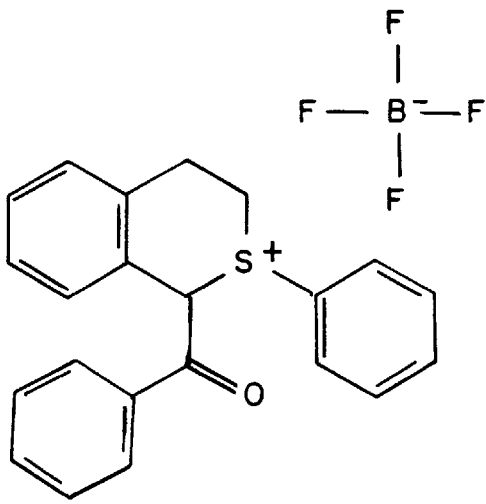
Figure 51I:
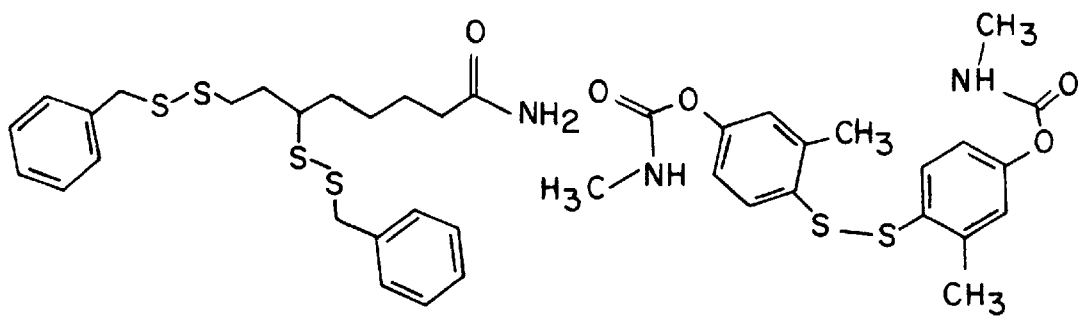
Figure 51J:
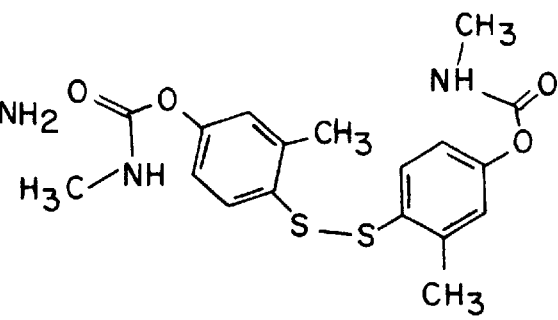

FIG. 47 is a graph showing results of the competitive binding experiments of PACAP27 (□), PACAP38 (○) and VIP (Δ) to [$^{125}$I]-PACAP27 in a membrane fraction of CHO cells transfected with pTS849 which expresses human PACAP receptor protein. The numerals on the abscissa indicate the concentrations (log M) of PACAP27, PACAP38 and VIP, and the numerals on the ordinate indicate the binding (%) of [$^{125}$I]-PACAP27, taking the specific binding as 100, when each peptide is added so as to give the final concentrations on the abscissa;

FIG. 48 is a graph showing changes in the amounts of intracellular cyclic AMP of CHO cells transfected with human PACAP receptor protein cDNA (pTS847-1) produced by PACAP27 (□), PACAP38 (○) and VIP (Δ). The numerals on the abscissa indicate the concentrations (log M) of PACAP27, PACAP38 and VIP, and the numerals on the ordinate indicate the relative concentrations of cyclic AMP in transformant CHO cells treated with peptides having respective concentrations, taking the concentration of inositol phosphate in untreated transformant CHO cells as 1;

FIG. 49 shows results of Northern hybridization using RNA prepared from the human brain, lung, liver, thymus, spleen, pancreas and placenta, and a human PACAP receptor protein cDNA probe. The bands represent that the RNA prepared from the human brain, lung, liver, thymus, spleen, pancreas placenta, and the human PACAP receptor protein cDNA probe exhibit cross reaction. The numerals on the left indicate the size of a molecular weight marker;

FIG. 50 shows results of norther hybridization using RNA prepared from the rat olfactory bulbs, amygdalae, cerebral basal ganglia, hippocampi, hypothalami, cerebral cortices, medulla oblongatas, cerebellums, vertebrae and pituitary glands, and a rat PACAP receptor protein cDNA probe. The bands represent that the RNA prepared from the rat olfactory bulbs, amygdalae, cerebral basal ganglia, hippocampi, hypothalamic cerebral cortices, medulla oblongatas, cerebellums, vertebrae and pituitary glands, and the rat PACAP receptor protein cDNA probe exhibit cross reaction. The numerals on the left indicate the size of a molecular weight marker.

FIGS. 51A–51J show a formula of the compound which was found by the screening using the membrane fraction of Sf9 cells which expressed human PACAP receptor Type I-A by baculovirus.

Figure 52:
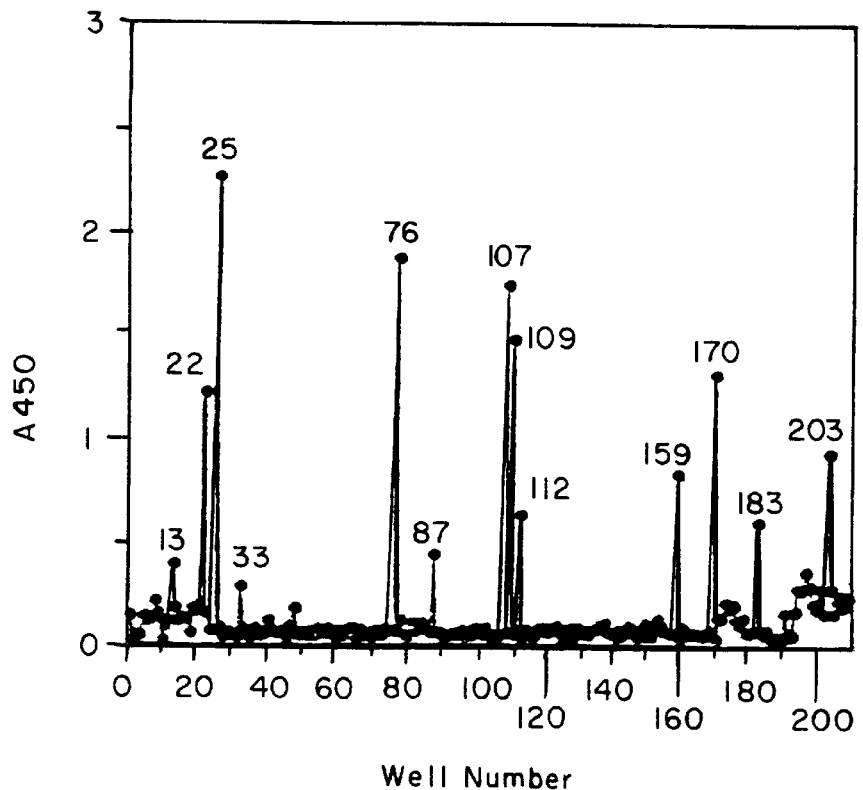

FIG. 52 is a graph which shows a typical sample of screening of hybridomas.

Figure 53:
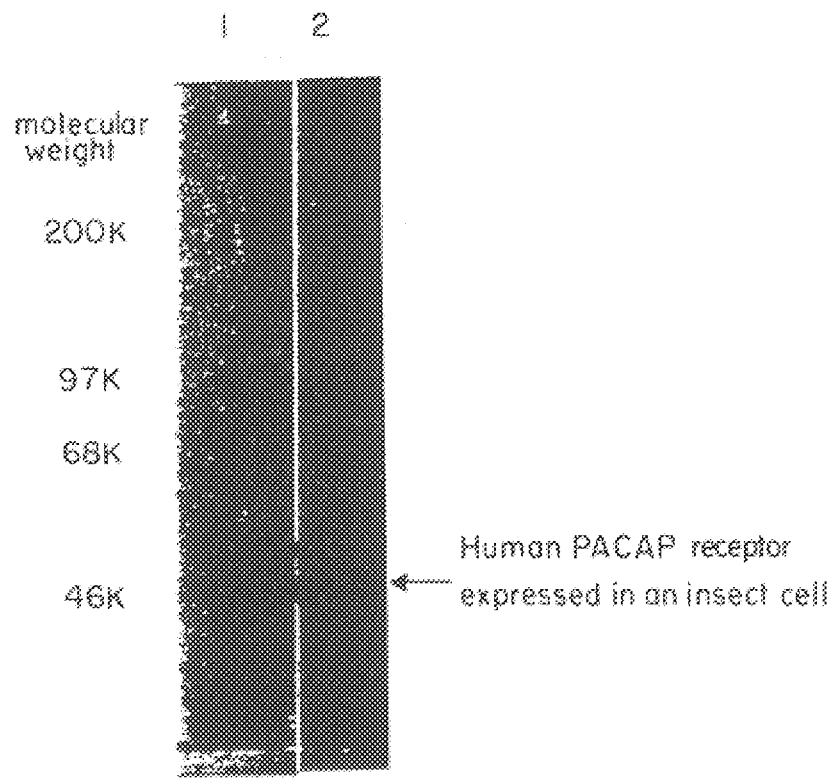

FIG. 53 shows a detection of PACAP receptor by Western blotting with the antibody of the present invention. Lane 1 shows rainbow coloured protein molecular weight markers and lane 2 shows a result of 320 ng of a membrane protein solubilized in an insect cell containing 20 ng of human PACAP receptor.

Figure 54:
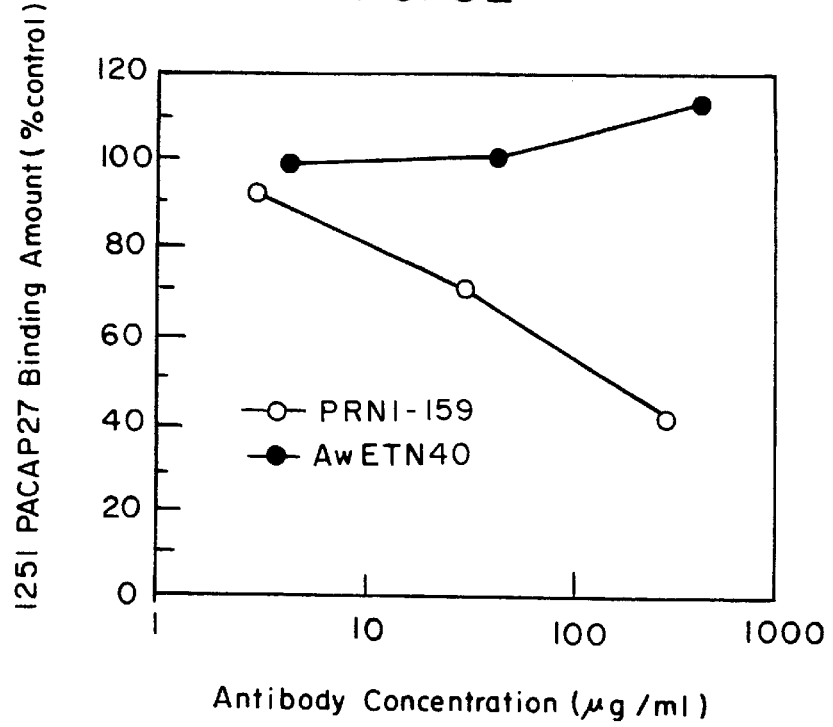

FIG. 54 is a graph which shows that the antibody of the present invention inhibits binding of PACAP27 and PACAP receptor.

DETAILED DESCRIPTION OF THE INVENTION

The present inventors obtained cDNA clones of the PACAP receptor proteins from the bovine brain cDNA library. Of these, λBPR35, λBPR114 and λBPR68 were cloned, and subcloned into pUC118 to obtain pBPR35, pBPR114 and pBPR68 (FIG. 1). Further, pBPR35 and pBPR68 were recombined at the BamHI site to prepare pBPR-T having a complete translation frame. The complete primary structure of bovine PACAP receptor protein based on pBPR-T was deduced (FIG. 2, pBPR-T). 84 nucleotides were not present in pBPR114, compared with pBPR-T. This is considered to occur by alternative splicing in a transcription product from a common gene.

The PACAP receptor protein which does not contain 84 nucleotides can be prepared by recombinating pBPR-T with pBPR114 at the BamHI and Ava II sites. The amino acid sequence of the recombinant protein was deduced (FIG. 3, pBPR-TD). The total number of amino acid residues and the molecular weight derived from these sequences are 513 residues (58.5 kilodaltons) for pBPR-T, and 485 residues (55.3 kilodaltons) for pBPR-TD. As to both the molecules, the N-terminal sequence up to the 37th Ala residue was deduced to be a signal sequence for passing through a membrane.

Further, the N-terminal sequence after this processing completely agreed with the N-terminal amino acid sequence of bovine PACAP receptor protein purified in this invention (FIG. 4). Analysis of hydrophobicity based on the amino acid sequence revealed in the present invention proved that bovine PACAP receptor protein has 7 hydrophobic amino acid clusters considered to be transmembrane domains in tandem (FIG. 5). Such structural features are common to peptide receptor proteins of the G protein coupling type [*European Journal of Pharmacology*, 227, 1–8 (1992)].

The present inventors further cloned λRPACAPR18, λRPACAPR46, λRPACAPR5 and λRPACAPR12 as cDNA clones of the PACAP protein from the rat brain cDNA library, and subcloned into pcDNA I or pUC118 to obtain pRPACAPR18, pRPACAPR46, pRPACAPR5 and pRPACAPR12 (FIG. 6). Further, pRPACAPR46 and pRPACAPR5 were recombined at the BamHI site to prepare pRPACAPR46-5 having a complete translation frame. Based on these, two kinds of complete primary structures of rat PACAP receptor protein were deduced (FIGS. 7 and 8, and FIGS. 9 and 10). The first methionine in each sequence is considered to be an initiation codon. It is conceivable that the difference between two kinds of sequences shown in FIGS. 7 and 8 and FIGS. 9 and 10 arises by alternative splicing in a transcription product from a common gene. The total number of amino acid residues and the molecular weight derived from these sequences are 467 residues (53.2 kilodaltons), and 495 residues (56.4 kilodaltons), respectively. As to both the molecules, the N-terminal sequence up to the 19th Ala residue was deduced to be a signal sequence for passing through a membrane. Further, the N-terminal sequence after this processing completely showed high homology with the N-terminal amino acid sequence of bovine PACAP receptor protein purified (FIG. 11).

In addition, the present inventors cloned λ#14 shown in FIG. 12 as a cDNA clone of the PACAP protein from the human pituitary cDNA library, and subcloned into pUC118 to obtain pTS847-1. Based on this, the complete primary structure of human PACAP receptor protein was deduced (FIG. 13). The first methionine in its sequence is considered to be an initiation codon. The total number of amino acid residues and the molecular weight derived from FIG. 13 are 525 residues and 59.3 kilodaltons, respectively. As to this molecule, the N-terminal sequence up to the 77th Ala residue was deduced to be a signal sequence for passing through a membrane. Further, the N-terminal sequence after this processing completely showed high homology with the N-terminal amino acid sequence of bovine PACAP receptor protein purified by Ohtaki et al (FIG. 14).

The present inventors found out that 84 nucleotides were inserted at the same sites of both rat and bovine Type I-B of PACAP receptor, and therefore deduced that there would also be a similar insertion at the same site of a human PACAP receptor. The inventors prepared a primer from the sequence flanking to the deduced insertion site and conducted PCR methods. As a result, the present inventors succeeded in cloning a cDNA encoding the insertion region of subtype of a human PACAP receptor and in identifying the amino acid sequence of the insertion region, by applying PCR method to cDNAs of human pituitay and amygdaloid nucleus. The present inventors further succeeded in preparing a cDNA encoding whole length of subtype of a human PACAP receptor by recombinating the above cDNAs with the cDNA of Type I-A of a human PACAP receptor. In more detail, the present inventors obtained pHPR15A, pHPR55A and pHPR66P as cDNA clones of the insertion region of a subtype of a human PACAP receptor by applying PCR method to cDNAs of human amygdaloid nucleus and human pituitary (FIG. 15). By recombinating the clones with human PACAP receptor Type I-A at the recognition sites of HpaI and AvaII, a cDNA for each subtype was constructed. The nucleotide sequences of cDNAs of the constructed subtypes and the amino acid sequence deduced therefrom are shown in FIGS. 16 to 18.

Figure 19A:
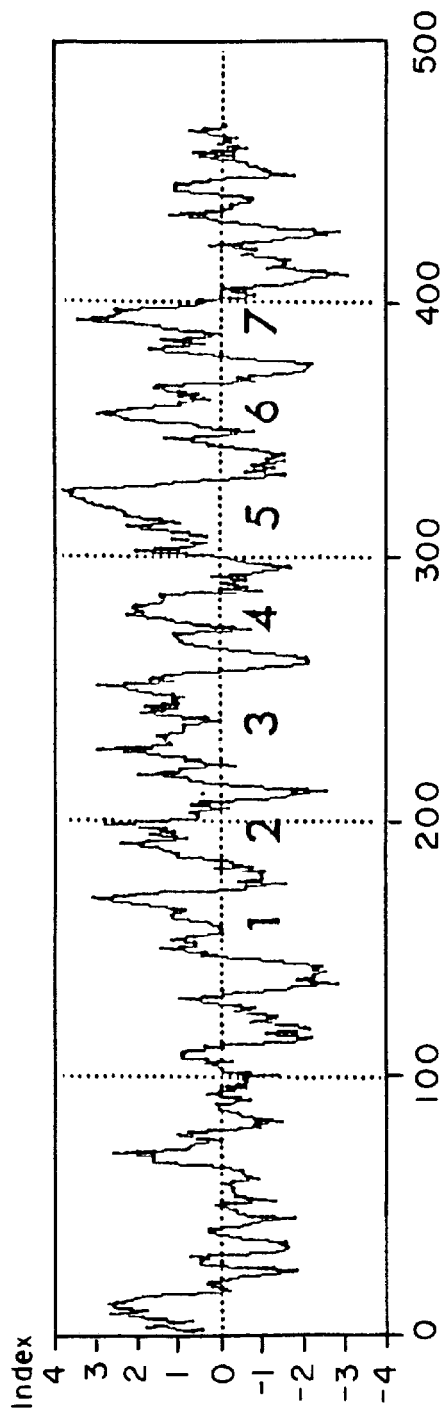
FIG. 19 shows graphs in which the degree of hydrophobicity of rat PACAP receptor protein encoded by pRPACAPR46-5 and pRPACAPR12 is shown as an index. A and B correspond to pRPACAPR46-5 and pRPACAPR12, respectively. The numerals 1 to 7 indicate portions deduced to be domains passing through a cell membrane from the degree of hydrophobicity. The upward arrow ▲ indicates the position of a sequence which does not exist in pRPACAPR46-5, but exists in pRPACAPR12.
Figure 19B:
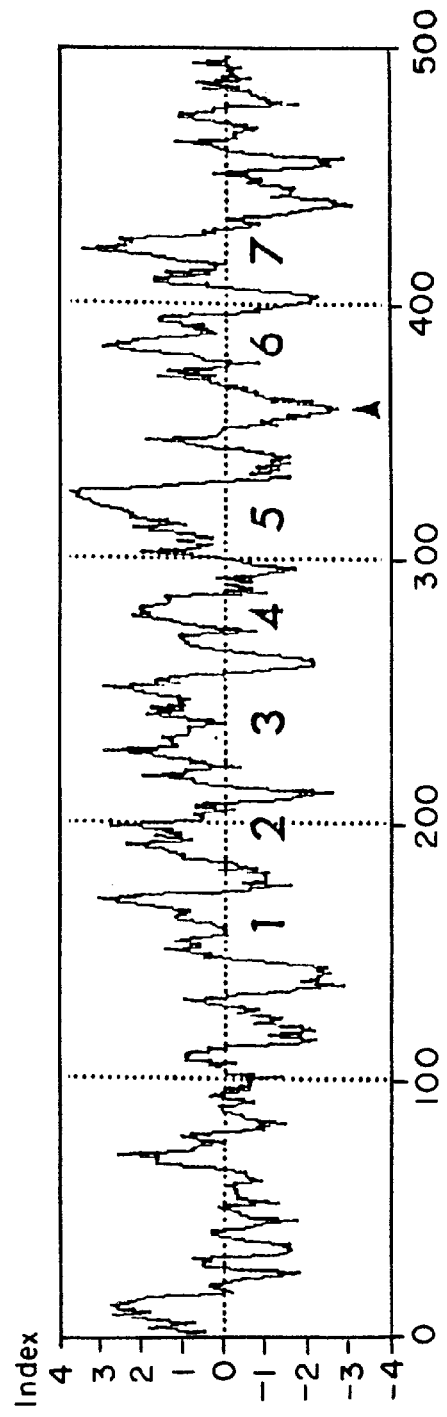
Figure 21:
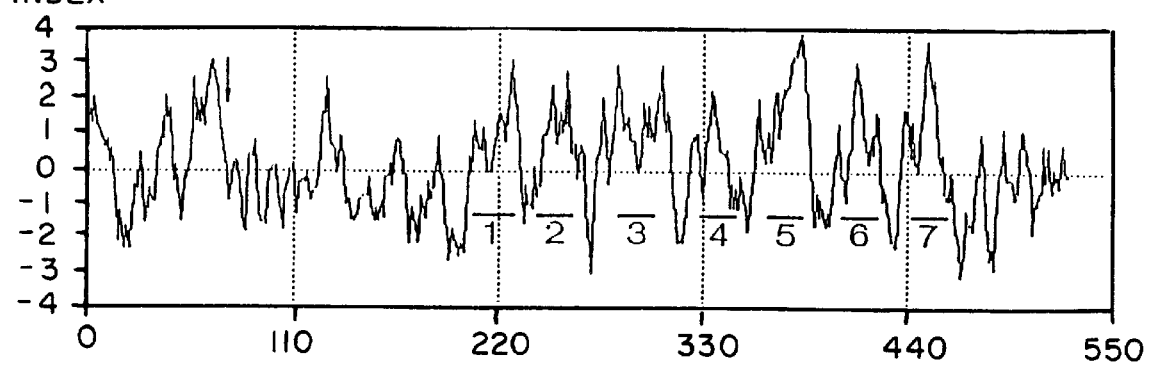
FIG. 21 shows a graph in which the degree of hydrophobicity of human PACAP receptor protein coded with pTS847-1 is shown as an index. The numerals 1 to 7 indicate portions deduced to be domains passing through a cell membrane from the degree of hydrophobicity.

Analysis of hydrophobicity based on the amino acid sequence revealed in the present invention proved that rat PACAP receptor protein has 7 hydrophobic amino acid clusters considered to be membrane permeable domains in tandem (FIG. 19(A) indicates a result of analysis of the protein shown in FIGS. 7 and 8, and FIG. 19(B) indicates a result of analysis of the protein shown in FIGS. 9 and 10). Such structural features are common to peptide receptor proteins of the G protein binding type [*European Journal of Pharmacology*, 227, 1–8 (1992)]. The peptides or ligands were extremely similar in structure, and the result of comparison at the amino acid sequence level with the structure of a VIP receptor used as a cDNA probe for cloning revealed extremely high similarity. As a whole, the similarity of the N-terminal portions is very low, whereas regions containing the first to seventh membrane permeable domains and the C-terminal intracellular domains conversely showed high similarity. It was further revealed that human PACAP receptor protein also has 7 hydrophobic amino acid clusters considered to be membrane permeable domains in tandem (FIG. 21).

Figure 22:
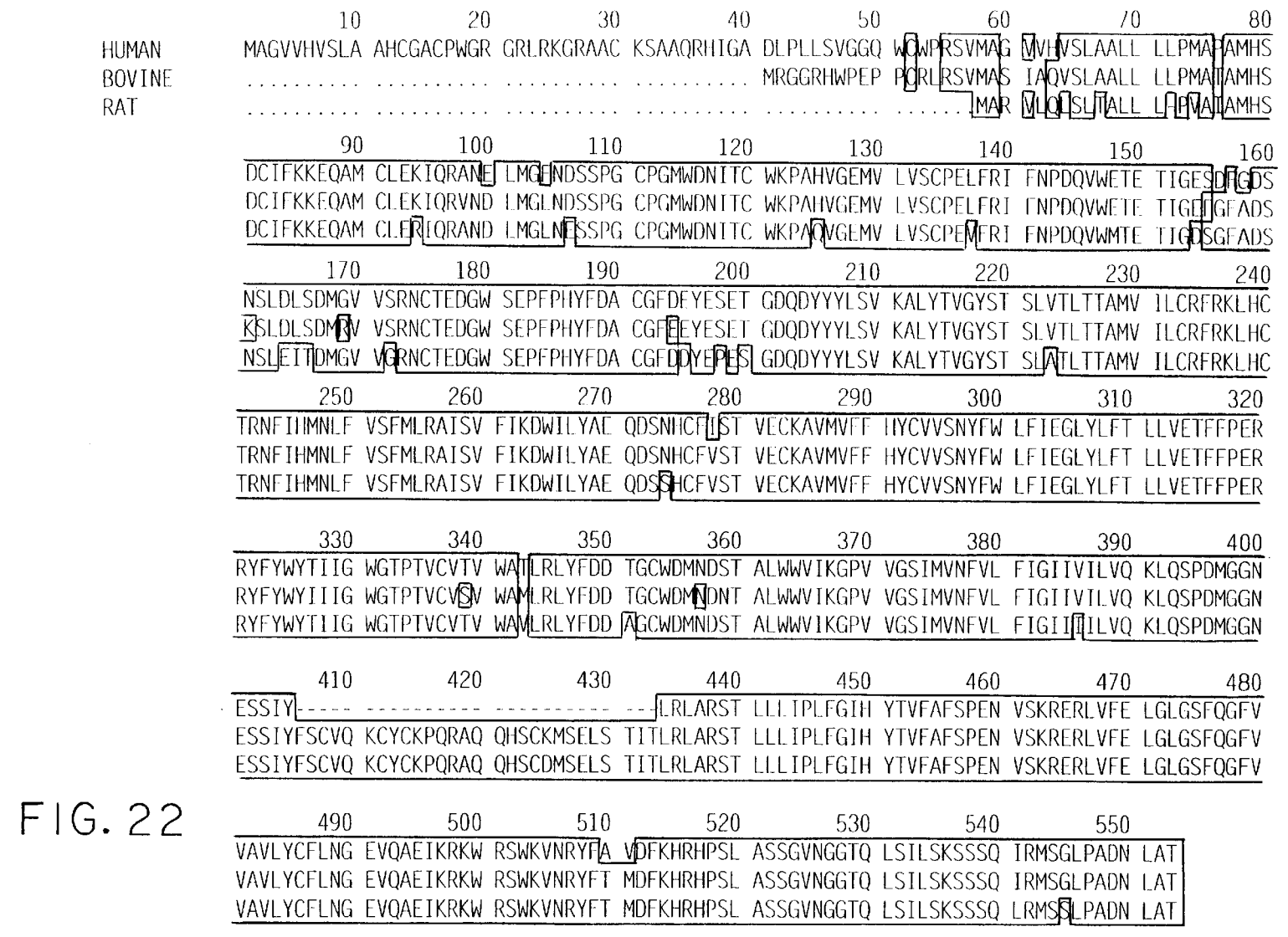

The amino acid sequences of bovine PACAP receptor protein, rat PACAP receptor protein and human PACAP receptor protein of the present invention showed very high homology (FIG. 22). All of these proteins were proved to shave amino acid sequences represented by SEQ ID NOs: 1 to 12.

The present inventors named rat PACAP receptor protein having the amino acid sequence of SEQ ID NO: 19 "Type I-A", and rat PACAP receptor protein having the amino acid sequence of SEQ ID NO: 21 "Type I-B". Bovine PACAP receptor protein having the amino acid sequence of SEQ ID NO: 15 is bovine PACAP receptor protein Type I-A corresponding to rat PACAP receptor protein Type I-A of SEQ ID NO: 19, and bovine PACAP receptor protein having the amino acid sequence of SEQ ID NO: 17 is bovine PACAP receptor protein Type I-B corresponding to rat PACAP receptor protein Type I-B of SEQ ID NO: 21.

Human PACAP receptor protein having the amino acid sequence of SEQ ID NO: 23 is human PACAP receptor protein Type I-A corresponding to rat PACAP receptor protein Type I-A of SEQ ID NO: 19, and human PACAP receptor protein having the amino acid sequence of SEQ ID NO: 25 which clone is obtained by recombinating pHPR15A is human PACAP receptor protein Type I-B. pHPR55A lacks 3 nucleotides, CAG, from pHPR15A, which lacks Ser as an amino acid. The human PACAP receptor protein having an amino acid sequence of SEQ ID NO:27 was named "Type I-B2" since the protein is thought to be a clone resulting from a sliding of the position of a splicing of Type I-B. Further, a human PACAP receptor protein having an amino acid sequence of SEQ ID NO:29, a recombinant clone of pHPR66P, which is thought to result from a transcription product of a common gene by an alternative splicing and the subtype was named Type I-C.

The origin of amino acid sequences of PACAP receptor proteins and nucleotide sequences of DNAs coding for said proteins represented by SEQ ID NO used in this specification are as follows:

[SEQ ID NO: 1-SEQ ID NO: 12]
These indicate amino acid sequences which bovine, rat and human PACAP receptor proteins have in common;
[SEQ ID NO: 13]
This indicates an N-terminal amino acid sequence of the purified bovine PACAP receptor protein;
[SEQ ID NO: 14]
This indicates an amino acid sequence of a protein in which a signal peptide is deleted from bovine PACAP receptor protein Type I-A encoded by in pBPR-T;
[SEQ ID NO: 15]
This indicates an amino acid sequence of bovine PACAP receptor protein Type I-A encoded by in pBPR-T;
[SEQ ID NO: 16]
This indicates an amino acid sequence of a protein in which a signal peptide is deleted from bovine PACAP receptor protein Type I-B encoded by in pBPR-TD;
[SEQ ID NO: 17]
This indicates an amino acid sequence of bovine PACAP receptor protein Type I-B encoded by in pBPR-TD;
[SEQ ID NO: 18]
This indicates an amino acid sequence of a protein in which a signal peptide is deleted from rat PACAP receptor protein Type I-A;
[SEQ ID NO: 19]
This indicates an amino acid sequence of rat PACAP receptor protein Type I-A;
[SEQ ID NO: 20]
This indicates an amino acid sequence of a protein in which a signal peptide is deleted from rat PACAP receptor protein Type I-B;
[SEQ ID NO: 21]
This indicates an amino acid sequence of rat PACAP receptor protein Type I-B;
[SEQ ID NO: 22]

This indicates an amino acid sequence of a protein in which a signal peptide is deleted from human PACAP receptor protein Type I-A;
[SEQ ID NO: 23]
This indicates an amino acid sequence of human PACAP receptor protein Type I-A;
[SEQ ID NO: 24]
This indicates an amino acid sequence of a protein in which a signal peptide is deleted from human PACAP receptor protein Type I-B;
[SEQ ID NO: 25]
This indicates an amino acid sequence of human PACAP receptor protein Type I-B;
[SEQ ID NO: 26]
This indicates an amino acid sequence of a protein in which a signal peptide is deleted from human PACAP receptor protein Type I-B2;
[SEQ ID NO: 27]
This indicates an amino acid sequence of human PACAP receptor protein Type I-B2;
[SEQ ID NO: 28]
This indicates an amino acid sequence of a protein in which a signal peptide is deleted from human PACAP receptor protein Type I-C;
[SEQ ID NO: 29]
This indicates an amino acid sequence of human PACAP receptor protein Type I-C;
[SEQ ID NO: 30]
This indicates a nucleotide sequence of cDNA coding for bovine PACAP receptor protein Type I-A;.
[SEQ ID NO: 31]
This indicates a nucleotide sequence of cDNA coding for bovine PACAP receptor protein Type I-B;
[SEQ ID NO: 32]
This indicates a nucleotide sequence of cDNA coding for rat PACAP receptor protein Type I-A;
[SEQ ID NO: 33]
This indicates a nucleotide sequence of cDNA coding for rat PACAP receptor protein Type I-B;
[SEQ ID NO: 34]
This indicates a nucleotide sequence of cDNA coding for human PACAP receptor protein Type I-A;
[SEQ ID NO: 35]
This indicates a nucleotide sequence of cDNA coding for human PACAP receptor protein Type I-B;
[SEQ ID NO: 36]
This indicates a nucleotide sequence of cDNA coding for human PACAP receptor protein Type I-B2;
[SEQ ID NO: 37]
This indicates a nucleotide sequence of cDNA coding for human PACAP receptor protein Type I-C;
[SEQ ID NO: 38]
This indicates a nucleotide sequence of DNA (pBPR-T) containing a nucleotide sequence of cDNA coding for bovine PACAP receptor protein Type I-A;
[SEQ ID NO: 39]
This indicates a nucleotide sequence of DNA (pBPR-TD) containing a nucleotide sequence of cDNA coding for bovine PACAP receptor protein Type I-B;
[SEQ ID NO: 40]
This indicates a nucleotide sequence of DNA (PRPACAPR 46-5) containing a nucleotide sequence of cDNA coding for rat PACAP receptor protein Type I-A;
[SEQ ID NO: 41]
This indicates a nucleotide sequence of DNA (pRPACAPR 12) containing a nucleotide sequence of cDNA coding for rat PACAP receptor protein Type I-B;
[SEQ ID NO: 42]
This indicates a nucleotide sequence of DNA (pTS847-1) containing a nucleotide sequence of cDNA coding for human PACAP receptor protein Type I-A;
[SEQ ID NO: 43]
This indicates a nucleotide sequence of DNA containing a nucleotide sequence of cDNA coding for human PACAP receptor protein Type I-B;
[SEQ ID NO: 44]
This indicates a nucleotide sequence of DNA containing a nucleotide sequence of cDNA coding for human PACAP receptor protein Type I-B2;
[SEQ ID NO: 45]
This indicates a nucleotide sequence of DNA containing a nucleotide sequence of cDNA coding for human PACAP receptor protein Type I-C;
[SEQ ID NO: 46]
This indicates an amino acid sequence of PACAP38.
[SEQ ID NO: 47]
This indicates an amino acid sequence of PACAP27.
[SEQ ID NO: 48]
This indicates a nucleotide sequence of an oligonucleotide used for screening of cDNA coding for rat PACAP receptor proteins Type I-A and Type I-B;
[SEQ ID NO: 49]
This indicates a nucleotide sequence of an oligonucleotide used for screening of cDNA coding for rat PACAP receptor proteins Type I-A and Type I-B.
[SEQ ID NO: 50]
This indicates an N-terminal amino acid sequence (sequence consisting of 16 amino acids) of bovine PACAP receptor protein.
[SEQ ID NO: 51]
This indicates a nucleotide sequence of an oligonucleotide used for screening of cDNA encoding bovine and human PACAP receptor proteins.
[SEQ ID NO: 52]
This indicates a nucleotide sequence of a primer prepared from cDNA encoding human PACAP receptor protein Type I-A.
[SEQ ID NO: 53]
This indicates a nucleotide sequence of a primer prepared from cDNA encoding human PACAP receptor protein Type I-A.
[SEQ ID NO: 54]
This indicates a nucleotide sequence of a probe prepared based on the nucleotide sequence at the insertion region of rat PACAP receptor protein Type I-B.
[SEQ ID NO: 55]
This indicates a nucleotide sequence of a probe prepared based on the nucleotide sequence at other insertion region than rat PACAP receptor protein Type I-B.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
EIA: Enzyme immunoassay
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gin: Glutamine Further, meanings of other abbreviations used in this specification are as follows:

VIP: Vasoactive intestinal peptide
Tris: Tris(hydroxymethyl)aminomethane
EDTA: Ethylenediaminetetraacetic acid
PMSF: Phenylmethylsulfonyl fluoride
BSA: Bovine serum albumin
CHAPS: 3-[(3-Cholamidopropyl)dimethylammonio]-1-propanesulfonate
Biotin-HSDP: N-[6-(biotinamido)hexyl]-3',-(2'-pyridylthio)-propionic acid amide "TM" used in this specification represents a registered trade mark.

The PACAP receptor proteins which are capable of binding a PACAP of the present invention may be derived from tissues of warm-blooded animals (for example, the cerebrums, pituitary glands and adrenals of rats, mice, hamsters, chickens, dogs, cats, sheep, monkeys, pigs, cattle or humans) or cells [for example, adrenal chromaffin cells, glial cells and established cell lines (such as PC12 cells, NB-OK cells and AR4-2J cells)], or may be produced by chemical synthesis. Any proteins may be used as long as they have PACAP receptor activity ("PACAP receptor activity" means the action of specifically binding to the PACAPs). Examples thereof include proteins having amino acid sequences containing at least one member selected from the group consisting of the amino acid sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12. Such proteins include, for example, proteins having only the amino acid sequences of SEQ ID NO: 1 to SEQ ID NO: 12, respectively, and proteins in which amino acids and (or) peptides are further bound to said proteins at their N-terminal sites and (or) C-terminal sites. Preferable examples of such proteins include proteins having amino acid sequences containing the amino acid sequences represented by SEQ ID NO:1 to SEQ ID NO:12. Specifically, they include proteins having the amino acid sequences represented by SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 or SEQ ID NO: 29. Preferably, the proteins having the amino acid sequences represented by SEQ ID NO: 14, SEQ ID NO: 15, SEQ ID NO: 16 or SEQ ID NO: 17 are bovine-derived proteins, the proteins having the amino acid sequences represented by SEQ ID NO: 18, SEQ ID NO: 19, SEQ ID NO: 20 or SEQ ID NO: 21 are rat-derived proteins, and the proteins having the amino acid sequences represented by SEQ ID NO: 22, SEQ ID NO: 23, SEQ ID NO: 24, SEQ ID NO: 25, SEQ ID NO: 26, SEQ ID NO: 27, SEQ ID NO: 28 or SEQ ID NO: 29 are human derived proteins.

The amino acid sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12 are amino acid sequences which the bovine-, rat- and human-derived PACAP receptors which lack signal peptide, that is PACAP receptors having the amino acid sequences represented by SEQ ID NO: 14, 16, 18, 20, 22, 24, 26 or 28, have in common (FIG. 22). Further, as apparent from FIG. 22, the amino acid sequences of the PACAP receptor proteins exhibit high homology among species of warm-blooded animals, so that proteins having usually 90–100%, preferably 95–100%, and more preferably 97–100% homology with the amino acid sequence(s) represented by SEQ ID NO: 14, SEQ ID NO: 16, SEQ ID NO: 18, SEQ ID NO: 20, SEQ ID NO: 22, SEQ ID NO: 24, SEQ ID NO: 26 and/or SEQ ID NO: 28 are also included in the PACAP receptor proteins of the present invention.

Further, for example, proteins having amino acid sequences containing the amino acid sequence represented by SEQ ID NO: 13 can also be used. Examples of such proteins include proteins having only the amino acid sequence of SEQ ID NO: 13, and proteins in which amino acids or peptides are further bound to said proteins at their C-terminal sites. Specifically, proteins having the amino acid sequence of SEQ ID NO: 14, SEQ ID NO: 15, SEQ ID NO: 16 or SEQ ID NO: 17 are used. In particular, bovine-derived proteins are preferred.

Furthermore, the PACAP receptor proteins of the present invention also comprise proteins in which the N-terminal Met residues are protected with protective groups (for example, $C_{1-6}$ acyl groups such as formyl and acetyl), proteins in which peptide bond between the 9th Lys residues and the 10th Glu residues in the amino acid sequences represented by SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28 are cleaved in vivo and the Glu residues are pyroglutaminated, proteins in which side chains of amino acids in molecules are protected with appropriate protective groups, and conjugated proteins such as so-called glicoproteins to which sugar chains are bound.

As used herein, "PACAP receptor protein" also includes a salt of said protein. Salts of the PACAP receptor proteins used in the present invention include, for example, salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

In producing the proteins of the present invention, when the proteins are extracted from animal tissues or cells, methods for purifying proteins can generally be employed. In particular, the proteins of the present invention are of the membrane binding type, so that solubilization of membrane fractions is required. Concrete purifying methods are shown below:

(1) Preparation of a membrane fraction suspension

A membrane fraction suspension can be prepared by treating an animal tissue, for example, by the method described in Biochem. Biophys. Res. Commun., 172, 709–714 (1990) or a method based thereon.

(2) Solubilization of a desired protein fraction from the membrane fraction suspension The membrane fraction obtained in (1) described above is solubilized by the method described in Biochem. Biophys. Res. Commun., 172, 709–714 (1990) or a method based thereon. Examples of solubilizing reagents which can be used therein include detergents having skeletons of bile acid (such as digitonin and CHAPS) and nonionic detergents (such as TWEEN 20™ and TRITON-X™). Specifically, the membrane fraction suspension is diluted with an appropriate buffer (for example, Tris buffer) to give a protein concentration of 0.1 to 5.0 mg/ml, preferably 0.5 to 2.0 mg/ml, and more preferably 1.0 mg/ml, the above-mentioned solubilizing reagent is added thereto to yield a concentration of 0.1 to 5.0%, preferably 0.5 to 2.0%, and more preferably 1.0%, and the mixture is stirred usually for 10 minutes to 72 hours, preferably for 30 minutes to 24 hours, followed by ultracentrifugation to obtain a supernatant thereof. The presence or absence of a desired protein can be detected by measuring the activity of said protein. For example, PACAP receptor activity can be supernatant thereof. The presence or absence of a desired protein can be detected by measuring the activity of said protein. For example, PACAP receptor activity can be measured by the method described in Biochem. Biophys. Res. Commun., 172, 709–714 (1990) or methods based thereon.

(3) Purification of the desired protein from the solubilized sample

Purification of the desired protein from the solubilized sample obtained in (2) described above can be conducted by anion-exchange chromatography [for example, DEAE-TOYOPEARL™ (Tosoh)], hydroxyapatite chromatography [for example, HCA-100™ (Mitsui Toatsu Chemicals)], affinity chromatography [for example, avidin-agarose (Pierce)], gel filtration [for example, SUPERROSE™ (Pharmacia)], etc. under appropriate conditions. In particular, the methods for producing the desired protein in the present invention are characterized in that the desired protein can be purified at high efficiency by use of affinity chromatography using the "biotinylated PACAPs" first discovered as ligands in the present invention. As said PACAPs, PACAP27 to PACAP38 described in EP-A-0404652 and PACAP23 to PACAP26 described in EP-A-0467279 are used. In particular, PACAP27 and PACAP38 are preferred. Examples of methods for biotinylating the PACAP include the method of introducing a cysteine residue into the carboxyl terminus of the PACAP to synthesize a PACAP derivative, and easily binding a commercially available biotinylating reagent through the cysteine residue. As the derivatives, for example, PACAP27-Cys and PACAP38-Cys are used. The derivatives can be produced by methods known in the art or methods based thereon, for example, solid phase methods. The biotinylating reagents used include, for example, the following reagents:

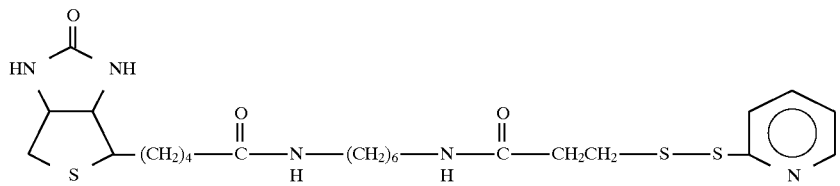

N-[6-(Biotinamido)hexyl]-3'-(2'-pyridylthio)-propionic acid amide (Cat. No. 21341, Pias)

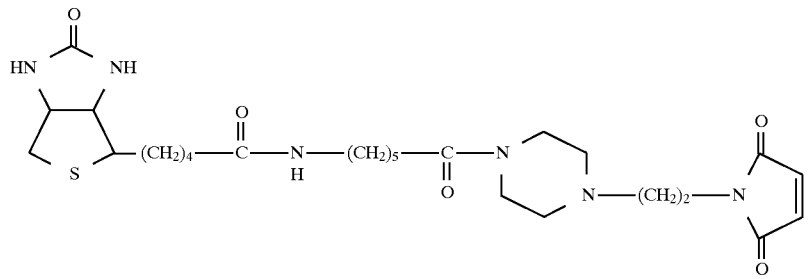

6-[N'{2-(N-Maleimido)ethyl}-N-piperazinylamido]hexyl biotinamide (Code No. 344-06391, Dojin Kagaku Kenkyusho)

The binding of the derivatives to the biotinylating reagents can be carried out by the method described in Biochem. Biophys. Res. Commun., 184, 123–160 (1990) or methods based thereon.

Examples of the biotinated PACAPs of the present invention include ones represented by the following formula:

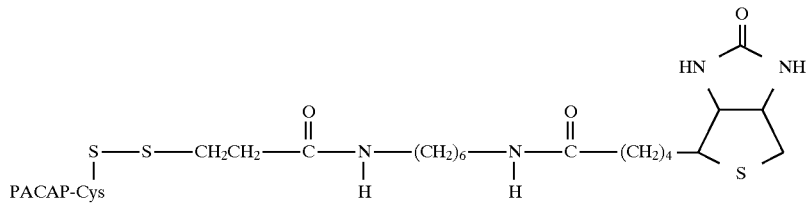

In particular, one represented by

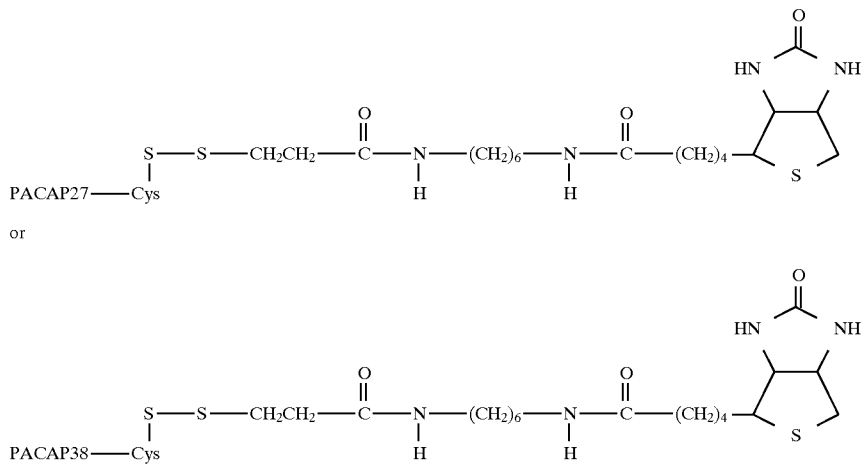

are preferred.

Of these biotinylated PACAPs, the method for producing biotinylated PACAP27 is described in detail in Example 1 (5) set out below. Other ligands can also be produced in accordance with the method of Example 1 (5-1).

The biotinylated PACAPs of the present invention thus obtained have binding ability to both PACAP receptor proteins and avidin. They can be therefore used for many purposes such as staining and flow cytophotometry of cells and tissues, as well as purification of PACAP receptor proteins.

On the other hand, when the proteins of the present invention are produced by chemical synthesis, they are produced by methods known in the art or methods based thereon. For example, either solid phase synthesis methods or liquid phase synthesis methods may be employed. Namely, the desired peptides can be produced by condensing partial peptides or amino acids which can constitute the proteins of the present invention with residual moieties, and eliminating protective groups when the products have the protective groups. Known condensing methods and elimination of the protective groups include, for example, methods described in (1) to (5) given below:

(1) M. Bodansky and M. A. Ondetti, *Peptide Synthesis*, Interscience Publishers, New York (1966);
(2) Schroeder and Luebke, *The Peptide*, Academic Press, New York (1965);
(3) N. Izumiya et al., *Peptide Gosei no Kiso to Jikken (Fundamentals and Experiments of Peptide Synthesis)*, Maruzen (1985);
(4) H. Yazima, S. Sakakibara et al., *Seikagaku Jikken Koza (Course of Biochemical Experiments)*, 1, *Chemistry of Proteins IV*, 205 (1977); and
(5) *Zoku Iyakuhin no Kaihatu (Development of Drugs) second series)*, 14, *Peptide Synthesis*, supervised by H. Yazima, Hirokawa Shoten.

After reaction, the PACAP receptor proteins of the present invention can be isolated by combinations of usual purification methods such as solvent extraction, distillation, reprecipitation, column chromatography, liquid chromatography, and recrystallization.

When the PACAP receptor proteins obtained by the above-mentioned methods are free forms, they can be converted to appropriate salts by known methods. Conversely, when the proteins are obtained in the salt state, they can be converted to the free forms by known methods.

The receptor fragments capable of binding a PACAP of the present invention may be any peptides e.g., a receptor fragment or a truncated receptor, as long as they have PACAP receptor activity. For example, sites of PACAP receptor protein molecules exposed out of cell membranes are used. Specifically, they are partial peptides deduced to be extracellular regions in hydrophobic plot analysis (FIG. 23 to FIG. 27). Examples thereof include:

(1) peptides having the amino acid sequence consisting of the 38th to 164th, 223rd to 232nd, 303rd to 317th or 416th to 424th amino acid residues of SEQ ID NO: 15 (bovine PACAP receptor protein Type I-A) (FIG. 23);
(2) peptides having the amino acid sequence consisting of the 38th to 164th, 223rd to 232nd, 303rd to 317th or 388th to 397th amino acid residues of SEQ ID NO: 17 (bovine PACAP receptor protein Type I-B) (FIG. 24);
(3) peptides having the amino acid sequence consisting of the 20th to 146th, 205th to 214th, 286th to 299th or 369th to 378th amino acid residues of SEQ ID NO: 19 (rat PACAP receptor protein Type I-A) (FIG. 25);
(4) peptides having the amino acid sequence consisting of the 20th to 146th, 205th to 214th, 286th to 299th or 397th to 406th amino acid residues of SEQ ID NO: 21 (rat PACAP receptor protein Type I-B) (FIG. 26); and (5) peptides having the amino acid sequence consisting of the 78th to 204th, 263rd to 272nd, 342nd to 357th or 427th to 436th amino acid residues of SEQ ID NO: 23 (human PACAP receptor protein Type I-A) (FIG. 27).

The receptor fragments capable of binding a PACAP can be produced by known methods for synthesizing the peptides of (1) to (5) described above or by cleaving the PACAP receptor proteins with appropriate peptidases.

Salts of the receptor fragments capable of binding a PACAP used in the present invention include, for example, salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The DNAs coding for the PACAP receptor proteins of the present invention may be any, as long as they have nucleotide sequences coding for the PACAP receptor proteins. Namely, the DNAs encoding the PACAP receptor proteins of the present invention may be any of cDNA, genomic DNA and synthetic DNA. Further, the DNAs may be ones encoding the PACAP receptor proteins derived from any warm-blooded animals (for example, rats, mice, hamsters, chickens, dogs, cats, sheep, monkeys, pigs, cattle, humans and so on), namely the above-mentioned PACAP receptor proteins of the present invention. Specifically, the DNAs having the nucleotide sequences of SEQ ID NO: 30 to SEQ ID NO: 45, respectively, are used. Screening of the DNAs can be conducted by general genetic engineering techniques or methods based thereon, for example, based on the examples 2 to 4 given below.

Expression vectors for the PACAP receptor proteins can be produced by (a) restricting desired DNA fragments from the DNAs encoding the PACAP receptor proteins, and (b) ligating the DNA fragments downstream from promoters in appropriate vectors.

The cloned DNAs encoding the PACAP receptor proteins can be used as such, or after digestion with restriction enzymes or addition of linkers if desired, depending on their purpose.

The DNA may have ATG as a translation initiation codon on the 5'-terminal side, and TAA, TGA or TAG as a translation termination codon on the 3'-terminal side. The translation initiation codon and translation termination codon may be added by use of an appropriate synthetic DNA adaptor. A promoter is further ligated upstream therefrom to express the DNA.

The vectors include plasmids derived from *Escherichia coli* (for example, pBR322, pBR325, pUC12 and pUC13), plasmids derived from *Bacillus subtilis* (for example, pUB110, pTP5 and pC194), plasmids derived from yeast (for example, pSH19 and pSH15, bacteriophages (for example, λ phage), and viruses such as retroviruses, vaccinia viruses and baculoviruses.

As the promoter used in the present invention, any promoter is available as long as it is suitable for expression corresponding to a host cell used for the gene expression.

When the host cell used for transformation is Escherichia, a trp promoter, a lac promoter, a recA promoter, a $\lambda P_L$ promoter or an lpp promoter is preferred. When the host cell is Bacillus, an SPO1 promoter, an SPO2 promoter or a penP promoter is preferred. When the host cell is yeast, a PHO5 promoter, a PGK promoter, a GAP promoter or an ADH promoter is preferred.

When the host cell is an animal cell, a SV40-derived promoter, a CMV-derived promoter, a retrovirus promoter, a metallothionein promoter, etc. are each usable.

An enhancer is also effectively utilized for expression.

Using the vectors containing the DNAs coding for the PACAP receptor proteins thus constructed, transformants are prepared.

Examples of the host cells include *Escherichia, Bacillus*, yeast, insects and animal cells.

Examples of the above-mentioned Escherichia include *E. coli* K12.DH1 [*Proc. Natl. Acad. Sci. U.S.A.*, 60, 160 (1968)], JM103 [*Nucleic Acids Research*, 9, 309 (1981)], JA221 [*Journal of Molecular Biology*, 120, 517, (1978)], HB101 [*Journal of Molecular Biology*, 41, 459 (1969)] and C600 [*Genetics*, 39, 440 (1954)].

Examples of the above-mentioned Bacillus include *Bacillus subtilis* M1114 [*Gene*, 24, 255 (1983)] and 207–21 [*Journal of Biochemistry*, 95, 87 (1984)].

Examples of the above-mentioned yeast include *Saccharomyces cerevisiae* AH22, AH22R⁻, NA87-11A, DKD-5D and 20B-12.

Examples of the insects include larvae of silk worms [Maeda et al., *Nature*, 315, 592 (1985)].

Examples of the animal cells include monkey cell COS-7, Vero, Chinese hamster cell (CHO), mouse L cell and human FL cell.

The transformation of the above-mentioned Escherichia is conducted, for example, according to the method described in *Proc. Natl. Acad. Sci. U.S.A.*, 69, 2110 (1972), *Gene*, 17, 107 (1982) or the like.

The transformation of the Bacillus is carried out, for example, according to the method described in *Molecular & General Genetics*, 168, 111 (1979) or the like.

The transformation of the yeast is performed, for example, according to the method described in *Proc. Natl. Acad. Sci. U.S.A.*, 75, 1929 (1978).

The transformation of the insects is conducted, for example, according to the method described in *Bio/Technology*, 6, 47–55 (1988) or the like.

The transformation of the animal cells is carried out, for example, according to the method described in *Virology*, 52, 456 (1973).

Thus, the transformants transformed with the expression vectors containing the cDNAs coding for the PACAP receptor proteins are obtained.

When the bacterial transformants are cultivated, a liquid medium is typically used for cultivation. Carbon sources, nitrogen sources, inorganic compounds and other nutrients necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins and growth promoting factors, etc. may be further added.

The pH of the medium is preferably about 5 to about 8.

When the Escherichia transformants are cultivated, M9 medium containing glucose and Casamino Acids [Miller, *Journal of Experiments in Molecular Genetics*, 431–433, Cold Spring Harbor Laboratory, New York (1972)] is preferably used to cultivate the transformants. In order to allow the promoters to act more efficiently, for example, drugs such as 3β-indolyl acrylic acid may be added thereto if necessary.

The Escherichia transformants are usually cultivated at about 15° to 43° C. for about 3 to 24 hours with aeration or agitation if necessary.

The Bacillus transformants are usually cultivated at about 30° to 40° C. for about 6 to 24 hours with aeration or agitation if necessary.

When the yeast transformants are cultivated, a preferred medium is Burkholder minimum medium [K. L. Bostian, Proc. Natl. Acad. Sci. U.S.A., 77, 4505 (1980)] or SD medium containing 0.5% Casamino Acids [G. A. Bitter et al., Proc. Natl. Acad. Sci. U.S.A., 81, 5330 (1984)]. The pH of the medium is preferably adjusted to about 5 to 8. The cultivation is usually carried out at about 20° to 35° C. for about 24 to 72 hours with aeration or agitation if necessary.

When the insect transformants are cultivated, examples of media used include Grace's insect medium [(T. C. C. Grace, Nature, 195, 788 (1962)] supplemented with an additive such as 10% inactivated bovine serum. The pH of the medium is preferably adjusted to about 6.2 to 6.4. The cultivation is usually carried out at about 27° C. for about 3 to 5 days with aeration or agitation if necessary.

When the animal cell transformants are cultured, examples of media used include MEM medium containing about 5 to 20% fetal calf serum (Science, 122, 501 (1952)], DMEM medium [Virology, 8, 396 (1959)], RPMI 1640 medium [Journal of the American Medical Association, 199, 519 (1967)] and 199 medium [Proceeding of the Society for the Biological Medicine, 73, 1 (1950)]. The pH is preferably about 6 to 8. The cell culture is usually carried out at about 30° to 40° C. for about 15 to 60 hours, with aeration or agitation if necessary.

The isolation and purification of the PACAP receptor proteins from the above-mentioned culture products can be carried out, for example, according to the following method.

When the PACAP receptor protein is to be extracted from cultured cells, the cells are collected by methods known in the art after cultivation. Then, the collected cells are suspended in an appropriate buffer solution, and disrupted by ultrasonic treatment, lysozyme treatment and/or freeze-thawing thereby releasing the PACAP receptor protein, followed by centrifugation to obtain a crude extract of the PACAP receptor protein. The buffer solution may contain a protein denaturant such as urea or guanidine hydrochloride, or a detergent such as Triton X-100.

When the PACAP receptor protein is secreted in the culture solution, a supernatant is separated from the cells by methods known in the art after termination of cultivation, and then collected. The separation and purification of the PACAP receptor protein contained in the culture supernatant or the extract thus obtained can be carried out by appropriate combinations of well-known separating and purifying methods. These known separating and purifying methods include methods utilizing a difference in solubility such as salting-out and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse phase high performance liquid chromatography, and methods utilizing a difference in isoelectric point such as isoelectric point electrophoresis.

Before or after purification, an appropriate protein modifying enzyme can also be reacted with the PACAP receptor protein produced by a recombinant to arbitrarily modify the protein or to partially eliminate a polypeptide therefrom. The protein modifying enzymes used include trypsin, chymotrypsin, arginyl endopeptidase and protein kinase.

The activity of the PACAP receptor proteins thus obtained can be measured by enzyme immunoassays. When the products have dephosphorylation activity, the measurement can also be conducted based upon said activity.

In the PACAP receptor proteins of the present invention, the amino acid sequences thereof may be partially modified (addition, elimination or substitution with other amino acids).

The PACAP receptor proteins and the DNAs coding for said proteins of the present invention thus obtained can be used for (i) acquisition of antibodies and antisera, (ii) construction of expression systems of recombinant receptor proteins, (iii) development of receptor binding assay preparation of probes and PCR primers in gene diagnosis, and (vi) detection of PACAPs or PACAP receptors in vivo. In particular, the information hitherto obtained suggests that the PACAPs are deeply related to the functions of the hypothalamus-pituitary gland system, the sympathetic nerve system and the central nerve system. Accordingly, elucidation of the structure and properties of the PACAP receptors can contribute to development of unique drugs acting on these systems.

The PACAP receptor proteins, the PACAP receptor fragments and the DNAs encoding said proteins of the present invention can be used as follows (1) to (3)

(1) The PACAPs are known to exhibit functions such as protection of nerve cells and growth maintenance of the nerve cells in vivo. A decrease in PACAP concentration in vivo is therefore considered to induce death of the nerve cells and to cause neuropathy such as Alzheimer's disease. Accordingly, for the PACAP receptor proteins of the present invention which specifically react with the PACAPS, the partial peptides thereof or the salts thereof, the PACAP concentration in vivo can be determined high sensitively, so that they can be effectively used as diagnostic composition for neuropathy such as Alzheimer's disease. When the PACAP receptor proteins of the present invention, the partial peptides thereof or the salts thereof are used as diagnostic composition which can determine the PACAP composition for neuropathy such as Alzheimer's disease. The diagnosis can be conducted by determining an amount of PACAP which binds to PACAP receptor proteins, the partial peptides thereof or the salts thereof of the present invention when contacting the test sample with PACAP receptor proteins, the partial peptides thereof of the salts thereof of the present invention. When the PACAP receptor proteins of the present invention, the partial peptides thereof of the salts thereof are used as diagnostic composition which can determine the PACAP concentration in test samples, they can be used, for example, in combination with competitive assays. For example, the methods described in the following (i) or (ii), or methods based thereon can be used:

(i) *Radioimmunoassay*, edited by H. Irie, Kodansha (1974), and (ii) *Radioimmunoassay* (*second series*), edited by H. Irie, Kodansha (1979)

Specifically, standard curves can be prepared by the receptor competitive binding experiment method described in Example 1 (3) given later, thereby measuring the PACAP concentration in test samples. The procedure of the method is shown below.

TABLE 1

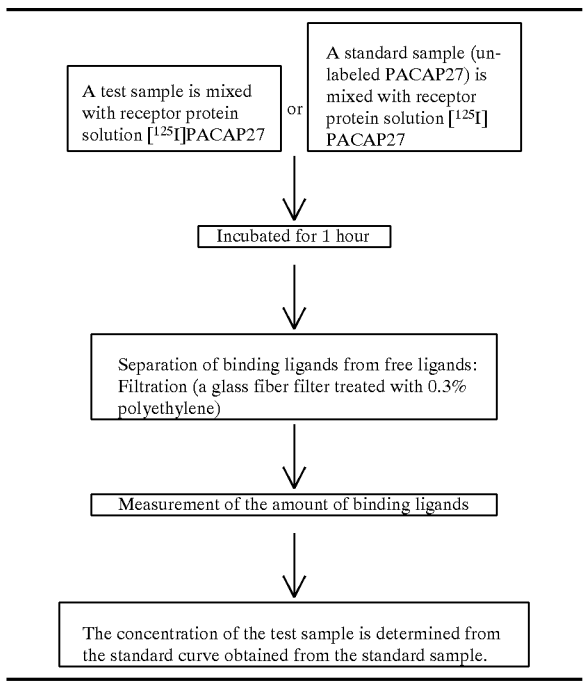

(2) In the case of a patient suffering from neuropathy (for example, Alzheimer's disease) in which the PACAP action is not sufficiently exhibited, because the PACAP can not be bound to the PACAP receptor in vivo due to a reduction in the amount of the PACAP receptor protein on the nerve cell membranes in vivo, causing the tendency of death of the nerve cells, the amount of the PACAP receptor protein in the nerve cells of the patient can be increased by (a) inserting the DNA of the present invention in the patient to express it, or by (b) inserting the DNA of the present invention in the nerve cells to express it, followed by implantation of the nerve cells in the patient, thereby sufficiently exhibiting the PACAP action. That is, the DNAs of the present invention can be used for gene therapy of neuropathy, because we can transform nerve cells in vitro or in vivo by using the DNAs of the present invention.

The above-mentioned gene therapy can be given according to methods known in the art. For example, they can be given orally as tablets, capsules, elixirs and microcpsules, or parenterally in the form of injections such as sterile solutions or suspensions with water or with pharmaceutically acceptable solutions other than water. For example, the DNAs of the present invention can be mixed with carriers, flavoring agents, excipients, vehicles, preservatives, stabilizing agents, binders, etc. in the form of unit dosage required for generally admitted pharmaceutical practice to prepare preparations. The amount of active ingredients in these preparations is adjusted so as to obtain appropriate doses within specified ranges. Additives which can be mixed with tablets, capsules, etc. include, for example, binders such as gelatin, corn starch, tragacanth and gum arabic; excipients such as crystalline cellulose; swelling agents such as corn starch, gelatin and alginic acid; lubricants such as magnesium stearate; sweeteners such as sucrose, lactose and saccharine; and flavoring agents such as peppermint, acamono oil and cherry. When the preparation unit is in the capsule form, liquid carriers such as fat and oil may further be added to materials of the above-mentioned types. Sterile compositions for injection can be formulated according to usual pharmaceutical practice such as dissolution or suspension of active substances and naturally occurring vegetable oils such as sesame oil and coconut oil in vehicles such as water for injection. Aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic surface active agents (for example, Polysolvate 80 and HCO-50). Oily solutions include sesame oil and soybean oil, and may be used in combination with solubilizing adjuvants such as benzyl benzoate, benzyl alcohol, etc. The preparations may further contain buffers (for example, phosphate buffer and sodium acetate buffer), soothing agents (for example, benzalkonium chloride and procaine hydrochloride), stabilizing agents (for example, human serum albumin and polyethylene glycol), preservatives (for example, benzyl alcohol and phenol), antioxidants, etc. The injections thus prepared are usually filled into appropriate ampuls. Although the dosage varies depending upon the symptom, the oral dosage is generally about 0.1 to 100 mg per day, preferably 1.0 to 50 mg, and more preferably 1.0 to 20 mg, for adults (taken as 60 kg). When the preparations are parenterally given, the dosage varies depending upon the object to which the preparations are given, the organ to which they are given, the symptom, the route of administration, etc. For example, when the preparations are given in the injection form, it is advantageous that they are intravenously injected in a dosage of about 0.01 to 30 mg per day, preferably 0.1 to 20 mg, and more preferably 0.1 to 10 mg, for adults (taken as 60 kg).

Figure 31:
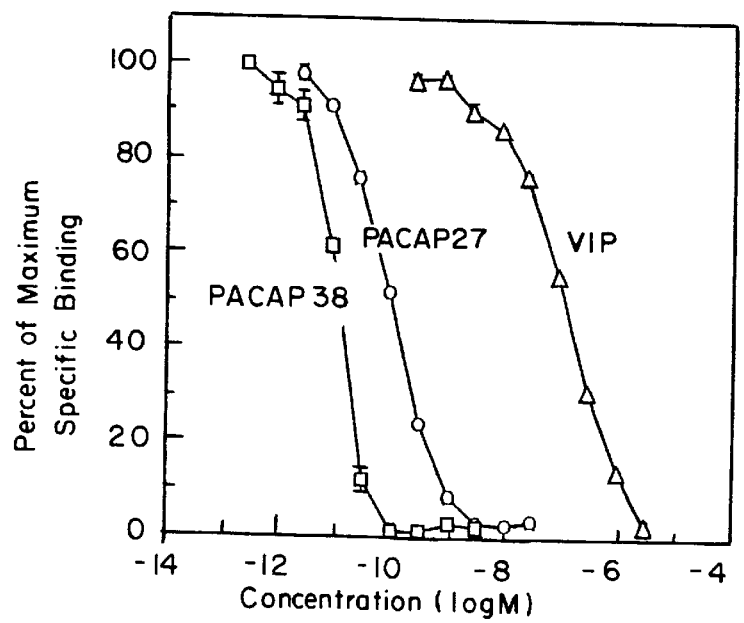
FIG. 31 is a graph showing results of the antagonistic binding experiment of purified bovine PACAP receptor protein. The numerals on the abscissa indicate the concentrations (log M) of PACAP38, PACAP27 and VIP, and the numerals on the ordinate indicate the binding (%) of [$^{125}$I]-PACAP27, taking the specific binding as 100, when each peptide is added so as to give the final concentrations on the abscissa.

(3) Example 1 below and FIG. 31 have proved that the PACAP receptor proteins of the present invention bind to the PACAPs. Further, Examples 5, 7 and 8 have revealed that the DNAs coding for bovine, rat and human PACAP receptor proteins can be expressed on cell membranes, and the PACAP receptor proteins expressed can react with the PACAPs to increase the amount of cyclic AMP and (or) the concentration of inositol phosphate in cells. Further Example 11 has revealed that compounds inhibiting the binding of PACAPs to PACAP receptors can be screened by using the membrane fractions of the Sf9 cells in which the human PACAP receptor is expressed by use of Baculoviridae. Accordingly, the present invention gives a method for determining
 (i) an effect of a test compound on PACAP receptor activity comprising comparing PACAP receptor activities in cases of (a) and (b);
  (a) contacting PACAP receptor with a PACAP;
  (b) contacting PACAP receptor with a PACAP and a test compound, or
 (ii) an effect of a test compound on binding of PACAP to PACAP receptor comprising comparing an amount of binding of PACAP to PACAP receptor in cases of (a) and (b);
  (a) contacting PACAP receptor with a PACAP;
  (b) contacting PACAP receptor with a PACAP and a test compound.

The present invention further gives an assay for quantifying a test compound's effect
(i) on PACAP receptor activity comprising comparing an amount of PACAP receptor activation in cases of (a) and (b);
 (a) contacting PACAP receptor with a PACAP;

(b) contacting PACAP receptor with a PACAP and a test compound, or (ii) on binding of PACAP to PACAP receptor comprising comparing an amount of binding of PACAP to PACAP receptor in cases of (a) and (b);

(a) contacting PACAP receptor with a PACAP;

(b) contacting PACAP receptor with a PACAP and a test compound.

As the PACAP receptor in the above screening method, the PACAP receptor of the present invention, the receptor fragment of the present invention or the PACAP receptor produced by cultivating a transformant containing the DNA encoding the PACAP receptor of the present invention.

Compounds or their salts obtained by the above screening method include compounds activating PACAP receptor or compounds antagonizing binding of a PACAP to a PACAP receptor.

As the above mentioned, compounds activating PACAP receptors (for example, peptides, proteins and natural or nonnatural compounds), namely, PACAP receptor antagonists, or compounds antagonistically inhibiting the binding of PACAPs to receptors (for example, peptides, proteins and natural or nonnatural compounds), namely PACAP receptor antagonists, can be screened by using the PACAP receptor proteins of the present invention, the partial peptides thereof or the salts thereof, or by the PACAP receptor proteins which are obtained by cultivating transformants containing a DNA encoding PACAP receptor protein. These PACAP receptor agonists or PACAP receptor antagonists can be further tested for use as drugs useful in protection of nerve cells and growth maintenance of nerve cells in vivo, for example, therapeutic composition for neuropathy such as Alzheimer's disease.

Until human PACAP receptor of the present invention was found, for example, when substances which inhibit a binding of PACAP to human PACAP receptor were screened, the following steps were necessary:

Obtaining a PACAP receptor of other than human such as bovine or porcine; screening substances which inhibit a binding of the bovine or porcine PACAP receptor and PACAP; and checking whether the picked substances have real affinity on human PACAP receptor.

Meanwhile, human PACAP receptor makes the screening of substances which inhibit binding of human PACAP receptor and PACAP easy and effective. The thus obtained PACAP receptor agonists or PACAP receptor antagonists may be further tested drugs useful for protecting nerve cells or maintaining growth of nerve cells in vivo such as for therapeutic composition for nervous diseases such as Alzheimer's disease or for maintaining growth of nerve cell in vitro.

The screening methods of the present invention will be described below in detail.

(I) Methods for Screening Compounds Antagonistically Inhibiting the Binding of PACAPs to PACAP Receptors PACAP receptor proteins used for screening are preferably membrane fractions of organs of warm-blooded animals. For example, human PACAP receptor protein expressed in large amounts by use of recombinants is suitable, because it is very difficult to obtain human-derived organs.

The above-mentioned methods are used for the production of the PACAP receptor proteins, and performed by expressing DNAs coding for said proteins in animal cells (for example, human cells) or insect cells. In particular, they are preferably expressed in the insect cells.

Complementary DNAs are used as the DNA fragments coding desired portions, but the DNA fragments are not necessarily limited thereto. For example, gene fragments or synthetic DNAs may be used. In order to introduce the DNA fragments coding for the PACAP receptor proteins into host cells and express them efficiently, it is preferred that said DNA fragments are ligated downstream from polyhedrin promoters of insect nuclear polyhedrosis viruses (NPVs) belonging to Baculoviridae. Vectors include two viruses of Autograph california NPV (ACNPV) belonging to Kinuwaba and Bombyx mori NPV (BmNPV) of silk worms. Baculoviridae has cyclic double stranded DNA (130 kb), and shows no infectivity to spinal animals and plants at all. Virus DNA is so long as 130 kb, so that it is difficult to directly insert the DNA fragment wanted to be expressed downstream from the polyhedrin promoter. Then, actually, a polyhedrin gene portion containing a promoter portion is cut out from a virus, and incorporated in an *E. coli* vector such as pUC18 to prepare a transfer vector. Subsequently, a desired DNA fragment is inserted downstream from a polyhedrin promoter of the transfer vector, and an insect cell is concurrently infected therewith, together with baculovirus DNA, followed by cultivation. Homologous recombination is allowed to take place in the insect cell to obtain a recombinant baculovirus. The recombinant virus forms the desired product freshly introduced, instead of forming a polyhedrin. When the virus is AcNPV, a yatoga caterpillar-derived established cell line (*Spodoptera frugiperda* cell; Sf cell) is used as a host cell. When the virus is BmNPV, a silk worm-derived established cell line (Bombyx mori N; BmN cell) is used. As expression systems using baculoviruses and insect cells, commercial systems can be employed (for example, MAXBAC™, Invitrogen), and procedures described in the experimental descriptions attached thereto and in *Bio/Technology*, 6, 47–55 (1988) can also be adopted. The amount and quality of the expressed receptor can be examined by methods known per se in the art, for example, the method described in P. Nambi et al. *J. Biol. Chem.*, 267, 19555–19559 (1992).

In the screening methods of the present invention, as the PACAP receptor proteins, either cells containing the proteins or proteins fractions of cells containing the proteins may be used. Further, membrane fractions of insect cells containing the proteins are most preferably used.

Said cells means host cells in which the PACAP receptor proteins are expressed. Said host cells include *E. coli, Bacillus subtilis,* yeast, insect cells and animal cells (for example, human cells), and the insect cells are preferred among others.

The membrane fractions means fractions in which cell membranes obtained by methods known per se in the art after cell disruption are contained in large amounts. The disruption of the cells is carried out preferably at 0° to 4° C., and physiological saline or a buffer such as 50 mM Tris-HCl is used. A protease inhibitor is preferably added to prevent decomposition of the protein. Methods for disrupting the cells include the method of crushing the cells with a Potter-Elvehjem type homogenizer, disruption with a Working blender or a Polytron homogenizer (Kinematica), disruption by ultrasonication, and disruption by allowing the cells to jet through a fine nozzle under pressing with a French press, etc. Fractionating methods utilizing centrifugal force such as differential centrifugation and density gradient centrifugation are mainly used for fractionation of the cell membranes. For example, a cell disrupted solution is centrifuged at a low speed (500 to 3000 rpm) for a short period of time (usually about 1 to 10 minutes), and the supernatant is further centrifuged at a high speed (15000 to 30000 rpm), usually for 30 minutes to 2 hours. The resulting precipitate is taken as the membrane fraction. In said membrane fraction, the expressed PACAP receptor protein and membrane compositions such as cell-derived phospholipids and membrane proteins are contained in large amounts.

The amount of the PACAP receptor proteins in the cells or the membrane fractions containing the PACAP receptor proteins is preferably $10^3$ to $10^8$ molecules per cell, and suitably $10^5$ to $10^7$ molecules per cell. A more expression amount results in higher PACAP binding activity per membrane fraction (specific activity). Not only construction of a high sensitive screening system becomes possible, but also a large amount of samples can be measured in the same lot.

In order to screen compounds antagonistically inhibiting the binding of a PACAP to a PACAP receptor, an appropriate PACAP receptor fraction and a labeled PACAP (for example, PACAP27 or PACAP38, hereinafter referred to as a PACAP) are required. Desirable examples of the PACAP receptor fractions include natural PACAP receptor proteins and recombinant PACAP receptor proteins equivalent thereto. As the labeled PACAPs, PACAP27 labeled with [$^{125}$I] (du Pont), etc. are commercially available. They can therefore be utilized.

When the compounds antagonistically inhibiting the binding of the PACAP to the PACAP receptor is screened, cells or cell membrane fractions containing the PACAP receptor protein are first suspended in a buffer suitable for screening, thereby preparing a receptor sample. The buffer may be any, as long as it is a buffer which does not inhibit the binding of the PACAP to the receptor, such as phosphate buffer or Tris-HCl buffer having a pH of 4 to 10 (preferably a pH of 6 to 8). For the purpose of decreasing non-specific binding, a surface active agent such as CHAPS, Tween-80™ (Kao-Atlas), digitonin or deoxycholate may also be added to the buffer. Further, for the purpose of inhibiting decomposition of the receptor or a ligand with a protease, a protease inhibitor such as PMSF, leupeptin, E-67 (Peptide Laboratory) or pepstatin can also be added. A definite amount (5000 to 500000 cpm) of [$^{125}$I]PACAP is added to 0.01 to 10 ml of the receptor solution, and $10^{-4}$ to $10^{-10}$M specimen compound, fermentation products, etc. are allowed to coexist at the same time. In order to know the non-specific binding (NSB), a reaction tube to which a ligand is added in large excess is prepared. Reaction is conducted at 0° to 50°C., desirably at 4° to 37° C. for 20 minutes to 24 hours, desirably for 30 minutes to 3 hours. After reaction, the reaction product is filtered through a glass fiber filter and washed with an appropriate amount of the same buffer, followed by measurement of [$^{125}$I] remaining on the glass fiber filter with a γ-counter. When the count ($B_0$-NSB) obtained by subtracting NSB from the count ($B_0$) in the absence of an antagonistic substance is taken as 100%, the specimen compound, the fermentation products, etc giving a non-specific binding (B-NSB) of 50% or less can be selected as potential materials having antagonistic ability.

Examples of kits for screening the compounds antagonistically inhibiting the binding of the PACAPs to the PACAP receptors of the present invention include the following:

1. Reagents for Screening

| (A) Buffer for Measurement | |
|---|---|
| Tris-HCl | 2.4 g |
| Magnesium acetate.4H$_2$O | 1.07 g |
| EGTA | 0.76 g |
| NaN$_3$ | 0.6 g |
| Leupeptin | 20 mg |

| -continued | |
|---|---|
| (A) Buffer for Measurement | |
| E-64 | 4 mg |

These are dissolved in 997 ml of distilled water.

| Pepstatin | 1 mg |
|---|---|
| PMSF | 0.09 g |

These are dissolved in 1 ml of DMSO, and the resulting solution is added to 997 ml of the above-mentioned water. About 2 ml of 6N HCl is added thereto to adjust to pH 7.2. One gram of BSA is dissolved therein, followed by storage at 4° C.

(B) Buffer for Washing

| CHAPS | 0.45 g |
|---|---|

This is dissolved in 900 ml of the buffer for measurement and the solution is stored at 4° C.

(C) PACAP Receptor Sample

A membrane fraction of insect cells (Sf9) in which a PACAP receptor protein is expressed is diluted with the buffer for measurement to 0.5 to 5 µg of protein/ml before use.

(D) [$^{125}$I] Labeled PACAP

| (3-[$^{125}$I]iodotyrosyl) PACAP (du Pont) | 185 kBq |
|---|---|

Fifty microliters of distilled water is added thereto to dissolve it, and 450 µl of the buffer for measurement is added thereto. The solution is stored at −20° C.

(E) PACAP Standard Solution

The PACAP (Peptide Laboratory) is diluted with 50% DMSO to $10^{-4}$M, and stored at −20° C. This is diluted 10 times with the buffer for measurement before use.

2. Assays (i) The membrane fraction of Sf9 cells containing the PACAP receptor protein [J. L. Vaughn et al., In Vitro, 13, 213–217 (1977)] is diluted with the buffer for measurement to give 1 µg of protein/ml, and 100 µl thereof is poured into each tube (Falcon).

(ii) After addition of 3 µl of $10^{-4}$ to $10^{-10}$M specimen or 10 µl or less of fermentation products, 2 µl of [$^{125}$I] labeled PACAP is added, followed by reaction at 25° C. for 60 minutes. In order to examine the non-specific bonding, 3 µl of $10^{-5}$M PACAP is added instead of the specimen.

(iii) The buffer for washing (1.5 ml) is added, and filtration is conducted through a glass fiber filter (GF/F, Whatman). Then, 1.5 ml of the same buffer is further added to the residue in the tube, and filtration is conducted again.

(iv) [$^{125}$I] remaining on the glass fiber filter is measured with a γ-counter, and the percent maximum binding (PMB) is determined from the following equation;

PMB=[(B-NBS)/(B$_0$-NBS)]×100

PMB: percent maximum binding
B: value when the specimen is added

NBS: non-specific binding

B$_0$: maximum binding (II) Methods for Screening Compounds Activating the PACAP Receptors The compounds antagonistically inhibiting the binding of the PACAPs to the PACAP receptor proteins selected by the methods of (I) described above is expected to contain compounds activating the PACAP receptor proteins similarly to the PACAPs (compounds having PACAP receptor agonist activity). Such compounds can be evaluated by secondary screening systems based on acceleration of cyclic AMP production as described below.

First, cells in which the PACAP receptor protein is expressed are subcultured to a 48-well plate for tissue culture in a ratio of 1×10$^5$ cells/well, and cultured for 2 days. Then, the medium is removed, and the plate is washed twice with serum-free medium. Subsequently, 300 µl of the same medium is added to each well as a reaction solution. The serum-free medium may be any, as long as it is a medium for cell culture, and bovine serum albumin, etc. may be added for the purpose of preventing the compounds added from being non-specifically adsorbed by the instruments, etc. Further, for the purpose of inhibiting decomposition of cyclic AMP produced to enhance assay sensitivity, addition of 3-isobutyl-1-methylxanthine (IBMX), a phosphodiesterase inhibitor, is effective. The specimen compound having a final concentration of $10^{-4}$ to $10^{-10}$M and fermentation products are added to each well. In order to know non-specific response, wells containing only the solvent in which the compounds are dissolved are prepared. Reaction is usually conducted at 4° to 42° C. for 10 minutes to 2 hours, preferably at room temperature to 37° C. for 20 minutes to 1 hour. After reaction, the supernatant is removed by suction. After washing with two portions of the reaction solution, cyclic AMP produced is extracted with 200 µl of 100% ethanol. Ethanol is removed with a centrifugal freeze dryer, and the residue is dissolved in 100 µl of a buffer for determination of cyclic AMP. Reagents for determination of cyclic AMP, including the buffer, may be ones commercially available as kits according to either radio immunoassay (RIA) or enzyme immunoassay (EIA) (Amersham, du Pont, etc.). When the production amount of cyclic AMP which has become clear by determination is statistically significantly high, compared with the case where the sample is not added or the case where only the solvent in which the sample is dissolved is added, such compound can be selected as potential compounds having PACAP receptor agonist activity. In order to eliminate the probability that the cyclic AMP production promoting action of the potential compounds is non-specific action to cells or action through receptors other than the PACAP receptor, it is necessary to confirm that the potential compounds exhibit no cyclic AMP production promoting action in cells in which the PACAP receptor protein is not allowed to be expressed. As an indication for PACAP receptor agonist activity, production promotion of inositol triphosphate or diacylglycerol and an increase in intracellular calcium concentration, as well as the production promotion of cyclic AMP, may be employed. However, the production promotion of cyclic AMP is superior from the viewpoint of treating the sample in large amounts. Such screening methods of the present invention are excellent methods by which compounds having action similar to that of the PACAP or higher than the PACAP and excellent in resistance against proteases, compared with the PACAP, a peptide, can be selected.

Antibodies or antiserum to the PACAP receptor proteins of the present invention, the partial peptides thereof or the salts thereof may be any antibodies or antiserum as long as they can recognize the PACAP receptor proteins, the partial peptides thereof or the salts thereof. For example, monoclonal antibodies such as PRN1-25a, PRN1-109a and PRN1-159a against a partial peptide (MHSDAIFKKEQAMC) are preferable. The partial peptide was prepared by substituting the 5th Cys(C) of a partial peptide which has a partial amino acid sequence (1st to 14th amino acid sequence of SEQ ID NO:14) common to bovine, rat or human PACAP receptor which has amino acid sequence of anyone of SEQ ID NO:14 to SEQ ID NO:29 to Ala(A), for the convenience of preparation of immunoantigen complexes.

Antibodies or antiserum to the PACAP receptor proteins of the present invention, the partial peptides thereof or the salts thereof can be produced by methods known per se in the art, using the PACAP receptor proteins, the partial peptides thereof or the salts thereof as antigens. The antibodies or antiserum thus obtained can be used for quantitative analysis or detection of the PACAP receptor proteins of the present invention, the peptides thereof or the salts thereof, more detailed utilities are as follows:

(1) By using the antibodies or antiserum for Western blotting or immune precipitation, the PACAP receptor proteins, the partial peptides thereof or the salts thereof can be detected.

(2) An affinity column to which the antibodies of the present invention are fixed, can purify the PACAP receptor proteins, the partial peptides thereof or the salts thereof.

(3) The antibodies of the present invention can be used as a PACAP receptor antagonist, as shown in Example 12, since the antibodies block PACAP action by inhibiting binding of PACAP and a PACAP receptor.

As a signal peptide of the PACAP receptor protein of the present invention, for example, a peptide which has 1st to 37th amino acid sequence of SEQ ID NO:15, a peptide which has 1st to 37th amino acid sequence of SEQ ID NO:17, a peptide which has 1st to 19th amino acid sequence of SEQ ID NO:19, a peptide which has 1st to 19th amino acid sequence of SEQ ID NO:21, a peptide which has 1st to 77th amino acid sequence of SEQ ID NO:23, a peptide which has 1st to 77th amino acid sequence of SEQ ID NO:25, a peptide which has 1st to 77th amino acid sequence of SEQ ID NO:27, a peptide which has 1st to 77th amino acid sequence of SEQ ID NO:29, a peptide which has 58th to 77th amino acid sequence of SEQ ID NO:23, a peptide which has 58th to 77th amino acid sequence of SEQ ID NO:25, a peptide which has 58th to 77th amino acid sequence of SEQ ID NO:27 or a peptide which has 58th to 77th amino acid sequence of SEQ ID NO:29 may be used. These signal peptides can be synthesized by conventional methods such as a peptide synthesizer or prepared by cutting the amino acid bond of the PACAP receptor of the present invention with an enzyme.

The salts of the signal peptides of the present invention include similar salts as those for PACAP receptors or partial peptides thereof.

A DNA which encodes a signal peptide may be any one which has a nucleotide sequence encoding the signal peptide and includes a DNA which has 1st to 111th nucleotide sequence of SEQ ID NO:30, a DNA which has 1st to 111th nucleotide sequence of SEQ ID NO:31, a DNA which has 1st to 57th nucleotide sequence of SEQ ID NO:32, a DNA which has 1st to 57th nucleotide sequence of SEQ ID NO:33, a DNA which has 1st to 231st nucleotide sequence of SEQ ID NO:34, a DNA which has 1st to 231st nucleotide sequence of SEQ ID NO:35, a DNA which has 1st to 231st nucleotide sequence of SEQ ID NO:36, a DNA which has 1st to 231st nucleotide sequence of SEQ ID No:37, a DNA which has 172nd to 231st nucleotide sequence of SEQ ID NO:34, a DNA which has 172nd to 231st nucleotide sequence of SEQ ID NO:35, a DNA which has 172nd to 231st nucleotide sequence of SEQ ID NO:36, a DNA which has 172nd to 231st nucleotide sequence of SEQ ID NO:37 or a DNA which comprises one of these DNAs. These DNAs encoding signal peptides of the present invention can be synthesized by conventional method such as a peptide synthesizer or prepared by cutting the DNA (cDNA is preferable) which encodes the PACAP receptor of the present invention with an appropriate restrictive enzyme.

The DNA coding for the signal peptide of the PACAP receptor proteins of the present invention may stimulate an expression of a membrane-bound peptide such as a receptor into a membrane. For example, a protein which does not or rately expresses into a membrane can be expressed on the membrane effectively by linking a DNA coding for a signal peptide of the PACAP receptor proteins of the present invention upstream from the DNA which rarely or does not express the desired protein on the membrane in an expression.

The present invention will be described in more detail through the following examples. It is understood of course that they are not intended to limit the scope of the invention.

Transformant *E. coli* pBPR-T containing pBPRT and transformant *E. coli* pBPR114 containing pBPR114 each obtained in Example 2 given later were deposited with the National Institute of Bioscience and Human-technology (NIBH), the Agency of Industrial Science and Technology, the Ministry of International Trade and Industry, Japan, under the accession numbers FERM BP-4338 and FERM BP-4339, respectively, on Jun. 15, 1993, and deposited with Institute for Fermentation, Osaka, Japan (IFO) under the accession numbers IFO 15572 and IFO 15571, respectively, on Nov. 5, 1993.

Transformant *E. coli* pRPACAPR 12 containing pRPACAPR 12 and transformant *E. coli* pRPACAPR 46-5 containing pRPACAPR each obtained in Example 3 given later were deposited with NIBH, under the accession numbers FERM BP-4254 and FERM BP-4255, respectively, on Apr. 5, 1993, and deposited with IFO under the accession numbers IFO 15469 and IFO 15470, respectively, on Apr. 15, 1993.

Transformant *E. coli* MV1184/pTS847-1 containing pTS847-1 obtained in Example 4 given below was deposited with the NIBH under the accession number FERM BP-4280, and deposited with IFO under the accession number IFO 15570 on Nov. 5, 1993.

Transformant *E. coli* pHPR15A containing pHPR15A obtained in Example 4 given below; Transformant *E. coli* pHPR55A containing pHPR55A and Transformant *E. coli* pHPR66P containing pHPR66P were deposited with the NIBH under the accession number FERM BP-451$_1$, FERM BP-4510 and FERM BP-4509, respectively on Dec. 22, 1993, and deposited with IFO under the accession number IFO 15603, 15604 and 15605, respectively on Dec. 20, 1993.

Hybridoma PRN1-159 obtained in Example 12 given below was deposited with NIBH under the accession number FERM BP-4554 on Feb. 8, 1994, and deposited with IFO under the accession number IFO 50427 on Feb. 8, 1994.

EXAMPLES

[Example 1]

Production (Purification) of Bovine-Derived PACAP Receptor Protein

The following procedure was conducted in a low temperature laboratory at 4° C.

(1) Preparation of Membrane Fractions

Membrane fractions were prepared from the bovine cerebrums according to a method in which the known method described in *Biochem. Biophys. Res. Commun.*, 172, 709–714 (1990) was partially modified. The fresh bovine cerebrums (1.5 kg) were homogenized 3 times in 6 liters of buffer A (20 mM Tris, 10 mM EDTA, 0.25M sucrose, 0.5 mM PMSF, 20 μg/ml leupeptin, 4 μg/ml E-64 and 1 μg/ml pepstatin, pH 7.4) with a Polytron homogenizer (Kinematica) for 30 seconds. The resulting homogenate was centrifuged with a high speed cooling centrifuge CR26H, Roter RR10A (Hitachi, Ltd.) at 680×g for 20 minutes to obtain a supernatant. The resulting supernatant was further ultracentrifuged with an ultracentrifuge SCP70H, Roter RPZ35T (Hitachi, Ltd.) at 100,000×g for 60 minutes to obtain pellets. The pellets were suspended in 400 ml of buffer B (20 mM Tris, 5 mM EDTA, 0.5 mM PMSF, 20 μg/ml leupeptin, 4 μg/ml E-64 and 1 μg/ml pepstatin, pH 7.4) to prepare a membrane fraction suspension.

(2) Solubilization of the PACAP Receptor Protein from the Membrane Fractions

The membrane fraction suspension obtained in (1) described above (400 ml) was diluted with 5 liters of buffer B to give a membrane protein concentration of 1 mg/ml, and digitonin was added thereto to provide a concentration of 1%. The resulting suspension was slowly stirred for 1 hour, and then, ultracentrifuged with an ultracentrifuge SCP70H, Roter RPZ35T (Hitachi, Ltd.) at 100,000×g for 1 hour to obtain a supernatant. The resulting supernatant was used as a solubilized membrane protein fraction.

(3) Assay of Receptor Activity of the PACAP Receptor Protein

PACAP receptor activity was assayed according to the saturation binding experiment method using [$^{125}$I]PACAP27 and the antagonistic binding experiment method [*Biochem. Biophys. Res. Commun.*, 171, 838–844 (1990) and *Biochem. Biophys. Res. Commun.*, 172, 709–714 (1990)]. The test sample (membrane fraction or solubilized membrane protein fraction) was appropriately diluted with buffer D (20 mM Tris, 5 mM magnesium chloride, 0.1% BSA and 0.05% digitonin, pH 7.4). In the saturation binding experiment, 0.1 ml of the diluted test sample was mixed with 10 μl of [$^{125}$I]PACAP27 (final concentration: 20 to 50 pM), and reacted at 25° C. for 1 hour. In the competitive binding experiment, the diluted test sample was mixed with 2 μl of [$^{125}$I]PACAP27 (final concentration: 100 pM) and 3 μl of an unlabeled peptide (PACAP27, PACAP38 or VIP) having a variable concentration, and reacted in a similar manner. To 0.1 ml of this reaction solution, 1.5 ml of buffer E (0.1% BSA, 0.05% CHAPS, 20 mM Tris and 5 mM magnesium chloride, pH 7.4) cooled with ice was added, and immediately, the mixed solution is filtered through a glass fiber filter. The glass fiber filter used had previously been treated with 0.3% polyethylene imine. The radioactivity of the filter was counted with a γ-ray counter, thereby determining [$^{125}$I]PACAP27 bound to the receptor. In order to determine the non-specific binding, the above-mentioned experiment was carried out in the presence of 1 μM PACAP27. The specific binding was calculated by subtracting the non-specific binding from the total binding measured in the absence of PACAP27. Results of the saturation binding experiment were subjected to Scatchard plot analysis to determine the dissociation constant and the maximum binding.

(4) Crude Purification of the PACAP Receptor Protein

A method for purifying the PACAP receptor from the solubilized membrane protein fraction by ion exchange chromatography and hydroxyapatite chromatography is described below.

The solubilized membrane protein fraction [2400 mg (4800 ml)] was loaded onto an ion exchange column (for example, anion exchange chromatography such as DEAE-TOYOPEARL) equilibrated with 1 liter of buffer C, at a flow rate of 9 ml/minute. Then, the concentration of sodium chloride in buffer C (20 mM Tris, 1 mM EDTA, 0.5 mM PMSF, 20 μg/ml leupeptin, 4 μg/ml E-64 and 1 μg/ml pepstatin, pH 7.4) supplemented with 0.1% digitonin was gradually increased from 0M to 1M for 170 minutes to elute the PACAP receptor from the column. The PACAP receptor activity of each eluted fraction was assayed by the above-mentioned method. The active fractions eluted from the ion exchange column were further loaded onto a hydroxyapatite column (HCA-100, 5 cm in diameter and 7 cm in length) at a flow rate of 7 ml/minute. This column was washed with 500 ml of 0.1M phosphate buffer containing 0.1% digitonin, and then, the PACAP receptor was eluted with 500 ml of 0.6M phosphate buffer containing 0.1% digitonin at a flow rate of 7 ml/minute. The active fractions were concentrated 10-fold using an ultrafilter, and further desalted by repetition of dilution and concentration with a 6-fold excess of buffer C in relation to the volume of the concentrated sample.

(5) Purification of the PACAP Receptor by Affinity Chromatography (5-1) Preparation of Affinity Ligand A method for preparing a biotinated PACAP used in affinity chromatography is described below. One equivalent of the PACAP27 derivative (having cysteine as the 28th amino acid residue, PACAP27-Cys) synthesized by the solid phase method was dissolved in 50 mM phosphate buffer (pH 7.0) supplemented with 3 mM EDTA and 0.5M NaCl to provide a concentration of $2 \times 10^{-4}$, and a 10 mM biotinylating reagent (biotin-HSDP) dissolved in DMF was added thereto to give 10 equivalents, followed by reaction overnight. The reaction product, biotinylated PACAP27 (PACAP27-Cys-biotin) represented by the following formula, was purified on a reverse phase HPL chromatography:

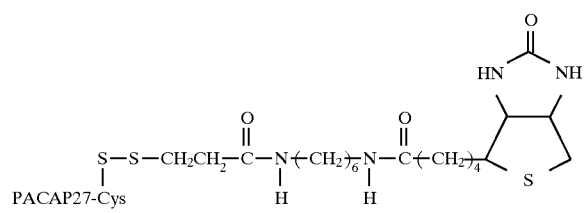

Figure 28:
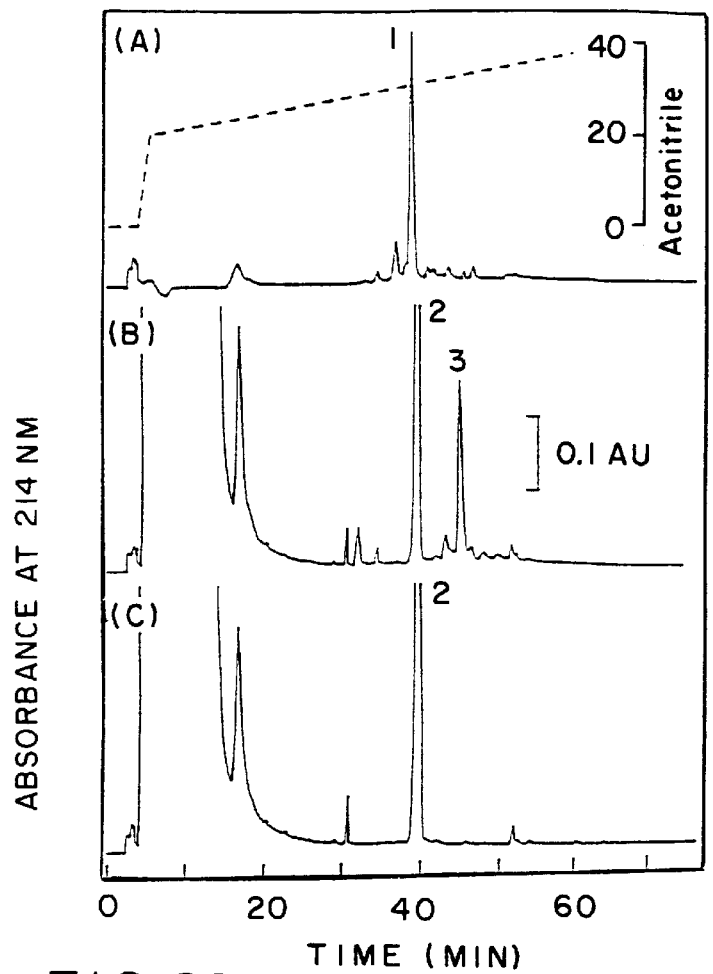
FIG. 28 is a graph showing absorption curves of biotinated PACAP27 by HPLC. Peak 1 of (A) indicates a peak of PACAP27-Cys, peak 3 of (B) indicates a peak of biotinated PACAP27-Cys, and peak 2 of (C) indicates a peak of the biotinating reagent.
Figure 23A:
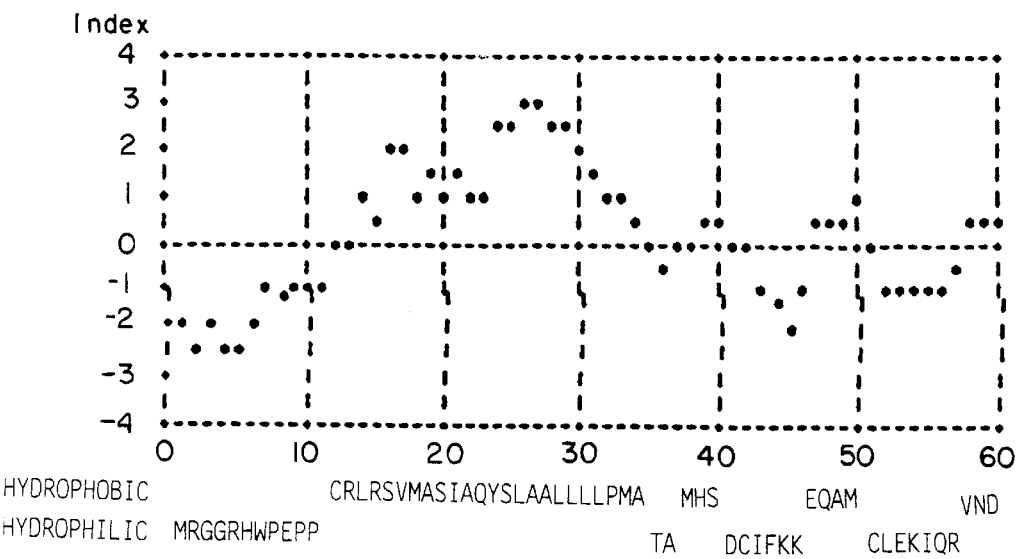
FIG. 23 is a series of graphs in which the degree of hydrophobicity of bovine PACAP receptor protein encoded by pBPR-T is shown as an index.
Figure 23B:
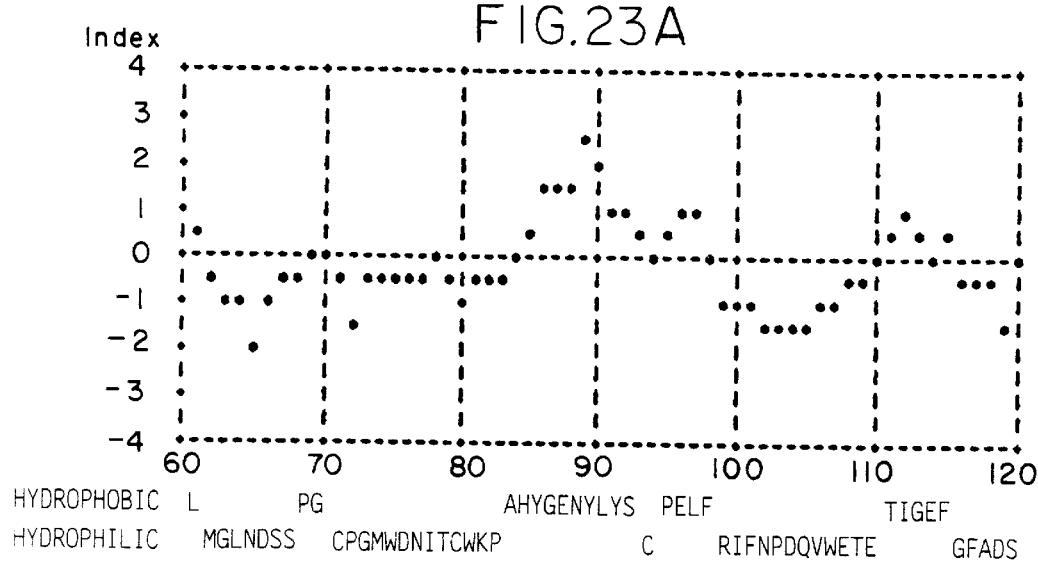
Figure 23C:
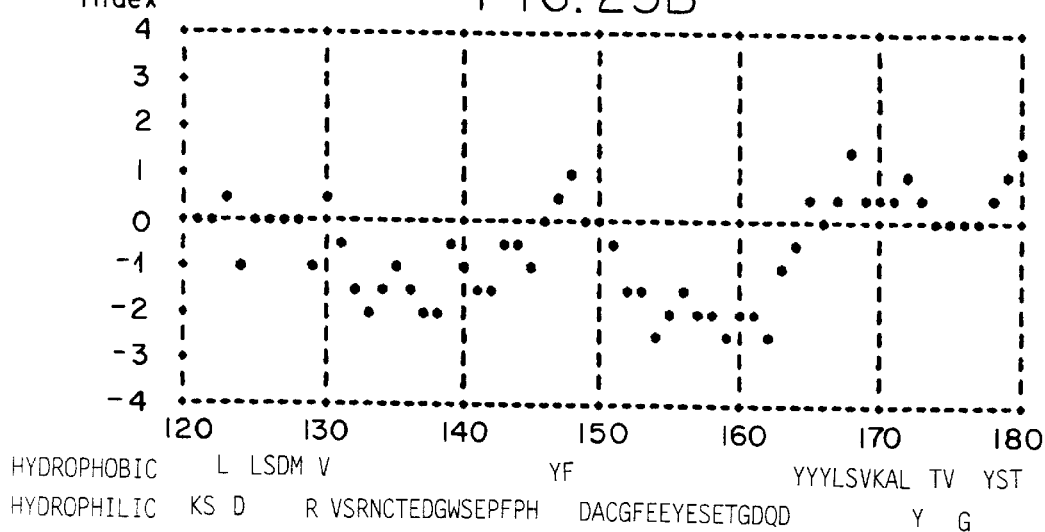
Figure 23D:
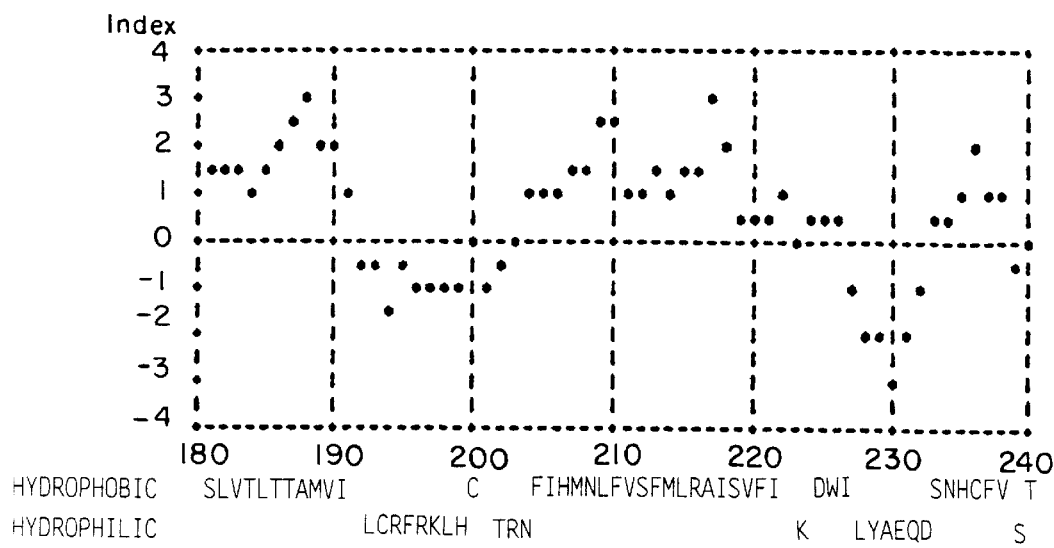
Figure 23E:
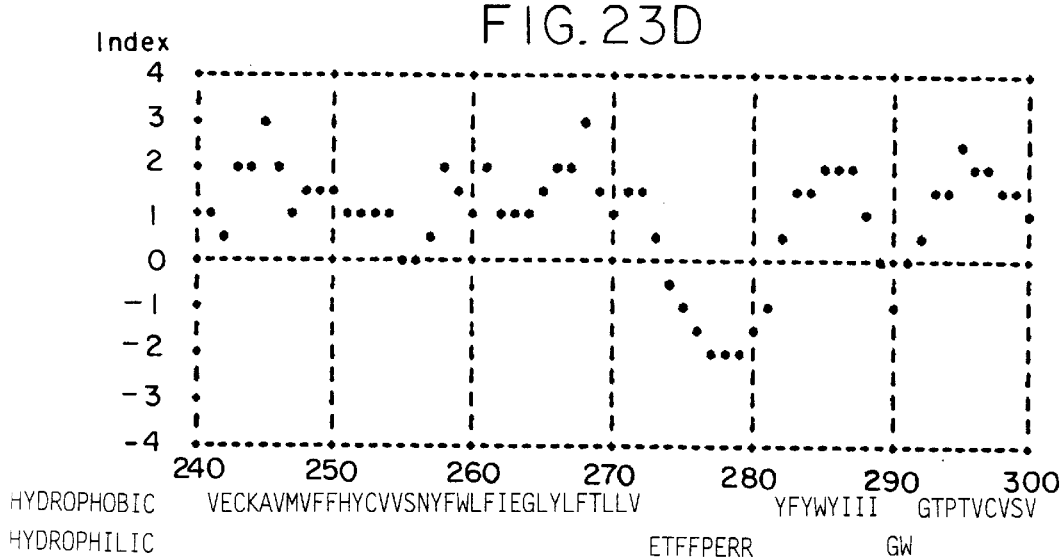
Figure 23F:
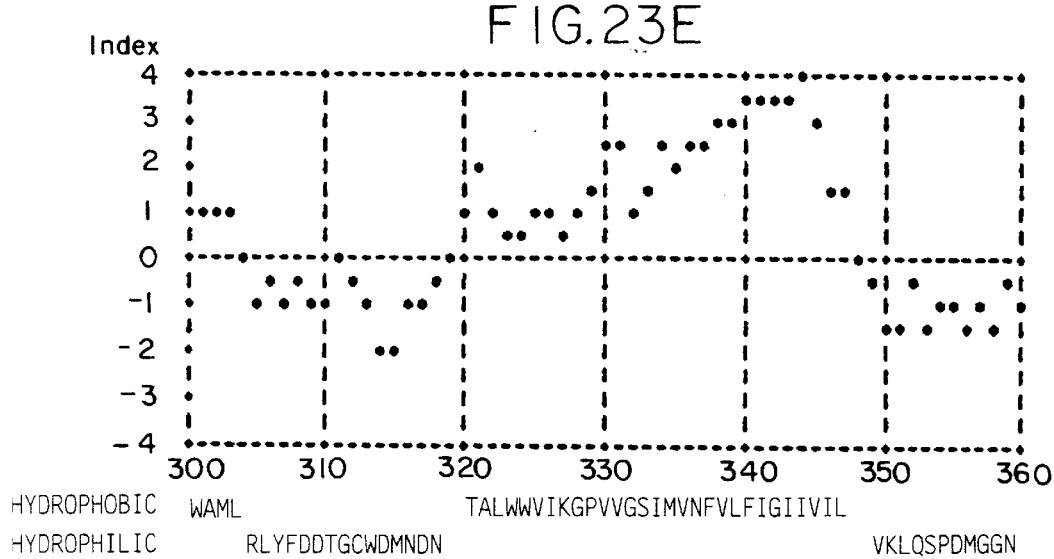
Figure 23G:
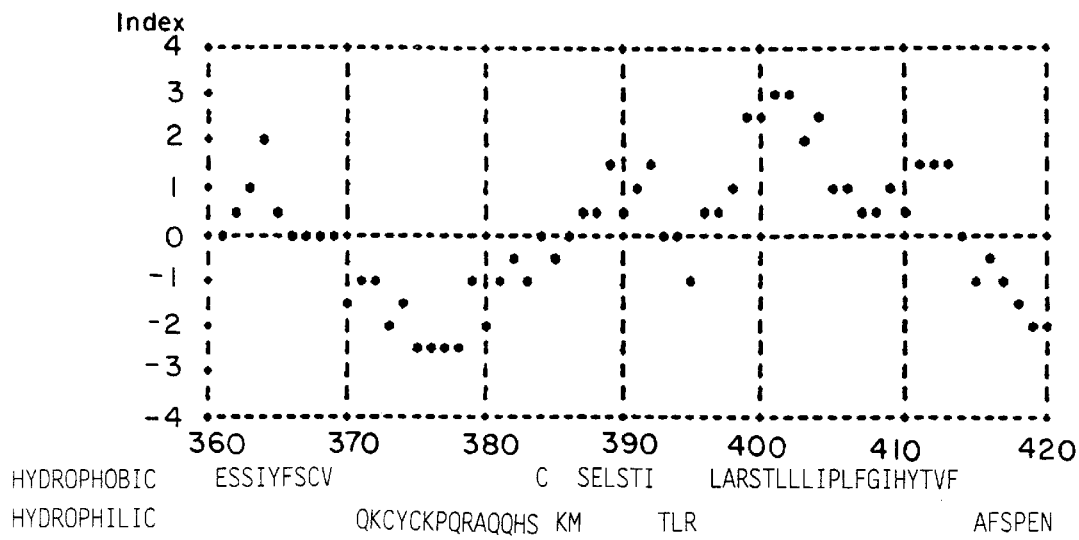
Figure 23H:
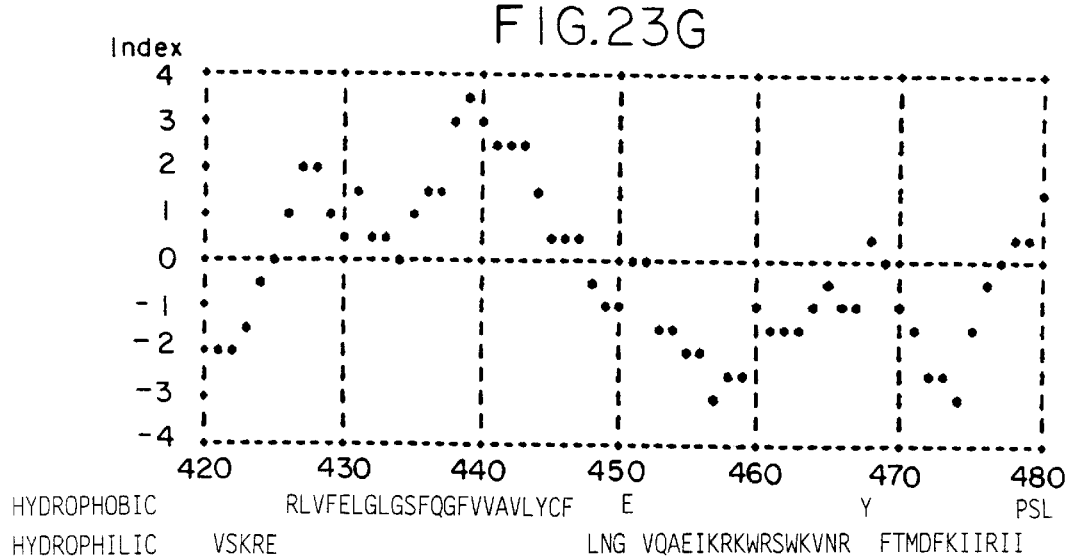
Figure 23I:
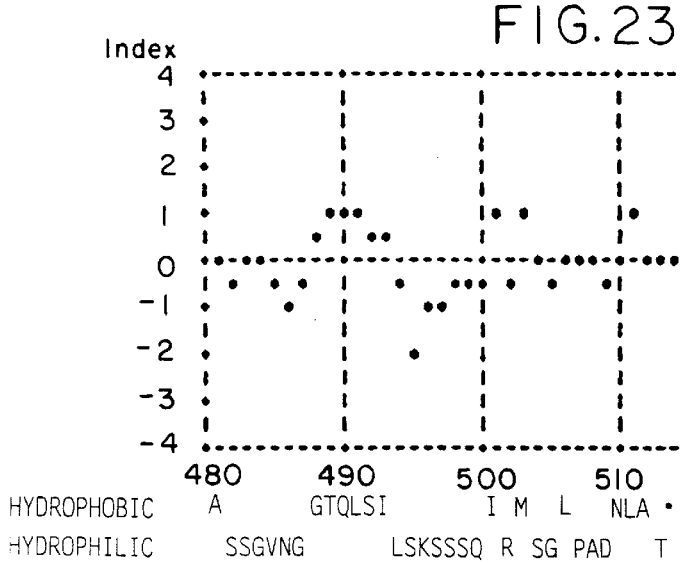
Figure 24A:
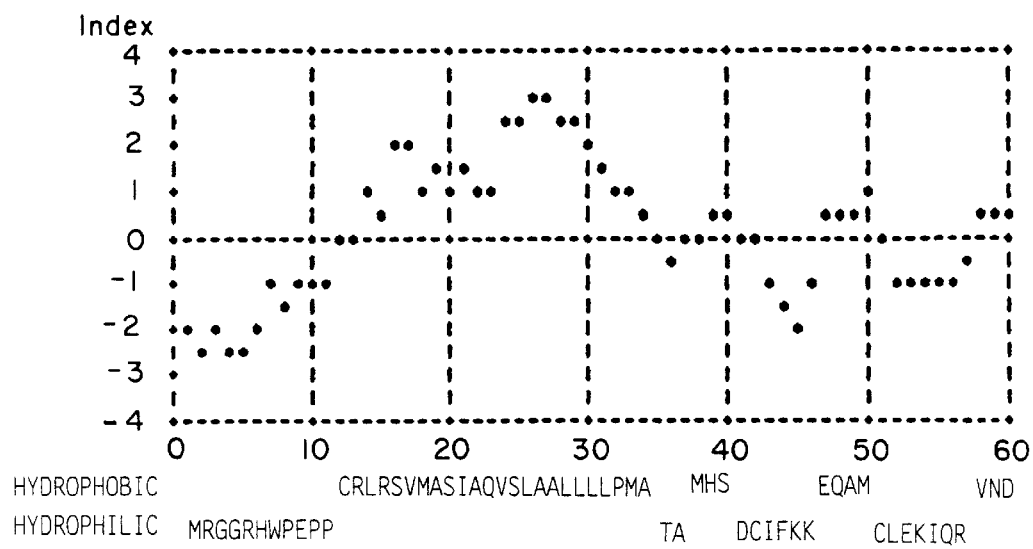
FIG. 24 is a series of graphs in which the degree of hydrophobicity of bovine PACAP receptor protein encoded-by pBPR-TD is shown as an index.
Figure 24B:
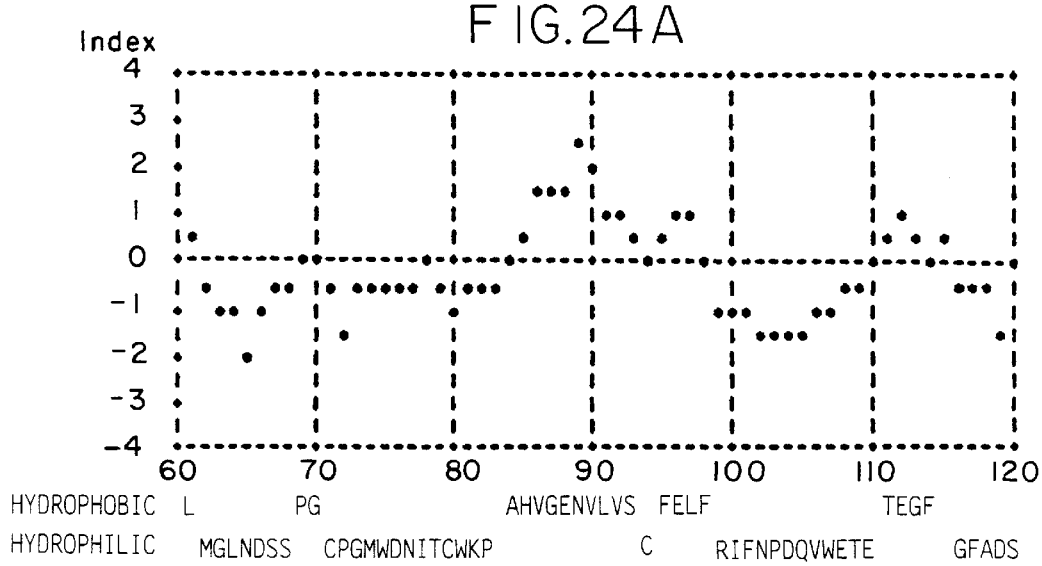
Figure 24C:
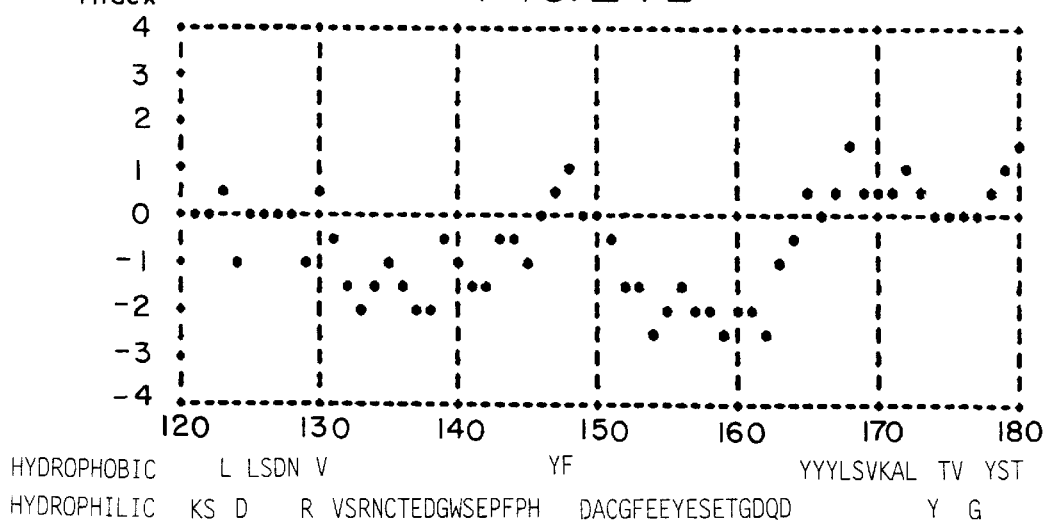
Figure 24D:
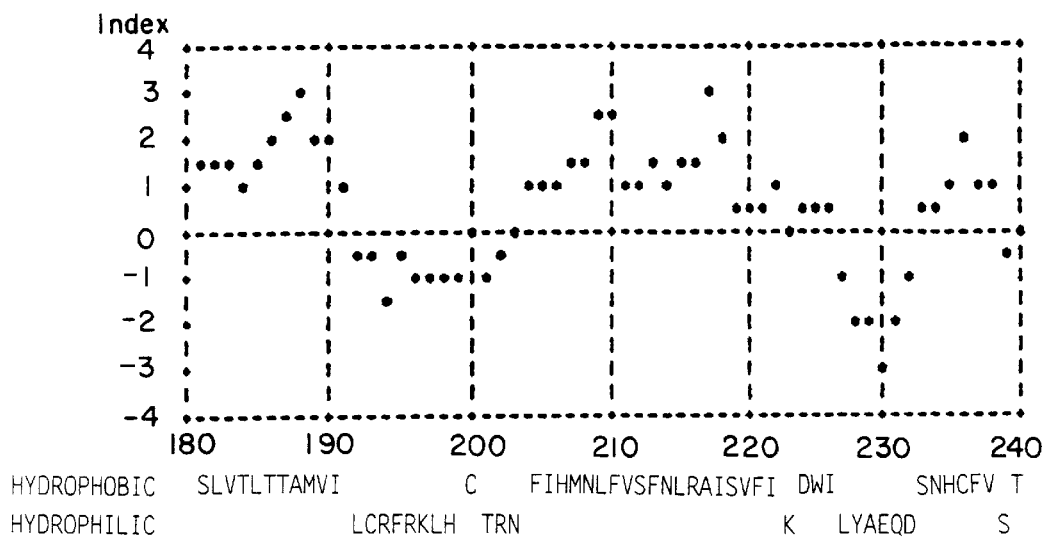
Figure 24E:
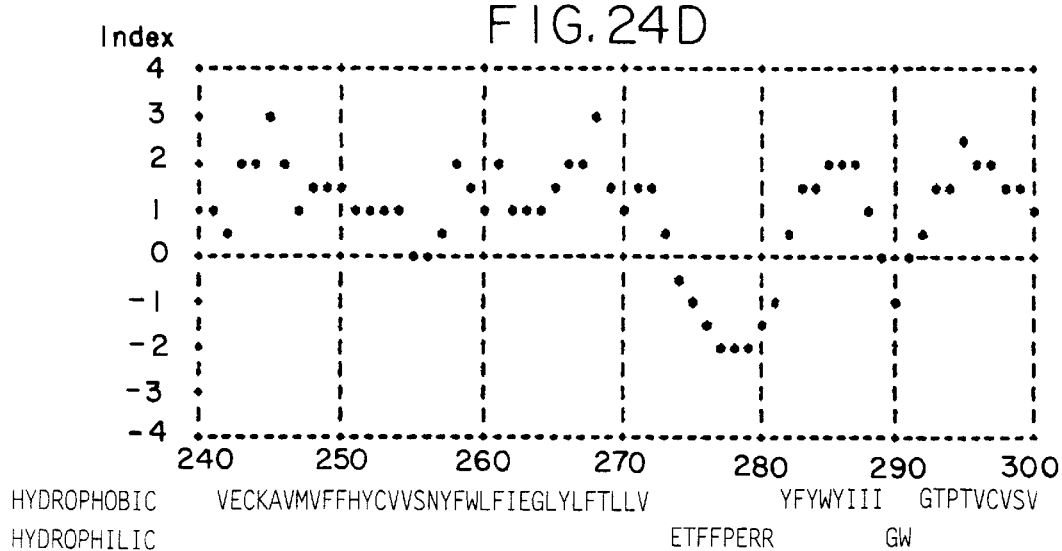
Figure 24F:
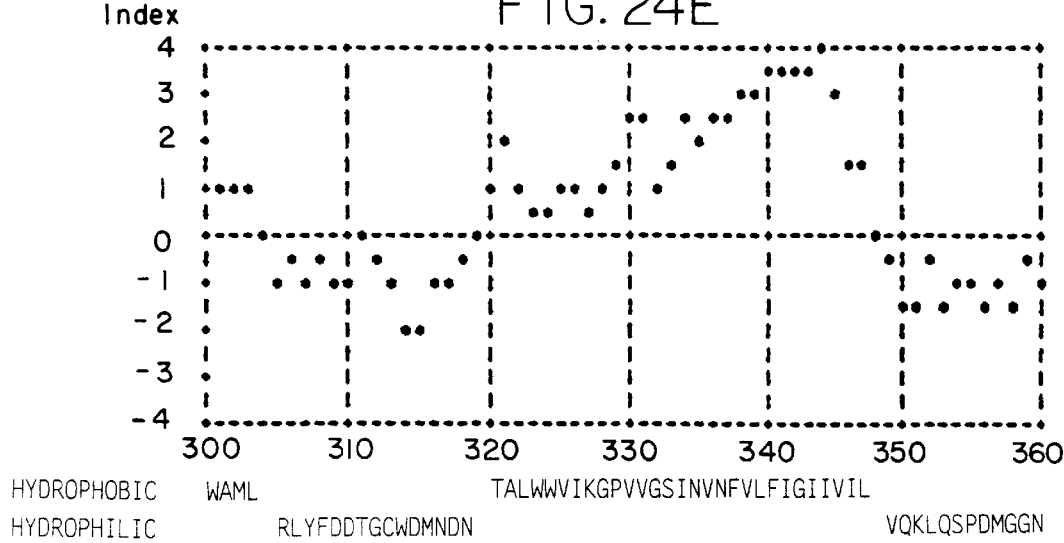
Figure 24G:
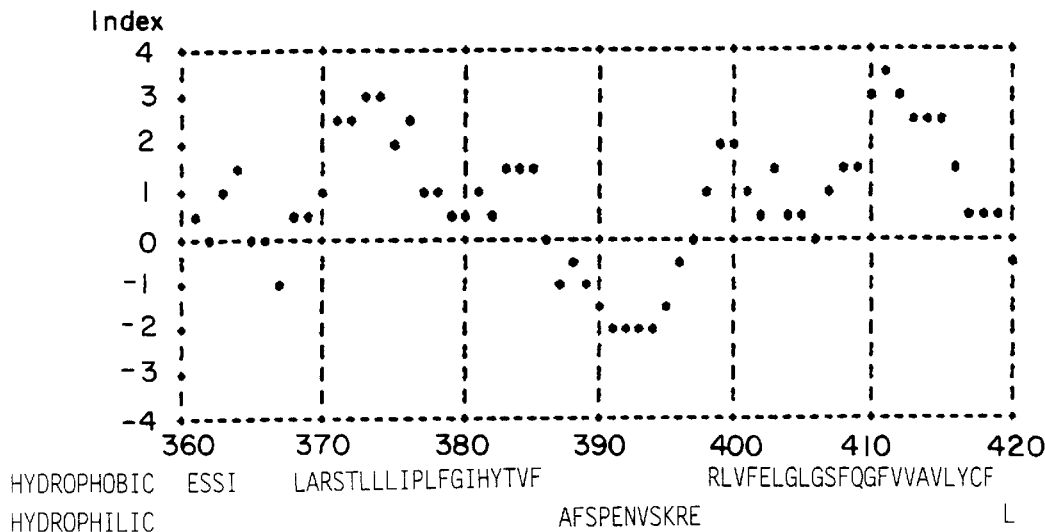
Figure 24H:
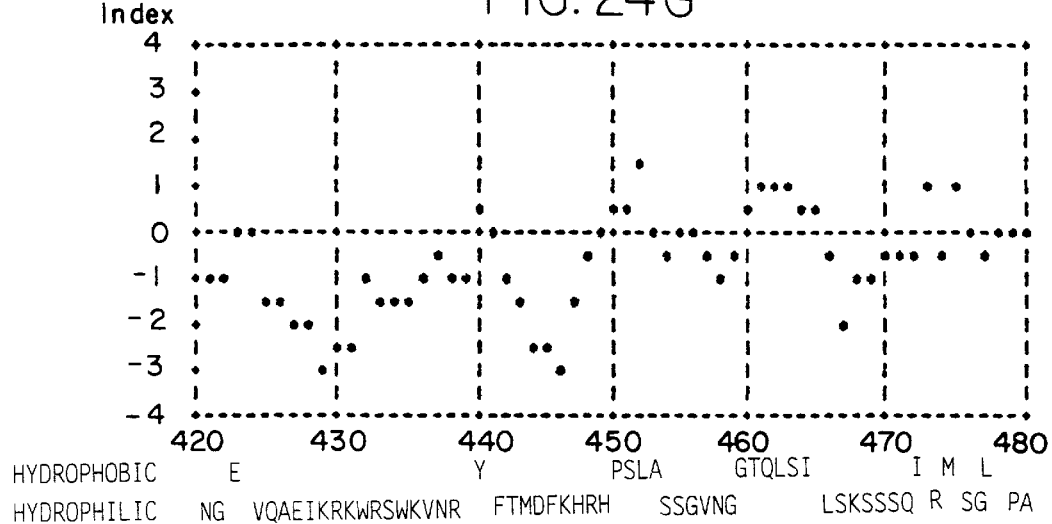
Figure 24I:
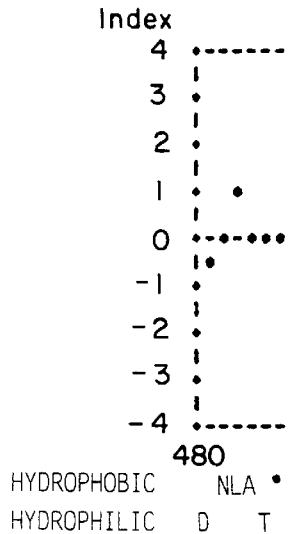
Figure 25A:
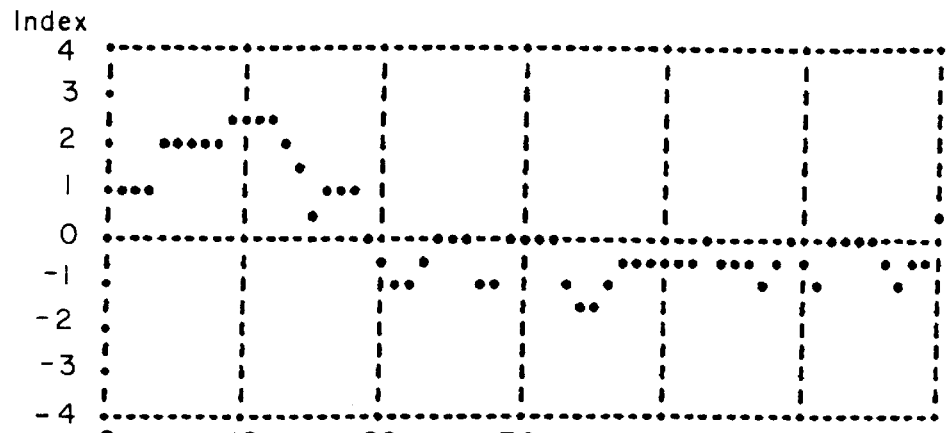
FIG. 25 is a series of graphs in which the degree of hydrophobicity of rat PACAP receptor protein encoded by pRPACAPR46-5 is shown as an index.
Figure 25B:
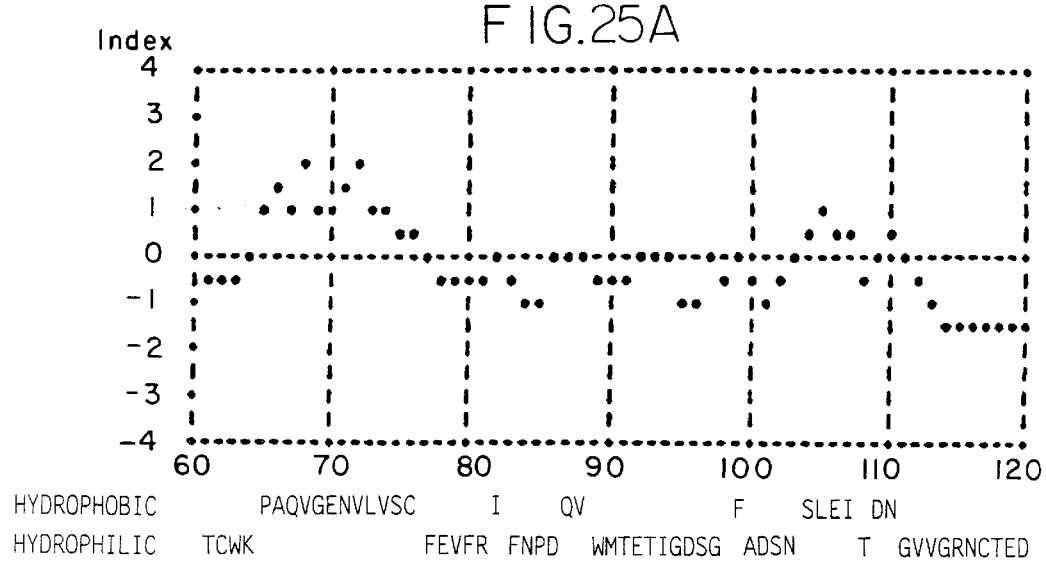
Figure 25C:
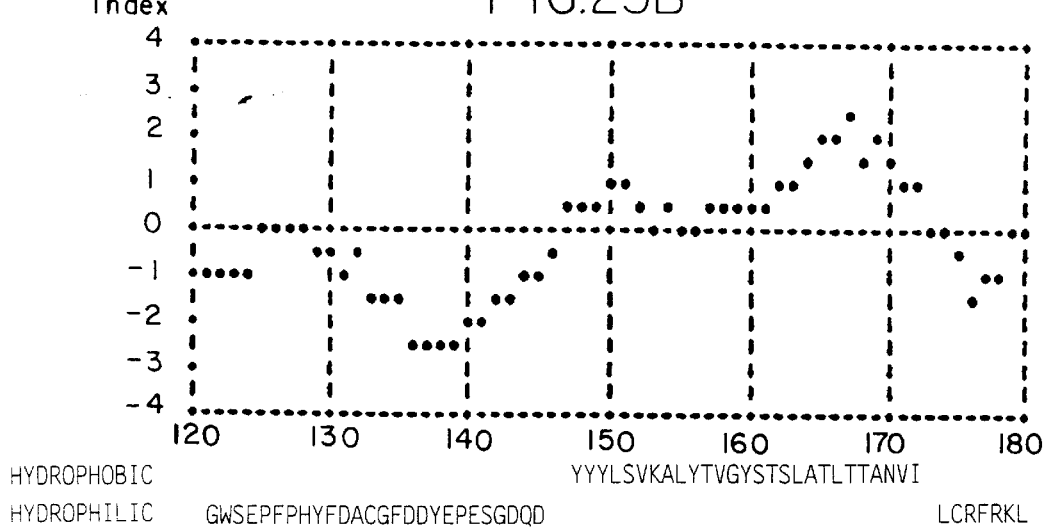
Figure 25D:
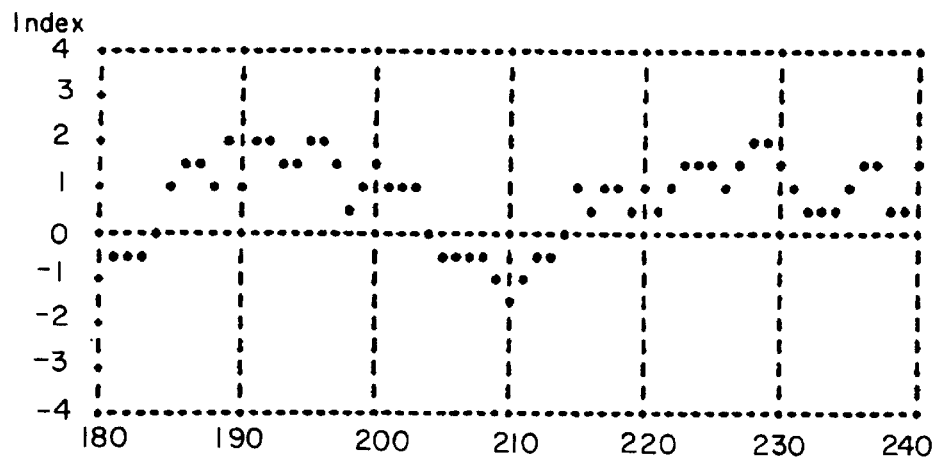
Figure 25E:
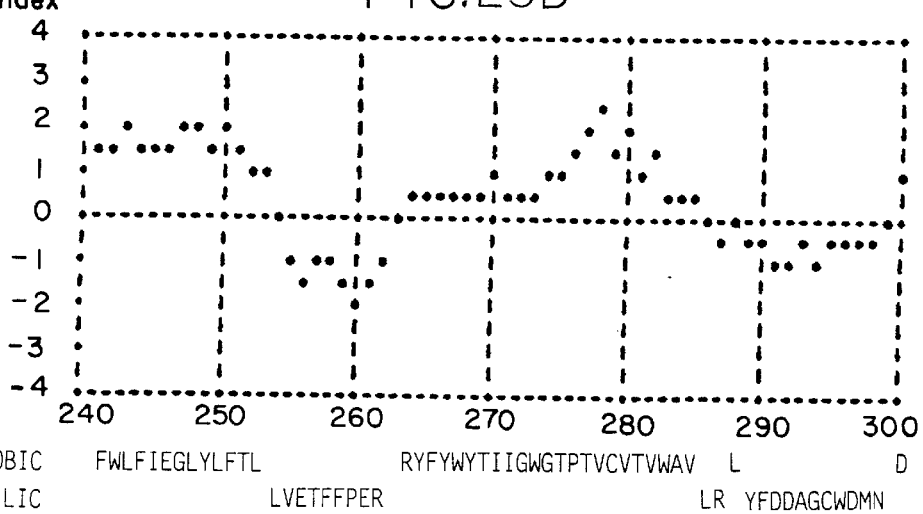
Figure 25F:
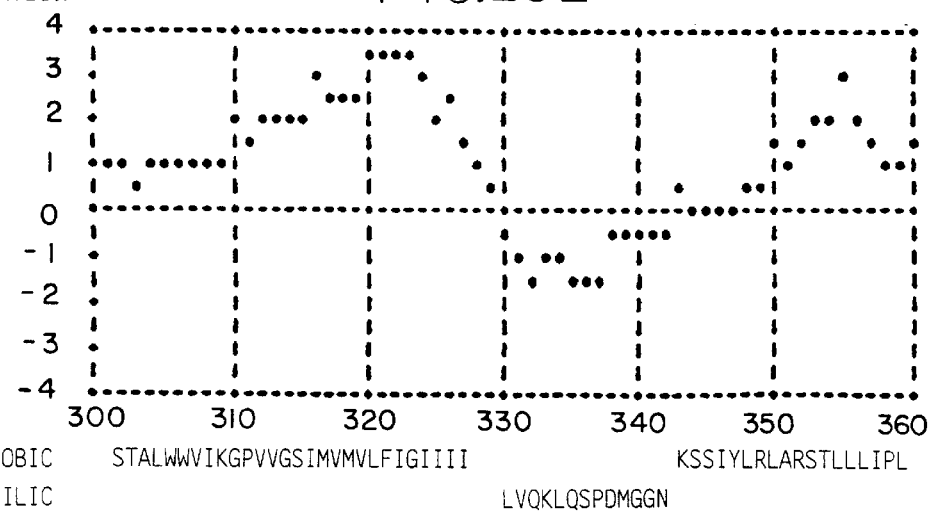
Figure 25G:
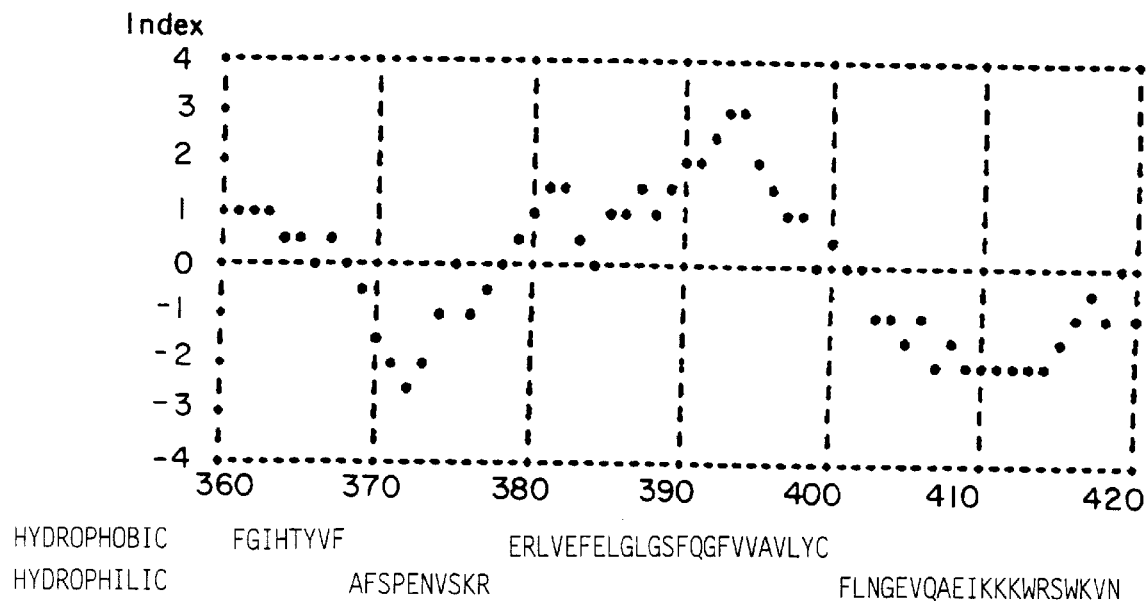
Figure 25H:
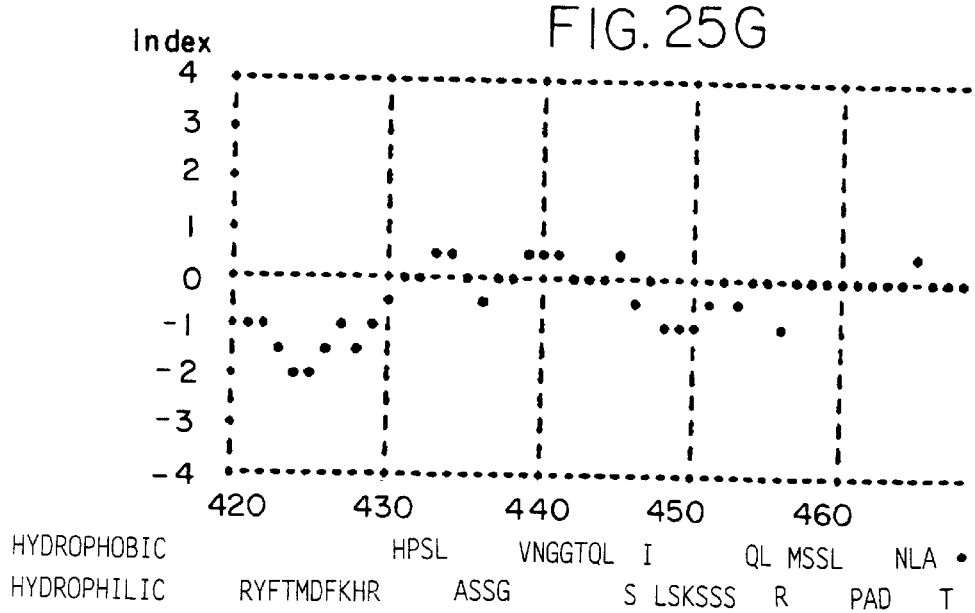
Figure 26A:
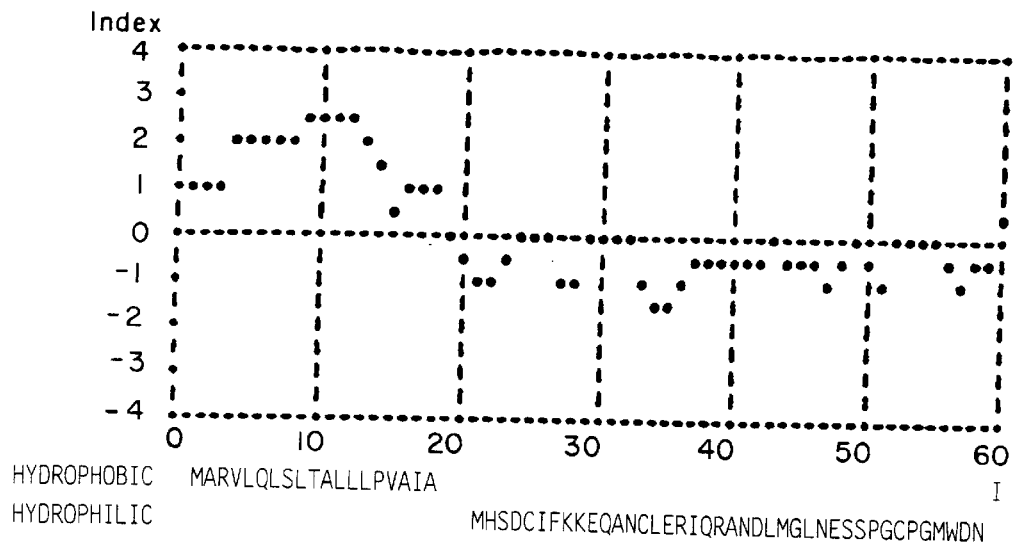
FIG. 26 is a series of graphs in which the degree of hydrophobicity of rat PACAP receptor protein encoded by pRPACAPR12 is shown as an index.
Figure 26B:
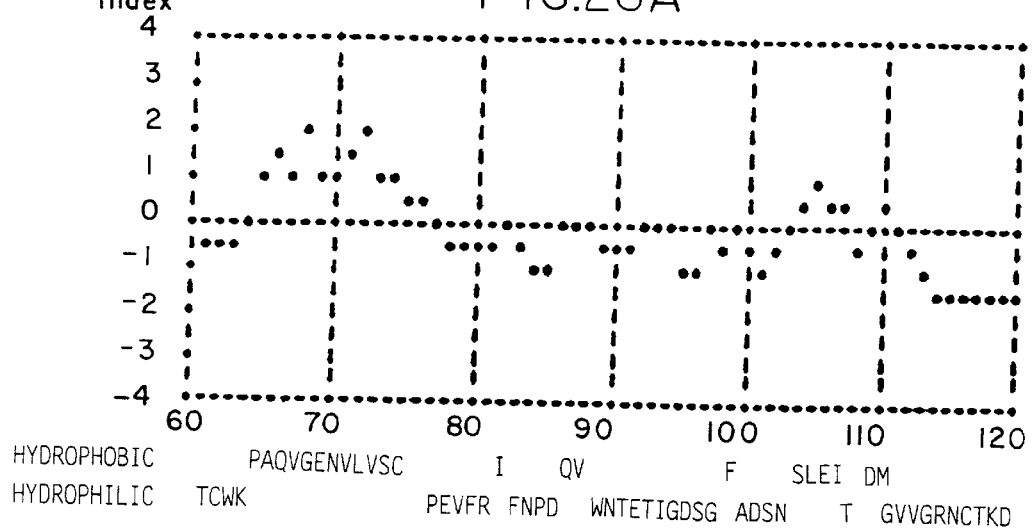
Figure 26C:
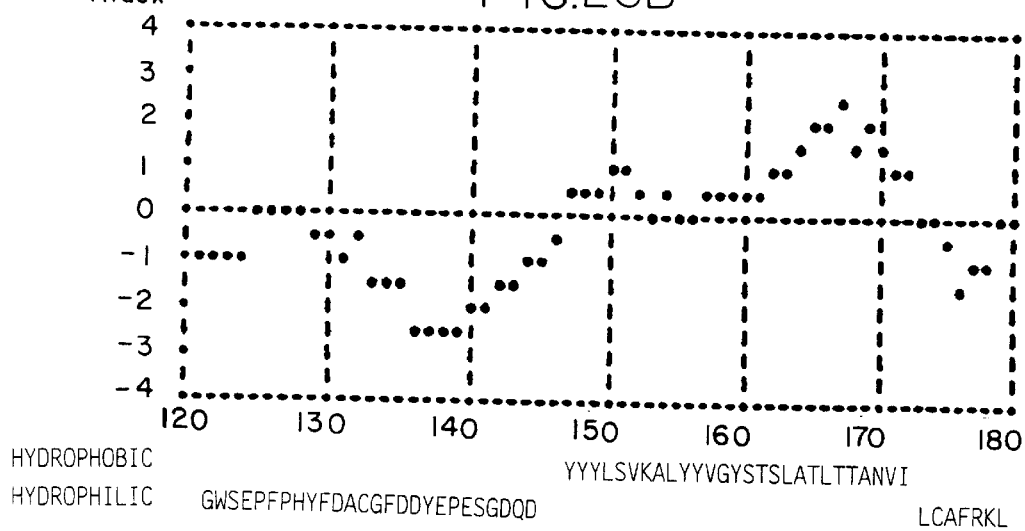
Figure 26D:
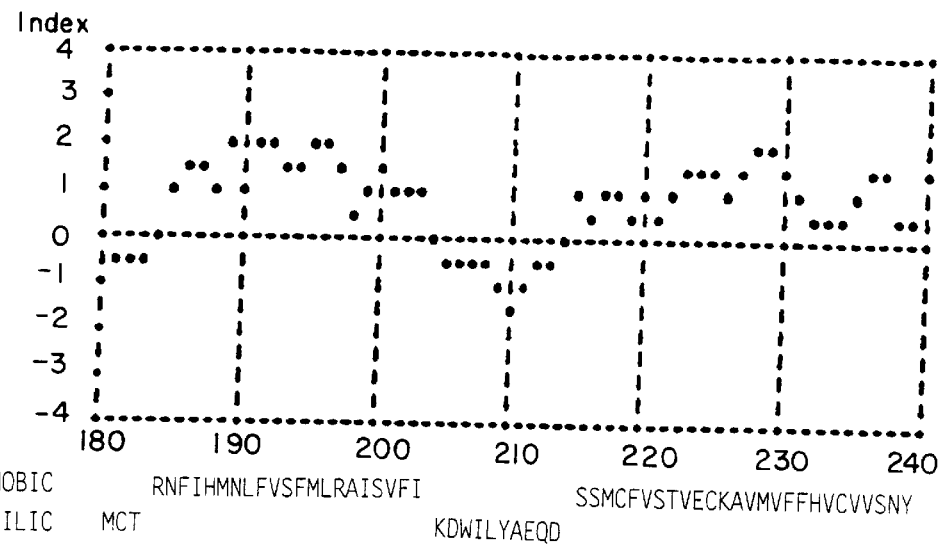
Figure 26E:
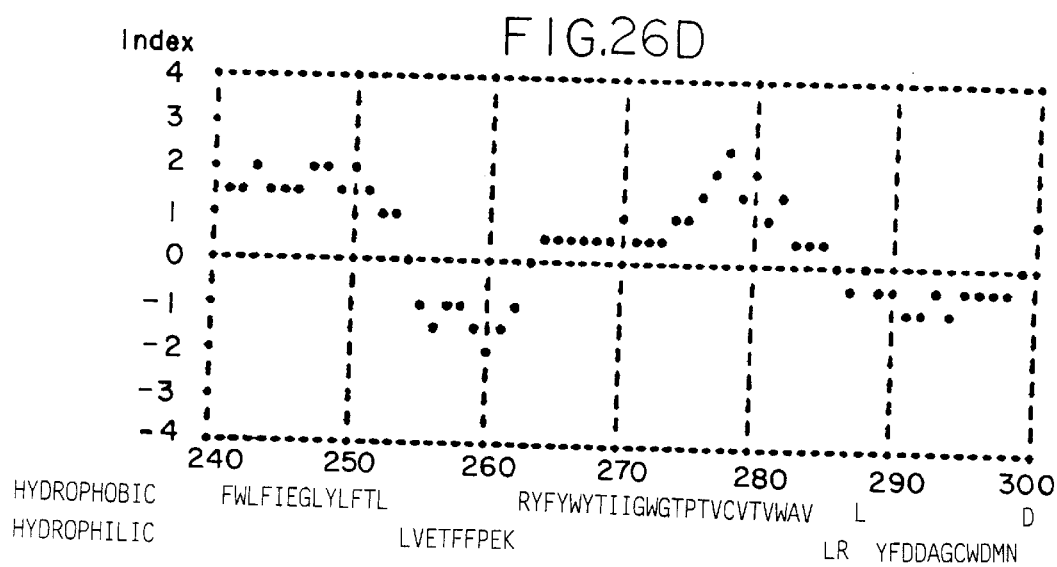
Figure 26F:
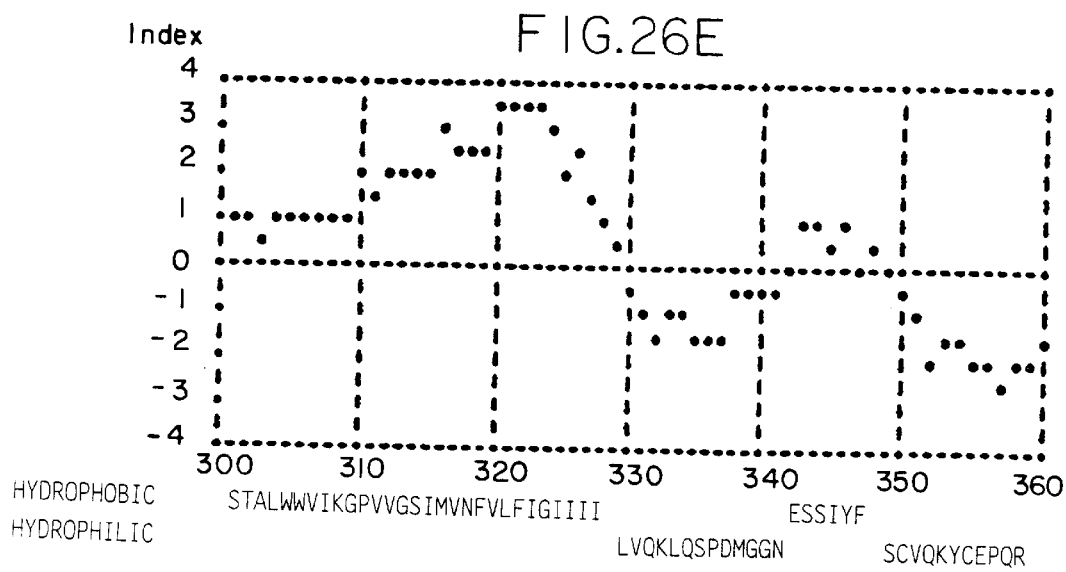
Figure 26G:
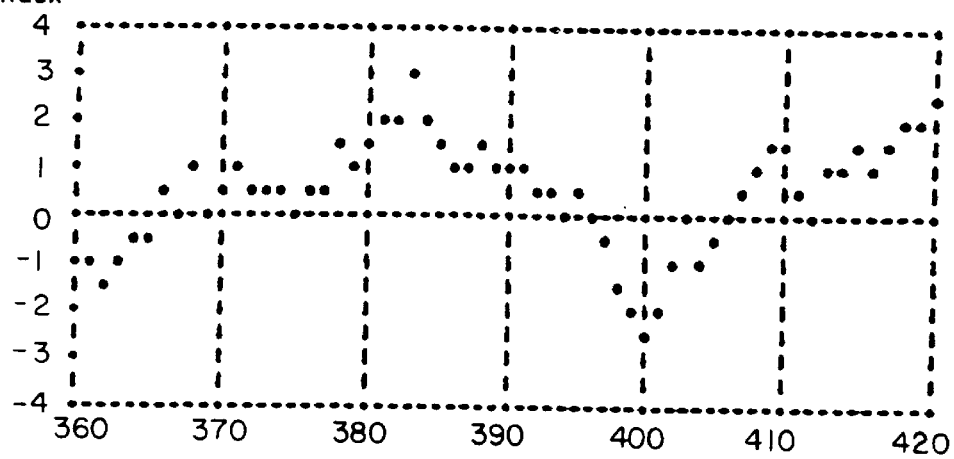
Figure 26H:
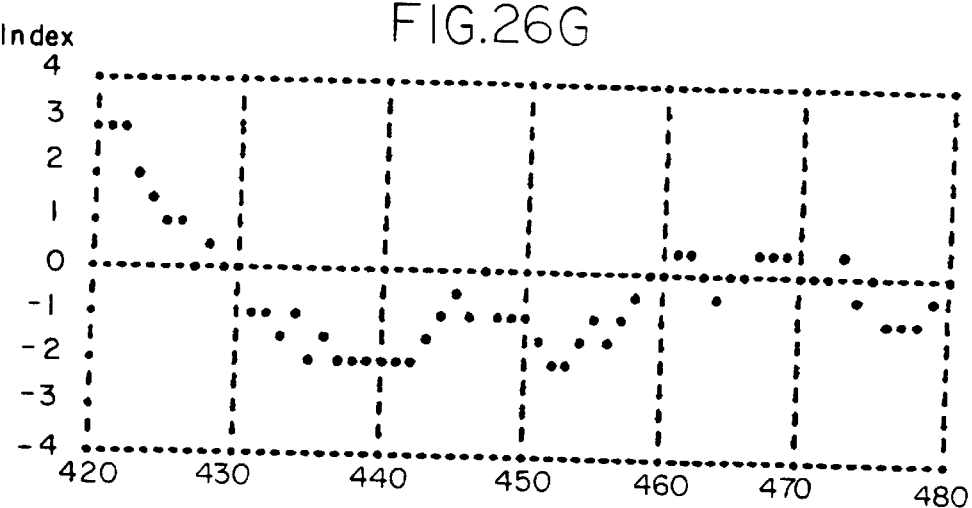
Figure 26I:
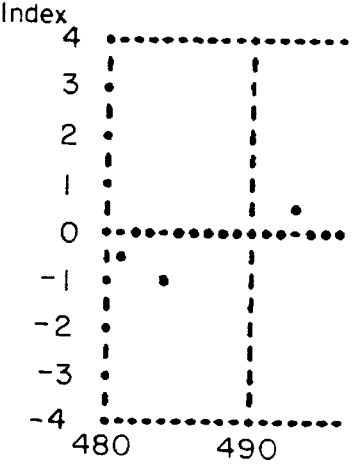
Figure 27A:
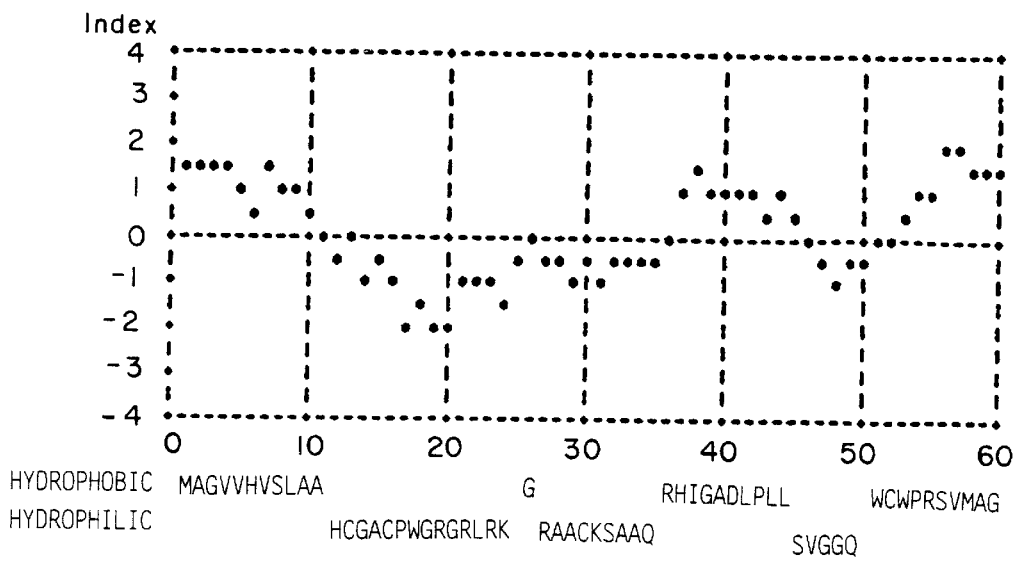
FIG. 27 is a series of graphs in which the degree of hydrophobicity of human PACAP receptor protein encoded by pTS847-1 is shown as an index.
Figure 27B:
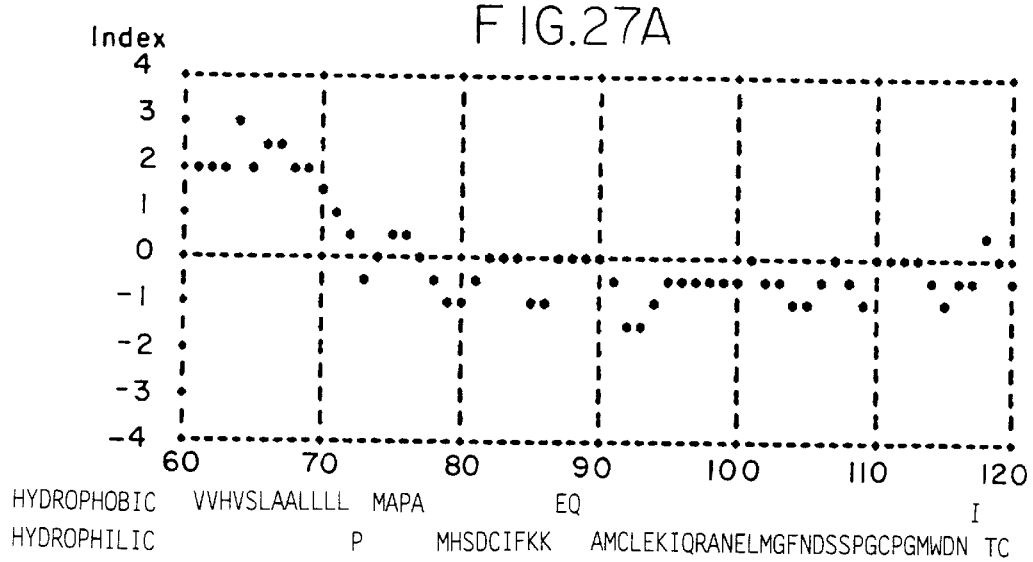
Figure 27C:
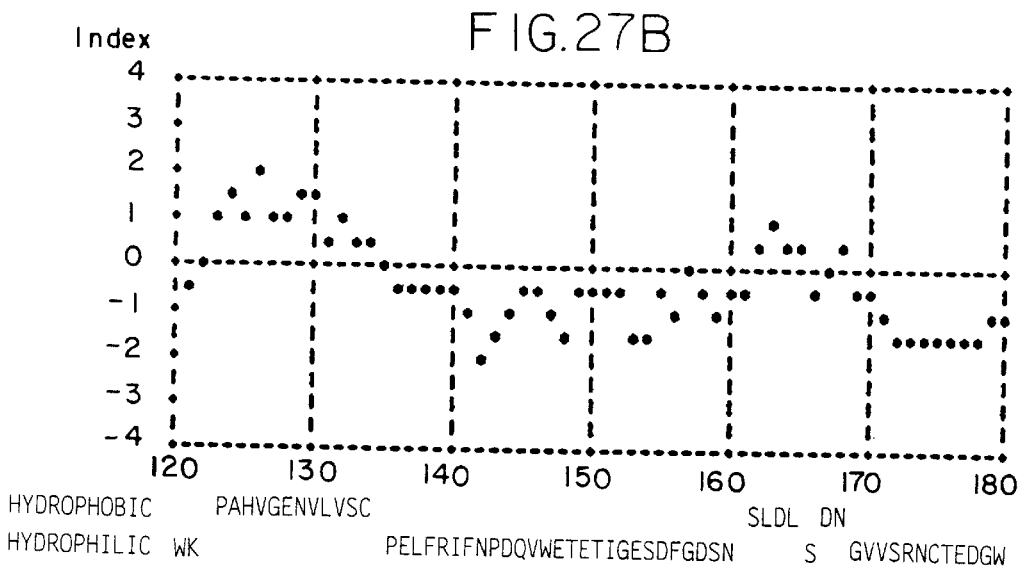
Figure 27D:
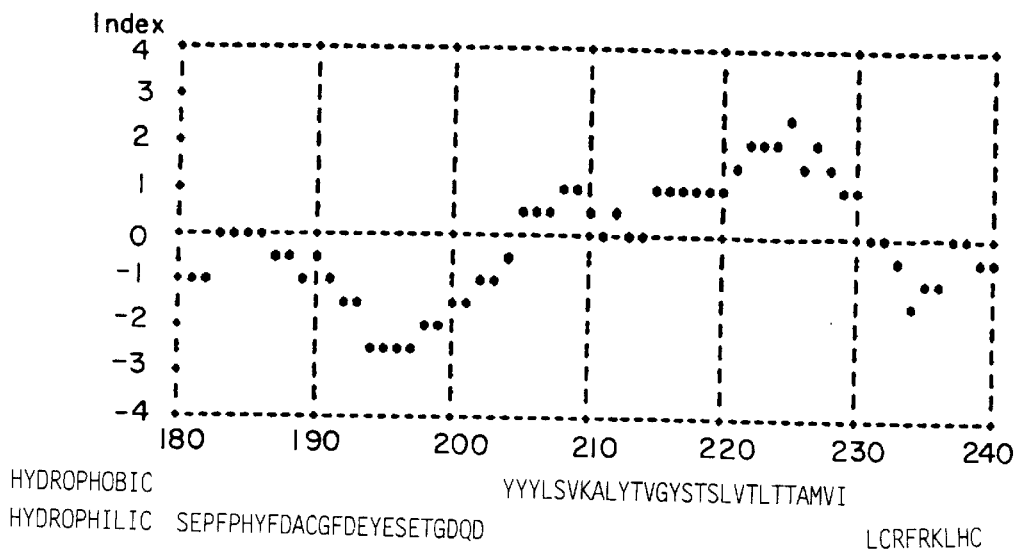
Figure 27E:
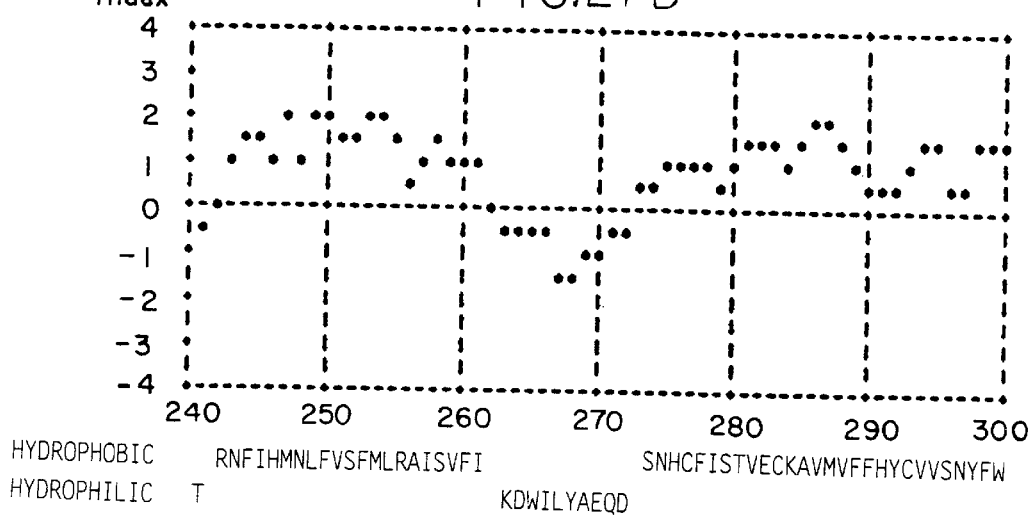
Figure 27F:
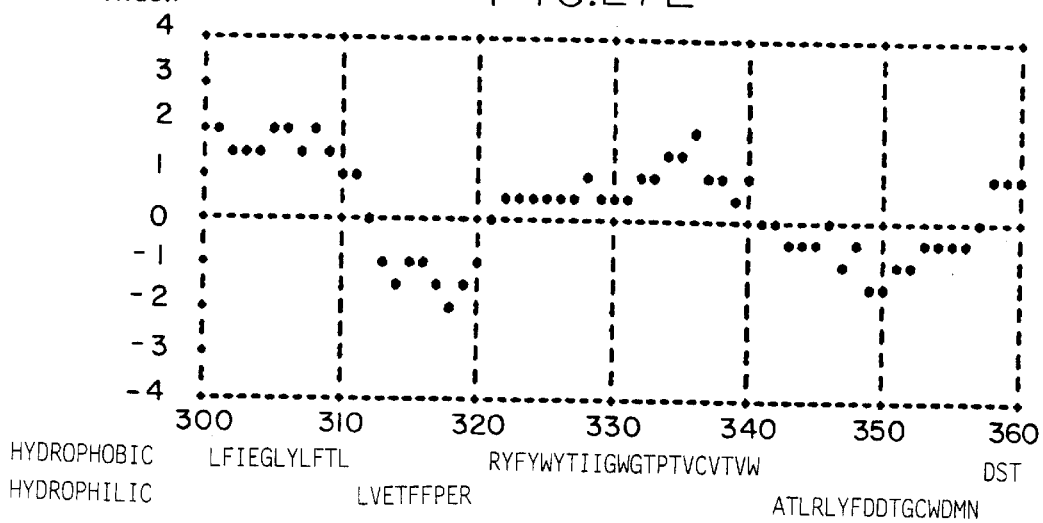
Figure 27G:
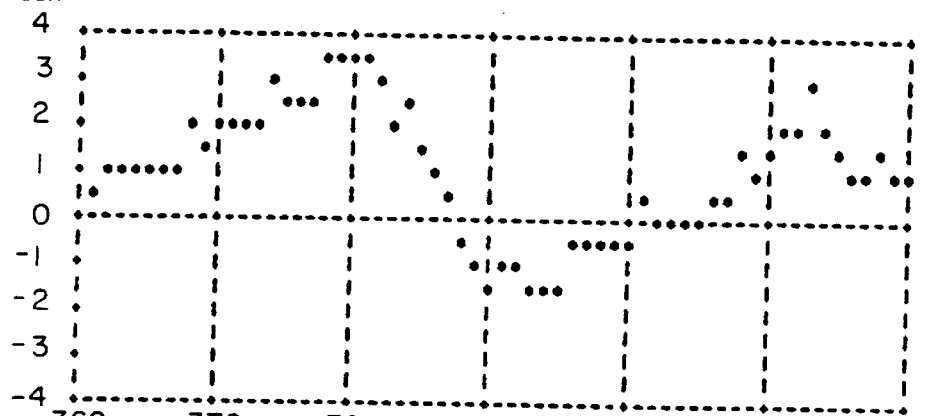
Figure 27I:
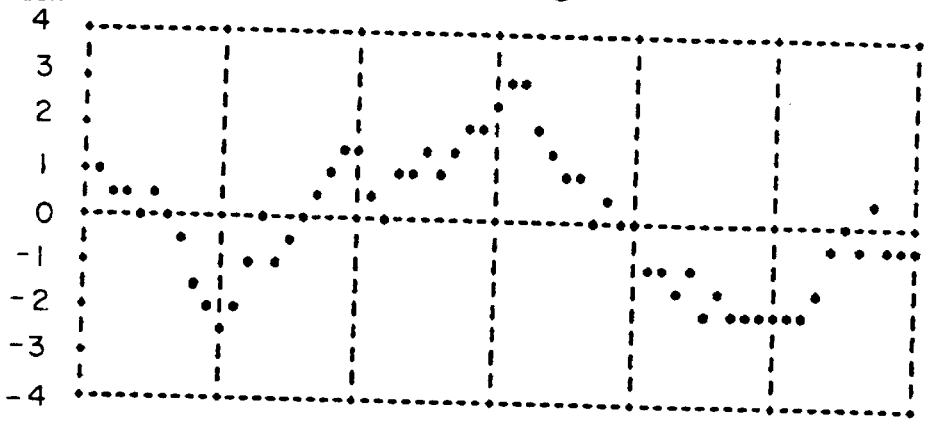
Figure 29:
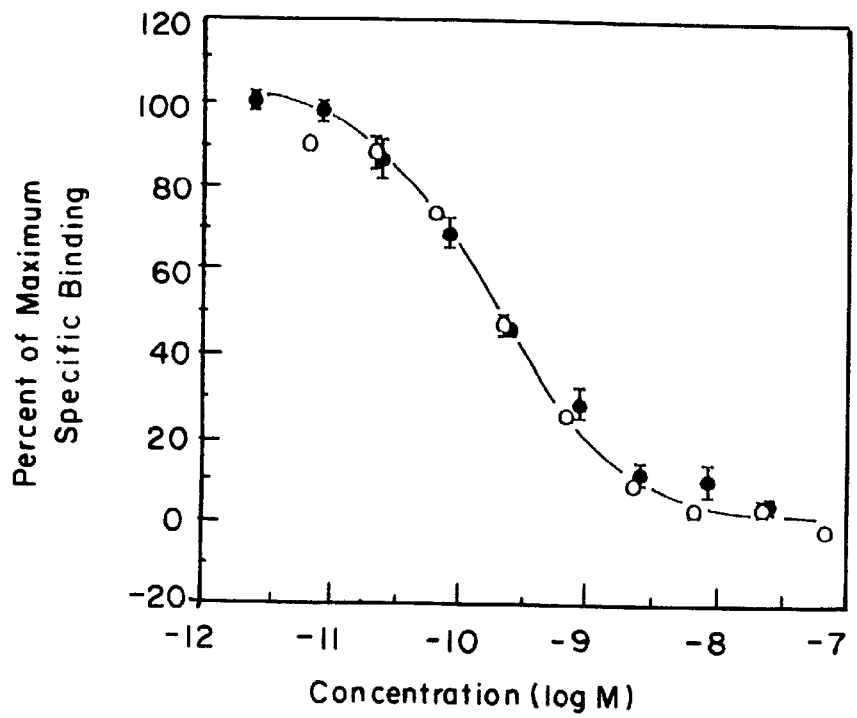
FIG. 29 is a graph showing results of the antagonistic binding experiments of PACAP27 (○) and biotinated PACAP27 (●). The numerals on the abscissa indicate the concentrations (log M) of PACAP27 and biotinated PACAP27, and the numerals on the ordinate indicate the binding (%) of [$^{125}$I]-PACAP27, taking the specific binding as 100, when each peptide is added so as to give the final concentrations on the abscissa.

Namely, the reaction product was loaded onto a reverse phase column (ODS 80-TM, Tosoh) equilibrated with 60 ml of distilled water containing 0.05% TFA, and the concentration of acetonitrile was gradually increased from 20% to 40% for 60 minutes at a flow rate of 1 ml/minute at room temperature to conduct separation. Peak fractions of biotinylated PACAP27 were fractionated, and chromatographed again under the same conditions (FIG. 28) to obtain pure biotinylated PACAP27, followed by lyophilization. It was confirmed by the competitive binding experiment that biotinylated PACAP27 has an affinity similar to that of PACAP (FIG. 29).

(5-2) Affinity Chromatography

Avidin-agarose was suspended in a solution containing the PACAP receptor protein crudely purified by the method described above, and gently stirred overnight. Avidin-agarose was removed by filtration to obtain a filtrate. About 20-fold equivalents of biotinated PACAP27 in relation to the amount of the receptor was added to this filtrate, and allowed to react overnight. Further, 80 ml of avidin-agarose was suspended therein, and gently stirred for 4 days. This avidin-agarose was packed into a column, and washed with 500 ml of buffer C containing 1M sodium chloride and 0.1% digitonin at a flow rate of 1.5 ml/minute, followed by elution of the PACAP receptor protein with 180 ml of a buffer (20 mM magnesium acetate 1M sodium chloride and 10% glycerol, pH 4.0) at a flow rate of 1.5 ml/minute. The eluate was immediately neutralized with 1/4 volume of 1M Tris (pH 7.5) with respect to the eluate.

(6) Final Purification after Affinity Chromatography

The PACAP receptor protein purified by the above-mentioned affinity chromatography was loaded onto a microcolumn (1.8 ml) of hydroxyapatite at a flow rate of 0.3 ml/minute, and washed with 20 ml of 0.1M phosphate buffer containing 0.1% digitonin at a flow rate of 0.3 ml/minute, followed by elution of the PACAP receptor from the column with 20 ml of 0.6M phosphate buffer containing 0.1% digitonin at a flow rate of 0.3 ml/minute. The active fractions eluted were concentrated using an ultrafilter (CENTRICON 10™, Amicon). The active fractions concentrated were gel filtered on a gel filtration column (for example, Superrose 6 Column, Pharmacia) equilibrated with 60 ml of buffer C containing 0.1% digitonin and 0.2M NaCl at a flow rate of 0.4 ml/minute. The active fractions eluted were used as a purified PACAP receptor protein sample.

One embodiment of the purification procedure conducted by the above-mentioned methods is summarized in Table 2.

Figure 30:
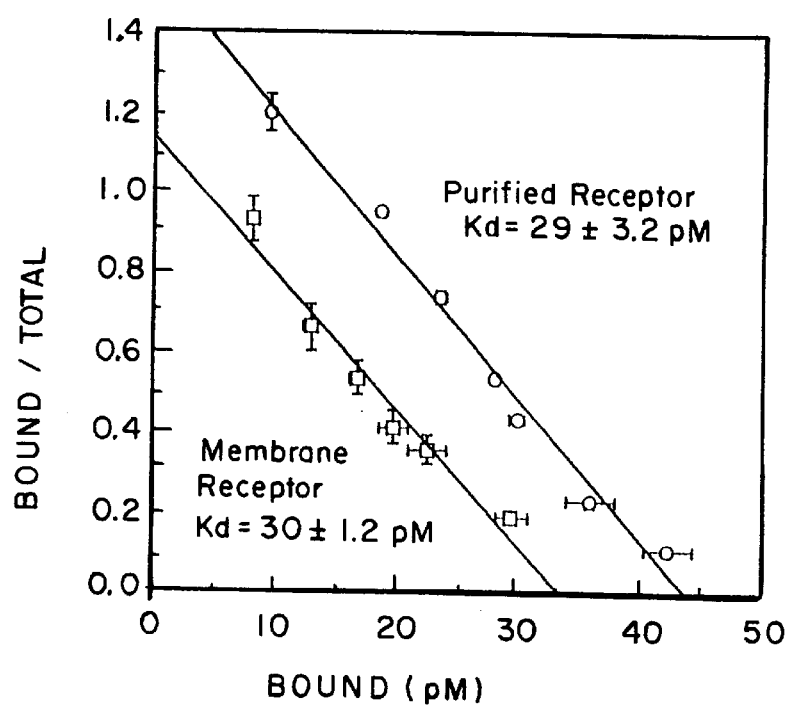
FIG. 30 is a graph showing Scatchard plot analysis of results of the saturation binding experiments of purified bovine PACAP receptor protein and membrane binding bovine receptor protein using [$^{125}$I]-PACAP27. Kd indicates the dissociation constant.

The specific activity (mole number of PACAP binding to unit weight of protein) of the final purified sample determined by the saturation binding experiment using [$^{125}$I] PACAP27 was usually 15,000 pmoles/mg of protein or more. Further, the calculation of the dissociation constant from results of the saturation binding experiment revealed that the dissociation constant of the final purified sample approximately agrees with that of the PACAP receptor existing in the membrane fractions, and that the purified PACAP receptor protein has a sufficiently high affinity for the PACAP (FIG. 30). Furthermore, results of the competitive binding experiment for the purified PACAP receptor protein proved that it has the property of reacting with PACAP27 and PACAP38, but not reacting with VIP (FIG. 31). Analysis results obtained by polyacrylamide electrophoresis for the final purified sample in the presence of sodium dodecylsulfate are shown in FIG. 28. The results indicate that the final purified sample is composed of a substantially pure protein (molecular weight: about 57,000). This protein having a molecular weight of about 57,000 is the PACAP receptor protein occurring in the bovine cerebrums.

TABLE 2

| | Total activity (pmole) | Total protein (mg) | Specific activity (pmole/mg) | Purification (fold) | Activity yield (%) |
|---|---|---|---|---|---|
| Membrane fraction | 8115 | 6400 | 1.3 | | |
| Solubilized product | 4561 | 2400 | 1.9 | 1 | 100 |
| Ion exchange | 4700 | 475 | 9.9 | 5.2 | 103 |
| Hydroxyapatite | 3349 | 134 | 25.0 | 13.2 | 73 |
| Avidin-agarose | 2046 | ND | ND | | 45 |
| Micro hydroxyapatite | 1717 | ND | ND | | 38 |

TABLE 2-continued

| | Total activity (pmole) | Total protein (mg) | Specific activity (pmole/mg) | Purification (fold) | Activity yield (%) |
|---|---|---|---|---|---|
| Gel filtration | 671 | 0.042 | 16000 | 8400 | 15 |

Total activity: The maximum binding of [$^{125}$I]PACAP27 obtained by the saturation binding experiment
ND: Not determined

[Example 2]

Screening of Bovine PACAP Receptor Protein cDNA and DNA Sequence Analysis (1) Preparation of Bovine Hippocampus Poly(A)$^+$ RNA Fractions and Construction of cDNA Library Using the Same Total RNA fractions were prepared from the bovine hippocampi according to the guanidine-fluoroacetate method [*Method in Enzymology*, 154, 3 (1987) and *Biochemistry*, 18, 5294 (1978)], and poly(A)$^+$ RNA fractions were further separated by the use of an oligo(dT) cellulose-spun-column (Pharmacia). Using these fractions as a starting material, a bovine hippocampus cDNA library in which a vector was λgt11 was constructed by the use of a cDNA cloning kit (Amersham). The library prepared had about 4×10$^6$ pfu (plaque forming unit) of independent clones.

(2) Preparation of Probe

A synthetic DNA was prepared as a probe, based on the N-terminal amino acid sequence having the amino acid sequence represented by SEQ ID NO: 38 of the bovine PACAP receptor protein obtained in Example 1. Sequence:

5' TGGATCTTCTCCAGGTGCATDGCCTGCTCCTTCTTGAAGATGTGGTC 3' (SEQ ID NO:51)
(D is G, A or T.)

(3) Screening

The λgt11 phage cDNA library (bovine brain, Clontech) (1.5×10$^6$ pfu) prepared in Example 2 (1) was mixed with magnesium sulfate-treated *E. coli* Y1090, and incubated at 37° C. for 15 minutes. Then, 0.5% agarose/LB was added thereto, followed by plating on a 1.5% agar/LB plate. A nitrocellulose filter was placed on the plate on which a plaque is formed, and the plaque transferred onto the filter. After alkali treatment of this filter, the DNA was fixed by heating at 80° C. for 3 hours. This filter was hybridized with the labeled probe in a hybridization buffer [0.5M phosphate buffer (pH 7.2), 1% bovine serum albumin, 7% SDS and 1 mM EDTA] overnight at 50° C. The labeling of the probe was conducted according to the method of phosphorylation of the 5'-terminus of the probe with [γ-$^{32}$P]ATP and T4 polynucleotide kinase (Nippon Gene). Washing was carried out with 2×SSC, 0.1% SDS at 48° C. for 1 hour, and then, hybridized clones were detected by autoradiography at −80° C. As a result, a cDNA encoding a N-terminal portion of the PACAP receptor was obtained, and the cDNA designated as λBPR35.

Further, the bovine brain-derived cDNA library (Clontech) (1.5×10$^6$ pfu). was screened, using the cDNA portion of λBPR35 as a probe, to obtain a cDNA encoding C-terminal portion of the PACAP receptor. At this time, a buffer was used which comprised 5×Denhardt's solution [0.02% bovine serum albumin (Sigma)], 5×SSPE (0.15M sodium chloride, 0.01M monosodium phosphate and 1 mM EDTA), 0.1% SDS and 100 μg/ml of heat-denatured salmon sperm DNA (Sigma), and incubation was conducted overnight at 65° C. together with the labeled probe to hybridize. The labeling of the probe was carried out by the use of a multi-prime DNA labeling kit (Amersham). Washing was carried out with 0.2×SSC, 0.1% SDS at 60° C. for 1 hour, and then, hybridized clones were detected by autoradiography at −80° C. A cDNA clone which encoded a portion of the PACAP receptor was obtained, and the cDNA was designated as λBPR114. Using the cDNA portion of the resulting pBPR114 as a probe, the cDNA library (4×10$^{-6}$ pfu) prepared from the bovine hippocampus poly(A)$^+$ RNA fractions was screened to obtain a cDNA encoding the C-terminal portion of the PACAP receptor. The conditions at this time were the same as those at the time when the above-mentioned λBPR114 was screened. As a result, a cDNA clone encoding a C-terminal portion of the PACAP receptor was obtained, and the cDNA was designated as λBPR68.

(4) Subcloning of cDNA Clones and DNA Sequence Analysis

An inserting portion of the resulting cDNA clone was cut out by cleavage with EcoRI, and subcloned into plasmid vector pUC118 to obtain pBPR35, pBPR114 or pBPR68. The plasmid was further cleaved stepwise by exonuclease digestion, or self cyclized or subcloned after cleavage with an appropriate restriction enzyme (NcoI, BamHI, etc.) to prepare a template DNA for sequence analysis. For sequence determination, the dideoxy chain termination method using RI marker dCTP and a fluorescent DNA sequencer (Applied Biosystems) were used, and for data analysis, a DNASIS (Hitachi Software Engineering) was used. Further, pBPR35 and pBPR68 were recombined at the BamHI sites to prepare pBPR-T. The BamHI and AvaII fragments of pBPR114 having disappeared regions can be recombined with pBPR-T by the use of known genetic engineering technique, thereby preparing PACAP receptor cDNA (pBPR-TD) containing no insertion.

Results of analysis revealed that pBPR-T has the nucleotide sequence of SEQ ID NO: 38, and that pBPR-TD has the nucleotide sequence of SEQ ID NO: 39.

[Example 3]

Screening of Rat PACAP Receptor Protein cDNA and DNA Sequence Analysis (1) Preparation of Rat Brain Poly(A)$^+$ RNA Fractions and Construction of cDNA Library Using the Same Total RNA fractions were prepared from the rat brains according to the guanidine-isothiocyanate method [*Biochemistry*, 18, 5294 (1979)], and poly(A)$^+$ RNA fractions were further separated by the use of an oligo(dT) cellulose-spun-column (Pharmacia). Using these-fractions as a starting material, a rat brain cDNA library in which a vector was λgt11 was constructed by the use of a cDNA cloning kit (Amersham). The library prepared had about 3×10$^6$ pfu (plaque forming unit) of independent clones.

(2) Preparation of Probe

Based on the cDNA nucleotide sequence of rat VIP receptor already reported, primers for PCR were synthesized with a DNA synthesizer (Model 391, PCR-MATE EP, Applied Biosystems).

Sequence: RVIPLR-1S
5' CAGA AAGCTT CGGACCATGCGCCCTCCGAGCCCACCG 3'
(SEQ ID NO: 48)
Sequence: RVIPLR-2A
5' GGGC TCTAGA CGGTCAGACCAGGGAGACCTCCGCTTG 3'
(SEQ ID NO: 49)

Using 5 μg of rat lung poly(A)⁺ RNA fractions prepared in a manner similar to that of the brain RNA fractions and a random primer, cDNA having only first strand was synthesized. Then, using this single stranded DNA as a template, and using the above-mentioned primers, rat VIP receptor cDNA fragments were amplified by the PCR method. The sequences of the resulting cDNA fragments were determined, and they are confirmed to be cDNA fragments of rat VIP receptor.

(3) Screening

The λgt11 cDNA library (3×10⁶ pfu) prepared in Example 3 (1) was mixed with magnesium sulfate-treated *E. coli* Y1090, and incubated at 37° C. for 15 minutes. Then, 0.5% agarose/LB was added thereto, followed by plating on a 1.5% agar/LB plate. A nitrocellulose filter was placed on the plate on which a plaque is formed, and the plaque was transferred onto the filter. After alkali treatment of this filter, the DNA was fixed by heating at 80° C. for 3 hours. This filter was hybridized with the probe labeled in hybribuffer S [0.2% poly(vinylpyrrolidone), 0.2% bovine serum albumin, 0.2% ficoll 400, 2×SSC and 0.17% yeast RNA) overnight at 55° C. The labeling of the probe was conducted by the use of a multi-prime labeling kit (Amersham). Washing was carried out with 2×SSC, 0.1% SDS at 50° C. for 1 hour, and then, hybridized clones were detected by autoradiography at −80° C. As a result, λRPACAPR18 was obtained.

Further, the rat brain-derived 5'-extended cDNA library (Clontech) (1.7×10⁶ pfu) was screened, using the cDNA portion of λRPACAPR18 as a probe, to obtain λRPACAPR46, λRPACAPR5, λRPACAPR12, etc. At this time, a buffer was used which comprised 50% formamide (Bethesda Research Laboratories), 5×Denhardt's solution [0.02% bovine serum albumin (Sigma)], 0.02% poly(vinylpyrrolidone (Sigma), 0.02% ficoll (Sigma), 5×SSPE (0.15M sodium chloride, 0.01M monosodium phosphate and 1 mM EDTA), 0.1% SDS and 100 μg/ml of heat-denatured salmon sperm DNA (Sigma), and incubation was conducted overnight at 42° C. together with the labeled probe to hybridize. Washing was carried out with 2×SSC, 0.1% SDS at 55° C. for 1 hour, and then, hybridized clones were detected by autoradiography at −80° C.

(4) Subcloning of cDNA Clones and DNA Sequence Analysis

An insert portion of the resulting cDNA clone was cut out by cleavage with EcoRI, and subcloned into plasmid vector pcDNAI or pUC118 to obtain pRPACAPR18 (pcDNAI), pRPACAPR46 (pcDNAI), pRPACAPR5 (pcDNAI) or pRPACAPR12 (pUC118). Further, pRPACAPR46 and pRPACAPR5 were recombined at the BamHI sites to prepare pRPACAPR46-5. The plasmid was further cleaved stepwise by exonuclease digestion, or self cyclized or subcloned after cleavage with an appropriate restriction enzyme (NcoI, PstI or BamHI) to prepare a template DNA for sequence analysis. For sequence determination, a fluorescent DNA sequencer (Applied Biosystems) was used, and for data analysis, a DNASIS (Hitachi Software Engineering) was used. Results of analysis revealed that pRPACAPR46-5 has the nucleotide sequence of SEQ ID NO: 40, and that pRPACAPR12 has the nucleotide sequence of SEQ ID NO: 41.

[Example 4]

Screening of Human PACAP Receptor Protein cDNA and DNA Sequence Analysis (1) Preparation of Probe The nucleotide sequence represented by SEQ ID NO: 51 corresponding to a complementary strand of the N-terminal amino acid sequence having the amino acid sequence represented by SEQ ID NO: 50 of the bovine PACAP receptor protein obtained in Example 1 was synthesized with a DNA synthesizer (Model 391, PCR-MATE EP, Applied Biosystems).

(2) Screening

The human pituitary gland-derived cDNA library (λgt11, Clontech) (1.4×10⁶ pfu) was mixed with magnesium sulfate-treated *E. coli* Y1090, and incubated at 37° C. for 30 minutes. Then, 0.6% agarose/LB was added thereto, followed by plating on a 1.5% agar/LB+50 μg/ml ampicillin plate. A nitrocellulose filter was placed on the plate on which a plaque is produced, and the plaque was transferred onto the filter. After alkali treatment and neutralization treatment of this filter, the DNA was fixed by heating at 80° C. for 3 hours. This filter was prehybridized in a hybridization buffer [7% SDS (Nakarai), 1% bovine serum albumin, 0.5M Na-PO₄ (pH 7.2) and 1 mM EDTA (Dojin)], and then hybridized with the probe labeled in the same buffer overnight at 55° C. For the labeling of the probe, terminal labeling was conducted using [γ-³²P]ATP (Du Pont NEN) and T4 kinase (Takara). Washing was carried out twice with 2×SSC, 0.1% SDS at 55° C. for 30 minutes, and then, hybridized clones were detected by autoradiography at −80° C. As a result, λ#14 was obtained.

(3) Subcloning of cDNA Clones and DNA Sequence Analysis

An insert portion of the resulting cDNA clone was cut out by cleavage with EcoRI, and subcloned into plasmid vector pUC118 to obtain pTS847-1. After further cleavage with an appropriate restriction enzyme (SacI, NcoI or HpaI), the plasmid was self cyclized to prepare a template DNA for sequence analysis. For sequence determination, a Bca Best Sequencing Kit (Takara) was used, and for data analysis, a DNASIS (Hitachi Software Engineering) was used. Results of analysis revealed that pTS847-1 has the nucleotide sequence of SEQ ID NO: 42. Among the nucleotide sequences, the nucleotide sequence coding for mature human PACAP receptor Type I-A is represented by SEQ ID NO:34. The deduced amino acid sequence of human PACAP receptor Type I-A is represented by SEQ ID NO:23.

(4) Preparation of a primer for PCR based on the nucleotide sequence of human PACAP receptor Type I-A A region into which the insertion region of human PACAP receptor being deduced to enter was amplified by PCR. Primers of following SEQ ID NO:52 and SEQ ID NO:53 were prepared based on the nucleotide sequence of pTS847 coding for human PACAP receptor Type I-A obtained in Example 4(3). Sequence:HPRF 5'CTGGGATATGAATGA-CAGCACAGC 3' (SEQ ID NO:52; a nucleotide sequence of 1132nd to 1155th of pTS847) Sequence:HPRR 5'TCTGGG-GAGAAGGCAAATACTGTG 3' (SEQ ID NO:53; a complementary nucleotide sequence of 1342nd to 1355th of pTS847)

(5) Application of PCR on human pituitary and amigdaloid nucleus

Two(2) ng of cDNA of human pituitary and amigdaloid nucleus (Quick-Clone cDNA, Clonetech) and each 0.5 μM of primers obtained Example 4(4), each 10 mM of dNTP were mixed in a PCR reaction buffer, and Taq polymerase was added thereto. Denaturing was conducted at 94° C. for 45 seconds, anealing was held at 60° C. for 45 seconds and elongation reaction was held at 72° C. for 2.5 minutes to obtain PCR product.

(6) Subcloning of PCR product and DNA sequence analysis

The resulting PCR product was inserted into Hinc II site of a plasmid pUC118 and was subjected to a subcloning. Of the clones subcloned, Southern blotting was conducted to screen subtypes. In order to screen a clone of human PACAP receptor Type I-B, the following probe of SEQ ID NO:54 was synthesized based on the sequence of the insertion region of rat PACAP receptor Type I-B. 5'TGCGTGCA-GAAATGCTACTGCAAGCCACAG 3' (SEQ ID NO:54)

In order to screen a clone of human PACAP receptor Type I-C, the following probe of SEQ ID NO:54 was synthesized based on the sequence of the insertion region which is different from Type I-B which was reported in rat (*Nature*, 365, p170–175, 1993). 5'GACCCCCTGCCTGTGCCCT-CAGACCAGCAT 3' (SEQ ID NO:55)

Clones of pHPR15A and pHPR55A were obtained from the Southern blot of SEQ ID NO:54 and a clone of pHRP66P was obtained from the Southern blot of SEQ ID NO:55 (FIG. 15). Dideoxy method using RI labelled dCTP was employed for the determination of the nucleotide sequences of these clones. DNASIS (Hitachi Soft Engineering Co. Ltd.) was used for analysis of the data. The nucleotide sequences of cDNA coding for human PACAP receptor Type I-B, Type I-B2 and Type I-C and the amino acid sequences deduced therefrom are shown in FIGS. 16, 17 and 18, respectively. The nucleotide sequences of cDNA coding for human PACAP receptor Type I-B, Type I-B2 and Type I-C are represented by SEQ ID NO:35, SEQ ID NO:36 and SEQ ID NO:37, respectively. The amino acid sequences deduced therefrom are represented by SEQ ID NO:25, SEQ ID NO:27 and SEQ ID NO:29, respectively.

[Example 5]

Expression of Bovine PACAP Receptor Protein cDNAs (1) Preparation of Transformants Containing Bovine PACAP Receptor Protein cDNAs cDNA clone pBPR35 of the bovine PACAP receptor protein obtained in Example 2 was digested with SmaI and BamHI, thereby cutting out a fragment (about 800 bp) from the plasmid. Then, a HindIII linker was added to the SmaI-digested terminus of this fragment. The resulting fragment was named "fragment A". On the other hand, two kinds of fragments were obtained by digesting pBPR68 with BamHI and SmaI. One of them, a fragment of about 1 kbp (named "fragment B"), was cut out. These fragment A and fragment B were ligated with each other at the respective BamHI-digested sites to prepare recombinant cDNA (pBPR-T). pBPR-T was inserted in the HindIII and EcoRV sites downstream of a CMV promoter of expression vector pRc/CMV to prepare an expression vector. This expression vector was introduced into a CHO cell by the calcium phosphate method using a CellPhect transfection kit (Pharmacia) to obtain a transformant. The transformant cells were selected with 500 μg/ml G-418 (trade mark: Geneticin, Lifetech Oriental).

(2) Preparation of Membrane Fraction of the Transformants

The transformants (CHO cells) cultivated for 3 days after subculture were separated using 0.2 mM EDTA/phosphate buffer, and suspended in 10 mM sodium carbonate buffer supplemented with 1 mM EDTA, 0.5 mM phenylmethyl-sulfonyl fluoride (PMSA), 20 μg/ml leupeptin, 4 μg/ml E-64 and 1 μg/ml pepstatin. The suspended cells were disrupted with a Polytron homogenizer (Kinematica). The disrupted product was centrifuged with a high speed cooling centrifuge (CR26H, Roter RR18, Hitachi, Ltd.) at 3,000 rpm for 10 minutes to obtain a supernatant. The resulting supernatant was further ultracentrifuged with an ultracentrifuge (SCP70H, Roter RPZ35T, Hitachi, Ltd.) at 30,000 rpm for 60 minutes to obtain pellets. The resulting pellets were suspended in a buffer [20 mM Tris-HCl (pH 7.4), 0.25M sucrose, 2 mM EDTA, 0.5 mM PMSF, 20 μg/ml leupeptin and 1 μg/ml pepstatin] to prepare a membrane fraction suspension.

Figure 33:
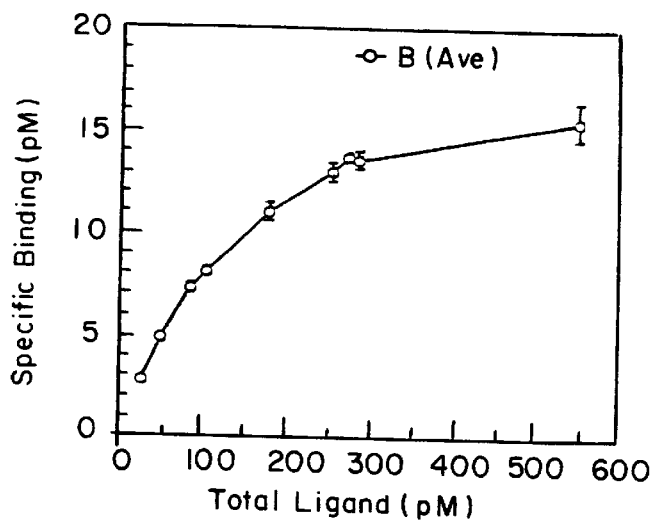
FIG. 33 is a graph showing results of the saturation binding experiment in a membrane fraction of CHO cells transfected with the bovine PACAP receptor protein cDNA (pBPR-T). The numerals on the abscissa indicate the concentration of [$^{125}$I]-PACAP27 added, and the numerals on the ordinate indicate the concentration of [$^{125}$I]-PACAP27 specifically bound to the membrane fraction.
Figure 34:
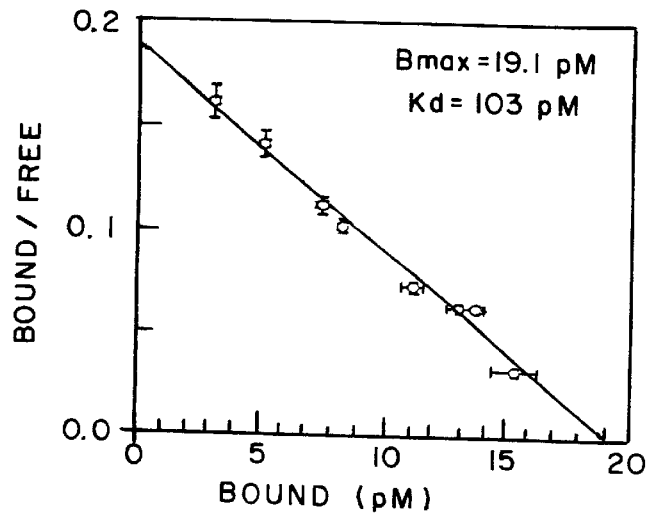
FIG. 34 is a graph showing Scatchard plot in the membrane fraction of CHO cells transfected with the bovine PACAP receptor protein cDNA (pBPR-T)
Figure 32:
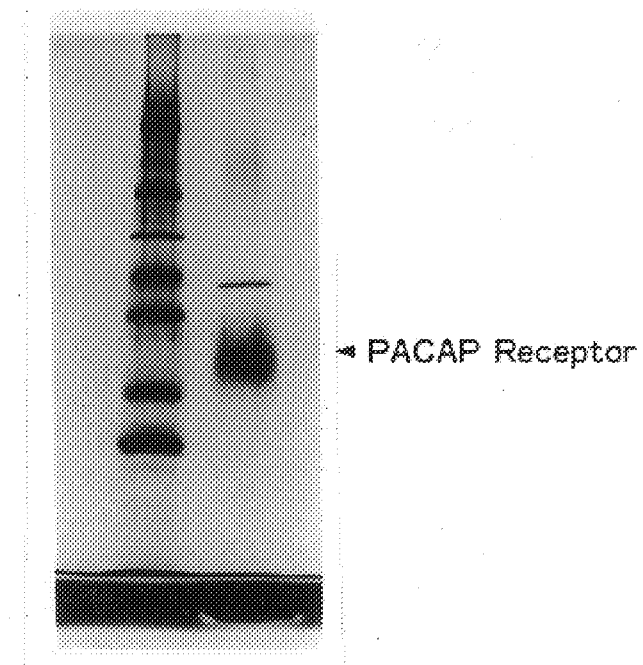
FIG. 32 shows analysis results of purified bovine PACAP receptor protein by polyacrylamide electrophoresis in the presence of sodium dodecylsulfate.

(3) Saturation Binding Experiment of Bovine PACAP Receptor Protein cDNA-Expressed CHO Cells The membrane fraction of the transformants obtained in (2) described above was reacted with 100 pM [$^{125}$I]-PACAP27 in a buffer [20 mM Tris-HCl (pH 7.4), 5 mM magnesium acetate, 2 mM EGTA, 0.5 mM PMSF, 20 μg/ml leupeptin, 4 μg/ml E-64 and 1 μg/ml pepstatin] at 25° C. for 75 minutes. Bound ligands were separated from free ligands through a glass fiber filter. The non-specific binding was examined in the presence of 1 μM PACAP27 (FIG. 33). The binding was examined with a a γ-ray counter. The dissociation constant and the maximum binding were examined by Scatchard plot analysis (FIG. 34).

Figure 35:
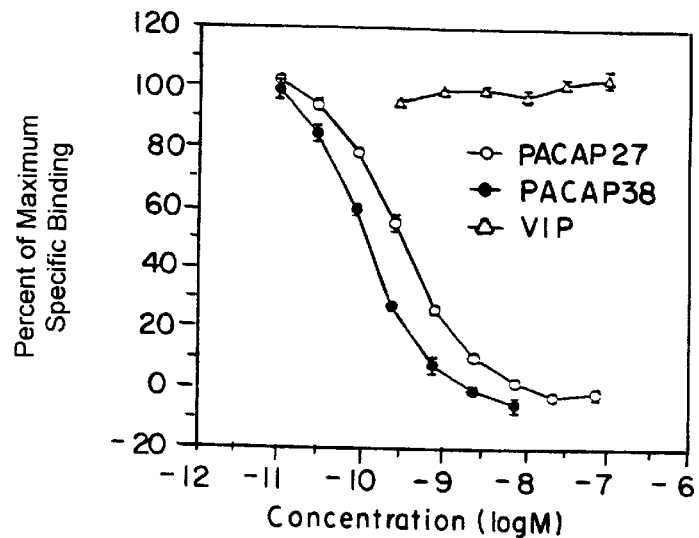
FIG. 35 is a graph showing results of the competitive binding experiments of PACAP27, PACAP38 and VIP to [$^{125}$I]-PACAP27 in the membrane fraction of CHO cells transfected with the bovine PACAP receptor protein cDNA (pBPR-T). The numerals on the abscissa indicate the concentrations (log M) of PACAP27, PACAP38 and VIP, and the numerals on the ordinate indicate the binding (%) of [$^{125}$I]-PACAP27, taking the specific binding as 100, when each peptide is added so as to give the final concentrations on the abscissa.

(4) Competitive Binding Experiment of Bovine PACAP Receptor Protein cDNA-Expressed CHO Cells Under the conditions of the binding experiment of (3) described above, PACAP27, PACAP38 and VIP were added to examine competition with [$^{125}$I]-PACAP27. Bovine PACAP receptor protein on the membrane fraction showed a high reactivity, but low in reactivity with VIP (FIG. 35).

Figure 36:
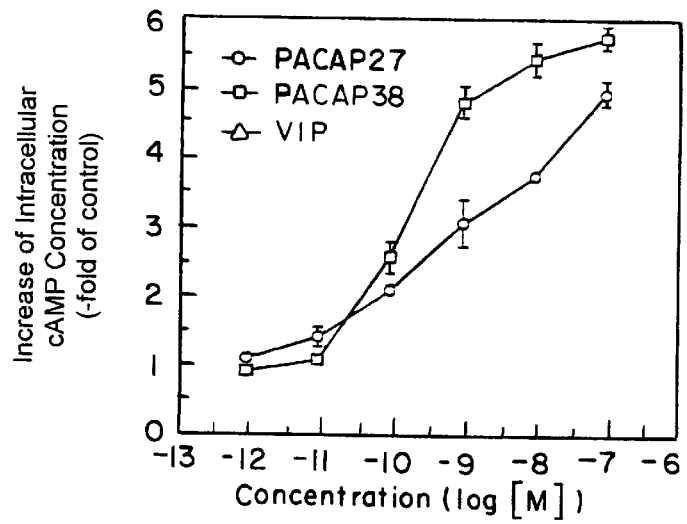
FIG. 36 is a graph showing changes in the amounts of intracellular cyclic AMP of CHO cells transfected with the bovine PACAP receptor protein cDNA (pBPR-T) produced by PACAP27, PACAP38 and VIP. The numerals on the abscissa indicate the concentrations (log M) of PACAP27, PACAP38 and VIP, and the numerals on the ordinate indicate the relative concentrations of cyclic AMP in the transformant CHO cells treated with peptides having respective concentrations, taking the concentration of cyclic AMP in untreated transformant CHO cells as 1.

(5) Assay of Intracellular Cyclic AMP Production of Bovine PACAP Receptor Protein cDNA-Expressed CHO Cells Three days after the transformants (CHO cells) were plated on a 24-well plate, the cells were washed with Hank's buffer (composition: 8 g/l NaCl, 0.4 g/l KCl, 0.06 g/l $Na_2HPO_4$, 1.0 g/l glucose, 0.2 g/l $MgSO_4$, 0.14 g/l $CaCl_2$ and 0.35 g/l $NaHCO_3$) supplemented with 0.05% BSA, and treated in the presence of 0.2 mM 3-isobutyl-1-methylxanthine at 37° C. for 1 hour. PACAP27, PACAP38 and VIP of various concentrations were added thereto, followed by cultivation at 37° C. for 30 minutes. After the cells were washed with the above-mentioned Hank's buffer supplemented with 0.05% BSA, intracellular cyclic AMP was extracted by the use of 500 μl of Hank's buffer and 100 μl of 20% perchloric acid, and neutralized with 1.5M KOH. The amount of cyclic AMP was assayed with a cAMP oxygen immunoassay system (BIOTRAK Amersham). The concentration of intracellular cyclic AMP increased depending on the concentrations of PACAP27 and PACAP38 (FIG. 36).

(6) Assay of Intracellular Inositol Phosphate of Bovine PACAP Receptor Protein cDNA-Expressed CHO Cells The pathway of signal transmission of inositol phosphate well known as the pathway of signal transmission together with cyclic AMP was examined. Three days after the transformants (CHO cells) were plated on a 24-well plate, 5 μCi myo-[$^3$H] inositol (19.1 Ci/mmole, Amersham) was added to the cell culture solution, followed by cultivation overnight at 37° C. The cells were washed with an assay buffer (20 mM HEPES, 140 mM NaCl, 4 mM KCl, 1 mM $Na_4HPO_4$, 1 mM $MgCl_2$, 1.25 mM $CaCl_2$, 10 mM LiCl, 10 mM glucose and 0.1% BSA). Then, PACAP27, PACAP38 and VIP of various concentrations were added to 500 μl of the assay buffer, and the mixtures were added to plates, followed by reaction with the cells at 37° C. for 20 minutes. One hundred microliters of 20% perchloric acid was added thereto to stop the reaction, and intracellular inositol phosphate was extracted. The extract was neutralized with 1.5M KOH. All inositol phosphate was separated from free inositol by the use of ion exchange chromatography (AGI-X8, Bio RAD). Thereafter, inositol phosphate was eluted with 1M ammonium formate/ 0.1M formic acid, and the amount of inositol phosphate was measured with a scintillation counter. The concentration of inositol phosphate increased depending on the concentrations of PACAP27 and PACAP38 (FIG. 37).

[Example 6]

Confirmation of Expression Site of Rat PACAP Receptor mRNA (1) Preparation of Poly(A)$^+$ RNA Total RNAs were prepared from the brains, lungs, livers, kidneys and testes of 8-week-old Sprague Dawley rats (males, Nippon Charles River) by the guanidine isothiocyanate method [*Biochemistry*, 18, 5294 (1979) and *Method in Enzymology*, 154 3 (1987)] and poly(A)$^+$ RNA prepared from the brains, lungs, livers, kidneys and testes was fractionated by formalin-modified agarose gel electrophoresis [*Proc. Natl. Acad. Sci. U.S.A.*, 77, 5794 (1980)] contained 2.2M formalin (Wako Pure Chemical Industries), followed by transfer to a nylon membrane filter (Pole).

(2) Preparation of Probe 374-bp fragment haveing the nucleotide sequence from the 76th to 450th of DNA (rat PACAP receptor cDNA pRPACAPR12) represented by the nucleotide sequence of SEQ ID NO:41 was labeled with $^{32}P$ by the use of a multi-prime labeling kit (Amersham) to prepare a probe.

(3) Northern Hybridization

Figure 38:
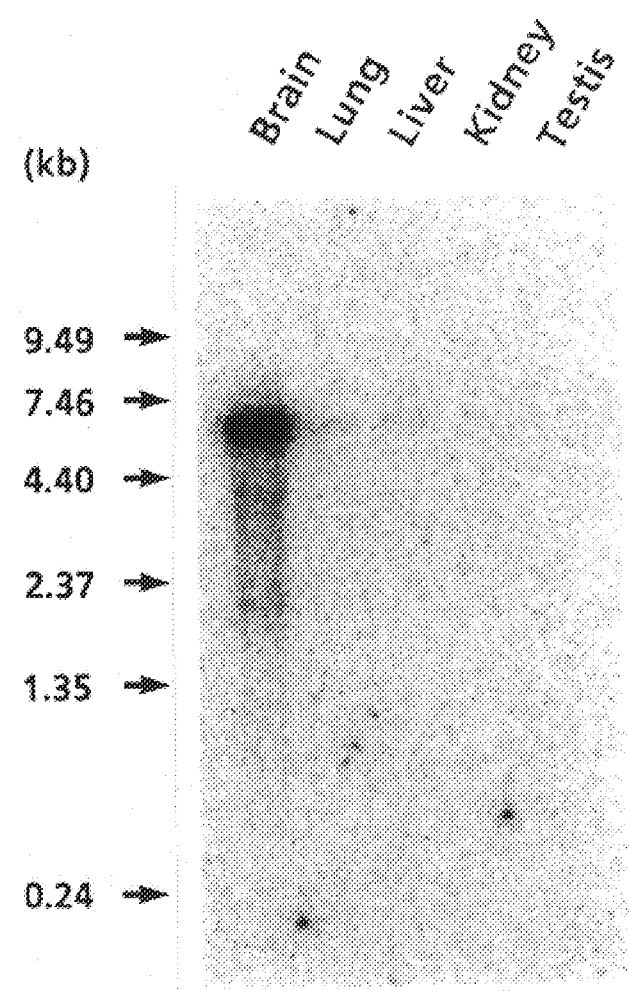
FIG. 38 shows results of northern hybridization using RNA prepared from the rat brains, lungs, livers, kidneys and testes, and a rat PACAP receptor protein cDNA probe. The bands represent that the RNA prepared from the rat brains, lungs, livers, kidneys and testes, and the rat PACAP receptor protein cDNA probe exhibit cross reaction. The numerals on the left indicate the size of a molecular weight marker.

The filter of (1) described above was treated at 80° C. for 2 hours to fix RNA, followed by hybridization in a hybridization buffer [50% formamide deionized, 5×SSPE, 5×Denhardt's solution, 0.5% SDS, and 100 μg/ml heterologous salmon sperm DNA heat denatured after ultrasonication (Wako Pure Chemical Industries)] overnight at 42° C. Subsequently, the probe obtained in (2) described above was heat denatured, and the heat-denatured probe was added thereto, followed by hybridization overnight at 42° C. Washing was conducted 5 times with 2×SSC, 0.1% SDS at 55° C. for 30 minutes, and further twice 0.1×SSC, 0.1% SDS at 50° C. for 20 minutes. Autoradiography was carried out for 12 hours using an image analyzer (Fuji BAS-2000) to detect desired bands. Results thereof revealed that PACAP receptor mRNA was most expressed in the brains, that expression thereof was also observed in the lungs and the livers, and that the size of mRNA was about 6.5 kb (FIG. 38).

[Example 7]

Expression of Rat PACAP Receptor Protein cDNA (1) Construction of Expression Vector for Animal Cells of Rat PACAP Receptor Protein cDNA Using plasmids pRPACAPR46-5 and pRPACAPR12 obtained in Example 3, an NcoI fragment having an N-terminal translation initiation codon was prepared. After repair of both ends of this fragment with Klenow fragments (Takara), HindIII linkers (Takara) were added thereto, and further cleaved with BamHI. Of the resulting fragments, a fragment containing the translation initiation codon was recovered by electrophoresis, and ligated with cDNA I obtained by cleaving BamHI-ApoI fragments of pRPACAPR46-5 and pRPACAPR12 with HindIII and EcoRI, respectively, to construct an expression vector in which NcoI-ApoI portions of the respective cDNA fragments were inserted. These plasmids were further cleaved double by the use of HindIII and XbaI, and DNA fragments containing cDNA portions were incorporated into other animal cell expression vectors, pRc/CMV, utilizing the same sites, to obtain expression vectors pRPR3-A (derived from pRPACAPR46-5) and pRPR4-B (derived from pRPACAPR12).

(2) Introduction of Expression Vector into CHO Cells 9.0×10$^5$ CHO cells were subcultured to each tissue culture flask having a bottom area of 25 cm$^2$ (Corning), and cultivated for 24 hours in a culture solution (culture solution A) composed of Ham's F12 medium (Flow), 10% fetal bovine serum, and penicillin and streptomycin as antibiotics. Expression vectors pRPR3-A (derived from pRPACAPR46-5) and pRPR4-B (derived from pRPACAPR12) obtained in (1) described above were introduced into CHO cells each in an amount of 10 μg with a gene introduction kit (CellPhect, Pharmacia) by the calcium phosphate method according to the formulation of the kit. After 24 hours, the culture solution was exchanged. After further 24 hours, the solution was-exchanged by culture solution A supplemented with 500 μg/ml of G418, and cDNA-introduced cells were selected, based on resistance to G418.

Figure 39:
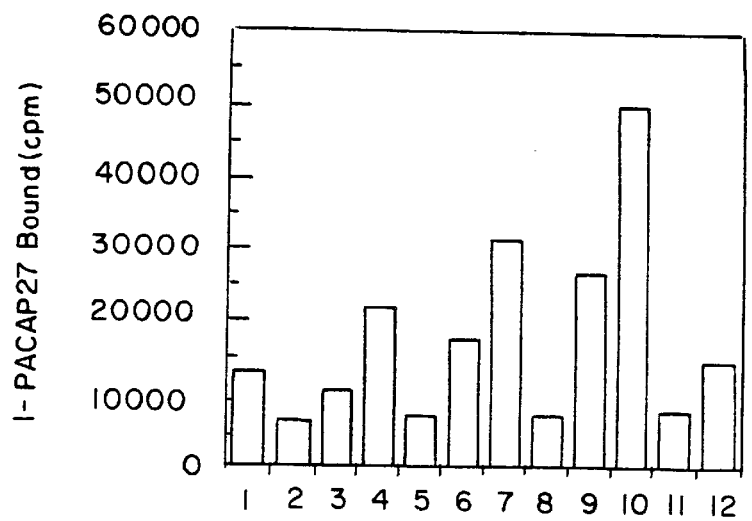
FIG. 39 shows results of measurements of the radioactivity, wherein each column indicates the binding of each CHO cell product with [$^{125}$I]-PACAP27 when cultured in each of the following combinations.

(3) Binding Experiment of PACAP Receptor Protein and [$^{125}I$]-PACAP27 on CHO Cell Membrane CHO cells exhibiting resistance to G418 were recovered by trypsin digestion, and subcultured to a 12-well plate for tissue culture. The cells were incubated until they covered the bottom surface of the tissue culture plates completely. Untreated CHO cells and rat VIP receptor cDNA-introduced CHO cells were also similarly cultivated. The cells were washed twice with a buffer for the binding experiment [Hank's solution (pH 7.4) containing 5 mM HEPES, 5% CHAPS and 0.1% BSA]. Then, the buffer and [$^{125}I$]-PACAP27 were successively added so as to give a final [$^{125}I$-PACAP27 concentration of 100 pM. The amount of the reaction solution per well was 500 μl. and the radioactivity was about 11.4×10$^4$ cpm. For analysis of specificity, samples containing unlabeled PACAP27 of a final concentration of 1 μm and VIP, in addition to the samples containing only the labeled products, were prepared. After incubation at 37° C. for 1 hour, the cells washed three times with the buffer for the binding experiment were dissolved with 1 ml of 0.5N NaOH and 0.1% SDS for each well, and the radioactivity contained therein was measured with a γ-counter. Results of measurements are shown in FIG. 39. Columns 1 to 12 in FIG. 39 indicate the radioactivity in CHO cells under the following conditions:

Column 1: untreated CHO cells+[$^{125}I$]-PACAP27

Column 2: untreated CHO cells+[$^{125}I$]-PACAP27+cold PACAP27

Column 3: untreated CHO cells+[$^{125}I$]-PACAP27 +cold VIP

Column 4: pRPR3-A-introduced CHO cells+[$^{125}I$]-PACAP27

Column 5: pRPR3-A-introduced CHO cells+[$^{125}I$]-PACAP27+cold PACAP27

Column 6: pRPR3-A-introduced CHO cells+[$^{125}$I]-PACAP27+cold VIP

Column 7: pRPR4-B-introduced CHO cells+[$^{125}$I]-PACAP27

Column 8: pRPR4-B-introduced CHO cells+[$^{125}$I]-PACAP27+cold PACAP27

Column 9: pRPR4-B-introduced CHO cells+[$^{125}$I]-PACAP27+cold VIP

Column 10: rat VIP receptor cDNA-introduced CHO cells+[$^{125}$I]-PACAP27

Column 11: rat VIP receptor cDNA-introduced CHO cells+[$^{125}$I]-PACAP27 +cold PACAP27

Column 12: rat VIP receptor cDNA-introduced CHO cells+[$^{125}$I]-PACAP27 +cold VIP FIG. 39 indicates that the radioactivities in the pRPR3-A-introduced CHO cells and the pRPR4-B-introduced CHO cells (column 4 and column 7, respectively) are higher than that in the untreated CHO cells (column 1). This fact proved that each of the pRPR3-A-introduced CHO cells and the pRPR4-B-introduced CHO cells produced PACAP receptors.

(4) Analysis of Specificity of Rat PACAP Receptor on CHO Cell Membrane Using [$^{125}$I]-PACAP27

The pRPR3-A-introduced and pRPR4-B-introduced CHO cells obtained in (2) described above were each disrupted in sodium carbonate buffer containing 1 mM EDTA, 0.5 mM PMSF, 20 µg/ml leupeptin, 4 µg/ml E-64 and 1 µg/ml pepstatin with a Polytron homogenizer (Kinematica) to prepare membrane fractions. Using the membrane fractions, complex binding experiments were conducted. For each of the membrane fractions of the pRPR3-A-introduced CHO cells and the pRPR4-B-introduced CHO cells, each of 10 µg and 15 µg (converted to a protein amount) thereof was ligated with 100 pM of [$^{125}$I]-PACAP27 in a buffer containing 20 mM Tris (pH 7.4), 1 mM EDTA, 0.05% CHAPS, 0.1% BSA and various protease inhibitors. For the competitive experiments, PACAP27 and VIP having each concentration were added. The reaction was conducted at 25° C. for 1 hour, and bound ligands were separated from free ligands by filtration through a filter. As to non-specific binding, a value in the case that 1 µM unlabeled PACAP27 was added and used as a standard. The amount of bound ligands was measured with a γ-counter. After elimination of the non-specific binding, it was examined whether or not concentration-dependent competition took place. Results thereof revealed that concentration-dependent competition took place. For VIP similar to PACAP27 in structure, competition was observed only at a concentration much higher than that of PACAP27, which showed that the PACAP receptor protein which was allowed to express was PACAP-specific (FIG. 40).

(5) Screening of Clones Highly Producing Rat PACAP Receptor Protein by Binding Experiment with [$^{125}$I]-PACAP27

The rat PACAP receptor protein cDNA-introduced CHO cells obtained in (2) described above were each subcultured to 10-cm diameter dishes at a low density. After cultivated until formation of colonies, each of the colonies was dispersed and recovered by suction. Cells derived from the respective colonies were separately subcultured in 6-well plates for tissue culture, followed by binding experiments using parts thereof in a manner similar to that of (4) described above (FIG. 41). Clones having relatively more bound [$^{125}$I]-PACAP27 when compared among wells were selected, and the reproducibility was further confirmed. As a result, clones A12 and B17 reproducibly binding to [$^{125}$I]-PACAP27 much more were selected from the pRPR3-A-introduced pRPR4-B-introduced CHO cells (FIG. 42).

(6) Assay of Intracellular Cyclic AMP of Rat PACAP Receptor Protein cDNA-Introduced CHO Cells From the binding experiment with [$^{125}$I]-PACAP27 of (3) described above, using CHO strains A12 and B17 highly producing rat PACAP receptor protein, the production promotion of intracellular cyclic AMP with PACAPs was detected in the following manner. Each 48-well plate for tissue culture was inoculated with each of the cell strains at a density of $1.0 \times 10^5$ cells/well, followed by cultivation for 3 days. The plate was washed twice with Ham's F12 medium supplemented with 0.1% BSA and 0.5 mM IBMX, and 500 µl/well of the same medium was added thereto. PACAP27, PACAP38 or VIP having each concentration was added thereto in a 1/100 amount, followed by standing at 37° C. for 40 minutes. The supernatant was removed, and extraction was conducted with 100% cold ethanol. The extract was evaporated to dryness with a centrifugal freeze dryer, and redissolved in the buffer attached to an EIA kit for assaying cyclic AMP (Amersham). Then, the amount of cyclic AMP was assayed according to the formulation of the kit. Results thereof revealed that both A12 and B17 promoted the production of intracellular cyclic AMP, depending on the concentrations, for PACAP27 and PACAP38, but a concentration much higher than that of the PACAPs was required to promote the production of intracellular cyclic AMP, for VIP (FIG. 43).

(7) Construction of Rat PACAP Receptor Protein cDNA Expression System Using Baculovirus Animal cell expression vectors pRPR3-A and pRPR4-B were each cleaved with HindIII, and the termini were repaired with Klenow fragments (Takara), followed by addition of BglII linkers. The resulting fragments were further cleaved with XbaI, and the termini were repaired with Klenow fragments, followed by addition of HindIII linkers. These DNAs were each digested double by the use of HindIII and BalII, thereby obtaining DNA fragments corresponding to translation regions. pBlneBacIII, a baculovirus transfer vector, was similarly digested double with HindIII and BglII, and subjected to ligation reaction with the above-mentioned DNA fragments. According to the formulation of a kit (Maxbac baculovirus expression system, Invitrogen) with which plasmid DNA confirmed in insertion was prepared, the resulting fragments, together with baculovirus genome DNA, were introduced into Sf9 cells. After cultivation at 27° C. for 2 days, virus particles appeared in the supernatant were recovered. Recombinant viruses were selected therefrom by the plaque assay in accordance with the formulation of the kit.

(8) Expression Using Rat PACAP Receptor Protein cDNA-Introduced Baculovirus

The recombinant plaques formed by the plaque assay were extracted with a micropipette, and dispersed in 1 ml of complete medium for Sf9 (Grace medium for insects (Gibco) containing necessary additives, inactivated calf serum and gentamicin]. A 25-cm$^2$ flask for tissue culture was inoculated with $2 \times 10^6$ Sf9 cells, together with 5 ml of the medium, and the cells were adhered to a bottom of the flask, followed by addition of 500 µl of the above-mentioned virus solution. After cultivation at 27° C. for 5 days, the cells were recovered by pipetting. The cells were pelletized by centrifugation, and suspended in a small amount of medium. Then, a 1/10 amount of the suspension was poured into each Eppendorf tube. After further centrifugation, the supernatant was replaced by the same buffer as with the binding experiment in animal cells (composition: Hank's solution (pH 7.4)

containing 5 mM HEPES, 5% CHAPS and 0.1% BSA]. Then, [$^{125}$I]-PACAP27 was added so as to give a final concentration of 100 pM, and unlabeled PACAP27 of a final concentration of 1 μM was added to a sample for analysis of specificity to make up a total solution amount of 500 μl. After standing at room temperature for 1 hour and binding, bound ligands, together with the cells, were pelletized by centrifugation. The pellets were further resuspended in the same buffer and centrifuged. After this procedure was repeated three times to conduct sufficient washing, the amount of radioligands remaining in the pellets was measured with a γ-counter. As a result, 4 virus clones showing a very high binding were obtained (FIG. 44).

[Example 8]

Expression of Human PACAP Receptor Protein cDNA (1) Preparation of Transformant in Baculovirus System Using Human PACAP Receptor Protein cDNA A fragment cut out by digestion with BamHI and PstI from animal cell expression vector pcDNAI/Amp in which human PACAP receptor protein was subcloned was inserted in the BamHI and PstI sites of transfer vector pBlueBacIII to prepare a recombinant transfer vector. Sf9 cells were transfected with this vector, together with baculovirus DNA (AcMAPV DNA), using the transfection module attached to the kit (MAXBAC, Inbitrogen). After transfection, the viruses appeared in the supernatant, so that the culture supernatant of the fourth day was used as a virus solution. Sf9 cells (2×10$^6$ cells) seeded on a 6-cm$^2$ dish were infected with this virus solution at room temperature for 30 minutes, and a medium containing 0.6% agarose was poured therein for fixing. Cell culture at a high humidity (a humidity of 100%) for 5 to 6 days resulted in development of virus plaques. Plaques caused by viruses in which human PACAP receptor protein was recombined could be judged by turning blue, and the viruses were recovered. The recombinants were purified by repetition of this plaque assay. Sf9 cells were infected with the purified recombinants, and cultivated for 48 to 72 hours, whereby PACAP receptor protein-expressed transformants could be obtained (FIG. 45).

(2) Construction of Cell Strain Expressing Human PACAP Receptor

An overall length fragment was cut out from human PACAP receptor cDNA-cloned pTS847-1 by digestion with EcoRI, and inserted in the EcoRI site of animal cell expression vector pRc/CMV so as to be arranged in a correct direction, thereby constructing pTS849. The resulting plasmids were introduced into CHO-K1 cells (ICN) by the calcium phosphate method, and plasmid-incorporated clones were selected with 500 μg/ml G-418 (Geneticin).

(3) Scatchard Plot Analysis Using Membrane Fraction of Human PACAP Receptor Protein-Expressed CHO-K1 Cells and Competitive Inhibition Analysis The human PACAP receptor-expressed CHO-K1 cells obtained in (2) described above were cultivated in ten 175-cm$^2$ flasks containing a medium supplemented with 500 μg/ml G-418 (trade mark: Geneticin, Lifetech Oriental). When the cells covered almost entire bottom surfaces of the flasks, the CHO-K1 cells were separated with PBS solution containing 1 mM EDTA. After washing with the same buffer, the CHO-K1 cells were suspended in 10 mM NaCO$_3$ buffer containing 1 mM EDTA, 0.5 mM PMSF, 20 μg/ml leupeptin, 20 μg/ml E-64 and 1 μg/ml pepstatin, and disrupted with a Polytron homogenizer (Kinematica). Then, the disrupted product was centrifuged with a high speed cooling centrifuge (CR26H, Roter RR18, Hitachi, Ltd.) at 3,000 rpm for 10 minutes. The resulting supernatant was further ultracentrifuged with an ultracentrifuge (SCP70H, Roter RP42, Hitachi, Ltd.) at 30,000 rpm for 60 minutes. The resulting pellets were suspended in a buffer containing 20 mM Tris-HCl (pH 7.4), 0.25M sucrose, 2 mM EDTA, 0.5 mM PMSF, 20 μg/ml leupeptin and 1 μg/ml pepstatin. The resulting suspension was used as a membrane fraction.

The preparation of [$^{125}$I]-PACAP27, the Scatchard plot analysis obtained from the saturation binding experiment, and the competitive inhibition experiment were carried out in accordance with the method described in Example 1 (3).

From results of Scatchard plot analysis, a single binding site existed in the membrane fraction of the human PACAP receptor protein-expressed CHO-K1 cells, and the dissociation constant (Kd) was 41±6.9 pM (FIG. 46). Further, results of the competitive inhibition experiment proved that PACAP27 and PACAP38 competed with [$^{125}$I]-PACAP27. On the other hand, it was revealed that VIP was 1,000 times weaker than PACAP27 (FIG. 47).

(4) Assay of Intracellular Cyclic AMP of Human PACAP Receptor Protein-Expressed CHO-K1 Cells The human PACAP receptor protein-expressed CHO-K1 cells obtained in (2) described above were cultivated in a 24-well plate containing a medium supplemented with 500 μg/ml G-418 (trade mark: Geneticin, Lifetech Oriental) until the cells almost covered an entire surface of the plate. After washing twice with Hank's buffer containing the culture buffer, 10 mM HEPES and 0.05% BSA, the CHO-K1 cells were cultivated in the above-mentioned buffer supplemented with 0.2 mM 3-isobutyl-1-methylxanthine at 37° C. for 60 minutes. Then, PACAP27, PACAP38 or VIP having each concentration was added thereto, followed by further cultivation at 37° C. for 30 minutes. After absorption of the buffer, the cells were washed twice with the culture buffer. Then, cAMP was extracted from the cells with 20% perchloric acid. After transfer to a 1.5-ml Eppendorf tube, the extract was centrifuged with a Tomy microcentrifuge at 12,000 rpm for 5 minutes, and the supernatant was neutralized with 1.5N KOH/60 mM HEPES to prepare a cell eluted solution. The concentration of cyclic AMP was determined by the acetylation method of a cAMP assay system (Amersham). Under these determination conditions, when nothing was added, the amount of intracellular cAMP was 0.7 pmole/well. For PACAP27 and PACAP38, the concentration of intracellular cAMP increased depending on the concentrations. In particular, when 0.1 mM of PACAP38 was added, accumulation of cyclic AMP about 30 times the basal level (about 21 pmoles/well) was observed (FIG. 48). VIP little raised the concentration of intracellular cyclic AMP, compared with PACAP27 and PACAP38 (FIG. 48).

[Example 9]

Expression of Human PACAP Receptor mRNA

Poly(A)$^+$ RNA (Clontech) from each human tissue was subjected to 1.1% agarose gel-modified gel electrophoresis containing 2.2M formalin for fractionation, followed by transfer to a nylon membrane filter. Then, RNA transferred was fixed to the nylon membrane with UV. A probe of human PACAP receptor cDNA (SacI-BglII fragment of pTS847-1, nucleotide No. 168–562) was prepared with a random prime labeling kit (Amersham) and [α-$^{32}$P]dCTP (Du Pont/NEN), and northern hybridization was carried out using this probe. As a result, human PACAP mRNA was most expressed in the brain, and the size thereof was about 7 kb. Expression was also observed in the lung, the liver, the pancreas and other organs, although weak (FIG. 49).

[Example 10]

Expression of PACAP mRNA in Rat Central Nerve System

All RNAs were prepared from the olfactory bulbs, amygdalae, cerebral basal ganglia, hippocampi, thalami, hypothalami, cerebral cortices, medulla oblongatas, cerebellums, spinal cords and pituitary glands of 8-week-old S. D. rats (♂) by the guanidine isothiocyanate method, and poly(A)$^+$ RNA was further prepared by the use of an oligo(dT) spun-column (Pharmacia). Five micrograms of poly(A)$^+$ RNA prepared from the above regions of the central nervous system was fractionated by 1.2% formalin-modified agarose gel electrophoresis [Proc. Natl. Acad. Sci. U.S.A., 77, 5794 (1980)] contained 2.2M formalin (Wako Pure Chemical Industries), followed by transfer to a nylon membrane filter (Pole).

(2) Preparation of Probe 374-bp fragment having the nucleotide sequence from the 76th to 450th of DNA (rat PACAP receptor cDNA pRPACAPR12) represented by the nucleotide sequence of SEQ ID NO: 41 was labeled with $^{32}P$ by the use of a multi-prime labeling kit (Amersham) to prepare a probe.

(3) Northern Hybridization

The filter of (1) described above was treated at 80° C. for 2 hours to fix RNA, followed by hybridization in a hybridization buffer [50% formamide deionized, 5×SSPE, 5×Denhardt's solution, 0.5% SDS, and 100 μg/ml heterologous salmon sperm DNA heat denatured after ultrasonication (Wako Pure Chemical Industries)] overnight at 42° C. Subsequently, the probe obtained in (2) described above was heat denatured, and the heat-denatured probe was added thereto, followed by hybridization overnight at 42° C. Washing was conducted 5 times with 2×SSC, 0.1% SDS at room temperature for 5 minutes, and further twice 0.1×SSC, 0.1% SDS at 50° C. for 20 minutes. Autoradiography was carried out for 7 days using a X-OMAT AR film (Kodak) to detect desired bands.

Results thereof revealed that rat PACAP receptor mRNA was expressed in almost all regions of the central nerve system, and that there was little expression in the cerebellums and pituitary glands (FIG. 50). From these results, the PACAPs are deduced to play an important role in the central nerve system.

[Example 11]

Screening of Human PACAP Receptor Antagonist Which Uses Cell Membrane Fraction of Sf9 cell Expressing cDNA of Human PACAP Receptor Protein (1) Preparation of Buffer for Assay
Composition of buffer
20 mM Tris-HCl, 2 mM EGTA, 5mM (CH$_3$COO)$_2$Mg.4H$_2$O, 0.5 mM PMSF, 1 μg/ml pepstatin, 20 μg/ml leupeptin, 4 μg/ml E-64, 0.03% NaN$_3$, 0.1% BSA, 0.05% CHAPS, pH7.2
Method for Preparation The agents other than peptidase inhibitor (PMSF, pepstatin, leupeptin, E-64) and BSA were dissolved into distilled water. While controlling pH of the aqueous solution with 6N HCl, peptidase inhibitor was added thereto. Pepstatin and PMSF were dissolved into DMSO and the DMSO solution was added to the distilled water solution with rapid agitation. Final concentration of DMSO was adjusted to 0.1%, thus pepstatin and PMSF were dissolved into 1 ml of DMSO to prepare 1 liter of buffer. Then the solution was mixed and BSA was added thereto.

(2) Sf9 cells which express human PACAP receptor protein obtained in Example 8 were disrupted by Polytron mixer in a buffer for homogenize (20 mM Tris-HCl, 2 mM EDTA, 0.5 mM PMSF, 1 μg/ml pepstatin, 20 μg/ml leupeptin, 4 μg/ml E-64, pH7.4). The disrupted cell solution was centrifuged at 3,000 rpm for 5 minutes and the supernatant was centrifuged at 30,000 rpm for 60 minutes. The resulting precipitate was treated as a membrane fraction. The membrane fraction was diluted with the buffer for assay to 2 μg protein/ml. The diluted solution was applied on a cell strainer (FALCON, 2350) and was divided into 100 μl in each tube (FALCON, 2053) with dispenser.

(3) Each 1 μl of 10 mM of the sample was added to the reaction tubes (final concentration: 100 μM, room temperature). DMF was added thereto for assay of the maximum binding amount, and 1 μl of DMF with 10 μM PACAP27 was added for assay of nonspecific binding amount (final concentration: 1 μM). The maximum binding amount was assayed twice respectively at the beginning and the end of the assay, and the nonspecific binding amount was assayed twice at the end of the assay.

(4) In radio isotope region, each 2 μl of 5 nM [$^{125}$I]-PACAP27 (DuPont) was added in the reaction tubes (final concentration: 100 pM). [$^{125}$I]-PACAP27 was placed on ice.

(5) The reaction tubes were incubated at 25° C. for 1 hour.

(6) 1.5 ml of a detergent buffer was added into the reaction tubes and the mixture was filtered on a glass fiber paper (Whatman, GF/F) using Sampling manifold (Millipore). 1.5 ml of a detergent buffer was further added to the reaction tubes and they were filtered. The glass fiber filtration paper (Whatman, GF/F) was previously immersed in a PEI (polyethyleneimine) solution (20 mM Tris-HCl, 0.3% PEI, pH7.4). The detergent buffer may be similar with the assay buffer but it is not necessary to contain. peptidase inhibitor.

(7) [$^{125}$I] remaining on the glass fiber filtration paper was counted by γ-counter. Based on the counts, inhibiting activity on a binding specificity [Percent Maximum Binding] of PACAP27 and a PACAP27 receptor of the samples were determined according to the following formula:

PMB=[(B-NSB)/B$_0$-NSB)×100

PMB: percent Maximum Binding
B: value when the samples are added,
NSB: non-specific binding amount
B$_0$: Maximum Binding As a result, substances No. 1 to 10 as shown in FIG. 51 were obtained as substances which inhibited a specific binding of PACAP27 and PACAP receptor. PMB of the compounds are shown in Table 3.

TABLE 3

| Test compound No. | Specific Binding % |
|---|---|
| 1 | 57 |
| 2 | 11 |
| 3 | 37 |
| 4 | 15 |
| 5 | 2 |
| 6 | −3 |

TABLE 3-continued

| Test compound No. | Specific Binding % |
|---|---|
| 7 | 50 |
| 8 | 15 |
| 9 | 20 |
| 10 | 34 |

[Example 12]

Preparation of Anti-PACAP Receptor Antibody (1) Preparation of a Partial Peptide of PACAP Receptor The 5th Cys(C) of the amino acid sequence, MESDCIFKKEQAMC, was substituted with Ala(A) for the convenience of a preparation of immunoantigen complexes to obtain a partial peptide, MHSDAIFKKQAMC, with a conventional method using a autosynthesizer (430A, AppliedBiosystem). The first amino acid sequence corresponds to 1st to 14th amino acid sequence of SEQ ID NO:14, which is a common sequence to bovine, rat or human PACAP receptor represented by the amino acid sequence of anyone of SEQ ID NO:14 to SEQ ID NO:29.

(2) Preparation of Immunogen

A complex of the synthetic peptide (MHSDAIFKKEQAMC) obtained in the above (1) and bovine thyroglobulin (BTG) was made and used as an immunogen. Thus, 21 mg of BTG was dissolved into 1.4 ml of 100 mM phosphate buffer (pH 6.8) and the solution was mixed with 2.35 mg of GMBS in 100 μl of DMF to react at room temperature for 40 minutes. The reactant was applied on Sephadex G-25 column™ (1×35 cm) equibilliated with 100 mM phosphate buffer and to obtain a fraction containing BTG. A half (1.5 ml) of the fraction was mixed with 2 mg of the synthesized peptide dissolved in 50% DMSO to react at 4° C. for two days. The reactant was dialyzed against physiological saline at 4° C. for two days and the dialyzate was divided into small amount and freeze-restored.

(3) Immunization

100 μg of the immunogen obtained in the above (2) was subcutanously given with a complete Freund's adjuvant to each female BALB/c mouse of 6 to 8 week old. Once or twice additional immunizations was conducted at three weeks intervals.

(4) Preparation of HRP-labelled partial peptide of receptor

HRP (Horse radish peroxidase)-labelled partial peptide necessary for assay for antibody value with EIA was prepared as follows:

Twenty (20) mg of HRP was dissolved into 1.5 ml of phosphate buffer (pH6.5) and the solution was mixed with 1.4 mg of GMBS [N-(6-maleimidebutylyloxy)succinimide] in 100 μl of DMF to react at room temperature for 40 minutes. The reactant was applied on Sephadex G-25 column™ (1×35 cm) equibilliated with 100 mM phosphate buffer and to obtain a fraction containing BTG. A half (1.5 ml) of the fraction was mixed with 2 mg of the synthesized peptide dissolved in 50% DMSO to react at 4° C. for two days. The reactant was applied on Ultrogel AcA44 column™ (1×35 cm) equibilliated with 100 mM phosphate buffer and to obtain a fraction containing HRP-labelled partial peptide. BSA(final concentration: 0.1%) and thimerosal (final concentration: 0.05%) were added to the fraction to be restored at 4° C.

(5) Assay of Antibody Titer

Antibody titer of antiserum of the mice immunized in the above (3) was assayed as follows:

100 μl of 100 μg/ml anti-mouse immuno globulin antibody (IgG fraction, Cuppel) dissolved in 100 mM carbonate buffer (pH 9.6) was added to a 96-well plate and kept at 4° C. for 24 hours to make an anti-mouse immunoglobulin bound microplate. After the plate was washed with phosphate bufferized physiological saline (PBS, pH 7.4), 300 μl of Blockace (Yukizirushi, Japan) diluted to 25% with PBS was added to the plate to react at 4° C. for at least 24 hours in order to block the remaining bind sites of the plate.

50 μl of Buffer A (0.1% BSA, 0.1M NaCl, 1 mM MgCl$_2$, 0.05% CHAPS and 0.1% NaN$_3$ in 20 mM phosphate buffer, pH 7.0) and 100 μl of mouse anti-partial peptide of PACAP receptor-antiserum diluted with Buffer A were added to each of the well of the above anti-mouse immunoglobulin bound microplate and to react at 4° C. for 16 hours. After the plate wase washed with PBS, 100 μl of HRP-labelled peptide diluted to 300 times with Buffer B (0.1% BSA, 0.4M NaCl and 2 mM EDTA in 20 mM phosphate buffer, pH 7.0) was added to react at 4° C. for 7 hours. Then, the plate was washed with PBS and 100 μl of TMB microwell peroxidase substrate system (Kirkegaard & Perry Lab, Inc.) was added to each well to react them at room temperature for 10 minutes. 100 μl of 1M phosphoric acid was added to each well to stop the reaction and their absorptions at 450 nm was assayed with a plate reader (MTP-120, Corona).

(6) Preparation of Anti-partial Peptide of PACAP Receptor Monoclonal Antibody

On mice which show relatively high antibody value, final immunization by intravenous injection of 200 to 300 μg of immunogen in 0.25 to 0.3 ml of physiological saline was conducted. Spleens were enucleated from the mice after 3 to 4 days of the final immunization and pressed and filtered through a stainless mesh and the filtrate was suspended in Eagle's Minimum Essential Medium (MEM) to obtain a spleen cell suspension. Mieloma cell P3-X63.Ag8.U1(P3U1 cell) derived from BALB/c mouse was used as a cell for cell fusion [Current Topics in Microbiology and Immunology, 81, 1(1978)]. The cell fusion was conducted according to the original method. Spleen cells and P3U1 cells were respectively washed 3 times with MEM having no serum, and then they were mixed at 5:1 in the ratio of spleen cells to P3U1 cells followed by centrifugation at 700 rpm for 15 minutes to make the cells precipitate. After thoroughly removing the supernatant, the precipitate was softly mixed and 0.4 ml of 45% polyethyleneglicol (PEG) 6000 (Kochlight) was added thereto and the mixture was maintained in water bath at 37° C. for 7 minutes for the hybridization. 15 ml of MEM was slowly added by 2 ml per minute thereto and the mixture was centrifuged at 750 rpm for 15 minutes to obtain the cell precipitate. The cells were suspended mildly into 200 ml of GIT medium containing 10% fetal calf serum (Wako Pure Chemical Industry, Japan) (GIT-10% FCS) and a 24 well multidish(Limbro) was seeded with 1 ml of the suspension to each well and incubated in an incubator with 5% carbonic acid at 37° C. After 24 hours of the incubation, 1 ml of GIT-10% FCS containing HAT (0.1 mM hypoxanthine, 0.4 μM aminopterin, 1.6 mM thymidine) (HAT medium) was added to each well and HAT selective cultivation began. After 4 and 8 days from the beginning of the cultivation, 1 ml of the culture solution was changed with new HAT medium. Growth of hybridoma was found after 8 to 10 days from the cell fusion and the supernatant when the culture solution changed yellow was taken and assayed according to the method described in Example 5.

Typical screening of hybridoma derived from mice immunized with a partial peptide of PACAP receptor is shown in FIG. 52. There are a few colonies of hybridoma in the wells and 3 wells were chosen, cloning of an antibody producing strain with limiting dilution analysis was conducted to obtain three hybridomas which produce anti-partial peptide of PACAP receptor (PRN1-25, PRN1-109 and PRN1-159). As a feeder cell for the cloning, thymus cells of BALB/c mouse was employed. One(1) to three(3)×10⁶ cells of these hybridomas were intraabdominally administered to BALB/c mice to which 0.5 ml of mineral oil was intrabdominally administered, and 10 to 15 days after the administration, ascites containing antibodies was collected.

Monoclonal antibodies were purified from the obtained ascites using a column to which Protein A was fixed. Thus, the ascites was diluted with equivalent binding buffer (3.5M NaCl, 0.05% NaN$_3$ in 1.5M glycine, pH 9.0) and the dilution was applied on Recombinant Protein A-agarose (Repligen) equilibrized with the binding buffer, washed with the buffer and antibodies were eluted with an elution buffer (0.1M citrate buffer with 0.05% NaN$_3$, pH 3.0). The purified monoclonal antibodies eluted were dialyzed against PBS containing 0.05% NaN$_3$ at 4° C. for two days and the dialysate was restored at 4° C. The monoclonal antibodies obtained are shown in Table 4.

TABLE 4

| Monoclonal antibodies | Type |
| --- | --- |
| PRN1-25a | IgG1 |
| PRN1-109a | IgG1 |
| PRN1-159a | IgG1 |

(7) Detection of PACAP Receptor by Western Blotting with Anti-partial Peptide of PACAP Receptor Antibody Human PACAP receptor was expressed in an insect cell using Baculo virus and a membrane fraction was prepared from the cell. Membrane protein was solubilized with digitonin from the membrane fraction and concentrated on DEAE-Toyopearl column. The concentrated membrane protein solution was isolated with SDS-polyacrylamide electrophoresis and transfered to PVDF membrane (Applied Biosystem). The PVDF membrane transfered with protein was immersed in 5% BSA solution at 37° C. for 1 hour to saturate adsorption sites. The PVDF membrane was washed and immersed in 10 μg/ml PRN1-159a antibody solution at room temperature for 1 hour. After washing, the membrane was immersed at room temperature for 2 hour in a solution with golden-colloid-labelled anti-mouse IgG and anti-mouse IgM antibodies (Amershum, Auroprobe BL plus GAM IgG+ IgM). After washing, the membrane was treated with a sensitizer (Amershum, Intense BL silver enhancement Kit) and a band of PACAP receptor which was recognized with the antibodies was detected (FIG. 53).

(8) Inhibition of PACAP binding by monoclonal antibodies

Membrane protein was solubilized with digitonin from the bovine brain membrane fraction and concentrated on DEAE-Toyopearl column. The concentrated membrane protein solution was diluted with assay buffer (20 mM Tris, 5 mM magnesium acetate, 2mM EGTA, 0.1% BSA, 0.05% digitonin, 0.03% NaN$_3$, 0.5 mM PMSF, 20 μg/ml leupeptin, 4 μg/ml E-64, 1 μg/ml pepstatin, pH 7.2) to 90 μl and was added with 10 μl of the purified monoclonal antibody solution. After mixing, the solution was kept at 4° C. for 16 hours and 2 μl of 5 nM radioactive iodine-labelled PACAP27 ([$^{125}$I]PACAP27) solution was added thereto to react at 25° C. for 1 hour. After completion of incubation, 1.5 ml of assay buffer detergent (digitonin in assay buffer was substituted with CHAPS of equivalent concentration) was added to the reaction solution and then the solution was filtered on a glass-fiber filter paper which was previously treated with 0.3% polyethyleneimine. The filter paper was further washed with equivalent amount of assay buffer detergent and the captured radio-activity was counted and radio-active PACAP27 bound to the receptor was determined. As shown in FIG. 54, PRN1-159a inhibited binding of [$^{125}$I]PACAP27 to the receptor.

It should be understood that the examples and embodiments described herein are for illustrative purposes only and that various modifications or changes in light thereof will be suggested to persons skilled and purview of this Application and the scope of the appended claims.

What is claimed is:

1. An isolated DNA coding for a receptor protein capable of binding a pituitary adenylate cyclase activating protein, wherein the receptor protein comprises the amino acid sequence of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO:

23, SEQ ID NO: 24, SEQ ID NO: 25, SEQ ID NO: 28 or SEQ ID NO: 29.

2. The DNA of claim 1 wherein the DNA is a cDNA.

3. A vector containing the DNA as claimed in claim 1.

4. A transformed host cell containing the DNA as claimed in claim 1.

5. A method for preparing the receptor protein or the salt thereof as claimed in claim 1 comprising cultivating a transformed host cell containing a DNA encoding said protein under conditions suitable for expression of said protein and recovering said protein.

6. An isolated DNA comprising the nucleotide sequence of SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

* * * * *

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Met His Ser Asp Cys Ile Phe Lys Lys Glu Gln Ala Met Cys Leu Glu
1               5                   1 0                 1 5

( 2 ) INFORMATION FOR SEQ ID NO:2:

( i ) SEQUENCE CHARACTERISTICS:

(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO:2:

Ser Ser Pro Gly Cys Pro Gly Met Trp Asp Asn Ile Thr Cys Trp Lys
 1               5                  10                  15
Pro Ala (2) INFORMATION FOR SEQ ID NO:3:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:3:

Val Gly Glu Met Val Leu Val Ser Cys Pro Glu
 1               5                  10

(2) INFORMATION FOR SEQ ID NO:4:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:4:

Phe Arg Ile Phe Asn Pro Asp Gln Val Trp Glu Thr Glu Thr Ile Gly
 1               5                  10                  15

(2) INFORMATION FOR SEQ ID NO:5:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:5:

Arg Asn Cys Thr Glu Asp Gly Trp Ser Glu Pro Phe Pro His Tyr Phe
 1               5                  10                  15
Asp Ala Cys Gly Phe
               20

(2) INFORMATION FOR SEQ ID NO:6:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:6:

Asp Gln Asp Tyr Tyr Tyr Leu Ser Val Lys Ala Leu Tyr Thr Val Gly
 1               5                  10                  15
Tyr Ser Thr Ser Leu
               20

( 2 ) INFORMATION FOR SEQ ID NO:7:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Thr Leu Thr Thr Ala Met Val Ile Leu Cys Arg Phe Arg Lys Leu His
 1               5                  10                  15
Cys Thr Arg Asn Phe Ile His Met Asn Leu Phe Val Ser Phe Met Leu
                20                  25                  30
Arg Ala Ile Ser Val Phe Ile Lys Asp Trp Ile Leu Tyr Ala Glu Gln
            35                  40                  45
Asp Ser
    50
```

( 2 ) INFORMATION FOR SEQ ID NO:8:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Ser Thr Val Glu Cys Lys Ala Val Met Val Phe Phe His Tyr Cys Val
 1               5                  10                  15
Val Ser Asn Tyr Phe Trp Leu Phe Ile Glu Gly Leu Tyr Leu Phe Thr
                20                  25                  30
Leu Leu Val Glu Thr Phe Phe Pro Glu Arg Arg Tyr Phe Tyr Trp Tyr
            35                  40                  45
Thr Ile Ile Gly Trp Gly Thr Pro Thr Val Cys Val
        50                  55                  60
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Thr Ala Leu Trp Trp Val Ile Lys Gly Pro Val Val Gly Ser Ile Met
 1               5                  10                  15
Val Asn Phe Val Leu Phe Ile Gly Ile Ile
                20                  25
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Ile Leu Val Gln Lys Leu Gln Ser Pro Asp Met Gly Gly Asn Glu Ser
 1               5                  10                  15
```

Ser Ile Tyr (2) INFORMATION FOR SEQ ID NO:11:

(i) SEQUENCE CHARACTERISTICS:
        (A) LENGTH: 76 amino acids
        (B) TYPE: amino acid
        (D) TOPOLOGY: linear (ii) MOLECULE TYPE: peptide (xi) SEQUENCE DESCRIPTION: SEQ ID NO:11:

```
Leu Arg Leu Ala Arg Ser Thr Leu Leu Leu Ile Pro Leu Phe Gly Ile
 1               5                  10                  15
His Tyr Thr Val Phe Ala Phe Ser Pro Glu Asn Val Ser Lys Arg Glu
            20                  25                  30
Arg Leu Val Phe Glu Leu Gly Leu Gly Ser Phe Gln Gly Phe Val Val
        35                  40                  45
Ala Val Leu Tyr Cys Phe Leu Asn Gly Glu Val Gln Ala Glu Ile Lys
    50                  55                  60
Arg Lys Trp Arg Ser Trp Lys Val Asn Arg Tyr Phe
65                  70                  75
```

(2) INFORMATION FOR SEQ ID NO:12:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:12:

```
Asp Phe Lys His Arg His Pro Ser Leu Ala Ser Ser Gly Val Asn Gly
 1               5                  10                  15
Gly Thr Gln Leu Ser Ile Leu Ser Lys Ser Ser Ser Gln Ile Arg Met
            20                  25                  30
Ser
```

(2) INFORMATION FOR SEQ ID NO:13:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:13:

```
Met His Ser Asp Cys Ile Phe Lys Lys Glu Gln Ala Met Cys Leu Glu
 1               5                  10                  15
Lys Ile Gln Arg Val Asn Asp Leu Met Gly Leu Asn Asp
            20                  25
```

(2) INFORMATION FOR SEQ ID NO:14:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:14:

```
Met His Ser Asp Cys Ile Phe Lys Lys Glu Gln Ala Met Cys Leu Glu
```

```
          1                       5                          10                         15

Lys    Ile    Gln    Arg    Val    Asn    Asp    Leu    Met    Gly    Leu    Asn    Asp    Ser    Pro
                             20                          25                         30

Gly    Cys    Pro    Gly    Met    Trp    Asp    Asn    Ile    Thr    Cys    Trp    Lys    Pro    Ala    His
                      35                          40                                45

Val    Gly    Glu    Met    Val    Leu    Val    Ser    Cys    Pro    Glu    Leu    Phe    Arg    Ile    Phe
                      50                          55                                60

Asn    Pro    Asp    Gln    Val    Trp    Glu    Thr    Glu    Thr    Ile    Gly    Glu    Phe    Gly    Phe
        65                          70                                 75                                        80

Ala    Asp    Ser    Lys    Ser    Leu    Asp    Leu    Ser    Asp    Met    Arg    Val    Val    Ser    Arg
                             85                          90                                       95

Asn    Cys    Thr    Glu    Asp    Gly    Trp    Ser    Glu    Pro    Phe    Pro    His    Tyr    Phe    Asp
                             100                         105                        110

Ala    Cys    Gly    Phe    Glu    Glu    Tyr    Glu    Ser    Glu    Thr    Gly    Asp    Gln    Asp    Tyr
                      115                         120                               125

Tyr    Tyr    Leu    Ser    Val    Lys    Ala    Leu    Tyr    Thr    Val    Gly    Tyr    Ser    Thr    Ser
               130                         135                               140

Leu    Val    Thr    Leu    Thr    Thr    Ala    Met    Val    Ile    Leu    Cys    Arg    Phe    Arg    Lys
        145                                150                         155                                      160

Leu    His    Cys    Thr    Arg    Asn    Phe    Ile    His    Met    Asn    Leu    Phe    Val    Ser    Phe
                             165                         170                        175

Met    Leu    Arg    Ala    Ile    Ser    Val    Phe    Ile    Lys    Asp    Trp    Ile    Leu    Tyr    Ala
                      180                         185                               190

Glu    Gln    Asp    Ser    Asn    His    Cys    Phe    Val    Ser    Thr    Val    Glu    Cys    Lys    Ala
                      195                         200                               205

Val    Met    Val    Phe    Phe    His    Tyr    Cys    Val    Val    Ser    Asn    Tyr    Phe    Trp    Leu
               210                         215                               220

Phe    Ile    Glu    Gly    Leu    Tyr    Leu    Phe    Thr    Leu    Leu    Val    Glu    Thr    Phe    Phe
        225                                230                         235                                      240

Pro    Glu    Arg    Arg    Tyr    Phe    Tyr    Trp    Tyr    Ile    Ile    Gly    Trp    Gly    Thr
                             245                         250                                      255

Pro    Thr    Val    Cys    Val    Ser    Val    Trp    Ala    Met    Leu    Arg    Leu    Tyr    Phe    Asp
                      260                         265                               270

Asp    Thr    Gly    Cys    Trp    Asp    Met    Asn    Asp    Asn    Thr    Ala    Leu    Trp    Trp    Val
                      275                         280                               285

Ile    Lys    Gly    Pro    Val    Val    Gly    Ser    Ile    Met    Val    Asn    Phe    Val    Leu    Phe
               290                         295                               300

Ile    Gly    Ile    Ile    Val    Ile    Leu    Val    Gln    Lys    Leu    Gln    Ser    Pro    Asp    Met
        305                                310                         315                                      320

Gly    Gly    Asn    Glu    Ser    Ser    Ile    Tyr    Phe    Ser    Cys    Val    Gln    Lys    Cys    Tyr
                             325                         330                               335

Cys    Lys    Pro    Gln    Arg    Ala    Gln    Gln    His    Ser    Cys    Lys    Met    Ser    Glu    Leu
                      340                         345                               350

Ser    Thr    Ile    Thr    Leu    Arg    Leu    Ala    Arg    Ser    Thr    Leu    Leu    Leu    Ile    Pro
                      355                         360                               365

Leu    Phe    Gly    Ile    His    Tyr    Thr    Val    Phe    Ala    Phe    Ser    Pro    Glu    Asn    Val
               370                         375                               380

Ser    Lys    Arg    Glu    Arg    Leu    Val    Phe    Glu    Leu    Gly    Leu    Gly    Ser    Phe    Gln
        385                                390                         395                                      400

Gly    Phe    Val    Val    Ala    Val    Leu    Tyr    Cys    Phe    Leu    Asn    Gly    Glu    Val    Gln
                      405                         410                               415

Ala    Glu    Ile    Lys    Arg    Lys    Trp    Arg    Ser    Trp    Lys    Val    Asn    Arg    Tyr    Phe
                      420                         425                               430
```

```
Thr  Met  Asp  Phe  Lys  His  Arg  His  Pro  Ser  Leu  Ala  Ser  Ser  Gly  Val
     435                 440                      445

Asn  Gly  Gly  Thr  Gln  Leu  Ser  Ile  Leu  Ser  Lys  Ser  Ser  Ser  Gln  Ile
450                      455                      460

Arg  Met  Ser  Gly  Leu  Pro  Ala  Asp  Asn  Leu  Ala  Thr
465                      470                      475
```

( 2 ) INFORMATION FOR SEQ ID NO:15:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Arg  Gly  Gly  Arg  His  Trp  Pro  Glu  Pro  Cys  Arg  Leu  Arg  Ser
 1              5                    10                        15

Val  Met  Ala  Ser  Ile  Ala  Gln  Val  Ser  Leu  Ala  Ala  Leu  Leu  Leu  Leu
               20              25                       30

Pro  Met  Ala  Thr  Ala  Met  His  Ser  Asp  Cys  Ile  Phe  Lys  Lys  Glu  Gln
               35                  40                       45

Ala  Met  Cys  Leu  Glu  Lys  Ile  Gln  Arg  Val  Asn  Asp  Leu  Met  Gly  Leu
      50                  55                       60

Asn  Asp  Ser  Ser  Pro  Gly  Cys  Pro  Gly  Met  Trp  Asp  Asn  Ile  Thr  Cys
 65                  70                       75                             80

Trp  Lys  Pro  Ala  His  Val  Gly  Glu  Met  Val  Leu  Val  Ser  Cys  Pro  Glu
                    85                  90                            95

Leu  Phe  Arg  Ile  Phe  Asn  Pro  Asp  Gln  Val  Trp  Glu  Thr  Glu  Thr  Ile
               100                 105                      110

Gly  Glu  Phe  Gly  Phe  Ala  Asp  Ser  Lys  Ser  Leu  Asp  Leu  Ser  Asp  Met
          115                      120                      125

Arg  Val  Val  Ser  Arg  Asn  Cys  Thr  Glu  Asp  Gly  Trp  Ser  Glu  Pro  Phe
     130                      135                 140

Pro  His  Tyr  Phe  Asp  Ala  Cys  Gly  Phe  Glu  Glu  Tyr  Glu  Ser  Glu  Thr
145                      150                 155                          160

Gly  Asp  Gln  Asp  Tyr  Tyr  Tyr  Leu  Ser  Val  Lys  Ala  Leu  Tyr  Thr  Val
                    165                 170                      175

Gly  Tyr  Ser  Thr  Ser  Leu  Val  Thr  Leu  Thr  Thr  Ala  Met  Val  Ile  Leu
               180                 185                      190

Cys  Arg  Phe  Arg  Lys  Leu  His  Cys  Thr  Arg  Asn  Phe  Ile  His  Met  Asn
          195                 200                 205

Leu  Phe  Val  Ser  Phe  Met  Leu  Arg  Ala  Ile  Ser  Val  Phe  Ile  Lys  Asp
     210                      215                 220

Trp  Ile  Leu  Tyr  Ala  Glu  Gln  Asp  Ser  Asn  His  Cys  Phe  Val  Ser  Thr
225                      230                 235                          240

Val  Glu  Cys  Lys  Ala  Val  Met  Val  Phe  Phe  His  Tyr  Cys  Val  Val  Ser
                    245                 250                      255

Asn  Tyr  Phe  Trp  Leu  Phe  Ile  Glu  Gly  Leu  Tyr  Leu  Phe  Thr  Leu  Leu
               260                 265                      270

Val  Glu  Thr  Phe  Phe  Pro  Glu  Arg  Arg  Tyr  Phe  Tyr  Trp  Tyr  Ile  Ile
          275                      280                 285

Ile  Gly  Trp  Gly  Thr  Pro  Thr  Val  Cys  Val  Ser  Val  Trp  Ala  Met  Leu
          290                 295                 300

Arg  Leu  Tyr  Phe  Asp  Asp  Thr  Gly  Cys  Trp  Asp  Met  Asn  Asp  Asn  Thr
305                      310                 315                          320
```

Ala  Leu  Trp  Trp  Val  Ile  Lys  Gly  Pro  Val  Val  Gly  Ser  Ile  Met  Val
                                    325                      330                     335

Asn  Phe  Val  Leu  Phe  Ile  Gly  Ile  Ile  Val  Ile  Leu  Val  Gln  Lys  Leu
                                    340                 345                     350

Gln  Ser  Pro  Asp  Met  Gly  Gly  Asn  Glu  Ser  Ser  Ile  Tyr  Phe  Ser  Cys
                          355                      360                     365

Val  Gln  Lys  Cys  Tyr  Cys  Lys  Pro  Gln  Arg  Ala  Gln  His  Ser  Cys
                     370                      375                     380

Lys  Met  Ser  Glu  Leu  Ser  Thr  Ile  Thr  Leu  Arg  Leu  Ala  Arg  Ser  Thr
                385                      390                     395                          400

Leu  Leu  Leu  Ile  Pro  Leu  Phe  Gly  Ile  His  Tyr  Thr  Val  Phe  Ala  Phe
                                    405                      410                     415

Ser  Pro  Glu  Asn  Val  Ser  Lys  Arg  Glu  Arg  Leu  Val  Phe  Glu  Leu  Gly
                                    420                      425                     430

Leu  Gly  Ser  Phe  Gln  Gly  Phe  Val  Val  Ala  Val  Leu  Tyr  Cys  Phe  Leu
                               435                      440                     445

Asn  Gly  Glu  Val  Gln  Ala  Glu  Ile  Lys  Arg  Lys  Trp  Arg  Ser  Trp  Lys
                          450                      455                     460

Val  Asn  Arg  Tyr  Phe  Thr  Met  Asp  Phe  Lys  His  Arg  His  Pro  Ser  Leu
                465                      470                     475                          480

Ala  Ser  Ser  Gly  Val  Asn  Gly  Gly  Thr  Gln  Leu  Ser  Ile  Leu  Ser  Lys
                                    485                      490                     495

Ser  Ser  Ser  Gln  Ile  Arg  Met  Ser  Gly  Leu  Pro  Ala  Asp  Asn  Leu  Ala
                               500                      505                     510

Thr ( 2 ) INFORMATION FOR SEQ ID NO:16:

( i ) SEQUENCE CHARACTERISTICS:
            ( A ) LENGTH: 448 amino acids
            ( B ) TYPE: amino acid
            ( D ) TOPOLOGY: linear ( i i ) MOLECULE TYPE: protein ( x i ) SEQUENCE DESCRIPTION: SEQ ID NO:16:

Met  His  Ser  Asp  Cys  Ile  Phe  Lys  Lys  Glu  Gln  Ala  Met  Cys  Leu  Glu
                1                   5                    10                      15

Lys  Ile  Gln  Arg  Val  Asn  Asp  Leu  Met  Gly  Leu  Asn  Asp  Ser  Ser  Pro
                               20                      25                      30

Gly  Cys  Pro  Gly  Met  Trp  Asp  Asn  Ile  Thr  Cys  Trp  Lys  Pro  Ala  His
                          35                       40                     45

Val  Gly  Glu  Met  Val  Leu  Val  Ser  Cys  Pro  Glu  Leu  Phe  Arg  Ile  Phe
                     50                       55                      60

Asn  Pro  Asp  Gln  Val  Trp  Glu  Thr  Glu  Thr  Ile  Gly  Glu  Phe  Gly  Phe
                65                       70                      75                           80

Ala  Asp  Ser  Lys  Ser  Leu  Asp  Leu  Ser  Asp  Met  Arg  Val  Val  Ser  Arg
                                    85                       90                          95

Asn  Cys  Thr  Glu  Asp  Gly  Trp  Ser  Glu  Pro  Phe  Pro  His  Tyr  Phe  Asp
                               100                      105                     110

Ala  Cys  Gly  Phe  Glu  Glu  Tyr  Glu  Ser  Glu  Thr  Gly  Asp  Gln  Asp  Tyr
                          115                      120                     125

Tyr  Tyr  Leu  Ser  Val  Lys  Ala  Leu  Tyr  Thr  Val  Gly  Tyr  Ser  Thr  Ser
                     130                      135                     140

Leu  Val  Thr  Leu  Thr  Thr  Ala  Met  Val  Ile  Leu  Cys  Arg  Phe  Arg  Lys
                145                      150                      155                         160

| | | | | | | | | | | | | | | |
|---|---|---|---|---|---|---|---|---|---|---|---|---|---|---|
| Leu | His | Cys | Thr | Arg 165 | Asn | Phe | Ile | His | Met 170 | Asn | Leu | Phe | Val | Ser 175 | Phe |
| Met | Leu | Arg | Ala 180 | Ile | Ser | Val | Phe | Ile 185 | Lys | Asp | Trp | Ile | Leu 190 | Tyr | Ala |
| Glu | Gln | Asp 195 | Ser | Asn | His | Cys | Phe 200 | Val | Ser | Thr | Val | Glu 205 | Cys | Lys | Ala |
| Val | Met 210 | Val | Phe | Phe | His | Tyr 215 | Cys | Val | Val | Ser | Asn 220 | Tyr | Phe | Trp | Leu |
| Phe 225 | Ile | Glu | Gly | Leu | Tyr 230 | Leu | Phe | Thr | Leu | Leu 235 | Val | Glu | Thr | Phe | Phe 240 |
| Pro | Glu | Arg | Arg | Tyr 245 | Phe | Tyr | Trp | Tyr | Ile 250 | Ile | Ile | Gly | Trp | Gly 255 | Thr |
| Pro | Thr | Val | Cys 260 | Val | Ser | Val | Trp | Ala 265 | Met | Leu | Arg | Leu | Tyr 270 | Phe | Asp |
| Asp | Thr | Gly 275 | Cys | Trp | Asp | Met | Asn 280 | Asp | Asn | Thr | Ala | Leu 285 | Trp | Trp | Val |
| Ile | Lys 290 | Gly | Pro | Val | Val | Gly 295 | Ser | Ile | Met | Val | Asn 300 | Phe | Val | Leu | Phe |
| Ile 305 | Gly | Ile | Ile | Val | Ile 310 | Leu | Val | Gln | Lys | Leu 315 | Gln | Ser | Pro | Asp | Met 320 |
| Gly | Gly | Asn | Glu | Ser 325 | Ser | Ile | Tyr | Leu | Arg 330 | Leu | Ala | Arg | Ser | Thr 335 | Leu |
| Leu | Leu | Ile | Pro 340 | Leu | Phe | Gly | Ile | His 345 | Tyr | Thr | Val | Phe | Ala 350 | Phe | Ser |
| Pro | Glu | Asn 355 | Val | Ser | Lys | Arg | Glu 360 | Arg | Leu | Val | Phe | Glu 365 | Leu | Gly | Leu |
| Gly | Ser 370 | Phe | Gln | Gly | Phe | Val 375 | Val | Ala | Val | Leu | Tyr 380 | Cys | Phe | Leu | Asn |
| Gly 385 | Glu | Val | Gln | Ala | Glu 390 | Ile | Lys | Arg | Lys | Trp 395 | Arg | Ser | Trp | Lys | Val 400 |
| Asn | Arg | Tyr | Phe | Thr 405 | Met | Asp | Phe | Lys | His 410 | Arg | His | Pro | Ser | Leu 415 | Ala |
| Ser | Ser | Gly | Val 420 | Asn | Gly | Gly | Thr | Gln 425 | Leu | Ser | Ile | Leu | Ser 430 | Lys | Ser |
| Ser | Ser | Gln 435 | Ile | Arg | Met | Ser | Gly 440 | Leu | Pro | Ala | Asp | Asn 445 | Leu | Ala | Thr |

(2) INFORMATION FOR SEQ ID NO:17:

(i) SEQUENCE CHARACTERISTICS:
    (A) LENGTH: 485 amino acids
    (B) TYPE: amino acid
    (D) TOPOLOGY: linear (ii) MOLECULE TYPE: protein (xi) SEQUENCE DESCRIPTION: SEQ ID NO:17:

| | | | | | | | | | | | | | | |
|---|---|---|---|---|---|---|---|---|---|---|---|---|---|---|
| Met 1 | Arg | Gly | Gly | Arg 5 | His | Trp | Pro | Glu | Pro 10 | Pro | Cys | Arg | Leu | Arg 15 | Ser |
| Val | Met | Ala | Ser 20 | Ile | Ala | Gln | Val | Ser 25 | Leu | Ala | Ala | Leu | Leu 30 | Leu | Leu |
| Pro | Met | Ala | Thr 35 | Ala | Met | His | Ser | Asp 40 | Cys | Ile | Phe | Lys | Lys 45 | Glu | Gln |
| Ala | Met 50 | Cys | Leu | Glu | Lys | Ile 55 | Gln | Arg | Val | Asn | Asp 60 | Leu | Met | Gly | Leu |
| Asn | Asp | Ser | Ser | Pro 65 | Gly | Cys | Pro | Gly | Met 70 | Trp | Asp | Asn | Ile | Thr 75 | Cys |

```
  65                         70                        75                         80
Trp Lys Pro Ala His Val Gly Glu Met Val Leu Val Ser Cys Pro Glu
                 85                  90                      95
Leu Phe Arg Ile Phe Asn Pro Asp Gln Val Trp Glu Thr Glu Thr Ile
            100             105                 110
Gly Glu Phe Gly Phe Ala Asp Ser Lys Ser Leu Asp Leu Ser Asp Met
            115             120                 125
Arg Val Val Ser Arg Asn Cys Thr Glu Asp Gly Trp Ser Glu Pro Phe
    130             135                 140
Pro His Tyr Phe Asp Ala Cys Gly Phe Glu Glu Tyr Glu Ser Glu Thr
145                 150             155                     160
Gly Asp Gln Asp Tyr Tyr Tyr Leu Ser Val Lys Ala Leu Tyr Thr Val
                165             170                 175
Gly Tyr Ser Thr Ser Leu Val Thr Leu Thr Ala Met Val Ile Leu
            180             185                 190
Cys Arg Phe Arg Lys Leu His Cys Thr Arg Asn Phe Ile His Met Asn
        195                 200             205
Leu Phe Val Ser Phe Met Leu Arg Ala Ile Ser Val Phe Ile Lys Asp
    210             215                 220
Trp Ile Leu Tyr Ala Glu Gln Asp Ser Asn His Cys Phe Val Ser Thr
225                 230             235                     240
Val Glu Cys Lys Ala Val Met Val Phe Phe His Tyr Cys Val Val Ser
                245             250                 255
Asn Tyr Phe Trp Leu Phe Ile Glu Gly Leu Tyr Leu Phe Thr Leu Leu
            260             265                 270
Val Glu Thr Phe Phe Pro Glu Arg Arg Tyr Phe Tyr Trp Tyr Ile Ile
        275             280                 285
Ile Gly Trp Gly Thr Pro Thr Val Cys Val Ser Val Trp Ala Met Leu
    290             295                 300
Arg Leu Tyr Phe Asp Asp Thr Gly Cys Trp Asp Met Asn Asp Asn Thr
305                 310             315                     320
Ala Leu Trp Trp Val Ile Lys Gly Pro Val Val Gly Ser Ile Met Val
                325             330                 335
Asn Phe Val Leu Phe Ile Gly Ile Ile Val Ile Leu Val Gln Lys Leu
            340             345                 350
Gln Ser Pro Asp Met Gly Gly Asn Glu Ser Ser Ile Tyr Leu Arg Leu
        355             360                 365
Ala Arg Ser Thr Leu Leu Leu Ile Pro Leu Phe Gly Ile His Tyr Thr
    370             375                 380
Val Phe Ala Phe Ser Pro Glu Asn Val Ser Lys Arg Glu Arg Leu Val
385                 390             395                     400
Phe Glu Leu Gly Leu Gly Ser Phe Gln Gly Phe Val Val Ala Val Leu
                405             410                 415
Tyr Cys Phe Leu Asn Gly Glu Val Gln Ala Glu Ile Lys Arg Lys Trp
            420             425                 430
Arg Ser Trp Lys Val Asn Arg Tyr Phe Thr Met Asp Phe Lys His Arg
        435             440                 445
His Pro Ser Leu Ala Ser Ser Gly Val Asn Gly Gly Thr Gln Leu Ser
    450             455                 460
Ile Leu Ser Lys Ser Ser Ser Gln Ile Arg Met Ser Gly Leu Pro Ala
465                 470             475                     480
Asp Asn Leu Ala Thr
                485
```

( 2 ) INFORMATION FOR SEQ ID NO:18:

( i ) SEQUENCE CHARACTERISTICS:
        ( A ) LENGTH: 448 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met His Ser Asp Cys Ile Phe Lys Lys Glu Gln Ala Met Cys Leu Glu
 1               5                  10                      15

Arg Ile Gln Arg Ala Asn Asp Leu Met Gly Leu Asn Glu Ser Ser Pro
                20              25                  30

Gly Cys Pro Gly Met Trp Asp Asn Ile Thr Cys Trp Lys Pro Ala Gln
            35                  40                  45

Val Gly Glu Met Val Leu Val Ser Cys Pro Glu Val Phe Arg Ile Phe
        50                  55                  60

Asn Pro Asp Gln Val Trp Met Thr Glu Thr Ile Gly Asp Ser Gly Phe
65                      70                  75                  80

Ala Asp Ser Asn Ser Leu Glu Ile Thr Asp Met Gly Val Val Gly Arg
                85                  90                      95

Asn Cys Thr Glu Asp Gly Trp Ser Glu Pro Phe Pro His Tyr Phe Asp
            100                 105                 110

Ala Cys Gly Phe Asp Asp Tyr Glu Pro Glu Ser Gly Asp Gln Asp Tyr
        115                 120                 125

Tyr Tyr Leu Ser Val Lys Ala Leu Tyr Thr Val Gly Tyr Ser Thr Ser
    130                 135                 140

Leu Ala Thr Leu Thr Thr Ala Met Val Ile Leu Cys Arg Phe Arg Lys
145                 150                 155                 160

Leu His Cys Thr Arg Asn Phe Ile His Met Asn Leu Phe Val Ser Phe
                165                 170                 175

Met Leu Arg Ala Ile Ser Val Phe Ile Lys Asp Trp Ile Leu Tyr Ala
            180                 185                 190

Glu Gln Asp Ser Ser His Cys Phe Val Ser Thr Val Glu Cys Lys Ala
        195                 200                 205

Val Met Val Phe Phe His Tyr Cys Val Val Ser Asn Tyr Phe Trp Leu
    210                 215                 220

Phe Ile Glu Gly Leu Tyr Leu Phe Thr Leu Leu Val Glu Thr Phe Phe
225                 230                 235                 240

Pro Glu Arg Arg Tyr Phe Tyr Trp Tyr Thr Ile Ile Gly Trp Gly Thr
                245                 250                 255

Pro Thr Val Cys Val Thr Val Trp Ala Val Leu Arg Leu Tyr Phe Asp
            260                 265                 270

Asp Ala Gly Cys Trp Asp Met Asn Asp Ser Thr Ala Leu Trp Trp Val
        275                 280                 285

Ile Lys Gly Pro Val Val Gly Ser Ile Met Val Asn Phe Val Leu Phe
    290                 295                 300

Ile Gly Ile Ile Ile Ile Leu Val Gln Lys Leu Gln Ser Pro Asp Met
305                 310                 315                 320

Gly Gly Asn Glu Ser Ser Ile Tyr Leu Arg Leu Ala Arg Ser Thr Leu
                325                 330                 335

Leu Leu Ile Pro Leu Phe Gly Ile His Tyr Thr Val Phe Ala Phe Ser
            340                 345                 350

Pro Glu Asn Val Ser Lys Arg Glu Arg Leu Val Phe Glu Leu Gly Leu
        355                 360                 365
```

Gly Ser Phe Gln Gly Phe Val Val Ala Val Leu Tyr Cys Phe Leu Asn
370                     375                     380

Gly Glu Val Gln Ala Glu Ile Lys Arg Lys Trp Arg Ser Trp Lys Val
385                 390                     395                 400

Asn Arg Tyr Phe Thr Met Asp Phe Lys His Arg His Pro Ser Leu Ala
            405                     410                 415

Ser Ser Gly Val Asn Gly Gly Thr Gln Leu Ser Ile Leu Ser Lys Ser
            420                 425                     430

Ser Ser Gln Leu Arg Met Ser Ser Leu Pro Ala Asp Asn Leu Ala Thr
        435                 440                 445

(2) INFORMATION FOR SEQ ID NO:19:

(i) SEQUENCE CHARACTERISTICS:
    (A) LENGTH: 467 amino acids
    (B) TYPE: amino acid
    (D) TOPOLOGY: linear (ii) MOLECULE TYPE: protein (xi) SEQUENCE DESCRIPTION: SEQ ID NO:19:

Met Ala Arg Val Leu Gln Leu Ser Leu Thr Ala Leu Leu Leu Pro Val
1               5                   10                  15

Ala Ile Ala Met His Ser Asp Cys Ile Phe Lys Lys Glu Gln Ala Met
            20                  25                  30

Cys Leu Glu Arg Ile Gln Arg Ala Asn Asp Leu Met Gly Leu Asn Glu
        35                  40                  45

Ser Ser Pro Gly Cys Pro Gly Met Trp Asp Asn Ile Thr Cys Trp Lys
    50                  55                  60

Pro Ala Gln Val Gly Glu Met Val Leu Val Ser Cys Pro Glu Val Phe
65                  70                  75                  80

Arg Ile Phe Asn Pro Asp Gln Val Trp Met Thr Glu Thr Ile Gly Asp
                85                  90                  95

Ser Gly Phe Ala Asp Ser Asn Ser Leu Glu Ile Thr Asp Met Gly Val
            100                 105                 110

Val Gly Arg Asn Cys Thr Glu Asp Gly Trp Ser Glu Pro Phe Pro His
        115                 120                 125

Tyr Phe Asp Ala Cys Gly Phe Asp Asp Tyr Glu Pro Glu Ser Gly Asp
    130                 135                 140

Gln Asp Tyr Tyr Tyr Leu Ser Val Lys Ala Leu Tyr Thr Val Gly Tyr
145                 150                 155                 160

Ser Thr Ser Leu Ala Thr Leu Thr Thr Ala Met Val Ile Leu Cys Arg
                165                 170                 175

Phe Arg Lys Leu His Cys Thr Arg Asn Phe Ile His Met Asn Leu Phe
            180                 185                 190

Val Ser Phe Met Leu Arg Ala Ile Ser Val Phe Ile Lys Asp Trp Ile
        195                 200                 205

Leu Tyr Ala Glu Gln Asp Ser Ser His Cys Phe Val Ser Thr Val Glu
    210                 215                 220

Cys Lys Ala Val Met Val Phe Phe His Tyr Cys Val Val Ser Asn Tyr
225                 230                 235                 240

Phe Trp Leu Phe Ile Glu Gly Leu Tyr Leu Phe Thr Leu Leu Val Glu
                245                 250                 255

Thr Phe Phe Pro Glu Arg Arg Tyr Phe Tyr Trp Tyr Thr Ile Ile Gly
            260                 265                 270

Trp Gly Thr Pro Thr Val Cys Val Thr Val Trp Ala Val Leu Arg Leu

|     | 275 |     |     |     | 280 |     |     |     | 285 |     |     |     |
|---|---|---|---|---|---|---|---|---|---|---|---|---|

Tyr Phe Asp Asp Ala Gly Cys Trp Asp Met Asn Asp Ser Thr Ala Leu
    290                 295             300

Trp Trp Val Ile Lys Gly Pro Val Val Gly Ser Ile Met Val Asn Phe
305             310             315                         320

Val Leu Phe Ile Gly Ile Ile Ile Ile Leu Val Gln Lys Leu Gln Ser
                325                 330                 335

Pro Asp Met Gly Gly Asn Glu Ser Ser Ile Tyr Leu Arg Leu Ala Arg
            340             345                 350

Ser Thr Leu Leu Leu Ile Pro Leu Phe Gly Ile His Tyr Thr Val Phe
        355             360             365

Ala Phe Ser Pro Glu Asn Val Ser Lys Arg Glu Arg Leu Val Phe Glu
    370             375             380

Leu Gly Leu Gly Ser Phe Gln Gly Phe Val Val Ala Val Leu Tyr Cys
385             390             395                         400

Phe Leu Asn Gly Glu Val Gln Ala Glu Ile Lys Arg Lys Trp Arg Ser
            405             410             415

Trp Lys Val Asn Arg Tyr Phe Thr Met Asp Phe Lys His Arg His Pro
            420             425             430

Ser Leu Ala Ser Ser Gly Val Asn Gly Gly Thr Gln Leu Ser Ile Leu
        435             440             445

Ser Lys Ser Ser Ser Gln Leu Arg Met Ser Ser Leu Pro Ala Asp Asn
    450             455             460

Leu Ala Thr
465

( 2 ) INFORMATION FOR SEQ ID NO:20:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Met His Ser Asp Cys Ile Phe Lys Lys Glu Gln Ala Met Cys Leu Glu
1               5                   10                  15

Arg Ile Gln Arg Ala Asn Asp Leu Met Gly Leu Asn Glu Ser Ser Pro
            20              25                  30

Gly Cys Pro Gly Met Trp Asp Asn Ile Thr Cys Trp Lys Pro Ala Gln
        35              40              45

Val Gly Glu Met Val Leu Val Ser Cys Pro Glu Val Phe Arg Ile Phe
    50              55              60

Asn Pro Asp Gln Val Trp Met Thr Glu Thr Ile Gly Asp Ser Gly Phe
65              70              75                          80

Ala Asp Ser Asn Ser Leu Glu Ile Thr Asp Met Gly Val Val Gly Arg
            85              90                  95

Asn Cys Thr Glu Asp Gly Trp Ser Glu Pro Phe Pro His Tyr Phe Asp
            100             105             110

Ala Cys Gly Phe Asp Asp Tyr Glu Pro Glu Ser Gly Asp Gln Asp Tyr
        115             120             125

Tyr Tyr Leu Ser Val Lys Ala Leu Tyr Thr Val Gly Tyr Ser Thr Ser
    130             135             140

Leu Ala Thr Leu Thr Thr Ala Met Val Ile Leu Cys Arg Phe Arg Lys
145             150             155                         160

|     |     |     |     |     |     |     |     |     |     |     |     |     |     |     |
|-----|-----|-----|-----|-----|-----|-----|-----|-----|-----|-----|-----|-----|-----|-----|
| Leu | His | Cys | Thr | Arg | Asn | Phe | Ile | His | Met | Asn | Leu | Phe | Val | Ser | Phe |
|     |     |     |     | 165 |     |     |     |     | 170 |     |     |     | 175 |     |
| Met | Leu | Arg | Ala | Ile | Ser | Val | Phe | Ile | Lys | Asp | Trp | Ile | Leu | Tyr | Ala |
|     |     |     | 180 |     |     |     | 185 |     |     |     |     | 190 |     |     |
| Glu | Gln | Asp | Ser | Ser | His | Cys | Phe | Val | Ser | Thr | Val | Glu | Cys | Lys | Ala |
|     |     | 195 |     |     |     | 200 |     |     |     |     | 205 |     |     |     |
| Val | Met | Val | Phe | Phe | His | Tyr | Cys | Val | Val | Ser | Asn | Tyr | Phe | Trp | Leu |
|     | 210 |     |     |     | 215 |     |     |     |     | 220 |     |     |     |     |
| Phe | Ile | Glu | Gly | Leu | Tyr | Leu | Phe | Thr | Leu | Leu | Val | Glu | Thr | Phe | Phe |
| 225 |     |     |     | 230 |     |     |     | 235 |     |     |     |     | 240 |
| Pro | Glu | Arg | Arg | Tyr | Phe | Tyr | Trp | Tyr | Thr | Ile | Ile | Gly | Trp | Gly | Thr |
|     |     |     | 245 |     |     |     | 250 |     |     |     | 255 |
| Pro | Thr | Val | Cys | Val | Thr | Val | Trp | Ala | Val | Leu | Arg | Leu | Tyr | Phe | Asp |
|     |     |     | 260 |     |     |     | 265 |     |     |     | 270 |
| Asp | Ala | Gly | Cys | Trp | Asp | Met | Asn | Asp | Ser | Thr | Ala | Leu | Trp | Trp | Val |
|     |     | 275 |     |     |     | 280 |     |     |     |     | 285 |
| Ile | Lys | Gly | Pro | Val | Val | Gly | Ser | Ile | Met | Val | Asn | Phe | Val | Leu | Phe |
|     | 290 |     |     |     | 295 |     |     |     |     | 300 |
| Ile | Gly | Ile | Ile | Ile | Ile | Leu | Val | Gln | Lys | Leu | Gln | Ser | Pro | Asp | Met |
| 305 |     |     |     | 310 |     |     |     |     | 315 |     |     |     |     | 320 |
| Gly | Gly | Asn | Glu | Ser | Ser | Ile | Tyr | Phe | Ser | Cys | Val | Gln | Lys | Cys | Tyr |
|     |     |     |     | 325 |     |     |     | 330 |     |     |     | 335 |
| Cys | Lys | Pro | Gln | Arg | Ala | Gln | Gln | His | Ser | Cys | Lys | Met | Ser | Glu | Leu |
|     |     |     | 340 |     |     |     |     | 345 |     |     |     | 350 |
| Ser | Thr | Ile | Thr | Leu | Arg | Leu | Ala | Arg | Ser | Thr | Leu | Leu | Leu | Ile | Pro |
|     |     | 355 |     |     |     | 360 |     |     |     |     | 365 |
| Leu | Phe | Gly | Ile | His | Tyr | Thr | Val | Phe | Ala | Phe | Ser | Pro | Glu | Asn | Val |
|     | 370 |     |     |     | 375 |     |     |     |     | 380 |
| Ser | Lys | Arg | Glu | Arg | Leu | Val | Phe | Glu | Leu | Gly | Leu | Gly | Ser | Phe | Gln |
| 385 |     |     |     |     | 390 |     |     |     |     | 395 |     |     |     |     | 400 |
| Gly | Phe | Val | Val | Ala | Val | Leu | Tyr | Cys | Phe | Leu | Asn | Gly | Glu | Val | Gln |
|     |     |     |     | 405 |     |     |     |     | 410 |     |     |     | 415 |
| Ala | Glu | Ile | Lys | Arg | Lys | Trp | Arg | Ser | Trp | Lys | Val | Asn | Arg | Tyr | Phe |
|     |     |     | 420 |     |     |     |     | 425 |     |     |     | 430 |
| Thr | Met | Asp | Phe | Lys | His | Arg | His | Pro | Ser | Leu | Ala | Ser | Ser | Gly | Val |
|     |     | 435 |     |     |     |     | 440 |     |     |     | 445 |
| Asn | Gly | Gly | Thr | Gln | Leu | Ser | Ile | Leu | Ser | Lys | Ser | Ser | Ser | Gln | Leu |
|     | 450 |     |     |     |     | 455 |     |     |     |     | 460 |
| Arg | Met | Ser | Ser | Leu | Pro | Ala | Asp | Asn | Leu | Ala | Thr |
| 465 |     |     |     |     | 470 |     |     |     | 475 |

( 2 ) INFORMATION FOR SEQ ID NO:21:

( i ) SEQUENCE CHARACTERISTICS:
        ( A ) LENGTH: 495 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ala | Arg | Val | Leu | Gln | Leu | Ser | Leu | Thr | Ala | Leu | Leu | Leu | Pro | Val |
| 1   |     |     |     | 5   |     |     |     |     | 10  |     |     |     |     | 15  |
| Ala | Ile | Ala | Met | His | Ser | Asp | Cys | Ile | Phe | Lys | Lys | Glu | Gln | Ala | Met |
|     |     |     | 20  |     |     |     |     | 25  |     |     |     |     | 30  |
| Cys | Leu | Glu | Arg | Ile | Gln | Arg | Ala | Asn | Asp | Leu | Met | Gly | Leu | Asn | Glu |
|     |     | 35  |     |     |     |     | 40  |     |     |     |     | 45  |

```
Ser  Ser  Pro  Gly  Cys  Pro  Gly  Met  Trp  Asp  Asn  Ile  Thr  Cys  Trp  Lys
     50                  55                      60

Pro  Ala  Gln  Val  Gly  Glu  Met  Val  Leu  Val  Ser  Cys  Pro  Glu  Val  Phe
65                       70                  75                           80

Arg  Ile  Phe  Asn  Pro  Asp  Gln  Val  Trp  Met  Thr  Glu  Thr  Ile  Gly  Asp
               85                      90                           95

Ser  Gly  Phe  Ala  Asp  Ser  Asn  Ser  Leu  Glu  Ile  Thr  Asp  Met  Gly  Val
               100                 105                      110

Val  Gly  Arg  Asn  Cys  Thr  Glu  Asp  Gly  Trp  Ser  Glu  Pro  Phe  Pro  His
          115                 120                      125

Tyr  Phe  Asp  Ala  Cys  Gly  Phe  Asp  Asp  Tyr  Glu  Pro  Glu  Ser  Gly  Asp
     130                 135                      140

Gln  Asp  Tyr  Tyr  Tyr  Leu  Ser  Val  Lys  Ala  Leu  Tyr  Thr  Val  Gly  Tyr
145                 150                      155                          160

Ser  Thr  Ser  Leu  Ala  Thr  Leu  Thr  Thr  Ala  Met  Val  Ile  Leu  Cys  Arg
                    165                      170                     175

Phe  Arg  Lys  Leu  His  Cys  Thr  Arg  Asn  Phe  Ile  His  Met  Asn  Leu  Phe
               180                      185                      190

Val  Ser  Phe  Met  Leu  Arg  Ala  Ile  Ser  Val  Phe  Ile  Lys  Asp  Trp  Ile
          195                      200                 205

Leu  Tyr  Ala  Glu  Gln  Asp  Ser  Ser  His  Cys  Phe  Val  Ser  Thr  Val  Glu
     210                      215                 220

Cys  Lys  Ala  Val  Met  Val  Phe  Phe  His  Tyr  Cys  Val  Val  Ser  Asn  Tyr
225                      230                      235                     240

Phe  Trp  Leu  Phe  Ile  Glu  Gly  Leu  Tyr  Leu  Phe  Thr  Leu  Leu  Val  Glu
                    245                 250                           255

Thr  Phe  Phe  Pro  Glu  Arg  Arg  Tyr  Phe  Tyr  Trp  Tyr  Thr  Ile  Ile  Gly
               260                 265                      270

Trp  Gly  Thr  Pro  Thr  Val  Cys  Val  Thr  Val  Trp  Ala  Val  Leu  Arg  Leu
          275                      280                      285

Tyr  Phe  Asp  Asp  Ala  Gly  Cys  Trp  Asp  Met  Asn  Asp  Ser  Thr  Ala  Leu
     290                 295                      300

Trp  Trp  Val  Ile  Lys  Gly  Pro  Val  Val  Gly  Ser  Ile  Met  Val  Asn  Phe
305                      310                 315                          320

Val  Leu  Phe  Ile  Gly  Ile  Ile  Ile  Ile  Leu  Val  Gln  Lys  Leu  Gln  Ser
               325                      330                          335

Pro  Asp  Met  Gly  Gly  Asn  Glu  Ser  Ser  Ile  Tyr  Phe  Ser  Cys  Val  Gln
               340                      345                 350

Lys  Cys  Tyr  Cys  Lys  Pro  Gln  Arg  Ala  Gln  Gln  His  Ser  Cys  Lys  Met
          355                 360                      365

Ser  Glu  Leu  Ser  Thr  Ile  Thr  Leu  Arg  Leu  Ala  Arg  Ser  Thr  Leu  Leu
     370                 375                      380

Leu  Ile  Pro  Leu  Phe  Gly  Ile  His  Tyr  Thr  Val  Phe  Ala  Phe  Ser  Pro
385                      390                      395                      400

Glu  Asn  Val  Ser  Lys  Arg  Glu  Arg  Leu  Val  Phe  Glu  Leu  Gly  Leu  Gly
               405                      410                          415

Ser  Phe  Gln  Gly  Phe  Val  Val  Ala  Val  Leu  Tyr  Cys  Phe  Leu  Asn  Gly
               420                      425                      430

Glu  Val  Gln  Ala  Glu  Ile  Lys  Arg  Lys  Trp  Arg  Ser  Trp  Lys  Val  Asn
               435                 440                      445

Arg  Tyr  Phe  Thr  Met  Asp  Phe  Lys  His  Arg  His  Pro  Ser  Leu  Ala  Ser
     450                 455                      460

Ser  Gly  Val  Asn  Gly  Gly  Thr  Gln  Leu  Ser  Ile  Leu  Ser  Lys  Ser  Ser
```

```
                    465                     470                     475                     480
      Ser  Gln  Leu  Arg  Met  Ser  Ser  Leu  Pro  Ala  Asp  Asn  Leu  Ala  Thr
                          485                     490                     495
```

( 2 ) INFORMATION FOR SEQ ID NO:22:

( i ) SEQUENCE CHARACTERISTICS:
        ( A ) LENGTH: 448 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
      Met  His  Ser  Asp  Cys  Ile  Phe  Lys  Lys  Glu  Gln  Ala  Met  Cys  Leu  Glu
      1                   5                        10                       15

Lys  Ile  Gln  Arg  Ala  Asn  Glu  Leu  Met  Gly  Phe  Asn  Asp  Ser  Ser  Pro
                          20                       25                       30

Gly  Cys  Pro  Gly  Met  Trp  Asp  Asn  Ile  Thr  Cys  Trp  Lys  Pro  Ala  His
                     35                       40                       45

Val  Gly  Glu  Met  Val  Leu  Val  Ser  Cys  Pro  Glu  Leu  Phe  Arg  Ile  Phe
                50                       55                       60

Asn  Pro  Asp  Gln  Val  Trp  Glu  Thr  Glu  Thr  Ile  Gly  Glu  Ser  Asp  Phe
      65                       70                       75                       80

Gly  Asp  Ser  Asn  Ser  Leu  Asp  Leu  Ser  Asp  Met  Gly  Val  Val  Ser  Arg
                          85                       90                       95

Asn  Cys  Thr  Glu  Asp  Gly  Trp  Ser  Glu  Pro  Phe  Pro  His  Tyr  Phe  Asp
                     100                      105                      110

Ala  Cys  Gly  Phe  Asp  Glu  Tyr  Glu  Ser  Glu  Thr  Gly  Asp  Gln  Asp  Tyr
                     115                      120                      125

Tyr  Tyr  Leu  Ser  Val  Lys  Ala  Leu  Tyr  Thr  Val  Gly  Tyr  Ser  Thr  Ser
                130                      135                      140

Leu  Val  Thr  Leu  Thr  Thr  Ala  Met  Val  Ile  Leu  Cys  Arg  Phe  Arg  Lys
      145                      150                      155                      160

Leu  His  Cys  Thr  Arg  Asn  Phe  Ile  His  Met  Asn  Leu  Phe  Val  Ser  Phe
                          165                      170                      175

Met  Leu  Arg  Ala  Ile  Ser  Val  Phe  Ile  Lys  Asp  Trp  Ile  Leu  Tyr  Ala
                     180                      185                      190

Glu  Gln  Asp  Ser  Asn  His  Cys  Phe  Ile  Ser  Thr  Val  Glu  Cys  Lys  Ala
                     195                      200                      205

Val  Met  Val  Phe  Phe  His  Tyr  Cys  Val  Val  Ser  Asn  Tyr  Phe  Trp  Leu
                210                      215                      220

Phe  Ile  Glu  Gly  Leu  Tyr  Leu  Phe  Thr  Leu  Leu  Val  Glu  Thr  Phe  Phe
      225                      230                      235                      240

Pro  Glu  Arg  Arg  Tyr  Phe  Tyr  Trp  Tyr  Thr  Ile  Ile  Gly  Trp  Gly  Thr
                          245                      250                      255

Pro  Thr  Val  Cys  Val  Thr  Val  Trp  Ala  Thr  Leu  Arg  Leu  Tyr  Phe  Asp
                     260                      265                      270

Asp  Thr  Gly  Cys  Trp  Asp  Met  Asn  Asp  Ser  Thr  Ala  Leu  Trp  Trp  Val
                     275                      280                      285

Ile  Lys  Gly  Pro  Val  Val  Gly  Ser  Ile  Met  Val  Asn  Phe  Val  Leu  Phe
                290                      295                      300

Ile  Gly  Ile  Ile  Val  Ile  Leu  Val  Gln  Lys  Leu  Gln  Ser  Pro  Asp  Met
      305                      310                      315                      320

Gly  Gly  Asn  Glu  Ser  Ser  Ile  Tyr  Leu  Arg  Leu  Ala  Arg  Ser  Thr  Leu
                          325                      330                      335
```

Leu Leu Ile Pro Leu Phe Gly Ile His Tyr Thr Val Phe Ala Phe Ser
        340             345                 350

Pro Glu Asn Val Ser Lys Arg Glu Arg Leu Val Phe Glu Leu Gly Leu
        355             360             365

Gly Ser Phe Gln Gly Phe Val Ala Val Leu Tyr Cys Phe Leu Asn
        370             375             380

Gly Glu Val Gln Ala Glu Ile Lys Arg Lys Trp Arg Ser Trp Lys Val
385                 390             395                 400

Asn Arg Tyr Phe Ala Val Asp Phe Lys His Arg His Pro Ser Leu Ala
            405             410                 415

Ser Ser Gly Val Asn Gly Gly Thr Gln Leu Ser Ile Leu Ser Lys Ser
            420             425             430

Ser Ser Gln Ile Arg Met Ser Gly Leu Pro Ala Asp Asn Leu Ala Thr
        435             440             445

( 2 ) INFORMATION FOR SEQ ID NO:23:

( i ) SEQUENCE CHARACTERISTICS:
       ( A ) LENGTH: 525 amino acids
       ( B ) TYPE: amino acid
       ( D ) TOPOLOGY: linear ( i i ) MOLECULE TYPE: protein ( x i ) SEQUENCE DESCRIPTION: SEQ ID NO:23:

Met Ala Gly Val Val His Val Ser Leu Ala Ala His Cys Gly Ala Cys
1               5                   10                  15

Pro Trp Gly Arg Gly Arg Leu Arg Lys Gly Arg Ala Ala Cys Lys Ser
            20              25                  30

Ala Ala Gln Arg His Ile Gly Ala Asp Leu Pro Leu Leu Ser Val Gly
        35              40                  45

Gly Gln Trp Cys Trp Pro Arg Ser Val Met Ala Gly Val Val His Val
    50              55                  60

Ser Leu Ala Ala Leu Leu Leu Leu Pro Met Ala Pro Ala Met His Ser
65              70              75                      80

Asp Cys Ile Phe Lys Lys Glu Gln Ala Met Cys Leu Glu Lys Ile Gln
            85                  90                  95

Arg Ala Asn Glu Leu Met Gly Phe Asn Asp Ser Ser Pro Gly Cys Pro
            100             105                 110

Gly Met Trp Asp Asn Ile Thr Cys Trp Lys Pro Ala His Val Gly Glu
        115                 120             125

Met Val Leu Val Ser Cys Pro Glu Leu Phe Arg Ile Phe Asn Pro Asp
    130                 135             140

Gln Val Trp Glu Thr Glu Thr Ile Gly Glu Ser Asp Phe Gly Asp Ser
145             150                 155                 160

Asn Ser Leu Asp Leu Ser Asp Met Gly Val Val Ser Arg Asn Cys Thr
            165             170                 175

Glu Asp Gly Trp Ser Glu Pro Phe Pro His Tyr Phe Asp Ala Cys Gly
            180             185                 190

Phe Asp Glu Tyr Glu Ser Glu Thr Gly Asp Gln Asp Tyr Tyr Leu
        195             200             205

Ser Val Lys Ala Leu Tyr Thr Val Gly Tyr Ser Thr Ser Leu Val Thr
        210             215             220

Leu Thr Thr Ala Met Val Ile Leu Cys Arg Phe Arg Lys Leu His Cys
225             230                 235                 240

Thr Arg Asn Phe Ile His Met Asn Leu Phe Val Ser Phe Met Leu Arg
            245             250                 255

|       |       |       |       |       |       |       |       |       |       |       |       |       |       |       |       |
|-------|-------|-------|-------|-------|-------|-------|-------|-------|-------|-------|-------|-------|-------|-------|-------|
| Ala   | Ile   | Ser   | Val   | Phe   | Ile   | Lys   | Asp   | Trp   | Ile   | Leu   | Tyr   | Ala   | Glu   | Gln   | Asp   |
|       |       |       | 260   |       |       |       | 265   |       |       |       |       | 270   |       |       |       |
| Ser   | Asn   | His   | Cys   | Phe   | Ile   | Ser   | Thr   | Val   | Glu   | Cys   | Lys   | Ala   | Val   | Met   | Val   |
|       |       | 275   |       |       |       |       | 280   |       |       |       |       | 285   |       |       |       |
| Phe   | Phe   | His   | Tyr   | Cys   | Val   | Val   | Ser   | Asn   | Tyr   | Phe   | Trp   | Leu   | Phe   | Ile   | Glu   |
|       | 290   |       |       |       |       | 295   |       |       |       |       | 300   |       |       |       |       |
| Gly   | Leu   | Tyr   | Leu   | Phe   | Thr   | Leu   | Leu   | Val   | Glu   | Thr   | Phe   | Phe   | Pro   | Glu   | Arg   |
| 305   |       |       |       |       | 310   |       |       |       |       | 315   |       |       |       |       | 320   |
| Arg   | Tyr   | Phe   | Tyr   | Trp   | Tyr   | Thr   | Ile   | Ile   | Gly   | Trp   | Gly   | Thr   | Pro   | Thr   | Val   |
|       |       |       |       | 325   |       |       |       |       | 330   |       |       |       |       | 335   |       |
| Cys   | Val   | Thr   | Val   | Trp   | Ala   | Thr   | Leu   | Arg   | Leu   | Tyr   | Phe   | Asp   | Asp   | Thr   | Gly   |
|       |       |       | 340   |       |       |       |       | 345   |       |       |       |       | 350   |       |       |
| Cys   | Trp   | Asp   | Met   | Asn   | Asp   | Ser   | Thr   | Ala   | Leu   | Trp   | Trp   | Val   | Ile   | Lys   | Gly   |
|       |       | 355   |       |       |       |       | 360   |       |       |       |       | 365   |       |       |       |
| Pro   | Val   | Val   | Gly   | Ser   | Ile   | Met   | Val   | Asn   | Phe   | Val   | Leu   | Phe   | Ile   | Gly   | Ile   |
|       | 370   |       |       |       |       | 375   |       |       |       |       | 380   |       |       |       |       |
| Ile   | Val   | Ile   | Leu   | Val   | Gln   | Lys   | Leu   | Gln   | Ser   | Pro   | Asp   | Met   | Gly   | Gly   | Asn   |
| 385   |       |       |       |       | 390   |       |       |       |       | 395   |       |       |       |       | 400   |
| Glu   | Ser   | Ser   | Ile   | Tyr   | Leu   | Arg   | Leu   | Ala   | Arg   | Ser   | Thr   | Leu   | Leu   | Leu   | Ile   |
|       |       |       |       | 405   |       |       |       |       | 410   |       |       |       |       | 415   |       |
| Pro   | Leu   | Phe   | Gly   | Ile   | His   | Tyr   | Thr   | Val   | Phe   | Ala   | Phe   | Ser   | Pro   | Glu   | Asn   |
|       |       |       | 420   |       |       |       |       | 425   |       |       |       |       | 430   |       |       |
| Val   | Ser   | Lys   | Arg   | Glu   | Arg   | Leu   | Val   | Phe   | Glu   | Leu   | Gly   | Leu   | Gly   | Ser   | Phe   |
|       |       | 435   |       |       |       |       | 440   |       |       |       |       | 445   |       |       |       |
| Gln   | Gly   | Phe   | Val   | Val   | Ala   | Val   | Leu   | Tyr   | Cys   | Phe   | Leu   | Asn   | Gly   | Glu   | Val   |
|       | 450   |       |       |       |       | 455   |       |       |       |       | 460   |       |       |       |       |
| Gln   | Ala   | Glu   | Ile   | Lys   | Arg   | Lys   | Trp   | Arg   | Ser   | Trp   | Lys   | Val   | Asn   | Arg   | Tyr   |
| 465   |       |       |       |       | 470   |       |       |       |       | 475   |       |       |       |       | 480   |
| Phe   | Ala   | Val   | Asp   | Phe   | Lys   | His   | Arg   | His   | Pro   | Ser   | Leu   | Ala   | Ser   | Ser   | Gly   |
|       |       |       |       | 485   |       |       |       |       | 490   |       |       |       |       | 495   |       |
| Val   | Asn   | Gly   | Gly   | Thr   | Gln   | Leu   | Ser   | Ile   | Leu   | Ser   | Lys   | Ser   | Ser   | Ser   | Gln   |
|       |       |       | 500   |       |       |       |       | 505   |       |       |       |       | 510   |       |       |
| Ile   | Arg   | Met   | Ser   | Gly   | Leu   | Pro   | Ala   | Asp   | Asn   | Leu   | Ala   | Thr   |       |       |       |
|       |       | 515   |       |       |       |       | 520   |       |       |       |       | 525   |       |       |       |

( 2 ) INFORMATION FOR SEQ ID NO:24:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

|       |       |       |       |       |       |       |       |       |       |       |       |       |       |       |       |
|-------|-------|-------|-------|-------|-------|-------|-------|-------|-------|-------|-------|-------|-------|-------|-------|
| Met   | His   | Ser   | Asp   | Cys   | Ile   | Phe   | Lys   | Lys   | Glu   | Gln   | Ala   | Met   | Cys   | Leu   | Glu   |
| 1     |       |       |       | 5     |       |       |       |       | 10    |       |       |       |       | 15    |       |
| Lys   | Ile   | Gln   | Arg   | Ala   | Asn   | Glu   | Leu   | Met   | Gly   | Phe   | Asn   | Asp   | Ser   | Ser   | Pro   |
|       |       |       | 20    |       |       |       |       | 25    |       |       |       |       | 30    |       |       |
| Gly   | Cys   | Pro   | Gly   | Met   | Trp   | Asp   | Asn   | Ile   | Thr   | Cys   | Trp   | Lys   | Pro   | Ala   | His   |
|       |       | 35    |       |       |       |       | 40    |       |       |       |       | 45    |       |       |       |
| Val   | Gly   | Glu   | Met   | Val   | Leu   | Val   | Ser   | Cys   | Pro   | Glu   | Leu   | Phe   | Arg   | Ile   | Phe   |
|       | 50    |       |       |       |       | 55    |       |       |       |       | 60    |       |       |       |       |
| Asn   | Pro   | Asp   | Gln   | Val   | Trp   | Glu   | Thr   | Glu   | Thr   | Ile   | Gly   | Glu   | Ser   | Asp   | Phe   |
| 65    |       |       |       |       | 70    |       |       |       |       | 75    |       |       |       |       | 80    |
| Gly   | Asp   | Ser   | Asn   | Ser   | Leu   | Asp   | Leu   | Ser   | Asp   | Met   | Gly   | Val   | Val   | Ser   | Arg   |

|   |   |   |   |   | 85 |   |   |   | 90 |   |   |   | 95 |   |
|---|---|---|---|---|---|---|---|---|---|---|---|---|---|---|
| Asn | Cys | Thr | Glu 100 | Asp | Gly | Trp | Ser | Glu 105 | Pro | Phe | Pro | His | Tyr 110 | Phe | Asp |
| Ala | Cys | Gly 115 | Phe | Asp | Glu | Tyr | Glu 120 | Ser | Glu | Thr | Gly | Asp 125 | Gln | Asp | Tyr |
| Tyr | Tyr 130 | Leu | Ser | Val | Lys 135 | Ala | Leu | Tyr | Thr | Val 140 | Gly | Tyr | Ser | Thr | Ser |
| Leu 145 | Val | Thr | Leu | Thr | Thr 150 | Ala | Met | Val | Ile | Leu 155 | Cys | Arg | Phe | Arg | Lys 160 |
| Leu | His | Cys | Thr | Arg 165 | Asn | Phe | Ile | His | Met 170 | Asn | Leu | Phe | Val | Ser 175 | Phe |
| Met | Leu | Arg | Ala 180 | Ile | Ser | Val | Phe | Ile 185 | Lys | Asp | Trp | Ile | Leu 190 | Tyr | Ala |
| Glu | Gln | Asp 195 | Ser | Asn | His | Cys | Phe 200 | Ile | Ser | Thr | Val | Glu 205 | Cys | Lys | Ala |
| Val | Met 210 | Val | Phe | Phe | His | Tyr 215 | Cys | Val | Val | Ser | Asn 220 | Tyr | Phe | Trp | Leu |
| Phe 225 | Ile | Glu | Gly | Leu | Tyr 230 | Leu | Phe | Thr | Leu | Leu 235 | Val | Glu | Thr | Phe | Phe 240 |
| Pro | Glu | Arg | Arg | Tyr 245 | Phe | Tyr | Trp | Tyr | Thr 250 | Ile | Ile | Gly | Trp | Gly 255 | Thr |
| Pro | Thr | Val | Cys 260 | Val | Thr | Val | Trp | Ala 265 | Thr | Leu | Arg | Leu | Tyr 270 | Phe | Asp |
| Asp | Thr | Gly 275 | Cys | Trp | Asp | Met | Asn 280 | Asp | Ser | Thr | Ala | Leu 285 | Trp | Trp | Val |
| Ile | Lys 290 | Gly | Pro | Val | Val | Gly 295 | Ser | Ile | Met | Val | Asn 300 | Phe | Val | Leu | Phe |
| Ile 305 | Gly | Ile | Ile | Val | Ile 310 | Leu | Val | Gln | Lys | Leu 315 | Gln | Ser | Pro | Asp | Met 320 |
| Gly | Gly | Asn | Glu | Ser 325 | Ser | Ile | Tyr | Phe | Ser 330 | Cys | Val | Gln | Lys | Cys 335 | Tyr |
| Cys | Lys | Pro | Gln 340 | Arg | Ala | Gln | His | Ser 345 | Cys | Lys | Met | Ser 350 | Glu | Leu |
| Ser | Thr | Ile 355 | Thr | Leu | Arg | Leu | Ala 360 | Arg | Ser | Thr | Leu | Leu 365 | Leu | Ile | Pro |
| Leu | Phe 370 | Gly | Ile | His | Tyr | Thr 375 | Val | Phe | Ala | Phe | Ser 380 | Pro | Glu | Asn | Val |
| Ser 385 | Lys | Arg | Glu | Arg | Leu 390 | Val | Phe | Glu | Leu | Gly 395 | Leu | Gly | Ser | Phe | Gln 400 |
| Gly | Phe | Val | Val | Ala 405 | Val | Leu | Tyr | Cys | Phe 410 | Leu | Asn | Gly | Glu | Val 415 | Gln |
| Ala | Glu | Ile | Lys 420 | Arg | Lys | Trp | Arg | Ser 425 | Trp | Lys | Val | Asn | Arg 430 | Tyr | Phe |
| Ala | Val | Asp 435 | Phe | Lys | His | Arg | His 440 | Pro | Ser | Leu | Ala | Ser 445 | Ser | Gly | Val |
| Asn | Gly 450 | Gly | Thr | Gln | Leu | Ser 455 | Ile | Leu | Ser | Lys | Ser 460 | Ser | Ser | Gln | Ile |
| Arg 465 | Met | Ser | Gly | Leu | Pro 470 | Ala | Asp | Asn | Leu | Ala 475 | Thr |

( 2 ) INFORMATION FOR SEQ ID NO:25:

( i ) SEQUENCE CHARACTERISTICS:
        ( A ) LENGTH: 553 amino acids
        ( B ) TYPE: amino acid (D) TOPOLOGY: linear (ii) MOLECULE TYPE: protein (xi) SEQUENCE DESCRIPTION: SEQ ID NO:25:

```
Met  Ala  Gly  Val  Val  His  Val  Ser  Leu  Ala  His  Cys  Gly  Ala  Cys
1                   5                        10                       15

Pro  Trp  Gly  Arg  Gly  Arg  Leu  Arg  Lys  Gly  Arg  Ala  Ala  Cys  Lys  Ser
            20                       25                       30

Ala  Ala  Gln  Arg  His  Ile  Gly  Ala  Asp  Leu  Pro  Leu  Leu  Ser  Val  Gly
           35                        40                       45

Gly  Gln  Trp  Cys  Trp  Pro  Arg  Ser  Val  Met  Ala  Gly  Val  Val  His  Val
     50                       55                       60

Ser  Leu  Ala  Ala  Leu  Leu  Leu  Pro  Met  Ala  Pro  Ala  Met  His  Ser
65                  70                       75                            80

Asp  Cys  Ile  Phe  Lys  Lys  Glu  Gln  Ala  Met  Cys  Leu  Glu  Lys  Ile  Gln
                    85                        90                            95

Arg  Ala  Asn  Glu  Leu  Met  Gly  Phe  Asn  Asp  Ser  Ser  Pro  Gly  Cys  Pro
               100                      105                     110

Gly  Met  Trp  Asp  Asn  Ile  Thr  Cys  Trp  Lys  Pro  Ala  His  Val  Gly  Glu
          115                      120                      125

Met  Val  Leu  Val  Ser  Cys  Pro  Glu  Leu  Phe  Arg  Ile  Phe  Asn  Pro  Asp
     130                     135                      140

Gln  Val  Trp  Glu  Thr  Glu  Thr  Ile  Gly  Glu  Ser  Asp  Phe  Gly  Asp  Ser
145                      150                      155                      160

Asn  Ser  Leu  Asp  Leu  Ser  Asp  Met  Gly  Val  Val  Ser  Arg  Asn  Cys  Thr
                    165                      170                      175

Glu  Asp  Gly  Trp  Ser  Glu  Pro  Phe  Pro  His  Tyr  Phe  Asp  Ala  Cys  Gly
               180                      185                      190

Phe  Asp  Glu  Tyr  Glu  Ser  Glu  Thr  Gly  Asp  Gln  Asp  Tyr  Tyr  Tyr  Leu
          195                      200                      205

Ser  Val  Lys  Ala  Leu  Tyr  Thr  Val  Gly  Tyr  Ser  Thr  Ser  Leu  Val  Thr
     210                      215                      220

Leu  Thr  Thr  Ala  Met  Val  Ile  Leu  Cys  Arg  Phe  Arg  Lys  Leu  His  Cys
225                      230                      235                      240

Thr  Arg  Asn  Phe  Ile  His  Met  Asn  Leu  Phe  Val  Ser  Phe  Met  Leu  Arg
                    245                      250                      255

Ala  Ile  Ser  Val  Phe  Ile  Lys  Asp  Trp  Ile  Leu  Tyr  Ala  Glu  Gln  Asp
                    260                      265                      270

Ser  Asn  His  Cys  Phe  Ile  Ser  Thr  Val  Glu  Cys  Lys  Ala  Val  Met  Val
          275                      280                      285

Phe  Phe  His  Tyr  Cys  Val  Val  Ser  Asn  Tyr  Phe  Trp  Leu  Phe  Ile  Glu
     290                      295                      300

Gly  Leu  Tyr  Leu  Phe  Thr  Leu  Leu  Val  Glu  Thr  Phe  Phe  Pro  Glu  Arg
305                      310                      315                      320

Arg  Tyr  Phe  Tyr  Trp  Tyr  Thr  Ile  Ile  Gly  Trp  Gly  Thr  Pro  Thr  Val
                    325                      330                      335

Cys  Val  Thr  Val  Trp  Ala  Thr  Leu  Arg  Leu  Tyr  Phe  Asp  Asp  Thr  Gly
                    340                      345                      350

Cys  Trp  Asp  Met  Asn  Asp  Ser  Thr  Ala  Leu  Trp  Trp  Val  Ile  Lys  Gly
          355                      360                      365

Pro  Val  Val  Gly  Ser  Ile  Met  Val  Asn  Phe  Val  Leu  Phe  Ile  Gly  Ile
     370                      375                      380

Ile  Val  Ile  Leu  Val  Gln  Lys  Leu  Gln  Ser  Pro  Asp  Met  Gly  Gly  Asn
385                      390                      395                      400
```

-continued

| Glu | Ser | Ser | Ile | Tyr | Phe | Ser | Cys | Val | Gln | Lys | Cys | Tyr | Cys | Lys | Pro |
|   |   |   |   | 405 |   |   |   |   | 410 |   |   |   |   | 415 |   |
| Gln | Arg | Ala | Gln | Gln | His | Ser | Cys | Lys | Met | Ser | Glu | Leu | Ser | Thr | Ile |
|   |   |   | 420 |   |   |   |   | 425 |   |   |   |   | 430 |   |   |
| Thr | Leu | Arg | Leu | Ala | Arg | Ser | Thr | Leu | Leu | Leu | Ile | Pro | Leu | Phe | Gly |
|   |   | 435 |   |   |   |   | 440 |   |   |   |   | 445 |   |   |   |
| Ile | His | Tyr | Thr | Val | Phe | Ala | Phe | Ser | Pro | Glu | Asn | Val | Ser | Lys | Arg |
|   | 450 |   |   |   |   | 455 |   |   |   |   | 460 |   |   |   |   |
| Glu | Arg | Leu | Val | Phe | Glu | Leu | Gly | Leu | Gly | Ser | Phe | Gln | Gly | Phe | Val |
| 465 |   |   |   |   | 470 |   |   |   |   | 475 |   |   |   |   | 480 |
| Val | Ala | Val | Leu | Tyr | Cys | Phe | Leu | Asn | Gly | Glu | Val | Gln | Ala | Glu | Ile |
|   |   |   |   | 485 |   |   |   |   | 490 |   |   |   |   | 495 |   |
| Lys | Arg | Lys | Trp | Arg | Ser | Trp | Lys | Val | Asn | Arg | Tyr | Phe | Ala | Val | Asp |
|   |   |   | 500 |   |   |   |   | 505 |   |   |   |   | 510 |   |   |
| Phe | Lys | His | Arg | His | Pro | Ser | Leu | Ala | Ser | Ser | Gly | Val | Asn | Gly | Gly |
|   |   | 515 |   |   |   |   | 520 |   |   |   |   | 525 |   |   |   |
| Thr | Gln | Leu | Ser | Ile | Leu | Ser | Lys | Ser | Ser | Ser | Gln | Ile | Arg | Met | Ser |
|   | 530 |   |   |   |   | 535 |   |   |   |   | 540 |   |   |   |   |
| Gly | Leu | Pro | Ala | Asp | Asn | Leu | Ala | Thr |
| 545 |   |   |   |   | 550 |   |   |   |

( 2 ) INFORMATION FOR SEQ ID NO:26:

( i ) SEQUENCE CHARACTERISTICS:
        ( A ) LENGTH: 475 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Met | His | Ser | Asp | Cys | Ile | Phe | Lys | Lys | Glu | Gln | Ala | Met | Cys | Leu | Glu |
| 1 |   |   |   | 5 |   |   |   |   | 10 |   |   |   |   | 15 |   |
| Lys | Ile | Gln | Arg | Ala | Asn | Glu | Leu | Met | Gly | Phe | Asn | Asp | Ser | Ser | Pro |
|   |   |   | 20 |   |   |   |   | 25 |   |   |   |   | 30 |   |   |
| Gly | Cys | Pro | Gly | Met | Trp | Asp | Asn | Ile | Thr | Cys | Trp | Lys | Pro | Ala | His |
|   |   | 35 |   |   |   |   | 40 |   |   |   |   | 45 |   |   |   |
| Val | Gly | Glu | Met | Val | Leu | Val | Ser | Cys | Pro | Glu | Leu | Phe | Arg | Ile | Phe |
|   | 50 |   |   |   |   | 55 |   |   |   |   | 60 |   |   |   |   |
| Asn | Pro | Asp | Gln | Val | Trp | Glu | Thr | Glu | Thr | Ile | Gly | Glu | Ser | Asp | Phe |
| 65 |   |   |   |   | 70 |   |   |   |   | 75 |   |   |   |   | 80 |
| Gly | Asp | Ser | Asn | Ser | Leu | Asp | Leu | Ser | Asp | Met | Gly | Val | Val | Ser | Arg |
|   |   |   |   | 85 |   |   |   |   | 90 |   |   |   |   | 95 |   |
| Asn | Cys | Thr | Glu | Asp | Gly | Trp | Ser | Glu | Pro | Phe | Pro | His | Tyr | Phe | Asp |
|   |   |   | 100 |   |   |   |   | 105 |   |   |   |   | 110 |   |   |
| Ala | Cys | Gly | Phe | Asp | Glu | Tyr | Glu | Ser | Glu | Thr | Gly | Asp | Gln | Asp | Tyr |
|   |   | 115 |   |   |   |   | 120 |   |   |   |   | 125 |   |   |   |
| Tyr | Tyr | Leu | Ser | Val | Lys | Ala | Leu | Tyr | Thr | Val | Gly | Tyr | Ser | Thr | Ser |
|   | 130 |   |   |   |   | 135 |   |   |   |   | 140 |   |   |   |   |
| Leu | Val | Thr | Leu | Thr | Thr | Ala | Met | Val | Ile | Leu | Cys | Arg | Phe | Arg | Lys |
| 145 |   |   |   |   | 150 |   |   |   |   | 155 |   |   |   |   | 160 |
| Leu | His | Cys | Thr | Arg | Asn | Phe | Ile | His | Met | Asn | Leu | Phe | Val | Ser | Phe |
|   |   |   |   | 165 |   |   |   |   | 170 |   |   |   |   | 175 |   |
| Met | Leu | Arg | Ala | Ile | Ser | Val | Phe | Ile | Lys | Asp | Trp | Ile | Leu | Tyr | Ala |
|   |   |   | 180 |   |   |   |   | 185 |   |   |   |   | 190 |   |   |
| Glu | Gln | Asp | Ser | Asn | His | Cys | Phe | Ile | Ser | Thr | Val | Glu | Cys | Lys | Ala |

-continued

|     |     | 195 |     |     |     | 200 |     |     |     | 205 |     |     |     |
|-----|-----|-----|-----|-----|-----|-----|-----|-----|-----|-----|-----|-----|-----|

Val Met Val Phe Phe His Tyr Cys Val Val Ser Asn Tyr Phe Trp Leu
210                     215                 220

Phe Ile Glu Gly Leu Tyr Leu Phe Thr Leu Leu Val Glu Thr Phe Phe
225                 230                 235                 240

Pro Glu Arg Arg Tyr Phe Tyr Trp Tyr Thr Ile Ile Gly Trp Gly Thr
                245                 250                 255

Pro Thr Val Cys Val Thr Val Trp Ala Thr Leu Arg Leu Tyr Phe Asp
            260             265                 270

Asp Thr Gly Cys Trp Asp Met Asn Asp Ser Thr Ala Leu Trp Trp Val
        275             280             285

Ile Lys Gly Pro Val Val Gly Ser Ile Met Val Asn Phe Val Leu Phe
    290             295             300

Ile Gly Ile Ile Val Ile Leu Val Gln Lys Leu Gln Ser Pro Asp Met
305             310             315                 320

Gly Gly Asn Glu Ser Ser Ile Tyr Phe Cys Val Gln Lys Cys Tyr Cys
                325             330             335

Lys Pro Gln Arg Ala Gln Gln His Ser Cys Lys Met Ser Glu Leu Ser
            340             345             350

Thr Ile Thr Leu Arg Leu Ala Arg Ser Thr Leu Leu Leu Ile Pro Leu
        355             360             365

Phe Gly Ile His Tyr Thr Val Phe Ala Phe Ser Pro Glu Asn Val Ser
    370             375             380

Lys Arg Glu Arg Leu Val Phe Glu Leu Gly Leu Gly Ser Phe Gln Gly
385             390             395             400

Phe Val Val Ala Val Leu Tyr Cys Phe Leu Asn Gly Glu Val Gln Ala
                405             410             415

Glu Ile Lys Arg Lys Trp Arg Ser Trp Lys Val Asn Arg Tyr Phe Ala
            420             425             430

Val Asp Phe Lys His Arg His Pro Ser Leu Ala Ser Ser Gly Val Asn
        435             440             445

Gly Gly Thr Gln Leu Ser Ile Leu Ser Lys Ser Ser Ser Gln Ile Arg
    450             455             460

Met Ser Gly Leu Pro Ala Asp Asn Leu Ala Thr
465             470             475

( 2 ) INFORMATION FOR SEQ ID NO:27:

( i ) SEQUENCE CHARACTERISTICS:
          ( A ) LENGTH: 552 amino acids
          ( B ) TYPE: amino acid
          ( D ) TOPOLOGY: linear ( i i ) MOLECULE TYPE: protein ( x i ) SEQUENCE DESCRIPTION: SEQ ID NO:27:

Met Ala Gly Val Val His Val Ser Leu Ala Ala His Cys Gly Ala Cys
1               5                   10                  15

Pro Trp Gly Arg Gly Arg Leu Arg Lys Gly Arg Ala Ala Cys Lys Ser
                20                  25                  30

Ala Ala Gln Arg His Ile Gly Ala Asp Leu Pro Leu Leu Ser Val Gly
            35                  40                  45

Gly Gln Trp Cys Trp Pro Arg Ser Val Met Ala Gly Val Val His Val
        50                  55                  60

Ser Leu Ala Ala Leu Leu Leu Leu Pro Met Ala Pro Ala Met His Ser
65                  70                  75                  80

-continued

```
Asp Cys Ile Phe Lys Lys Glu Gln Ala Met Cys Leu Glu Lys Ile Gln
                 85                  90                  95
Arg Ala Asn Glu Leu Met Gly Phe Asn Asp Ser Ser Pro Gly Cys Pro
            100                 105                 110
Gly Met Trp Asp Asn Ile Thr Cys Trp Lys Pro Ala His Val Gly Glu
        115                 120                 125
Met Val Leu Val Ser Cys Pro Glu Leu Phe Arg Ile Phe Asn Pro Asp
        130                 135                 140
Gln Val Trp Glu Thr Glu Thr Ile Gly Glu Ser Asp Phe Gly Asp Ser
145                 150                 155                 160
Asn Ser Leu Asp Leu Ser Asp Met Gly Val Val Ser Arg Asn Cys Thr
                165                 170                 175
Glu Asp Gly Trp Ser Glu Pro Phe Pro His Tyr Phe Asp Ala Cys Gly
            180                 185                 190
Phe Asp Glu Tyr Glu Ser Glu Thr Gly Asp Gln Asp Tyr Tyr Tyr Leu
        195                 200                 205
Ser Val Lys Ala Leu Tyr Thr Val Gly Tyr Ser Thr Ser Leu Val Thr
        210                 215                 220
Leu Thr Thr Ala Met Val Ile Leu Cys Arg Phe Arg Lys Leu His Cys
225                 230                 235                 240
Thr Arg Asn Phe Ile His Met Asn Leu Phe Val Ser Phe Met Leu Arg
                245                 250                 255
Ala Ile Ser Val Phe Ile Lys Asp Trp Ile Leu Tyr Ala Glu Gln Asp
            260                 265                 270
Ser Asn His Cys Phe Ile Ser Thr Val Glu Cys Lys Ala Val Met Val
        275                 280                 285
Phe Phe His Tyr Cys Val Val Ser Asn Tyr Phe Trp Leu Phe Ile Glu
        290                 295                 300
Gly Leu Tyr Leu Phe Thr Leu Leu Val Glu Thr Phe Phe Pro Glu Arg
305                 310                 315                 320
Arg Tyr Phe Tyr Trp Tyr Thr Ile Ile Gly Trp Gly Thr Pro Thr Val
                325                 330                 335
Cys Val Thr Val Trp Ala Thr Leu Arg Leu Tyr Phe Asp Asp Thr Gly
            340                 345                 350
Cys Trp Asp Met Asn Asp Ser Thr Ala Leu Trp Trp Val Ile Lys Gly
        355                 360                 365
Pro Val Val Gly Ser Ile Met Val Asn Phe Val Leu Phe Ile Gly Ile
        370                 375                 380
Ile Val Ile Leu Val Gln Lys Leu Gln Ser Pro Asp Met Gly Gly Asn
385                 390                 395                 400
Glu Ser Ser Ile Tyr Phe Cys Val Gln Lys Cys Tyr Cys Lys Pro Gln
                405                 410                 415
Arg Ala Gln Gln His Ser Cys Lys Met Ser Glu Leu Ser Thr Ile Thr
            420                 425                 430
Leu Arg Leu Ala Arg Ser Thr Leu Leu Leu Ile Pro Leu Phe Gly Ile
        435                 440                 445
His Tyr Thr Val Phe Ala Phe Ser Pro Glu Asn Val Ser Lys Arg Glu
        450                 455                 460
Arg Leu Val Phe Glu Leu Gly Leu Gly Ser Phe Gln Gly Phe Val Val
465                 470                 475                 480
Ala Val Leu Tyr Cys Phe Leu Asn Gly Glu Val Gln Ala Glu Ile Lys
                485                 490                 495
Arg Lys Trp Arg Ser Trp Lys Val Asn Arg Tyr Phe Ala Val Asp Phe
            500                 505                 510
```

-continued

```
        Lys   His   Arg   His   Pro   Ser   Leu   Ala   Ser   Ser   Gly   Val   Asn   Gly   Gly   Thr
                    515                     520                           525

Gln   Leu   Ser   Ile   Leu   Ser   Lys   Ser   Ser   Ser   Gln   Ile   Arg   Met   Ser   Gly
              530                           535                           540

Leu   Pro   Ala   Asp   Asn   Leu   Ala   Thr
        545                           550
```

(2) INFORMATION FOR SEQ ID NO:28:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:28:

```
        Met   His   Ser   Asp   Cys   Ile   Phe   Lys   Lys   Glu   Gln   Ala   Met   Cys   Leu   Glu
        1                       5                         10                          15

Lys   Ile   Gln   Arg   Ala   Asn   Glu   Leu   Met   Gly   Phe   Asn   Asp   Ser   Ser   Pro
                          20                          25                          30

Gly   Cys   Pro   Gly   Met   Trp   Asp   Asn   Ile   Thr   Cys   Trp   Lys   Pro   Ala   His
                    35                          40                          45

Val   Gly   Glu   Met   Val   Leu   Val   Ser   Cys   Pro   Glu   Leu   Phe   Arg   Ile   Phe
              50                          55                          60

Asn   Pro   Asp   Gln   Val   Trp   Glu   Thr   Glu   Thr   Ile   Gly   Glu   Ser   Asp   Phe
        65                          70                          75                          80

Gly   Asp   Ser   Asn   Ser   Leu   Asp   Leu   Ser   Asp   Met   Gly   Val   Val   Ser   Arg
                                85                          90                          95

Asn   Cys   Thr   Glu   Asp   Gly   Trp   Ser   Glu   Pro   Phe   Pro   His   Tyr   Phe   Asp
                          100                         105                         110

Ala   Cys   Gly   Phe   Asp   Glu   Tyr   Glu   Ser   Glu   Thr   Gly   Asp   Gln   Asp   Tyr
                    115                         120                         125

Tyr   Tyr   Leu   Ser   Val   Lys   Ala   Leu   Tyr   Thr   Val   Gly   Tyr   Ser   Thr   Ser
              130                         135                         140

Leu   Val   Thr   Leu   Thr   Thr   Ala   Met   Val   Ile   Leu   Cys   Arg   Phe   Arg   Lys
        145                         150                         155                         160

Leu   His   Cys   Thr   Arg   Asn   Phe   Ile   His   Met   Asn   Leu   Phe   Val   Ser   Phe
                          165                         170                         175

Met   Leu   Arg   Ala   Ile   Ser   Val   Phe   Ile   Lys   Asp   Trp   Ile   Leu   Tyr   Ala
                    180                         185                         190

Glu   Gln   Asp   Ser   Asn   His   Cys   Phe   Ile   Ser   Thr   Val   Glu   Cys   Lys   Ala
              195                         200                         205

Val   Met   Val   Phe   Phe   His   Tyr   Cys   Val   Val   Ser   Asn   Tyr   Phe   Trp   Leu
        210                         215                         220

Phe   Ile   Glu   Gly   Leu   Tyr   Leu   Phe   Thr   Leu   Leu   Val   Glu   Thr   Phe   Phe
        225                         230                         235                         240

Pro   Glu   Arg   Arg   Tyr   Phe   Tyr   Trp   Tyr   Thr   Ile   Ile   Gly   Trp   Gly   Thr
                          245                         250                         255

Pro   Thr   Val   Cys   Val   Thr   Val   Trp   Ala   Thr   Leu   Arg   Leu   Tyr   Phe   Asp
                    260                         265                         270

Asp   Thr   Gly   Cys   Trp   Asp   Met   Asn   Asp   Ser   Thr   Ala   Leu   Trp   Trp   Val
              275                         280                         285

Ile   Lys   Gly   Pro   Val   Val   Gly   Ser   Ile   Met   Val   Asn   Phe   Val   Leu   Phe
                    290                         295                         300

Ile   Gly   Ile   Ile   Val   Ile   Leu   Val   Gln   Lys   Leu   Gln   Ser   Pro   Asp   Met
```

-continued

```
                305                           310                           315                           320
        Gly   Gly   Asn   Glu   Ser   Ser   Ile   Tyr   Leu   Thr   Asn   Leu   Ser   Pro   Arg   Val
                                325                           330                           335
        Pro   Lys   Lys   Ala   Arg   Glu   Asp   Pro   Leu   Pro   Val   Pro   Ser   Asp   Gln   His
                                340                           345                           350
        Ser   Leu   Pro   Phe   Leu   Arg   Leu   Ala   Arg   Ser   Thr   Leu   Leu   Leu   Ile   Pro
                                355                           360                           365
        Leu   Phe   Gly   Ile   His   Tyr   Thr   Val   Phe   Ala   Phe   Ser   Pro   Glu   Asn   Val
                    370                           375                           380
        Ser   Lys   Arg   Glu   Arg   Leu   Val   Phe   Glu   Leu   Gly   Leu   Gly   Ser   Phe   Gln
        385                           390                           395                                 400
        Gly   Phe   Val   Val   Ala   Val   Leu   Tyr   Cys   Phe   Leu   Asn   Gly   Glu   Val   Gln
                                405                           410                           415
        Ala   Glu   Ile   Lys   Arg   Lys   Trp   Arg   Ser   Trp   Lys   Val   Asn   Arg   Tyr   Phe
                          420                           425                           430
        Ala   Val   Asp   Phe   Lys   His   Arg   His   Pro   Ser   Leu   Ala   Ser   Ser   Gly   Val
                          435                           440                           445
        Asn   Gly   Gly   Thr   Gln   Leu   Ser   Ile   Leu   Ser   Lys   Ser   Ser   Ser   Gln   Ile
              450                           455                           460
        Arg   Met   Ser   Gly   Leu   Pro   Ala   Asp   Asn   Leu   Ala   Thr
        465                     470                           475
```

(2) INFORMATION FOR SEQ ID NO:29:

(i) SEQUENCE CHARACTERISTICS:
      (A) LENGTH: 553 amino acids
      (B) TYPE: amino acid
      (D) TOPOLOGY: linear (ii) MOLECULE TYPE: protein (xi) SEQUENCE DESCRIPTION: SEQ ID NO:29:

```
        Met   Ala   Gly   Val   Val   His   Val   Ser   Leu   Ala   Ala   His   Cys   Gly   Ala   Cys
        1                       5                           10                              15
        Pro   Trp   Gly   Arg   Gly   Arg   Leu   Arg   Lys   Gly   Arg   Ala   Ala   Cys   Lys   Ser
                          20                            25                            30
        Ala   Ala   Gln   Arg   His   Ile   Gly   Ala   Asp   Leu   Pro   Leu   Leu   Ser   Val   Gly
                    35                            40                            45
        Gly   Gln   Trp   Cys   Trp   Pro   Arg   Ser   Val   Met   Ala   Gly   Val   Val   His   Val
              50                            55                            60
        Ser   Leu   Ala   Ala   Leu   Leu   Leu   Leu   Pro   Met   Ala   Pro   Ala   Met   His   Ser
        65                            70                            75                            80
        Asp   Cys   Ile   Phe   Lys   Lys   Glu   Gln   Ala   Met   Cys   Leu   Glu   Lys   Ile   Gln
                                85                            90                            95
        Arg   Ala   Asn   Glu   Leu   Met   Gly   Phe   Asn   Asp   Ser   Ser   Pro   Gly   Cys   Pro
                          100                           105                           110
        Gly   Met   Trp   Asp   Asn   Ile   Thr   Cys   Trp   Lys   Pro   Ala   His   Val   Gly   Glu
                    115                           120                           125
        Met   Val   Leu   Val   Ser   Cys   Pro   Glu   Leu   Phe   Arg   Ile   Phe   Asn   Pro   Asp
                    130                           135                           140
        Gln   Val   Trp   Glu   Thr   Glu   Thr   Ile   Gly   Glu   Ser   Asp   Phe   Gly   Asp   Ser
        145                           150                           155                           160
        Asn   Ser   Leu   Asp   Leu   Ser   Asp   Met   Gly   Val   Val   Ser   Arg   Asn   Cys   Thr
                                165                           170                           175
        Glu   Asp   Gly   Trp   Ser   Glu   Pro   Phe   Pro   His   Tyr   Phe   Asp   Ala   Cys   Gly
                          180                           185                           190
```

| | | | | | | | | | | | | | |
|---|---|---|---|---|---|---|---|---|---|---|---|---|---|
|Phe|Asp|Glu<br>195|Tyr|Glu|Ser|Glu|Thr<br>200|Gly|Asp|Gln|Asp<br>205|Tyr|Tyr|Leu|
|Ser|Val<br>210|Lys|Ala|Leu|Tyr<br>215|Thr|Val|Gly|Tyr|Ser<br>220|Thr|Ser|Leu|Val|Thr|
|Leu<br>225|Thr|Thr|Ala|Met|Val<br>230|Ile|Leu|Cys|Arg|Phe<br>235|Arg|Lys|Leu|His|Cys<br>240|
|Thr|Arg|Asn|Phe|Ile<br>245|His|Met|Asn|Leu|Phe<br>250|Val|Ser|Phe|Met|Leu<br>255|Arg|
|Ala|Ile|Ser|Val<br>260|Phe|Ile|Lys|Asp|Trp<br>265|Ile|Leu|Tyr|Ala|Glu<br>270|Gln|Asp|
|Ser|Asn|His<br>275|Cys|Phe|Ile|Ser|Thr<br>280|Val|Glu|Cys|Lys|Ala<br>285|Val|Met|Val|
|Phe|Phe<br>290|His|Tyr|Cys|Val|Val<br>295|Ser|Asn|Tyr|Phe|Trp<br>300|Leu|Phe|Ile|Glu|
|Gly<br>305|Leu|Tyr|Leu|Phe|Thr<br>310|Leu|Leu|Val|Glu|Thr<br>315|Phe|Phe|Pro|Glu|Arg<br>320|
|Arg|Tyr|Phe|Tyr|Trp<br>325|Tyr|Thr|Ile|Ile|Gly<br>330|Trp|Gly|Thr|Pro|Thr<br>335|Val|
|Cys|Val|Thr|Val<br>340|Trp|Ala|Thr|Leu|Arg<br>345|Leu|Tyr|Phe|Asp|Asp<br>350|Thr|Gly|
|Cys|Trp|Asp<br>355|Met|Asn|Asp|Ser|Thr<br>360|Ala|Leu|Trp|Trp|Val<br>365|Ile|Lys|Gly|
|Pro|Val<br>370|Val|Gly|Ser|Ile|Met<br>375|Val|Asn|Phe|Val|Leu<br>380|Phe|Ile|Gly|Ile|
|Ile<br>385|Val|Ile|Leu|Val|Gln<br>390|Lys|Leu|Gln|Ser|Pro<br>395|Asp|Met|Gly|Gly|Asn<br>400|
|Glu|Ser|Ser|Ile|Tyr<br>405|Leu|Thr|Asn|Leu|Ser<br>410|Pro|Arg|Val|Pro|Lys<br>415|Lys|
|Ala|Arg|Glu|Asp<br>420|Pro|Leu|Pro|Val|Pro<br>425|Ser|Asp|Gln|His|Ser<br>430|Leu|Pro|
|Phe|Leu|Arg<br>435|Leu|Ala|Arg|Ser|Thr<br>440|Leu|Leu|Leu|Ile|Pro<br>445|Leu|Phe|Gly|
|Ile|His<br>450|Tyr|Thr|Val|Phe|Ala<br>455|Phe|Ser|Pro|Glu|Asn<br>460|Val|Ser|Lys|Arg|
|Glu<br>465|Arg|Leu|Val|Phe|Glu<br>470|Leu|Gly|Leu|Gly|Ser<br>475|Phe|Gln|Gly|Phe|Val<br>480|
|Val|Ala|Val|Leu|Tyr<br>485|Cys|Phe|Leu|Asn|Gly<br>490|Glu|Val|Gln|Ala|Glu<br>495|Ile|
|Lys|Arg|Lys|Trp<br>500|Arg|Ser|Trp|Lys|Val<br>505|Asn|Arg|Tyr|Phe|Ala<br>510|Val|Asp|
|Phe|Lys|His<br>515|Arg|His|Pro|Ser|Leu<br>520|Ala|Ser|Ser|Gly|Val<br>525|Asn|Gly|Gly|
|Thr|Gln<br>530|Leu|Ser|Ile|Leu|Ser<br>535|Lys|Ser|Ser|Ser|Gln<br>540|Ile|Arg|Met|Ser|
|Gly<br>545|Leu|Pro|Ala|Asp|Asn<br>550|Leu|Ala|Thr|

( 2 ) INFORMATION FOR SEQ ID NO:30:

( i ) SEQUENCE CHARACTERISTICS:
        ( A ) LENGTH: 1539 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
   ( A ) NAME/KEY: mat_peptide
   ( B ) LOCATION: 1..1539

( x i ) SEQUENCE DESCRIPTION: SEQ ID NO:30:

| | | | | | | |
|---|---|---|---|---|---|---|
| ATGAGAGGCG | GGCGGCACTG | GCCCGAGCCG | CCTTGCAGGC | TGAGAAGCGT | CATGGCCAGC | 60 |
| ATCGCGCAGG | TCTCCCTGGC | TGCTCTCCTC | CTGCTGCCTA | TGGCCACCGC | CATGCATTCC | 120 |
| GACTGCATCT | TCAAGAAGGA | GCAAGCCATG | TGCCTGGAGA | AGATCCAGAG | GGTGAATGAC | 180 |
| CTGATGGGCT | TGAATGACTC | CTCCCCAGGG | TGCCCTGGGA | TGTGGGACAA | CATCACGTGT | 240 |
| TGGAAGCCCG | CCCACGTGGG | TGAGATGGTC | CTGGTCAGTT | GCCCTGAACT | CTTCCGAATC | 300 |
| TTCAACCCAG | ACCAAGTCTG | GGAGACGGAA | ACCATCGGAG | AGTTCGGTTT | TGCAGACAGT | 360 |
| AAATCCTTGG | ATCTCTCAGA | CATGAGGGTG | GTGAGCCGGA | ATTGCACGGA | GGATGGATGG | 420 |
| TCAGAGCCAT | TCCCTCATTA | TTTCGATGCC | TGTGGGTTTG | AGGAGTACGA | ATCTGAGACT | 480 |
| GGGGACCAGG | ATTACTACTA | CCTGTCAGTG | AAGGCCCTGT | ACACAGTTGG | CTACAGCACG | 540 |
| TCCCTCGTCA | CCCTCACCAC | TGCCATGGTC | ATCCTGTGTC | GTTTCCGGAA | GCTGCACTGC | 600 |
| ACCCGCAACT | TCATCCACAT | GAACCTCTTC | GTGTCGTTTA | TGCTGAGGGC | CATCTCCGTC | 660 |
| TTCATCAAAG | ACTGGATCCT | CTATGCTGAG | CAGGACAGCA | ATCACTGCTT | TGTCTCCACT | 720 |
| GTGGAATGCA | AGGCTGTGAT | GGTTTTCTTC | CACTACTGTG | TTGTATCCAA | CTACTTCTGG | 780 |
| CTGTTCATCG | AGGGCCTGTA | TCTCTTCACC | CTGCTGGTGG | AGACCTTCTT | CCCCGAGAGG | 840 |
| AGATATTTCT | ACTGGTACAT | CATCATTGGC | TGGGGACAC | CAACTGTGTG | TGTGTCTGTG | 900 |
| TGGGCTATGC | TGAGGCTCTA | CTTCGATGAC | ACAGGCTGCT | GGGATATGAA | TGACAACACG | 960 |
| GCTCTGTGGT | GGGTGATCAA | AGGCCCTGTA | GTTGGCTCCA | TAATGGTTAA | TTTTGTGCTC | 1020 |
| TTCATCGGCA | TCATTGTCAT | CCTTGTGCAG | AAACTTCAGT | CTCCAGACAT | GGGAGGCAAC | 1080 |
| GAGTCCAGCA | TCTACTTCAG | CTGCGTGCAG | AAATGCTACT | GCAAGCCACA | GCGGGCTCAG | 1140 |
| CAGCACTCTT | GCAAGATGTC | AGAACTGTCC | ACCATTACTC | TACGGCTCGC | CAGGTCCACC | 1200 |
| TTGCTGCTCA | TCCCACTCTT | TGGAATCCAC | TACACTGTCT | TTGCTTTCTC | CCCGGAGAAC | 1260 |
| GTCAGCAAGA | GGGAGAGACT | GGTGTTTGAG | CTGGGTCTGG | GCTCCTTCCA | GGGCTTTGTG | 1320 |
| GTGGCTGTTC | TCTATTGCTT | TCTGAATGGA | GAGGTGCAGG | CGGAGATCAA | GAGGAAGTGG | 1380 |
| CGGAGCTGGA | AGGTGAACCG | CTACTTCACC | ATGGACTTCA | AGCACCGGCA | CCCATCCCTG | 1440 |
| GCCAGCAGCG | GGGTGAACGG | GGGCACCCAG | CTCTCCATCC | TGAGCAAGAG | CAGCTCCCAG | 1500 |
| ATCCGCATGT | CTGGGCTTCC | GGCCGACAAC | CTGGCCACC | | | 1539 |

( 2 ) INFORMATION FOR SEQ ID NO:31:

( i ) SEQUENCE CHARACTERISTICS:
      ( A ) LENGTH: 1455 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: mat_peptide
      ( B ) LOCATION: 1..1455

( x i ) SEQUENCE DESCRIPTION: SEQ ID NO:31:

| | | | | | | |
|---|---|---|---|---|---|---|
| ATGAGAGGCG | GGCGGCACTG | GCCCGAGCCG | CCTTGCAGGC | TGAGAAGCGT | CATGGCCAGC | 60 |
| ATCGCGCAGG | TCTCCCTGGC | TGCTCTCCTC | CTGCTGCCTA | TGGCCACCGC | CATGCATTCC | 120 |
| GACTGCATCT | TCAAGAAGGA | GCAAGCCATG | TGCCTGGAGA | AGATCCAGAG | GGTGAATGAC | 180 |

| | | | | | |
|---|---|---|---|---|---|
| CTGATGGGCT | TGAATGACTC | CTCCCCAGGG | TGCCCTGGGA | TGTGGGACAA | CATCACGTGT | 240 |
| TGGAAGCCCG | CCCACGTGGG | TGAGATGGTC | CTGGTCAGTT | GCCCTGAACT | CTTCCGAATC | 300 |
| TTCAACCCAG | ACCAAGTCTG | GGAGACGGAA | ACCATCGGAG | AGTTCGGTTT | TGCAGACAGT | 360 |
| AAATCCTTGG | ATCTCTCAGA | CATGAGGGTG | GTGAGCCGGA | ATTGCACGGA | GGATGGATGG | 420 |
| TCAGAGCCAT | TCCCTCATTA | TTTCGATGCC | TGTGGGTTTG | AGGAGTACGA | ATCTGAGACT | 480 |
| GGGGACCAGG | ATTACTACTA | CCTGTCAGTG | AAGGCCCTGT | ACACAGTTGG | CTACAGCACG | 540 |
| TCCCTCGTCA | CCCTCACCAC | TGCCATGGTC | ATCCTGTGTC | GTTTCCGGAA | GCTGCACTGC | 600 |
| ACCCGCAACT | TCATCCACAT | GAACCTCTTC | GTGTCGTTTA | TGCTGAGGGC | CATCTCCGTC | 660 |
| TTCATCAAAG | ACTGGATCCT | CTATGCTGAG | CAGGACAGCA | ATCACTGCTT | TGTCTCCACT | 720 |
| GTGGAATGCA | AGGCTGTGAT | GGTTTTCTTC | CACTACTGTG | TTGTATCCAA | CTACTTCTGG | 780 |
| CTGTTCATCG | AGGGCCTGTA | TCTCTTCACC | CTGCTGGTGG | AGACCTTCTT | CCCCGAGAGG | 840 |
| AGATATTTCT | ACTGGTACAT | CATCATTGGC | TGGGGACAC | CAACTGTGTG | TGTGTCTGTG | 900 |
| TGGGCTATGC | TGAGGCTCTA | CTTCGATGAC | ACAGGCTGCT | GGGATATGAA | TGACAACACG | 960 |
| GCTCTGTGGT | GGGTGATCAA | AGGCCCTGTA | GTTGGCTCCA | TAATGGTTAA | TTTTGTGCTC | 1020 |
| TTCATCGGCA | TCATTGTCAT | CCTTGTGCAG | AAACTTCAGT | CTCCAGACAT | GGGAGGCAAC | 1080 |
| GAGTCCAGCA | TCTACTTACG | GCTCGCCAGG | TCCACCTTGC | TGCTCATCCC | ACTCTTTGGA | 1140 |
| ATCCACTACA | CTGTCTTTGC | TTTCTCCCCG | GAGAACGTCA | GCAAGAGGGA | GAGACTGGTG | 1200 |
| TTTGAGCTGG | GTCTGGGCTC | CTTCCAGGGC | TTTGTGGTGG | CTGTTCTCTA | TTGCTTTCTG | 1260 |
| AATGGAGAGG | TGCAGGCGGA | GATCAAGAGG | AAGTGGCGGA | GCTGGAAGGT | GAACCGCTAC | 1320 |
| TTCACCATGG | ACTTCAAGCA | CCGGCACCCA | TCCCTGGCCA | GCAGCGGGGT | GAACGGGGC | 1380 |
| ACCCAGCTCT | CCATCCTGAG | CAAGAGCAGC | TCCCAGATCC | GCATGTCTGG | GCTTCCGGCC | 1440 |
| GACAACCTGG | CCACC | | | | | 1455 |

( 2 ) INFORMATION FOR SEQ ID NO:32:

( i ) SEQUENCE CHARACTERISTICS:
        ( A ) LENGTH: 1401 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 1..1401

( x i ) SEQUENCE DESCRIPTION: SEQ ID NO:32:

| | | | | | |
|---|---|---|---|---|---|
| ATGGCCAGAG | TCCTGCAGCT | CTCCCTGACT | GCTCTCCTGC | TGCCTGTGGC | TATTGCTATG | 60 |
| CACTCTGACT | GCATCTTCAA | GAAGGAGCAA | GCCATGTGCC | TGGAGAGGAT | CCAGAGGGCC | 120 |
| AACGACCTGA | TGGGACTAAA | CGAGTCTTCC | CCAGGTTGCC | CTGGCATGTG | GGACAATATC | 180 |
| ACATGTTGGA | AGCCAGCTCA | AGTAGGTGAG | ATGGTCCTTG | TAAGCTGCCC | TGAGGTCTTC | 240 |
| CGGATCTTCA | ACCCGGACCA | AGTCTGGATG | ACAGAAACCA | TAGGAGATTC | TGGTTTTGCC | 300 |
| GATAGTAATT | CCTTGGAGAT | CACAGACATG | GGGGTCGTGG | GCCGGAACTG | CACAGAGGAC | 360 |
| GGCTGGTCGG | AGCCCTTCCC | CCACTACTTC | GATGCTTGTG | GGTTTGATGA | TTATGAGCCT | 420 |
| GAGTCTGGAG | ATCAGGATTA | TTACTACCTG | TCGGTGAAGG | CTCTCTACAC | AGTCGGCTAC | 480 |
| AGCACTTCCC | TCGCCACCCT | CACTACTGCC | ATGGTCATCT | TGTGCCGCTT | CCGGAAGCTG | 540 |

-continued

| | | | | | |
|---|---|---|---|---|---|
| CATTGCACTC | GCAACTTCAT | CCACATGAAC | CTGTTTGTAT | CCTTCATGCT | GAGGGCTATC | 600
| TCCGTCTTCA | TCAAGGACTG | GATCTTGTAC | GCCGAGCAGG | ACAGCAGTCA | CTGCTTCGTT | 660
| TCCACCGTGG | AGTGCAAAGC | TGTCATGGTT | TTCTTCCACT | ACTGCGTGGT | GTCCAACTAC | 720
| TTCTGGCTGT | TCATTGAAGG | CCTGTACCTC | TTTACACTGC | TGGTGGAGAC | CTTCTTCCCT | 780
| GAGAGGAGAT | ATTTCTACTG | GTACACCATC | ATCGGCTGGG | GGACACCTAC | TGTGTGTGTA | 840
| ACAGTGTGGG | CTGTGCTGAG | GCTCTATTTT | GATGATGCAG | GATGCTGGGA | TATGAATGAC | 900
| AGCACAGCTC | TGTGGTGGGT | GATCAAAGGC | CCCGTGGTTG | GCTCTATAAT | GGTTAACTTT | 960
| GTGCTTTTCA | TCGGCATCAT | CATCATCCTT | GTACAGAAGC | TGCAGTCCCC | AGACATGGGA | 1020
| GGCAACGAGT | CCAGCATCTA | CTTACGGCTG | GCCCGCTCCA | CCCTACTGCT | CATCCCACTC | 1080
| TTCGGAATCC | ACTACACAGT | ATTCGCCTTC | TCTCCAGAGA | ACGTCAGCAA | GAGGGAAAGA | 1140
| CTTGTGTTTG | AGCTTGGGCT | GGGCTCCTTC | CAGGGCTTTG | TGGTGGCTGT | ACTCTACTGC | 1200
| TTCCTGAATG | GGGAGGTACA | GGCAGAGATT | AAGAGGAAAT | GGAGGAGCTG | GAAGGTGAAC | 1260
| CGTTACTTCA | CTATGGACTT | CAAGCACCGG | CACCCGTCCC | TGGCCAGCAG | TGGAGTAAAT | 1320
| GGGGGAACCC | AGCTGTCCAT | CCTGAGCAAG | AGCAGCTCCC | AGCTCCGCAT | GTCCAGCCTC | 1380
| CCGGCCGACA | ACTTGGCCAC | C | | | | 1401

(2) INFORMATION FOR SEQ ID NO:33:

(i) SEQUENCE CHARACTERISTICS:
        (A) LENGTH: 1485 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat_peptide
        (B) LOCATION: 1..1485

(xi) SEQUENCE DESCRIPTION: SEQ ID NO:33:

| | | | | | |
|---|---|---|---|---|---|
| ATGGCCAGAG | TCCTGCAGCT | CTCCCTGACT | GCTCTCCTGC | TGCCTGTGGC | TATTGCTATG | 60
| CACTCTGACT | GCATCTTCAA | GAAGGAGCAA | GCCATGTGCC | TGGAGAGGAT | CCAGAGGGCC | 120
| AACGACCTGA | TGGGACTAAA | CGAGTCTTCC | CCAGGTTGCC | CTGGCATGTG | GACAATATC | 180
| ACATGTTGGA | AGCCAGCTCA | AGTAGGTGAG | ATGGTCCTTG | TAAGCTGCCC | TGAGGTCTTC | 240
| CGGATCTTCA | ACCCGGACCA | AGTCTGGATG | ACAGAAACCA | TAGGAGATTC | TGGTTTTGCC | 300
| GATAGTAATT | CCTTGGAGAT | CACAGACATG | GGGTCGTGG | GCCGGAACTG | CACAGAGGAC | 360
| GGCTGGTCGG | AGCCCTTCCC | CCACTACTTC | GATGCTTGTG | GGTTTGATGA | TTATGAGCCT | 420
| GAGTCTGGAG | ATCAGGATTA | TTACTACCTG | TCGGTGAAGG | CTCTCTACAC | AGTCGGCTAC | 480
| AGCACTTCCC | TCGCCACCCT | CACTACTGCC | ATGGTCATCT | TGTGCCGCTT | CCGGAAGCTG | 540
| CATTGCACTC | GCAACTTCAT | CCACATGAAC | CTGTTTGTAT | CCTTCATGCT | GAGGGCTATC | 600
| TCCGTCTTCA | TCAAGGACTG | GATCTTGTAC | GCCGAGCAGG | ACAGCAGTCA | CTGCTTCGTT | 660
| TCCACCGTGG | AGTGCAAAGC | TGTCATGGTT | TTCTTCCACT | ACTGCGTGGT | GTCCAACTAC | 720
| TTCTGGCTGT | TCATTGAAGG | CCTGTACCTC | TTTACACTGC | TGGTGGAGAC | CTTCTTCCCT | 780
| GAGAGGAGAT | ATTTCTACTG | GTACACCATC | ATCGGCTGGG | GGACACCTAC | TGTGTGTGTA | 840
| ACAGTGTGGG | CTGTGCTGAG | GCTCTATTTT | GATGATGCAG | GATGCTGGGA | TATGAATGAC | 900
| AGCACAGCTC | TGTGGTGGGT | GATCAAAGGC | CCCGTGGTTG | GCTCTATAAT | GGTTAACTTT | 960
| GTGCTTTTCA | TCGGCATCAT | CATCATCCTT | GTACAGAAGC | TGCAGTCCCC | AGACATGGGA | 1020

| | | | | | | |
|---|---|---|---|---|---|---|
| GGCAACGAGT | CCAGCATCTA | CTTCAGCTGC | GTGCAGAAAT | GCTACTGCAA | GCCACAGCGG | 1080 |
| GCTCAGCAGC | ACTCTTGCAA | GATGTCAGAA | CTATCCACCA | TTACTCTACG | GCTGGCCCGC | 1140 |
| TCCACCCTAC | TGCTCATCCC | ACTCTTCGGA | ATCCACTACA | CAGTATTCGC | CTTCTCTCCA | 1200 |
| GAGAACGTCA | GCAAGAGGGA | AAGACTTGTG | TTTGAGCTTG | GCTGGGCTC | CTTCCAGGGC | 1260 |
| TTTGTGGTGG | CTGTACTCTA | CTGCTTCCTG | AATGGGGAGG | TACAGGCAGA | GATTAAGAGG | 1320 |
| AAATGGAGGA | GCTGGAAGGT | GAACCGTTAC | TTCACTATGG | ACTTCAAGCA | CCGGCACCCG | 1380 |
| TCCCTGGCCA | GCAGTGGAGT | AAATGGGGGA | ACCCAGCTGT | CCATCCTGAG | CAAGAGCAGC | 1440 |
| TCCCAGCTCC | GCATGTCCAG | CCTCCCGGCC | GACAACTTGG | CCACC | | 1485 |

( 2 ) INFORMATION FOR SEQ ID NO:34:

( i ) SEQUENCE CHARACTERISTICS:
  ( A ) LENGTH: 1575 base pairs
  ( B ) TYPE: nucleic acid
  ( C ) STRANDEDNESS: double
  ( D ) TOPOLOGY: linear ( i i ) MOLECULE TYPE: cDNA ( i x ) FEATURE:
  ( A ) NAME/KEY: mat_peptide
  ( B ) LOCATION: 1..1575

( x i ) SEQUENCE DESCRIPTION: SEQ ID NO:34:

| | | | | | | |
|---|---|---|---|---|---|---|
| ATGGCTGGTG | TCGTGCACGT | TTCCCTGGCT | GCTCACTGCG | GGGCCTGTCC | GTGGGGCCGG | 60 |
| GGCAGACTCC | GCAAAGGACG | CGCAGCCTGC | AAGTCCGCGG | CCCAGAGACA | CATTGGGGCT | 120 |
| GACCTGCCGC | TGCTGTCAGT | GGGAGGCCAG | TGGTGCTGGC | CAAGAAGTGT | CATGGCTGGT | 180 |
| GTCGTGCACG | TTTCCCTGGC | TGCTCTCCTC | CTGCTGCCTA | TGGCCCCTGC | CATGCATTCT | 240 |
| GACTGCATCT | TCAAGAAGGA | GCAAGCCATG | TGCCTGGAGA | AGATCCAGAG | GCCAATGAG | 300 |
| CTGATGGGCT | TCAATGATTC | CTCTCCAGGC | TGTCCTGGGA | TGTGGGACAA | CATCACGTGT | 360 |
| TGGAAGCCCG | CCCATGTGGG | TGAGATGGTC | CTGGTCAGCT | GCCCTGAGCT | CTTCCGAATC | 420 |
| TTCAACCCAG | ACCAAGTCTG | GGAGACCGAA | ACCATTGGAG | AGTCTGATTT | TGGTGACAGT | 480 |
| AACTCCTTAG | ATCTCTCAGA | CATGGGAGTG | GTGAGCCGGA | ACTGCACGGA | GGATGGCTGG | 540 |
| TCGGAACCCT | TCCCTCATTA | CTTTGATGCC | TGTGGGTTTG | ATGAATATGA | ATCTGAGACT | 600 |
| GGGGACCAGG | ATTATTACTA | CCTGTCAGTG | AAGGCCTCT | ACACGGTTGG | CTACAGCACA | 660 |
| TCCCTCGTCA | CCCTCACCAC | TGCCATGGTC | ATCCTTTGTC | GCTTCCGGAA | GCTGCACTGC | 720 |
| ACACGCAACT | TCATCCACAT | GAACCTGTTT | GTGTCGTTCA | TGCTGAGGGC | GATCTCCGTC | 780 |
| TTCATCAAAG | ACTGGATTCT | GTATGCGGAG | CAGGACAGCA | ACCACTGCTT | CATCTCCACT | 840 |
| GTGGAATGTA | AGGCCGTCAT | GGTTTTCTTC | CACTACTGTG | TTGTGTCCAA | CTACTTCTGG | 900 |
| CTGTTCATCG | AGGGCCTGTA | CCTCTTCACT | CTGCTGGTGG | AGACCTTCTT | CCCTGAAAGG | 960 |
| AGATACTTCT | ACTGGTACAC | CATCATTGGC | TGGGGGTCCC | CAACTGTGTG | TGTGACAGTG | 1020 |
| TGGGCTACGC | TGAGACTCTA | CTTTGATGAC | ACAGGCTGCT | GGGATATGAA | TGACAGCACA | 1080 |
| GCTCTGTGGT | GGGTGATCAA | AGGCCCTGTG | GTTGGCTCTA | TCATGGTTAA | CTTTGTGCTT | 1140 |
| TTTATTGGCA | TTATCGTCAT | CCTTGTGCAG | AAACTTCAGT | CTCCAGACAT | GGGAGGCAAT | 1200 |
| GAGTCCAGCA | TCTACTTGCG | ACTGGCCCGG | TCCACCCTGC | TGCTCATCCC | ACTATTCGGA | 1260 |
| ATCCACTACA | CAGTATTTGC | CTTCTCCCCA | GAGAATGTCA | GCAAAAGGGA | AAGACTCGTG | 1320 |
| TTTGAGCTGG | GGCTGGGCTC | CTTCCAGGGC | TTTGTGGTGG | CTGTTCTCTA | CTGTTTTCTG | 1380 |

| | | | | | | |
|---|---|---|---|---|---|---|
| AATGGTGAGG | TACAAGCGGA | GATCAAGCGA | AAATGGCGAA | GCTGGAAGGT | GAACCGTTAC | 1440 |
| TTCGCTGTGG | ACTTCAAGCA | CCGACACCCG | TCTCTGGCCA | GCAGTGGGGT | GAATGGGGGC | 1500 |
| ACCCAGCTCT | CCATCCTGAG | CAAGAGCAGC | TCCCAAATCC | GCATGTCTGG | CCTCCCTGCT | 1560 |
| GACAATCTGG | CCACC | | | | | 1575 |

(2) INFORMATION FOR SEQ ID NO:35:

(i) SEQUENCE CHARACTERISTICS:
        (A) LENGTH: 1659 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat_peptide
        (B) LOCATION: 1..1659

(xi) SEQUENCE DESCRIPTION: SEQ ID NO:35:

| | | | | | | |
|---|---|---|---|---|---|---|
| ATGGCTGGTG | TCGTGCACGT | TTCCCTGGCT | GCTCACTGCG | GGGCCTGTCC | GTGGGGCCGG | 60 |
| GGCAGACTCC | GCAAAGGACG | CGCAGCCTGC | AAGTCCGCGG | CCCAGAGACA | CATTGGGGCT | 120 |
| GACCTGCCGC | TGCTGTCAGT | GGGAGGCCAG | TGGTGCTGGC | CAAGAAGTGT | CATGGCTGGT | 180 |
| GTCGTGCACG | TTTCCCTGGC | TGCTCTCCTC | CTGCTGCCTA | TGGCCCCTGC | CATGCATTCT | 240 |
| GACTGCATCT | TCAAGAAGGA | GCAAGCCATG | TGCCTGGAGA | AGATCCAGAG | GGCCAATGAG | 300 |
| CTGATGGGCT | TCAATGATTC | CTCTCCAGGC | TGTCCTGGGA | TGTGGGACAA | CATCACGTGT | 360 |
| TGGAAGCCCG | CCCATGTGGG | TGAGATGGTC | CTGGTCAGCT | GCCCTGAGCT | CTTCCGAATC | 420 |
| TTCAACCCAG | ACCAAGTCTG | GGAGACCGAA | ACCATTGGAG | AGTCTGATTT | TGGTGACAGT | 480 |
| AACTCCTTAG | ATCTCTCAGA | CATGGGAGTG | GTGAGCCGGA | ACTGCACGGA | GGATGGCTGG | 540 |
| TCGGAACCCT | TCCCTCATTA | CTTTGATGCC | TGTGGGTTTG | ATGAATATGA | ATCTGAGACT | 600 |
| GGGGACCAGG | ATTATTACTA | CCTGTCAGTG | AAGGCCCTCT | ACACGGTTGG | CTACAGCACA | 660 |
| TCCCTCGTCA | CCCTCACCAC | TGCCATGGTC | ATCCTTTGTC | GCTTCCGGAA | GCTGCACTGC | 720 |
| ACACGCAACT | TCATCCACAT | GAACCTGTTT | GTGTCGTTCA | TGCTGAGGGC | GATCTCCGTC | 780 |
| TTCATCAAAG | ACTGGATTCT | GTATGCGGAG | CAGGACAGCA | ACCACTGCTT | CATCTCCACT | 840 |
| GTGGAATGTA | AGGCCGTCAT | GGTTTTCTTC | CACTACTGTG | TTGTGTCCAA | CTACTTCTGG | 900 |
| CTGTTCATCG | AGGGCCTGTA | CCTCTTCACT | CTGCTGGTGG | AGACCTTCTT | CCCTGAAAGG | 960 |
| AGATACTTCT | ACTGGTACAC | CATCATTGGC | TGGGGACCC | CAACTGTGTG | TGTGACAGTG | 1020 |
| TGGGCTACGC | TGAGACTCTA | CTTTGATGAC | ACAGGCTGCT | GGGATATGAA | TGACAGCACA | 1080 |
| GCTCTGTGGT | GGGTGATCAA | AGGCCCTGTG | GTTGGCTCTA | TCATGGTTAA | CTTTGTGCTT | 1140 |
| TTTATTGGCA | TTATCGTCAT | CCTTGTGCAG | AAACTTCAGT | CTCCAGACAT | GGGAGGCAAT | 1200 |
| GAGTCCAGCA | TCTACTTCAG | CTGCGTGCAG | AAATGCTACT | GCAAGCCACA | GCGGGCTCAG | 1260 |
| CAGCACTCTT | GCAAGATGTC | AGAACTGTCC | ACCATTACTC | TGCGACTGGC | CCGGTCCACC | 1320 |
| CTGCTGCTCA | TCCCACTATT | CGGAATCCAC | TACACAGTAT | TTGCCTTCTC | CCCAGAGAAT | 1380 |
| GTCAGCAAAA | GGGAAAGACT | CGTGTTTGAG | CTGGGGCTGG | GCTCCTTCCA | GGGCTTTGTG | 1440 |
| GTGGCTGTTC | TCTACTGTTT | TCTGAATGGT | GAGGTACAAG | CGGAGATCAA | GCGAAAATGG | 1500 |
| CGAAGCTGGA | AGGTGAACCG | TTACTTCGCT | GTGGACTTCA | AGCACCGACA | CCCGTCTCTG | 1560 |
| GCCAGCAGTG | GGGTGAATGG | GGGCACCCAG | CTCTCCATCC | TGAGCAAGAG | CAGCTCCCAA | 1620 |
| ATCCGCATGT | CTGGCCTCCC | TGCTGACAAT | CTGGCCACC | | | 1659 |

( 2 ) INFORMATION FOR SEQ ID NO:36:

( i ) SEQUENCE CHARACTERISTICS:
        ( A ) LENGTH: 1656 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 1..1656

( x i ) SEQUENCE DESCRIPTION: SEQ ID NO:36:

| | | | | | | |
|---|---|---|---|---|---|---|
| ATGGCTGGTG | TCGTGCACGT | TTCCCTGGCT | GCTCACTGCG | GGGCCTGTCC | GTGGGGCCGG | 60 |
| GGCAGACTCC | GCAAAGGACG | CGCAGCCTGC | AAGTCCGCGG | CCCAGAGACA | CATTGGGGCT | 120 |
| GACCTGCCGC | TGCTGTCAGT | GGGAGGCCAG | TGGTGCTGGC | CAAGAAGTGT | CATGGCTGGT | 180 |
| GTCGTGCACG | TTTCCCTGGC | TGCTCTCCTC | CTGCTGCCTA | TGGCCCCTGC | CATGCATTCT | 240 |
| GACTGCATCT | TCAAGAAGGA | GCAAGCCATG | TGCCTGGAGA | AGATCCAGAG | GCCAATGAG | 300 |
| CTGATGGGCT | TCAATGATTC | CTCTCCAGGC | TGTCCTGGGA | TGTGGGACAA | CATCACGTGT | 360 |
| TGGAAGCCCG | CCCATGTGGG | TGAGATGGTC | CTGGTCAGCT | GCCCTGAGCT | CTTCCGAATC | 420 |
| TTCAACCCAG | ACCAAGTCTG | GGAGACCGAA | ACCATTGGAG | AGTCTGATTT | TGGTGACAGT | 480 |
| AACTCCTTAG | ATCTCTCAGA | CATGGGAGTG | GTGAGCCGGA | ACTGCACGGA | GGATGGCTGG | 540 |
| TCGGAACCCT | TCCCTCATTA | CTTTGATGCC | TGTGGGTTTG | ATGAATATGA | ATCTGAGACT | 600 |
| GGGGACCAGG | ATTATTACTA | CCTGTCAGTG | AAGGCCCTCT | ACACGGTTGG | CTACAGCACA | 660 |
| TCCCTCGTCA | CCCTCACCAC | TGCCATGGTC | ATCCTTTGTC | GCTTCCGGAA | GCTGCACTGC | 720 |
| ACACGCAACT | TCATCCACAT | GAACCTGTTT | GTGTCGTTCA | TGCTGAGGGC | GATCTCCGTC | 780 |
| TTCATCAAAG | ACTGGATTCT | GTATGCGGAG | CAGGACAGCA | ACCACTGCTT | CATCTCCACT | 840 |
| GTGGAATGTA | AGGCCGTCAT | GGTTTTCTTC | CACTACTGTG | TTGTGTCCAA | CTACTTCTGG | 900 |
| CTGTTCATCG | AGGGCCTGTA | CCTCTTCACT | CTGCTGGTGG | AGACCTTCTT | CCCTGAAAGG | 960 |
| AGATACTTCT | ACTGGTACAC | CATCATTGGC | TGGGGGACCC | CAACTGTGTG | TGTGACAGTG | 1020 |
| TGGGCTACGC | TGAGACTCTA | CTTTGATGAC | ACAGGCTGCT | GGGATATGAA | TGACAGCACA | 1080 |
| GCTCTGTGGT | GGGTGATCAA | AGGCCCTGTG | GTTGGCTCTA | TCATGGTTAA | CTTTGTGCTT | 1140 |
| TTTATTGGCA | TTATCGTCAT | CCTTGTGCAG | AAACTTCAGT | CTCCAGACAT | GGGAGGCAAT | 1200 |
| GAGTCCAGCA | TCTACTTCTG | CGTGCAGAAA | TGCTACTGCA | AGCCACAGCG | GGCTCAGCAG | 1260 |
| CACTCTTGCA | AGATGTCAGA | ACTGTCCACC | ATTACTCTGC | GACTGGCCCG | GTCCACCCTG | 1320 |
| CTGCTCATCC | CACTATTCGG | AATCCACTAC | ACAGTATTTG | CCTTCTCCCC | AGAGAATGTC | 1380 |
| AGCAAAAGGG | AAAGACTCGT | GTTTGAGCTG | GGGCTGGGCT | CCTTCCAGGG | CTTTGTGGTG | 1440 |
| GCTGTTCTCT | ACTGTTTTCT | GAATGGTGAG | GTACAAGCGG | AGATCAAGCG | AAAATGGCGA | 1500 |
| AGCTGGAAGG | TGAACCGTTA | CTTCGCTGTG | GACTTCAAGC | ACCGACACCC | GTCTCTGGCC | 1560 |
| AGCAGTGGGG | TGAATGGGGG | CACCCAGCTC | TCCATCCTGA | GCAAGAGCAG | CTCCCAAATC | 1620 |
| CGCATGTCTG | GCCTCCCTGC | TGACAATCTG | GCCACC | | | 1656 |

( 2 ) INFORMATION FOR SEQ ID NO:37:

( i ) SEQUENCE CHARACTERISTICS:
        ( A ) LENGTH: 1659 base pairs
        ( B ) TYPE: nucleic acid ( C ) STRANDEDNESS: double
( D ) TOPOLOGY: linear ( i i ) MOLECULE TYPE: cDNA ( i x ) FEATURE:
( A ) NAME/KEY: mat_peptide
( B ) LOCATION: 1..1659

( x i ) SEQUENCE DESCRIPTION: SEQ ID NO:37:

| | | | | | | |
|---|---|---|---|---|---|---|
| ATGGCTGGTG | TCGTGCACGT | TTCCCTGGCT | GCTCACTGCG | GGGCCTGTCC | GTGGGGCCGG | 60 |
| GGCAGACTCC | GCAAAGGACG | CGCAGCCTGC | AAGTCGCGG | CCCAGAGACA | CATTGGGGCT | 120 |
| GACCTGCCGC | TGCTGTCAGT | GGGAGGCCAG | TGGTGCTGGC | CAAGAAGTGT | CATGGCTGGT | 180 |
| GTCGTGCACG | TTTCCCTGGC | TGCTCTCCTC | CTGCTGCCTA | TGGCCCCTGC | CATGCATTCT | 240 |
| GACTGCATCT | TCAAGAAGGA | GCAAGCCATG | TGCCTGGAGA | AGATCCAGAG | GGCCAATGAG | 300 |
| CTGATGGGCT | TCAATGATTC | CTCTCCAGGC | TGTCCTGGGA | TGTGGGACAA | CATCACGTGT | 360 |
| TGGAAGCCCG | CCCATGTGGG | TGAGATGGTC | CTGGTCAGCT | GCCCTGAGCT | CTTCCGAATC | 420 |
| TTCAACCCAG | ACCAAGTCTG | GGAGACCGAA | ACCATTGGAG | AGTCTGATTT | GGTGACAGT | 480 |
| AACTCCTTAG | ATCTCTCAGA | CATGGGAGTG | GTGAGCCGGA | ACTGCACGGA | GGATGGCTGG | 540 |
| TCGGAACCCT | TCCCTCATTA | CTTTGATGCC | TGTGGGTTTG | ATGAATATGA | ATCTGAGACT | 600 |
| GGGGACCAGG | ATTATTACTA | CCTGTCAGTG | AAGGCCCTCT | ACACGGTTGG | CTACAGCACA | 660 |
| TCCCTCGTCA | CCCTCACCAC | TGCCATGGTC | ATCCTTTGTC | GCTTCCGGAA | GCTGCACTGC | 720 |
| ACACGCAACT | TCATCCACAT | GAACCTGTTT | GTGTCGTTCA | TGCTGAGGGC | GATCTCCGTC | 780 |
| TTCATCAAAG | ACTGGATTCT | GTATGCGGAG | CAGGACAGCA | ACCACTGCTT | CATCTCCACT | 840 |
| GTGGAATGTA | AGGCCGTCAT | GGTTTTCTTC | CACTACTGTG | TTGTGTCCAA | CTACTTCTGG | 900 |
| CTGTTCATCG | AGGGCCTGTA | CCTCTTCACT | CTGCTGGTGG | AGACCTTCTT | CCCTGAAAGG | 960 |
| AGATACTTCT | ACTGGTACAC | CATCATTGGC | TGGGGACCC | CAACTGTGTG | TGTGACAGTG | 1020 |
| TGGGCTACGC | TGAGACTCTA | CTTTGATGAC | ACAGGCTGCT | GGGATATGAA | TGACAGCACA | 1080 |
| GCTCTGTGGT | GGGTGATCAA | AGGCCCTGTG | GTTGGCTCTA | TCATGGTTAA | CTTTGTGCTT | 1140 |
| TTTATTGGCA | TTATCGTCAT | CCTTGTGCAG | AAACTTCAGT | CTCCAGACAT | GGGAGGCAAT | 1200 |
| GAGTCCAGCA | TCTACTTAAC | AAATTTAAGC | CCGCGAGTCC | CAAGAAAGC | CCGAGAGGAC | 1260 |
| CCCCTGCCTG | TGCCCTCAGA | CCAGCATTCA | CTCCCTTTCC | TGCGACTGGC | CCGGTCCACC | 1320 |
| CTGCTGCTCA | TCCCACTATT | CGGAATCCAC | TACACAGTAT | TTGCCTTCTC | CCCAGAGAAT | 1380 |
| GTCAGCAAAA | GGGAAAGACT | CGTGTTTGAG | CTGGGGCTGG | GCTCCTTCCA | GGGCTTTGTG | 1440 |
| GTGGCTGTTC | TCTACTGTTT | TCTGAATGGT | GAGGTACAAG | CGGAGATCAA | GCGAAAATGG | 1500 |
| CGAAGCTGGA | AGGTGAACCG | TTACTTCGCT | GTGGACTTCA | AGCACCGACA | CCCGTCTCTG | 1560 |
| GCCAGCAGTG | GGGTGAATGG | GGGCACCCAG | CTCTCCATCC | TGAGCAAGAG | CAGCTCCCAA | 1620 |
| ATCCGCATGT | CTGGCCTCCC | TGCTGACAAT | CTGGCCACC | | | 1659 |

( 2 ) INFORMATION FOR SEQ ID NO:38:

( i ) SEQUENCE CHARACTERISTICS:
( A ) LENGTH: 2814 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: mat_peptide -continued (B) LOCATION: 498..2036

(xi) SEQUENCE DESCRIPTION: SEQ ID NO:38:

| | | | | | | |
|---|---|---|---|---|---|---|
| TGGCCTGCAC | CCCACCCCCC | AGCCTGCGAA | GACGGGGGGA | GGCGGTGGTC | GGTCGCCTCC | 60 |
| CTCCTGCCCC | CGGCCTGGCT | TCGCGGTGGA | GGCGGTGCCT | CTCCGGCAAG | GCAGACCAGG | 120 |
| CTGGGCGGAC | GCGCGGCGCG | GGGCGGGCTA | GGGAAGGCCG | GGGGCCTCGC | GCTCGGGCCC | 180 |
| CGGGCGGCGA | CTGACAGCGG | CGGCGGCGGC | GGCAGCGGCT | CCAAGGCGAG | CGTGGTCCCC | 240 |
| GCGTGCGCAC | AAGCTCGCCG | CCGCGCAGGG | ACCCACGGAC | ACCGGCGCCG | GGCGGACACA | 300 |
| CAGACGCGGA | GATCGGGCTC | TACGCGCGCT | ACTCAGCGCA | CGAGCTCCCC | ATCCCTGGGC | 360 |
| GGAGCGGGGC | GCGGACTCGC | CGCTGCGCGC | CCTCCCCGCG | GAGTCTGCCC | CGGGCAGACC | 420 |
| CGCAGCCCGC | GGCCCCGCCG | CGAGGCCCCT | GGGTGAGCAG | CCTGTAGACA | CCTGGGGTTG | 480 |
| AGCAGTGGCG | GCTGTGAATG | AGAGGCGGGC | GGCACTGGCC | CGAGCCGCCT | TGCAGGCTGA | 540 |
| GAAGCGTCAT | GGCCAGCATC | GCGCAGGTCT | CCCTGGCTGC | TCTCCTCCTG | CTGCCTATGG | 600 |
| CCACCGCCAT | GCATTCCGAC | TGCATCTTCA | AGAAGGAGCA | AGCCATGTGC | CTGGAGAAGA | 660 |
| TCCAGAGGGT | GAATGACCTG | ATGGGCTTGA | ATGACTCCTC | CCCAGGGTGC | CCTGGGATGT | 720 |
| GGGACAACAT | CACGTGTTGG | AAGCCCGCCC | ACGTGGGTGA | GATGGTCCTG | GTCAGTTGCC | 780 |
| CTGAACTCTT | CCGAATCTTC | AACCCAGACC | AAGTCTGGGA | GACGGAAACC | ATCGGAGAGT | 840 |
| TCGGTTTTGC | AGACAGTAAA | TCCTTGGATC | TCTCAGACAT | GAGGGTGGTG | AGCCGGAATT | 900 |
| GCACGGAGGA | TGGATGGTCA | GAGCCATTCC | CTCATTATTT | CGATGCCTGT | GGGTTTGAGG | 960 |
| AGTACGAATC | TGAGACTGGG | GACCAGGATT | ACTACTACCT | GTCAGTGAAG | GCCCTGTACA | 1020 |
| CAGTTGGCTA | CAGCACGTCC | CTCGTCACCC | TCACCACTGC | CATGGTCATC | CTGTGTCGTT | 1080 |
| TCCGGAAGCT | GCACTGCACC | CGCAACTTCA | TCCACATGAA | CCTCTTCGTG | TCGTTTATGC | 1140 |
| TGAGGGCCAT | CTCCGTCTTC | ATCAAAGACT | GGATCCTCTA | TGCTGAGCAG | GACAGCAATC | 1200 |
| ACTGCTTTGT | CTCCACTGTG | GAATGCAAGG | CTGTGATGGT | TTTCTTCCAC | TACTGTGTTG | 1260 |
| TATCCAACTA | CTTCTGGCTG | TTCATCGAGG | GCCTGTATCT | CTTCACCCTG | CTGGTGGAGA | 1320 |
| CCTTCTTCCC | CGAGAGGAGA | TATTTCTACT | GGTACATCAT | CATTGGCTGG | GGGACACCAA | 1380 |
| CTGTGTGTGT | GTCTGTGTGG | GCTATGCTGA | GGCTCTACTT | CGATGACACA | GGCTGCTGGG | 1440 |
| ATATGAATGA | CAACACGGCT | CTGTGGTGGG | TGATCAAAGG | CCCTGTAGTT | GGCTCCATAA | 1500 |
| TGGTTAATTT | TGTGCTCTTC | ATCGGCATCA | TTGTCATCCT | TGTGCAGAAA | CTTCAGTCTC | 1560 |
| CAGACATGGG | AGGCAACGAG | TCCAGCATCT | ACTTCAGCTG | CGTGCAGAAA | TGCTACTGCA | 1620 |
| AGCCACAGCG | GGCTCAGCAG | CACTCTTGCA | AGATGTCAGA | ACTGTCCACC | ATTACTCTAC | 1680 |
| GGCTCGCCAG | GTCCACCTTG | CTGCTCATCC | CACTCTTTGG | AATCCACTAC | ACTGTCTTTG | 1740 |
| CTTTCTCCCC | GGAGAACGTC | AGCAAGAGGG | AGAGACTGGT | GTTTGAGCTG | GGTCTGGGCT | 1800 |
| CCTTCCAGGG | CTTTGTGGTG | GCTGTTCTCT | ATTGCTTTCT | GAATGGAGAG | GTGCAGGCGG | 1860 |
| AGATCAAGAG | GAAGTGGCGG | AGCTGGAAGG | TGAACCGCTA | CTTCACCATG | GACTTCAAGC | 1920 |
| ACCGGCACCC | ATCCCTGGCC | AGCAGCGGGG | TGAACGGGGG | CACCCAGCTC | TCCATCCTGA | 1980 |
| GCAAGAGCAG | CTCCCAGATC | CGCATGTCTG | GCTTCCGGC | CGACAACCTG | GCCACCTGAG | 2040 |
| CCCACCCTGC | CCCCTCCTCT | CCTCTGTACG | CAGGCTGGGG | CTGTGGTGGG | GCGCCGGCCC | 2100 |
| ACGCATGTTG | TGCCTCTTCT | CGCCTTCGGG | CAGGCCCCGG | GCTGGGCGCC | TGGCCCCGA | 2160 |
| GGTTGGAGAA | GGATGCGGGA | CAGGCAGCTG | TTTAGCCTTC | CTGTTTTGGC | GCTGGCCCAA | 2220 |
| CCACCGTGGG | TCCCTGGGCC | TGCACCCAGA | CATGTAATAC | TCCTTAATTG | GGAAGTCATC | 2280 |

-continued

| | | | | | | |
|---|---|---|---|---|---|---|
| CATTCTTTCC | CTTTCCCAAG | TCCTTGCTTA | TTAAGAGGTT | CAAGTCACCT | ACCCAATTCA | 2340 |
| GAAGCTTAAG | TAACCACTAA | CCACCGTGAC | TGCGTGGGAG | GCCTCCCATG | GGCTGAGCTA | 2400 |
| CTGACTTGGC | TTTGGGGGCC | TTGGGCTGGG | GCCCTCCTTA | AAGCCCCCCC | TGAAATTGTC | 2460 |
| GGACCTCAAA | GTGTGACTCC | TTTGAGTCTA | CTCGCCACCC | CCGTGGCCCT | TTGCAGCCCT | 2520 |
| GGTCCAGTCA | CCGAGGTTAC | TGGAAGTCCA | GCTTGGATGG | CCAGACAGCT | TTTTGGCACA | 2580 |
| GGCAGACCCA | TGCTCACCCA | ACATTTTAGT | GTCCAGGTGC | CCAGGTGCCC | AGGTGCCCAG | 2640 |
| CTCCTGGGCA | TCAGACAGTG | GGAAAGCTCC | AGGGATCTAC | CATTCAGAGA | CTTCAGTTTG | 2700 |
| GATGTAGGGC | TAAGGCCAGA | GAAAAGTTCT | GGAGCTTTTC | ATTTGGCCCA | AGAAAAAACT | 2760 |
| GCCAAGATCC | AGAAAAGTGG | ATCTGAGTGG | AATTTAGATG | CAAAGAGCTT | GGAG | 2814 |

( 2 ) INFORMATION FOR SEQ ID NO:39:

( i ) SEQUENCE CHARACTERISTICS:
        ( A ) LENGTH: 2730 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 498..1952

( x i ) SEQUENCE DESCRIPTION: SEQ ID NO:39:

| | | | | | | |
|---|---|---|---|---|---|---|
| TGGCCTGCAC | CCCACCCCCC | AGCCTGCGAA | GACGGGGGA | GGCGGTGGTC | GGTCGCCTCC | 60 |
| CTCCTGCCCC | CGGCCTGGCT | TCGCGGTGGA | GGCGGTGCCT | CTCCGGCAAG | GCAGACCAGG | 120 |
| CTGGGCGGAC | GCGCGGCGCG | GGGCGGGCTA | GGGAAGGCCG | GGGGCCTCGC | GCTCGGGCCC | 180 |
| CGGGCGGCGA | CTGACAGCGG | CGGCGGCGGC | GGCAGCGGCT | CCAAGGCGAG | CGTGGTCCCC | 240 |
| GCGTGCGCAC | AAGCTCGCCG | CCGCGCAGGG | ACCACGGAC | ACCGGCGCCG | GCGGACACA | 300 |
| CAGACGCGGA | GATCGGGCTC | TACGCGCGCT | ACTCAGCGCA | CGAGCTCCCC | ATCCCTGGGC | 360 |
| GGAGCGGGGC | GCGGACTCGC | CGCTGCGCGC | CCTCCCCGCG | GAGTCTGCCC | CGGGCAGACC | 420 |
| CGCAGCCCGC | GGCCCCGCCG | CGAGGCCCCT | GGGTGAGCAG | CCTGTAGACA | CCTGGGGTTG | 480 |
| AGCAGTGGCG | GCTGTGAATG | AGAGGCGGGC | GGCACTGGCC | CGAGCCGCCT | TGCAGGCTGA | 540 |
| GAAGCGTCAT | GGCCAGCATC | GCGCAGGTCT | CCCTGGCTGC | TCTCCTCCTG | CTGCCTATGG | 600 |
| CCACCGCCAT | GCATTCCGAC | TGCATCTTCA | AGAAGGAGCA | AGCCATGTGC | CTGGAGAAGA | 660 |
| TCCAGAGGGT | GAATGACCTG | ATGGGCTTGA | ATGACTCCTC | CCCAGGGTGC | CCTGGGATGT | 720 |
| GGGACAACAT | CACGTGTTGG | AAGCCCGCCC | ACGTGGGTGA | GATGGTCCTG | GTCAGTTGCC | 780 |
| CTGAACTCTT | CCGAATCTTC | AACCCAGACC | AAGTCTGGGA | GACGGAAACC | ATCGGAGAGT | 840 |
| TCGGTTTTGC | AGACAGTAAA | TCCTTGGATC | TCTCAGACAT | GAGGGTGGTG | AGCCGGAATT | 900 |
| GCACGGAGGA | TGGATGGTCA | GAGCCATTCC | CTCATTATTT | CGATGCCTGT | GGGTTTGAGG | 960 |
| AGTACGAATC | TGAGACTGGG | GACCAGGATT | ACTACTACCT | GTCAGTGAAG | GCCCTGTACA | 1020 |
| CAGTTGGCTA | CAGCACGTCC | CTCGTCACCC | TCACCACTGC | CATGGTCATC | CTGTGTCGTT | 1080 |
| TCCGGAAGCT | GCACTGCACC | CGCAACTTCA | TCCACATGAA | CCTCTTCGTG | TCGTTTATGC | 1140 |
| TGAGGGCCAT | CTCCGTCTTC | ATCAAAGACT | GGATCCTCTA | TGCTGAGCAG | GACAGCAATC | 1200 |
| ACTGCTTTGT | CTCCACTGTG | GAATGCAAGG | CTGTGATGGT | TTTCTTCCAC | TACTGTGTTG | 1260 |
| TATCCAACTA | CTTCTGGCTG | TTCATCGAGG | GCCTGTATCT | CTTCACCCTG | CTGGTGGAGA | 1320 |
| CCTTCTTCCC | CGAGAGGAGA | TATTTCTACT | GGTACATCAT | CATTGGCTGG | GGGACACCAA | 1380 |

| | | | | | | |
|---|---|---|---|---|---|---|
|CTGTGTGTGT|GTCTGTGTGG|GCTATGCTGA|GGCTCTACTT|CGATGACACA|GGCTGCTGGG|1440|
|ATATGAATGA|CAACACGGCT|CTGTGGTGGG|TGATCAAAGG|CCCTGTAGTT|GGCTCCATAA|1500|
|TGGTTAATTT|TGTGCTCTTC|ATCGGCATCA|TTGTCATCCT|TGTGCAGAAA|CTTCAGTCTC|1560|
|CAGACATGGG|AGGCAACGAG|TCCAGCATCT|ACTTACGGCT|CGCCAGGTCC|ACCTTGCTGC|1620|
|TCATCCCACT|CTTTGGAATC|CACTACACTG|TCTTTGCTTT|CTCCCCGGAG|AACGTCAGCA|1680|
|AGAGGGAGAG|ACTGGTGTTT|GAGCTGGGTC|TGGGCTCCTT|CCAGGGCTTT|GTGGTGGCTG|1740|
|TTCTCTATTG|CTTTCTGAAT|GGAGAGGTGC|AGGCGGAGAT|CAAGAGGAAG|TGGCGGAGCT|1800|
|GGAAGGTGAA|CCGCTACTTC|ACCATGGACT|TCAAGCACCG|GCACCCATCC|CTGGCCAGCA|1860|
|GCGGGGTGAA|CGGGGGCACC|CAGCTCTCCA|TCCTGAGCAA|GAGCAGCTCC|CAGATCCGCA|1920|
|TGTCTGGGCT|TCCGGCCGAC|AACCTGGCCA|CCTGAGCCCA|CCCTGCCCCC|TCCTCTCCTC|1980|
|TGTACGCAGG|CTGGGGCTGT|GGTGGGGCGC|CGGCCCACGC|ATGTTGTGCC|TCTTCTCGCC|2040|
|TTCGGGCAGG|CCCCGGGCTG|GGCGCCTGGC|CCCCGAGGTT|GGAGAAGGAT|GCGGGACAGG|2100|
|CAGCTGTTTA|GCCTTCCTGT|TTTGGCGCTG|GCCCAACCAC|CGTGGGTCCC|TGGGCCTGCA|2160|
|CCCAGACATG|TAATACTCCT|TAATTGGGAA|GTCATCCATT|CTTTCCCTTT|CCCAAGTCCT|2220|
|TGCTTATTAA|GAGGTTCAAG|TCACCTACCC|AATTCAGAAG|CTTAAGTAAC|CACTAACCAC|2280|
|CGTGACTGCG|TGGGAGGCCT|CCCATGGGCT|GAGCTACTGA|CTTGGCTTTG|GGGGCCTTGG|2340|
|GCTGGGGCCC|TCCTTAAAGC|CCCCCCTGAA|ATTGTCGGAC|CTCAAAGTGT|GACTCCTTTG|2400|
|AGTCTACTCG|CCACCCCCGT|GGCCCTTTGC|AGCCCTGGTC|CAGTCACCGA|GGTTACTGGA|2460|
|AGTCCAGCTT|GGATGGCCAG|ACAGCTTTTT|GGCACAGGCA|GACCCATGCT|CACCCAACAT|2520|
|TTTAGTGTCC|AGGTGCCCAG|GTGCCCAGGT|GCCCAGCTCC|TGGGCATCAG|ACAGTGGGAA|2580|
|AGCTCCAGGG|ATCTACCATT|CAGAGACTTC|AGTTTGGATG|TAGGGCTAAG|GCCAGAGAAA|2640|
|AGTTCTGGAG|CTTTTCATTT|GGCCCAAGAA|AAAACTGCCA|AGATCCAGAA|AAGTGGATCT|2700|
|GAGTGGAATT|TAGATGCAAA|GAGCTTGGAG| | | |2730|

( 2 ) INFORMATION FOR SEQ ID NO:40:

( i ) SEQUENCE CHARACTERISTICS:
        ( A ) LENGTH: 1869 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 77..1477

( x i ) SEQUENCE DESCRIPTION: SEQ ID NO:40:

| | | | | | | |
|---|---|---|---|---|---|---|
|CGAGTGGACA|GTGGCAGGCG|GTGACTGAAT|CTCCAAGTCT|GGAAACAATA|GCCAGAGATA|60|
|GTGGCTGGGA|AGCACCATGG|CCAGAGTCCT|GCAGCTCTCC|CTGACTGCTC|TCCTGCTGCC|120|
|TGTGGCTATT|GCTATGCACT|CTGACTGCAT|CTTCAAGAAG|GAGCAAGCCA|TGTGCCTGGA|180|
|GAGGATCCAG|AGGGCCAACG|ACCTGATGGG|ACTAAACGAG|TCTTCCCCAG|GTTGCCCTGG|240|
|CATGTGGGAC|AATATCACAT|GTTGGAAGCC|AGCTCAAGTA|GGTGAGATGG|TCCTTGTAAG|300|
|CTGCCCTGAG|GTCTTCCGGA|TCTTCAACCC|GGACCAAGTC|TGGATGACAG|AAACCATAGG|360|
|AGATTCTGGT|TTTGCCGATA|GTAATTCCTT|GGAGATCACA|GACATGGGGG|TCGTGGGCCG|420|
|GAACTGCACA|GAGGACGGCT|GGTCGGAGCC|CTTCCCCCAC|TACTTCGATG|CTTGTGGGTT|480|

| | | | | | | |
|---|---|---|---|---|---|---|
| TGATGATTAT | GAGCCTGAGT | CTGGAGATCA | GGATTATTAC | TACCTGTCGG | TGAAGGCTCT | 540 |
| CTACACAGTC | GGCTACAGCA | CTTCCCTCGC | CACCCTCACT | ACTGCCATGG | TCATCTTGTG | 600 |
| CCGCTTCCGG | AAGCTGCATT | GCACTCGCAA | CTTCATCCAC | ATGAACCTGT | TTGTATCCTT | 660 |
| CATGCTGAGG | GCTATCTCCG | TCTTCATCAA | GGACTGGATC | TTGTACGCCG | AGCAGGACAG | 720 |
| CAGTCACTGC | TTCGTTTCCA | CCGTGGAGTG | CAAAGCTGTC | ATGGTTTTCT | TCCACTACTG | 780 |
| CGTGGTGTCC | AACTACTTCT | GGCTGTTCAT | TGAAGGCCTG | TACCTCTTTA | CACTGCTGGT | 840 |
| GGAGACCTTC | TTCCCTGAGA | GGAGATATTT | CTACTGGTAC | ACCATCATCG | GCTGGGGGAC | 900 |
| ACCTACTGTG | TGTGTAACAG | TGTGGGCTGT | GCTGAGGCTC | TATTTTGATG | ATGCAGGATG | 960 |
| CTGGATATG | AATGACAGCA | CAGCTCTGTG | GTGGGTGATC | AAAGGCCCCG | TGGTTGGCTC | 1020 |
| TATAATGGTT | AACTTTGTGC | TTTTCATCGG | CATCATCATC | ATCCTTGTAC | AGAAGCTGCA | 1080 |
| GTCCCCAGAC | ATGGGAGGCA | ACGAGTCCAG | CATCTACTTA | CGGCTGGCCC | GCTCCACCCT | 1140 |
| ACTGCTCATC | CCACTCTTCG | GAATCCACTA | CACAGTATTC | GCCTTCTCTC | AGAGAACGT | 1200 |
| CAGCAAGAGG | GAAAGACTTG | TGTTTGAGCT | TGGGCTGGGC | TCCTTCCAGG | GCTTTGTGGT | 1260 |
| GGCTGTACTC | TACTGCTTCC | TGAATGGGGA | GGTACAGGCA | GAGATTAAGA | GGAAATGGAG | 1320 |
| GAGCTGGAAG | GTGAACCGTT | ACTTCACTAT | GGACTTCAAG | CACCGGCACC | CGTCCCTGGC | 1380 |
| CAGCAGTGGA | GTAAATGGGG | GAACCCAGCT | GTCCATCCTG | AGCAAGAGCA | GCTCCCAGCT | 1440 |
| CCGCATGTCC | AGCCTCCCGG | CCGACAACTT | GGCCACCTGA | GGCCTGTCTC | CCTCCTCCTT | 1500 |
| CTGCACAGGC | TGGGGCTGCG | GGCCAGTGCC | TGAGCATGTT | TGTGCCTCTC | CCCTCTCCTT | 1560 |
| GGGCAGGCCC | TGGGTAGGAA | GCTGGGCTCC | TCCCCAAAGG | GGAAGAGAGA | GATAGGGTAT | 1620 |
| AGGCTGATAT | TGCTCCTCCT | GTTTGGGTCC | CACCTACTGT | GATTCATTGA | GCCTGATTTG | 1680 |
| ACATGTAAAT | ACACCTCAAA | TTTGGAAAGT | TGCCCCATCT | CTGCCCCCAA | CCCATGCCCC | 1740 |
| TGCTCACCTC | TGCCAGGCCC | CAGCTCAACC | TACTGTGTCA | AGGCCAGCCT | CAGTGATAGT | 1800 |
| CTGATCCCAG | GTACAAGGCC | TTGTGAGCTG | AGGCTGAAAG | GCCTGTTTTG | GAGAGGCTGG | 1860 |
| GGTAGTGCC | | | | | | 1869 |

( 2 ) INFORMATION FOR SEQ ID NO:41:

( i ) SEQUENCE CHARACTERISTICS:
        ( A ) LENGTH: 2548 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 77..1561

( x i ) SEQUENCE DESCRIPTION: SEQ ID NO:41:

| | | | | | | |
|---|---|---|---|---|---|---|
| CGAGTGGACA | GTGGCAGGCG | GTGACTGAAT | CTCCAAGTCT | GGAAACAATA | GCCAGAGATA | 60 |
| GTGGCTGGGA | AGCACCATGG | CCAGAGTCCT | GCAGCTCTCC | CTGACTGCTC | TCCTGCTGCC | 120 |
| TGTGGCTATT | GCTATGCACT | CTGACTGCAT | CTTCAAGAAG | GAGCAAGCCA | TGTGCCTGGA | 180 |
| GAGGATCCAG | AGGGCCAACG | ACCTGATGGG | ACTAAACGAG | TCTTCCCCAG | GTTGCCCTGG | 240 |
| CATGTGGGAC | AATATCACAT | GTTGGAAGCC | AGCTCAAGTA | GGTGAGATGG | TCCTTGTAAG | 300 |
| CTGCCCTGAG | GTCTTCCGGA | TCTTCAACCC | GGACCAAGTC | TGGATGACAG | AAACCATAGG | 360 |
| AGATTCTGGT | TTTGCCGATA | GTAATTCCTT | GGAGATCACA | GACATGGGGG | TCGTGGGCCG | 420 |
| GAACTGCACA | GAGGACGGCT | GGTCGGAGCC | CTTCCCCCAC | TACTTCGATG | CTTGTGGGTT | 480 |

```
TGATGATTAT  GAGCCTGAGT  CTGGAGATCA  GGATTATTAC  TACCTGTCGG  TGAAGGCTCT     540

CTACACAGTC  GGCTACAGCA  CTTCCCTCGC  CACCCTCACT  ACTGCCATGG  TCATCTTGTG     600

CCGCTTCCGG  AAGCTGCATT  GCACTCGCAA  CTTCATCCAC  ATGAACCTGT  TTGTATCCTT     660

CATGCTGAGG  GCTATCTCCG  TCTTCATCAA  GGACTGGATC  TTGTACGCCG  AGCAGGACAG     720

CAGTCACTGC  TTCGTTTCCA  CCGTGGAGTG  CAAAGCTGTC  ATGGTTTTCT  TCCACTACTG     780

CGTGGTGTCC  AACTACTTCT  GGCTGTTCAT  TGAAGGCCTG  TACCTCTTTA  CACTGCTGGT     840

GGAGACCTTC  TTCCCTGAGA  GGAGATATTT  CTACTGGTAC  ACCATCATCG  GCTGGGGGAC     900

ACCTACTGTG  TGTGTAACAG  TGTGGGCTGT  GCTGAGGCTC  TATTTTGATG  ATGCAGGATG     960

CTGGGATATG  AATGACAGCA  CAGCTCTGTG  GTGGGTGATC  AAAGGCCCCG  TGGTTGGCTC    1020

TATAATGGTT  AACTTTGTGC  TTTTCATCGG  CATCATCATC  ATCCTTGTAC  AGAAGCTGCA    1080

GTCCCCAGAC  ATGGGAGGCA  ACGAGTCCAG  CATCTACTTC  AGCTGCGTGC  AGAAATGCTA    1140

CTGCAAGCCA  CAGCGGGCTC  AGCAGCACTC  TTGCAAGATG  TCAGAACTAT  CCACCATTAC    1200

TCTACGGCTG  GCCCGCTCCA  CCCTACTGCT  CATCCCACTC  TTCGGAATCC  ACTACACAGT    1260

ATTCGCCTTC  TCTCCAGAGA  ACGTCAGCAA  GAGGGAAAGA  CTTGTGTTTG  AGCTTGGGCT    1320

GGGCTCCTTC  CAGGGCTTTG  TGGTGGCTGT  ACTCTACTGC  TTCCTGAATG  GGGAGGTACA    1380

GGCAGAGATT  AAGAGGAAAT  GGAGGAGCTG  GAAGGTGAAC  CGTTACTTCA  CTATGGACTT    1440

CAAGCACCGG  CACCCGTCCC  TGGCCAGCAG  TGGAGTAAAT  GGGGGAACCC  AGCTGTCCAT    1500

CCTGAGCAAG  AGCAGCTCCC  AGCTCCGCAT  GTCCAGCCTC  CCGGCCGACA  ACTTGGCCAC    1560

CTGAGGCCTG  TCTCCCTCCT  CCTTCTGCAC  AGGCTGGGGC  TGCGGGCCAG  TGCCTGAGCA    1620

TGTTTGTGCC  TCTCCCTCT   CCTTGGGCAG  GCCCTGGGTA  GGAAGCTGGG  CTCCTCCCCA    1680

AAGGGGAAGA  GAGAGATAGG  GTATAGGCTG  ATATTGCTCC  TCCTGTTTGG  GTCCCACCTA    1740

CTGTGATTCA  TTGAGCCTGA  TTTGACATGT  AAATACACCT  CAAATTTGGA  AAGTTGCCCC    1800

ATCTCTGCCC  CCAACCCATG  CCCCTGCTCA  CCTCTGCCAG  GCCCAGCTC   AACCTACTGT    1860

GTCAAGGCCA  GCCTCAGTGA  TAGTCTGATC  CCAGGTACAA  GGCCTTGTGA  GCTGAGGCTG    1920

AAAGGCCTGT  TTTGGAGAGG  CTGGGGTAGT  GCCCACCCCA  GCAGCCTTTC  AGCAAATTGA    1980

CTTTGGATGT  GGACCCTTCT  CAGCCTGTAC  CAAGTACTGC  AGTTGGCTAG  GGATGCAGCT    2040

CAGTTTCCTG  AGCATCCTTT  GGAGCAGGTC  AACCTGAGGC  TCCTTTTGCT  TACCCGACAT    2100

CTAAGTTGTC  CAGGTGCTCG  GCTCCTGTGT  GCCTGGATGA  CGGGAGGGCT  CCGGGGTCTT    2160

TCAGTCAAAG  ACTTACATTG  AGGTGGGGTG  AGAGTCAGAG  AAAAGTTCTG  GTGCTTTTCA    2220

TTTGTTCTAA  GAGCTGAGAG  CCAGGAATGC  AGAGTCAATT  GGGAAGGAGA  TGGGATAGCT    2280

GATGATCTTA  CCATGTCCAT  GACTGTGCCC  CTGATTCAAG  ACCGGATCAT  GTGGTGGCTT    2340

TATTTCTACA  CTTCTTGTCC  ACAATGGACA  GTCTGAGGAA  GCTCTTCTTT  CAGCCACAAC    2400

AACCACAGAA  AGCCCTTTCT  TCTCCCTCT   TGTTTCTCCA  TAAGTCAAAG  CCATGTTTAG    2460

AACGGACCAG  CCACCTTGCG  ATGAAATCAC  TGAGTTCTGA  AGCAACTTTC  AATTTCCACG    2520

AGCCAAGTCC  TGGGTCCAGG  GACGCCCC                                         2548
```

( 2 ) INFORMATION FOR SEQ ID NO:42:

( i ) SEQUENCE CHARACTERISTICS:
        ( A ) LENGTH: 1664 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
    ( A ) NAME/KEY: mat_peptide
    ( B ) LOCATION: 74..1648

( x i ) SEQUENCE DESCRIPTION: SEQ ID NO:42:

| | | | | | | |
|---|---|---|---|---|---|---|
| AGCCCAGAGA | CACATTGGGG | CTGACCTGCC | GCTGCTGTCA | GTGGGAGGCC | AGTGGTGCTG | 60 |
| GCCAAGAAGT | GTCATGGCTG | GTGTCGTGCA | CGTTTCCCTG | GCTGCTCACT | GCGGGGCCTG | 120 |
| TCCGTGGGGC | CGGGGCAGAC | TCCGCAAAGG | ACGCGCAGCC | TGCAAGTCCG | CGGCCCAGAG | 180 |
| ACACATTGGG | GCTGACCTGC | CGCTGCTGTC | AGTGGGAGGC | CAGTGGTGCT | GGCCAAGAAG | 240 |
| TGTCATGGCT | GGTGTCGTGC | ACGTTTCCCT | GGCTGCTCTC | CTCCTGCTGC | CTATGGCCCC | 300 |
| TGCCATGCAT | TCTGACTGCA | TCTTCAAGAA | GGAGCAAGCC | ATGTGCCTGG | AGAAGATCCA | 360 |
| GAGGGCCAAT | GAGCTGATGG | GCTTCAATGA | TTCCTCTCCA | GGCTGTCCTG | GGATGTGGGA | 420 |
| CAACATCACG | TGTTGGAAGC | CCGCCCATGT | GGGTGAGATG | GTCCTGGTCA | GCTGCCCTGA | 480 |
| GCTCTTCCGA | ATCTTCAACC | CAGACCAAGT | CTGGGAGACC | GAAACCATTG | AGAGTCTGA | 540 |
| TTTTGGTGAC | AGTAACTCCT | TAGATCTCTC | AGACATGGGA | GTGGTGAGCC | GGAACTGCAC | 600 |
| GGAGGATGGC | TGGTCGGAAC | CCTTCCCTCA | TTACTTTGAT | GCCTGTGGGT | TGATGAATA | 660 |
| TGAATCTGAG | ACTGGGGACC | AGGATTATTA | CTACCTGTCA | GTGAAGGCCC | TCTACACGGT | 720 |
| TGGCTACAGC | ACATCCCTCG | TCACCCTCAC | CACTGCCATG | GTCATCCTTT | GTCGCTTCCG | 780 |
| GAAGCTGCAC | TGCACACGCA | ACTTCATCCA | CATGAACCTG | TTTGTGTCGT | TCATGCTGAG | 840 |
| GGCGATCTCC | GTCTTCATCA | AAGACTGGAT | TCTGTATGCG | GAGCAGGACA | GCAACCACTG | 900 |
| CTTCATCTCC | ACTGTGGAAT | GTAAGGCCGT | CATGGTTTTC | TTCCACTACT | GTGTTGTGTC | 960 |
| CAACTACTTC | TGGCTGTTCA | TCGAGGGCCT | GTACCTCTTC | ACTCTGCTGG | TGGAGACCTT | 1020 |
| CTTCCCTGAA | AGGAGATACT | TCTACTGGTA | CACCATCATT | GGCTGGGGGT | CCCCAACTGT | 1080 |
| GTGTGTGACA | GTGTGGGCTA | CGCTGAGACT | CTACTTTGAT | GACACAGGCT | GCTGGGATAT | 1140 |
| GAATGACAGC | ACAGCTCTGT | GGTGGGTGAT | CAAAGGCCCT | GTGGTTGGCT | CTATCATGGT | 1200 |
| TAACTTTGTG | CTTTTTATTG | GCATTATCGT | CATCCTTGTG | CAGAAACTTC | AGTCTCCAGA | 1260 |
| CATGGGAGGC | AATGAGTCCA | GCATCTACTT | GCGACTGGCC | CGGTCCACCC | TGCTGCTCAT | 1320 |
| CCCACTATTC | GGAATCCACT | ACACAGTATT | TGCCTTCTCC | CCAGAGAATG | TCAGCAAAAG | 1380 |
| GGAAAGACTC | GTGTTTGAGC | TGGGGCTGGG | CTCCTTCCAG | GGCTTTGTGG | TGGCTGTTCT | 1440 |
| CTACTGTTTT | CTGAATGGTG | AGGTACAAGC | GGAGATCAAG | CGAAAATGGC | GAAGCTGGAA | 1500 |
| GGTGAACCGT | TACTTCGCTG | TGGACTTCAA | GCACCGACAC | CCGTCTCTGG | CCAGCAGTGG | 1560 |
| GGTGAATGGG | GGCACCCAGC | TCTCCATCCT | GAGCAAGAGC | AGCTCCCAAA | TCCGCATGTC | 1620 |
| TGGCCTCCCT | GCTGACAATC | TGGCCACCTG | AGCCATGCTC | CCCT | | 1664 |

( 2 ) INFORMATION FOR SEQ ID NO:43:

( i ) SEQUENCE CHARACTERISTICS:
        ( A ) LENGTH: 1748 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 74..1732

( x i ) SEQUENCE DESCRIPTION: SEQ ID NO:43:

| | | | | | | |
|---|---|---|---|---|---|---|
| AGCCCAGAGA | CACATTGGGG | CTGACCTGCC | GCTGCTGTCA | GTGGGAGGCC | AGTGGTGCTG | 60 |
| GCCAAGAAGT | GTCATGGCTG | GTGTCGTGCA | CGTTTCCCTG | GCTGCTCACT | GCGGGGCCTG | 120 |
| TCCGTGGGGC | CGGGGCAGAC | TCCGCAAAGG | ACGCGCAGCC | TGCAAGTCCG | CGGCCCAGAG | 180 |
| ACACATTGGG | GCTGACCTGC | CGCTGCTGTC | AGTGGGAGGC | CAGTGGTGCT | GGCCAAGAAG | 240 |
| TGTCATGGCT | GGTGTCGTGC | ACGTTTCCCT | GGCTGCTCTC | CTCCTGCTGC | CTATGGCCCC | 300 |
| TGCCATGCAT | TCTGACTGCA | TCTTCAAGAA | GGAGCAAGCC | ATGTGCCTGG | AGAAGATCCA | 360 |
| GAGGGCCAAT | GAGCTGATGG | GCTTCAATGA | TTCCTCTCCA | GGCTGTCCTG | GGATGTGGGA | 420 |
| CAACATCACG | TGTTGGAAGC | CCGCCCATGT | GGGTGAGATG | GTCCTGGTCA | GCTGCCCTGA | 480 |
| GCTCTTCCGA | ATCTTCAACC | CAGACCAAGT | CTGGGAGACC | GAAACCATTG | GAGAGTCTGA | 540 |
| TTTTGGTGAC | AGTAACTCCT | TAGATCTCTC | AGACATGGGA | GTGGTGAGCC | GGAACTGCAC | 600 |
| GGAGGATGGC | TGGTCGGAAC | CCTTCCCTCA | TTACTTTGAT | GCCTGTGGGT | TGATGAATA | 660 |
| TGAATCTGAG | ACTGGGGACC | AGGATTATTA | CTACCTGTCA | GTGAAGGCCC | TCTACACGGT | 720 |
| TGGCTACAGC | ACATCCCTCG | TCACCCTCAC | CACTGCCATG | GTCATCCTTT | GTCGCTTCCG | 780 |
| GAAGCTGCAC | TGCACACGCA | ACTTCATCCA | CATGAACCTG | TTTGTGTCGT | TCATGCTGAG | 840 |
| GGCGATCTCC | GTCTTCATCA | AAGACTGGAT | TCTGTATGCG | GAGCAGGACA | GCAACCACTG | 900 |
| CTTCATCTCC | ACTGTGGAAT | GTAAGGCCGT | CATGGTTTTC | TTCCACTACT | GTGTTGTGTC | 960 |
| CAACTACTTC | TGGCTGTTCA | TCGAGGGCCT | GTACCTCTTC | ACTCTGCTGG | TGGAGACCTT | 1020 |
| CTTCCCTGAA | AGGAGATACT | TCTACTGGTA | CACCATCATT | GGCTGGGGGA | CCCCAACTGT | 1080 |
| GTGTGTGACA | GTGTGGGCTA | CGCTGAGACT | CTACTTTGAT | GACACAGGCT | GCTGGGATAT | 1140 |
| GAATGACAGC | ACAGCTCTGT | GGTGGGTGAT | CAAAGGCCCT | GTGGTTGGCT | CTATCATGGT | 1200 |
| TAACTTTGTG | CTTTTTATTG | GCATTATCGT | CATCCTTGTG | CAGAAACTTC | AGTCTCCAGA | 1260 |
| CATGGGAGGC | AATGAGTCCA | GCATCTACTT | CAGCTGCGTG | CAGAAATGCT | ACTGCAAGCC | 1320 |
| ACAGCGGGCT | CAGCAGCACT | CTTGCAAGAT | GTCAGAACTG | TCCACCATTA | CTCTGCGACT | 1380 |
| GGCCCGGTCC | ACCCTGCTGC | TCATCCCACT | ATTCGGAATC | CACTACACAG | TATTTGCCTT | 1440 |
| CTCCCCAGAG | AATGTCAGCA | AAAGGGAAAG | ACTCGTGTTT | GAGCTGGGGC | TGGGCTCCTT | 1500 |
| CCAGGGCTTT | GTGGTGGCTG | TTCTCTACTG | TTTTCTGAAT | GGTGAGGTAC | AAGCGGAGAT | 1560 |
| CAAGCGAAAA | TGGCGAAGCT | GGAAGGTGAA | CCGTTACTTC | GCTGTGGACT | TCAAGCACCG | 1620 |
| ACACCCGTCT | CTGGCCAGCA | GTGGGGTGAA | TGGGGCACC | CAGCTCTCCA | TCCTGAGCAA | 1680 |
| GAGCAGCTCC | CAAATCCGCA | TGTCTGGCCT | CCCTGCTGAC | AATCTGGCCA | CCTGAGCCAT | 1740 |
| GCTCCCCT | | | | | | 1748 |

( 2 ) INFORMATION FOR SEQ ID NO:44:

( i ) SEQUENCE CHARACTERISTICS:
        ( A ) LENGTH: 1745 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 74..1729

( x i ) SEQUENCE DESCRIPTION: SEQ ID NO:44:

| | | | | | | |
|---|---|---|---|---|---|---|
| AGCCCAGAGA | CACATTGGGG | CTGACCTGCC | GCTGCTGTCA | GTGGGAGGCC | AGTGGTGCTG | 60 |

| | | | | | |
|---|---|---|---|---|---|
| GCCAAGAAGT | GTCATGGCTG | GTGTCGTGCA | CGTTTCCCTG | GCTGCTCACT | GCGGGGCCTG | 120 |
| TCCGTGGGGC | CGGGGCAGAC | TCCGCAAAGG | ACGCGCAGCC | TGCAAGTCCG | CGGCCCAGAG | 180 |
| ACACATTGGG | GCTGACCTGC | CGCTGCTGTC | AGTGGGAGGC | CAGTGGTGCT | GGCCAAGAAG | 240 |
| TGTCATGGCT | GGTGTCGTGC | ACGTTTCCCT | GGCTGCTCTC | CTCCTGCTGC | CTATGGCCCC | 300 |
| TGCCATGCAT | TCTGACTGCA | TCTTCAAGAA | GGAGCAAGCC | ATGTGCCTGG | AGAAGATCCA | 360 |
| GAGGGCCAAT | GAGCTGATGG | GCTTCAATGA | TTCCTCTCCA | GGCTGTCCTG | GGATGTGGGA | 420 |
| CAACATCACG | TGTTGGAAGC | CCGCCCATGT | GGGTGAGATG | GTCCTGGTCA | GCTGCCCTGA | 480 |
| GCTCTTCCGA | ATCTTCAACC | CAGACCAAGT | CTGGGAGACC | GAAACCATTG | AGAGTCTGA | 540 |
| TTTTGGTGAC | AGTAACTCCT | TAGATCTCTC | AGACATGGGA | GTGGTGAGCC | GGAACTGCAC | 600 |
| GGAGGATGGC | TGGTCGGAAC | CCTTCCCTCA | TTACTTTGAT | GCCTGTGGGT | TGATGAATA | 660 |
| TGAATCTGAG | ACTGGGGACC | AGGATTATTA | CTACCTGTCA | GTGAAGGCCC | TCTACACGGT | 720 |
| TGGCTACAGC | ACATCCCTCG | TCACCCTCAC | CACTGCCATG | GTCATCCTTT | GTCGCTTCCG | 780 |
| GAAGCTGCAC | TGCACACGCA | ACTTCATCCA | CATGAACCTG | TTTGTGTCGT | TCATGCTGAG | 840 |
| GGCGATCTCC | GTCTTCATCA | AAGACTGGAT | TCTGTATGCG | GAGCAGGACA | GCAACCACTG | 900 |
| CTTCATCTCC | ACTGTGGAAT | GTAAGGCCGT | CATGGTTTTC | TTCCACTACT | GTGTTGTGTC | 960 |
| CAACTACTTC | TGGCTGTTCA | TCGAGGGCCT | GTACCTCTTC | ACTCTGCTGG | TGGAGACCTT | 1020 |
| CTTCCCTGAA | AGGAGATACT | TCTACTGGTA | CACCATCATT | GGCTGGGGGA | CCCCAACTGT | 1080 |
| GTGTGTGACA | GTGTGGGCTA | CGCTGAGACT | CTACTTTGAT | GACACAGGCT | GCTGGGATAT | 1140 |
| GAATGACAGC | ACAGCTCTGT | GGTGGGTGAT | CAAAGGCCCT | GTGGTTGGCT | CTATCATGGT | 1200 |
| TAACTTTGTG | CTTTTTATTG | GCATTATCGT | CATCCTTGTG | CAGAAACTTC | AGTCTCCAGA | 1260 |
| CATGGGAGGC | AATGAGTCCA | GCATCTACTT | CTGCGTGCAG | AAATGCTACT | GCAAGCCACA | 1320 |
| GCGGGCTCAG | CAGCACTCTT | GCAAGATGTC | AGAACTGTCC | ACCATTACTC | TGCGACTGGC | 1380 |
| CCGGTCCACC | CTGCTGCTCA | TCCCACTATT | CGGAATCCAC | TACACAGTAT | TTGCCTTCTC | 1440 |
| CCCAGAGAAT | GTCAGCAAAA | GGGAAAGACT | CGTGTTTGAG | CTGGGGCTGG | GCTCCTTCCA | 1500 |
| GGGCTTTGTG | GTGGCTGTTC | TCTACTGTTT | TCTGAATGGT | GAGGTACAAG | CGGAGATCAA | 1560 |
| GCGAAAATGG | CGAAGCTGGA | AGGTGAACCG | TTACTTCGCT | GTGGACTTCA | AGCACCGACA | 1620 |
| CCCGTCTCTG | GCCAGCAGTG | GGGTGAATGG | GGGCACCCAG | CTCTCCATCC | TGAGCAAGAG | 1680 |
| CAGCTCCCAA | ATCCGCATGT | CTGGCCTCCC | TGCTGACAAT | CTGGCCACCT | GAGCCATGCT | 1740 |
| CCCCT | | | | | | 1745 |

( 2 ) INFORMATION FOR SEQ ID NO:45:

( i ) SEQUENCE CHARACTERISTICS:
        ( A ) LENGTH: 1748 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 74..1732

( x i ) SEQUENCE DESCRIPTION: SEQ ID NO:45:

| | | | | | |
|---|---|---|---|---|---|
| AGCCCAGAGA | CACATTGGGG | CTGACCTGCC | GCTGCTGTCA | GTGGGAGGCC | AGTGGTGCTG | 60 |
| GCCAAGAAGT | GTCATGGCTG | GTGTCGTGCA | CGTTTCCCTG | GCTGCTCACT | GCGGGGCCTG | 120 |
| TCCGTGGGGC | CGGGGCAGAC | TCCGCAAAGG | ACGCGCAGCC | TGCAAGTCCG | CGGCCCAGAG | 180 |

```
ACACATTGGG  GCTGACCTGC  CGCTGCTGTC  AGTGGGAGGC  CAGTGGTGCT  GGCCAAGAAG   240

TGTCATGGCT  GGTGTCGTGC  ACGTTTCCCT  GGCTGCTCTC  CTCCTGCTGC  CTATGGCCCC   300

TGCCATGCAT  TCTGACTGCA  TCTTCAAGAA  GGAGCAAGCC  ATGTGCCTGG  AGAAGATCCA   360

GAGGGCCAAT  GAGCTGATGG  GCTTCAATGA  TTCCTCTCCA  GGCTGTCCTG  GATGTGGGA    420

CAACATCACG  TGTTGGAAGC  CCGCCCATGT  GGGTGAGATG  GTCCTGGTCA  GCTGCCCTGA   480

GCTCTTCCGA  ATCTTCAACC  CAGACCAAGT  CTGGGAGACC  GAAACCATTG  GAGAGTCTGA   540

TTTTGGTGAC  AGTAACTCCT  TAGATCTCTC  AGACATGGGA  GTGGTGAGCC  GGAACTGCAC   600

GGAGGATGGC  TGGTCGGAAC  CCTTCCCTCA  TTACTTTGAT  GCCTGTGGGT  TTGATGAATA   660

TGAATCTGAG  ACTGGGGACC  AGGATTATTA  CTACCTGTCA  GTGAAGGCCC  TCTACACGGT   720

TGGCTACAGC  ACATCCCTCG  TCACCCTCAC  CACTGCCATG  GTCATCCTTT  GTCGCTTCCG   780

GAAGCTGCAC  TGCACACGCA  ACTTCATCCA  CATGAACCTG  TTTGTGTCGT  TCATGCTGAG   840

GGCGATCTCC  GTCTTCATCA  AAGACTGGAT  TCTGTATGCG  GAGCAGGACA  GCAACCACTG   900

CTTCATCTCC  ACTGTGGAAT  GTAAGGCCGT  CATGGTTTTC  TTCCACTACT  GTGTTGTGTC   960

CAACTACTTC  TGGCTGTTCA  TCGAGGGCCT  GTACCTCTTC  ACTCTGCTGG  TGGAGACCTT  1020

CTTCCCTGAA  AGGAGATACT  TCTACTGGTA  CACCATCATT  GGCTGGGGGA  CCCCAACTGT  1080

GTGTGTGACA  GTGTGGGCTA  CGCTGAGACT  CTACTTTGAT  GACACAGGCT  GCTGGGATAT  1140

GAATGACAGC  ACAGCTCTGT  GGTGGGTGAT  CAAAGGCCCT  GTGGTTGGCT  CTATCATGGT  1200

TAACTTTGTG  CTTTTTATTG  GCATTATCGT  CATCCTTGTG  CAGAAACTTC  AGTCTCCAGA  1260

CATGGGAGGC  AATGAGTCCA  GCATCTACTT  AACAAATTTA  AGCCCGCGAG  TCCCCAAGAA  1320

AGCCCGAGAG  GACCCCCTGC  CTGTGCCCTC  AGACCAGCAT  TCACTCCCTT  TCCTGCGACT  1380

GGCCCGGTCC  ACCCTGCTGC  TCATCCCACT  ATTCGGAATC  CACTACACAG  TATTTGCCTT  1440

CTCCCCAGAG  AATGTCAGCA  AAAGGGAAAG  ACTCGTGTTT  GAGCTGGGGC  TGGGCTCCTT  1500

CCAGGGCTTT  GTGGTGGCTG  TTCTCTACTG  TTTTCTGAAT  GGTGAGGTAC  AAGCGGAGAT  1560

CAAGCGAAAA  TGGCGAAGCT  GGAAGGTGAA  CCGTTACTTC  GCTGTGGACT  TCAAGCACCG  1620

ACACCCGTCT  CTGGCCAGCA  GTGGGGTGAA  TGGGGCACCC  CAGCTCTCCA  TCCTGAGCAA  1680

GAGCAGCTCC  CAAATCCGCA  TGTCTGGCCT  CCCTGCTGAC  AATCTGGCCA  CCTGAGCCAT  1740

GCTCCCCT                                                                1748
```

(2) INFORMATION FOR SEQ ID NO:46:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:46:

```
His  Ser  Asp  Gly  Ile  Phe  Thr  Asp  Ser  Tyr  Ser  Arg  Tyr  Arg  Lys  Gln
 1              5                        10                          15

Met  Ala  Val  Lys  Lys  Tyr  Leu  Ala  Ala  Val  Leu  Gly  Lys  Arg  Tyr  Lys
                20                        25                      30

Gln  Arg  Val  Lys  Asn  Lys
                35
```

(2) INFORMATION FOR SEQ ID NO:47:

(i) SEQUENCE CHARACTERISTICS:

(A) LENGTH: 27 amino acids
(B) TYPE: amino acid
(D) TOPOLOGY: linear (ii) MOLECULE TYPE: protein (xi) SEQUENCE DESCRIPTION: SEQ ID NO:47:

His Ser Asp Gly Ile Phe Thr Asp Ser Tyr Ser Arg Tyr Arg Lys Gln
1               5                   10                  15
Met Ala Val Lys Lys Tyr Leu Ala Ala Val Leu
            20                  25

(2) INFORMATION FOR SEQ ID NO:48:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: Other nucleic acid, Synthetic DNA (xi) SEQUENCE DESCRIPTION: SEQ ID NO:48:

CAGAAAGCTT CGGACCATGC GCCCTCCGAG CCCACCG                    37

(2) INFORMATION FOR SEQ ID NO:49:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: Other nucleic acid, Synthetic DNA (xi) SEQUENCE DESCRIPTION: SEQ ID NO:49:

GGGCTCTAGA CGGTCAGACC AGGGAGACCT CCGCTTG                    37

(2) INFORMATION FOR SEQ ID NO:50:

(i) SEQUENCE CHARACTERISTICS:
(A) LENGTH: 16 amino acids
(B) TYPE: amino acid
(D) TOPOLOGY: linear (ii) MOLECULE TYPE: protein (xi) SEQUENCE DESCRIPTION: SEQ ID NO:50:

Asp Cys Ile Phe Lys Lys Glu Gln Ala Met Cys Leu Glu Lys Ile Gln
1               5                   10                  15

(2) INFORMATION FOR SEQ ID NO:51:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: Other nucleic acid, Synthetic DNA (xi) SEQUENCE DESCRIPTION: SEQ ID NO:51:

TGGATCTTCT CCAGGTGCAT DGCCTGCTCC TTCTTGAAGA TGTGGTC          47

(2) INFORMATION FOR SEQ ID NO:52:

(i) SEQUENCE CHARACTERISTICS:
(A) LENGTH: 24 base pairs
(B) TYPE: nucleic acid

-continued (C) STRANDEDNESS: single
(D) TOPOLOGY: linear (i i) MOLECULE TYPE: Other nucleic acid, Synthetic DNA (x i) SEQUENCE DESCRIPTION: SEQ ID NO:52:

CTGGGATATG AATGACAGCA CAGC    24

(2) INFORMATION FOR SEQ ID NO:53:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: Other nucleic acid, Synthetic DNA (x i) SEQUENCE DESCRIPTION: SEQ ID NO:53:

TCTGGGGAGA AGGCAAATAC TGTG    24

(2) INFORMATION FOR SEQ ID NO:54:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: Other nucleic acid, Synthetic DNA (x i) SEQUENCE DESCRIPTION: SEQ ID NO:54:

TGCGTGCAGA AATGCTACTG CAAGCCACAG    30

(2) INFORMATION FOR SEQ ID NO:55:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: Other nucleic acid, Synthetic DNA (x i) SEQUENCE DESCRIPTION: SEQ ID NO:55:

GACCCCCTGC CTGTGCCCTC AGACCAGCAT    30

(2) INFORMATION FOR SEQ ID NO:56:

(i) SEQUENCE CHARACTERISTICS:
(A) LENGTH: 1324 amino acids
(B) TYPE: amino acid
(C) STRANDEDNESS: single
(D) TOPOLOGY: linear (x i) SEQUENCE DESCRIPTION: SEQ ID NO:56:

```
Gly  Glx  Met  Arg  Pro  Pro  Ser  Pro  Pro  His  Val  Arg  Trp  Leu  Cys  Val
 1                   5                        10                       15

Leu  Ala  Gly  Ala  Leu  Ala  Cys  Ala  Leu  Arg  Pro  Ala  Gly  Ser  Gln  Ala
               20                       25                       30

Ala  Ser  Pro  Gln  His  Glu  Cys  Glu  Tyr  Leu  Gln  Leu  Ile  Glu  Ile  Gln
          35                       40                       45

Arg  Gln  Gln  Cys  Leu  Glu  Glu  Ala  Gln  Leu  Glu  Asn  Glu  Thr  Thr  Gly
     50                       55                       60

Cys  Ser  Lys  Met  Trp  Asp  Asn  Leu  Thr  Cys  Trp  Pro  Thr  Thr  Pro  Arg
65                       70                       75                       80
```

-continued

```
Gly Gln Ala Val Val Leu Asp Cys Pro Leu Ile Phe Gln Leu Phe Ala
                 85                  90                  95

Pro Ile His Gly Tyr Asn Ile Ser Arg Ser Cys Thr Glu Glu Gly Trp
            100                 105                 110

Ser Gln Leu Glu Pro Gly Pro Tyr His Ile Ala Cys Gly Leu Asn Asp
        115                 120                 125

Arg Ala Ser Ser Leu Asp Glu Gln Gln Gln Thr Lys Phe Tyr Asn Thr
    130                 135                 140

Val Lys Thr Gly Tyr Thr Ile Gly Tyr Ser Leu Ser Leu Ala Ser Leu
145                 150                 155                 160

Leu Val Ala Met Ala Ile Leu Ser Leu Phe Arg Lys Leu His Cys Thr
                165                 170                 175

Arg Asn Tyr Ile His Met His Leu Phe Met Ser Phe Ile Leu Arg Ala
            180                 185                 190

Thr Ala Val Phe Ile Lys Asp Met Ala Leu Phe Asn Ser Gly Glu Ile
        195                 200                 205

Asp His Cys Ser Glu Ala Ser Val Gly Cys Lys Ala Ala Val Val Phe
    210                 215                 220

Phe Gln Tyr Cys Val Met Ala Asn Phe Phe Trp Leu Leu Val Glu Gly
225                 230                 235                 240

Leu Tyr Leu Tyr Thr Leu Leu Ala Val Ser Phe Phe Ser Glu Arg Lys
                245                 250                 255

Tyr Phe Trp Gly Tyr Ile Leu Ile Gly Trp Gly Val Pro Ser Val Phe
            260                 265                 270

Ile Thr Ile Trp Thr Val Val Arg Ile Tyr Phe Glu Asp Phe Gly Cys
        275                 280                 285

Trp Asp Thr Ile Ile Asn Ser Ser Leu Trp Trp Ile Ile Lys Ala Pro
    290                 295                 300

Ile Leu Leu Ser Ile Leu Val Asn Phe Val Leu Phe Ile Cys Ile Ile
305                 310                 315                 320

Arg Ile Leu Val Gln Lys Leu Arg Pro Pro Asp Ile Gly Lys Asn Asp
                325                 330                 335

Ser Ser Pro Tyr Ser Arg Leu Ala Lys Ser Thr Leu Leu Leu Ile Pro
            340                 345                 350

Leu Phe Gly Ile His Tyr Val Met Phe Ala Phe Phe Pro Asp Asn Phe
        355                 360                 365

Lys Ala Gln Val Lys Met Val Phe Glu Leu Val Val Gly Ser Phe Gln
    370                 375                 380

Gly Phe Val Val Ala Ile Leu Tyr Cys Phe Leu Asn Gly Glu Val Gln
385                 390                 395                 400

Ala Glu Leu Arg Arg Lys Trp Arg Arg Trp His Leu Gln Gly Val Leu
                405                 410                 415

Gly Trp Ser Ser Lys Ser Gln His Pro Trp Gly Gly Ser Asn Gly Ala
            420                 425                 430

Thr Cys Ser Thr Gln Val Ser Met Leu Thr Arg Val Ser Pro Ser Ala
        435                 440                 445

Arg Arg Ser Ser Ser Phe Gln Ala Glu Val Ser Leu Val Asn His Ala
    450                 455                 460

Asp Pro Phe Asn Asx Cys Trp Ile Asn Asp Trp Ser Thr Glu Met Pro
465                 470                 475                 480

Ala Arg Asp Asn Asx Ala Ser Glu Gln Glu Asn Cys Glu Asp Gly Thr
                485                 490                 495

Asn Arg Ser Ala Met Arg Pro Pro Ser Pro Pro His Val Arg Trp Leu
            500                 505                 510
```

```
Cys Val Leu Ala Gly Ala Leu Ala Cys Ala Leu Arg Pro Ala Gly Ser
        515                 520                 525
Gln Ala Ala Ser Pro Gln His Glu Cys Glu Tyr Leu Gln Leu Ile Glu
        530                 535                 540
Ile Gln Arg Gln Gln Cys Leu Glu Glu Ala Gln Leu Glu Asn Glu Thr
545                 550                 555                 560
Thr Gly Cys Ser Lys Met Trp Asp Asn Leu Thr Cys Trp Pro Thr Thr
                565                 570                 575
Pro Arg Gly Gln Ala Val Val Leu Asp Cys Pro Leu Ile Phe Gln Leu
            580                 585                 590
Phe Ala Pro Ile His Gly Tyr Asn Ile Ser Arg Ser Cys Thr Glu Glu
            595                 600                 605
Gly Trp Ser Gln Leu Glu Pro Gly Pro Tyr His Ile Ala Cys Gly Leu
        610                 615                 620
Asn Asp Arg Ala Ser Ser Leu Asp Glu Gln Gln Gln Thr Lys Phe Tyr
625                 630                 635                 640
Asn Thr Val Lys Thr Gly Tyr Thr Ile Gly Tyr Ser Leu Ser Leu Ala
            645                 650                 655
Ser Leu Leu Val Ala Met Ala Ile Leu Ser Leu Phe Arg Lys Leu His
            660                 665                 670
Cys Thr Arg Asn Tyr Ile His Met His Leu Phe Met Ser Phe Ile Leu
        675                 680                 685
Arg Ala Thr Ala Val Phe Ile Lys Asp Met Ala Leu Phe Asn Ser Gly
        690                 695                 700
Glu Ile Asp His Cys Ser Glu Ala Ser Val Gly Cys Lys Ala Ala Val
705                 710                 715                 720
Val Phe Phe Gln Tyr Cys Val Met Ala Asn Phe Phe Trp Leu Leu Val
                725                 730                 735
Glu Gly Leu Tyr Leu Tyr Thr Leu Leu Ala Val Ser Phe Phe Ser Glu
            740                 745                 750
Arg Lys Asn Asx Asn Asx Asp Leu Thr Met Arg Pro Pro Ser Pro Pro
        755                 760                 765
His Val Arg Trp Leu Cys Val Leu Ala Gly Ala Leu Ala Cys Ala Leu
    770                 775                 780
Arg Pro Ala Gly Ser Gln Ala Ala Ser Pro Gln His Glu Cys Glu Tyr
785                 790                 795                 800
Leu Gln Leu Ile Glu Ile Gln Arg Gln Gln Cys Leu Glu Glu Ala Gln
                805                 810                 815
Leu Glu Asn Glu Thr Thr Gly Cys Ser Lys Met Trp Asp Asn Leu Thr
            820                 825                 830
Cys Trp Pro Thr Thr Pro Arg Gly Gln Ala Val Val Leu Asp Cys Pro
        835                 840                 845
Leu Ile Phe Gln Leu Phe Ala Pro Ile His Gly Tyr Asn Ile Ser Arg
    850                 855                 860
Ser Cys Thr Glu Glu Gly Trp Ser Gln Leu Glu Pro Gly Pro Tyr His
865                 870                 875                 880
Ile Ala Cys Gly Leu Asn Asp Arg Ala Ser Ser Leu Asp Glu Gln Gln
                885                 890                 895
Gln Thr Lys Phe Tyr Asn Thr Val Lys Thr Gly Tyr Thr Ile Gly Tyr
            900                 905                 910
Ser Leu Ser Leu Ala Ser Leu Leu Val Ala Met Ala Ile Leu Ser Leu
        915                 920                 925
Phe Arg Lys Leu His Cys Thr Arg Asn Tyr Ile His Met His Leu Phe
```

|     |     |     |     |     | 930 |     |     |     |     | 935 |     |     |     |     | 940 |
| --- | --- | --- | --- | --- | --- | --- | --- | --- | --- | --- | --- | --- | --- | --- | --- |
| Met | Ser | Phe | Ile | Leu | Arg | Ala | Thr | Ala | Val | Phe | Ile | Lys | Asp | Met | Ala |
| 945 |     |     |     |     | 950 |     |     |     |     | 955 |     |     |     |     | 960 |
| Leu | Phe | Asn | Ser | Gly | Glu | Ile | Asp | His | Cys | Ser | Glu | Ala | Ser | Val | Gly |
|     |     |     |     | 965 |     |     |     |     | 970 |     |     |     |     | 975 |     |
| Cys | Lys | Ala | Ala | Val | Val | Phe | Phe | Gln | Tyr | Cys | Val | Met | Ala | Asn | Phe |
|     |     |     | 980 |     |     |     |     | 985 |     |     |     |     | 990 |     |     |
| Phe | Trp | Leu | Leu | Val | Glu | Gly | Leu | Tyr | Leu | Tyr | Thr | Leu | Leu | Ala | Val |
|     |     | 995 |     |     |     |     | 1000 |     |     |     |     | 1005 |     |     |     |
| Ser | Phe | Phe | Ser | Glu | Arg | Lys | Arg | Pro | Pro | Asn | Asx | Ala | Asn | Asx | Asn |
|     |     | 1010 |     |     |     | 1015 |     |     |     |     | 1020 |     |     |     |     |
| Asx | Ala | Met | Trp | Ala | Asp | Pro | Met | Arg | Pro | Pro | Ser | Pro | Pro | His | Val |
| 1025 |     |     |     |     | 1030 |     |     |     |     | 1035 |     |     |     |     | 1040 |
| Arg | Trp | Leu | Cys | Val | Leu | Ala | Gly | Ala | Leu | Ala | Cys | Ala | Leu | Arg | Pro |
|     |     |     |     | 1045 |     |     |     |     | 1050 |     |     |     |     | 1055 |     |
| Ala | Gly | Ser | Gln | Ala | Ala | Ser | Pro | Gln | His | Glu | Cys | Glu | Tyr | Leu | Gln |
|     |     |     |     | 1060 |     |     |     |     | 1065 |     |     |     |     | 1070 |     |
| Leu | Ile | Glu | Ile | Gln | Arg | Gln | Gln | Cys | Leu | Glu | Glu | Ala | Gln | Leu | Glu |
|     |     |     | 1075 |     |     |     |     | 1080 |     |     |     |     | 1085 |     |     |
| Asn | Glu | Thr | Thr | Gly | Cys | Ser | Lys | Met | Trp | Asp | Asn | Leu | Thr | Cys | Trp |
|     |     | 1090 |     |     |     |     | 1095 |     |     |     |     | 1100 |     |     |     |
| Pro | Thr | Thr | Pro | Arg | Gly | Gln | Ala | Val | Val | Leu | Asp | Cys | Pro | Leu | Ile |
| 1105 |     |     |     |     | 1110 |     |     |     |     | 1115 |     |     |     |     | 1120 |
| Phe | Gln | Leu | Phe | Ala | Pro | Ile | His | Gly | Tyr | Asn | Ile | Ser | Arg | Ser | Cys |
|     |     |     |     | 1125 |     |     |     |     | 1130 |     |     |     |     | 1135 |     |
| Thr | Glu | Glu | Gly | Trp | Ser | Gln | Leu | Glu | Pro | Gly | Pro | Tyr | His | Ile | Ala |
|     |     |     |     | 1140 |     |     |     |     | 1145 |     |     |     |     | 1150 |     |
| Cys | Gly | Leu | Asn | Asp | Arg | Ala | Ser | Ser | Leu | Asp | Glu | Gln | Gln | Gln | Thr |
|     |     |     |     | 1155 |     |     |     |     | 1160 |     |     |     |     | 1165 |     |
| Lys | Phe | Tyr | Asn | Thr | Val | Lys | Thr | Gly | Tyr | Thr | Ile | Gly | Tyr | Ser | Leu |
|     |     | 1170 |     |     |     |     | 1175 |     |     |     |     | 1180 |     |     |     |
| Ser | Leu | Ala | Ser | Leu | Leu | Val | Ala | Met | Ala | Ile | Leu | Ser | Leu | Phe | Arg |
| 1185 |     |     |     |     | 1190 |     |     |     |     | 1195 |     |     |     |     | 1200 |
| Lys | Leu | His | Cys | Thr | Arg | Asn | Tyr | Ile | His | Met | His | Leu | Phe | Met | Ser |
|     |     |     |     | 1205 |     |     |     |     | 1210 |     |     |     |     | 1215 |     |
| Phe | Ile | Leu | Arg | Ala | Thr | Ala | Val | Phe | Ile | Lys | Asp | Met | Ala | Leu | Phe |
|     |     |     | 1220 |     |     |     |     | 1225 |     |     |     |     | 1230 |     |     |
| Asn | Ser | Gly | Glu | Ile | Asp | His | Cys | Ser | Glu | Ala | Ser | Val | Gly | Cys | Lys |
|     |     |     | 1235 |     |     |     |     | 1240 |     |     |     |     | 1245 |     |     |
| Ala | Ala | Val | Val | Phe | Phe | Gln | Tyr | Cys | Val | Met | Ala | Asn | Phe | Phe | Trp |
|     | 1250 |     |     |     |     | 1255 |     |     |     |     | 1260 |     |     |     |     |
| Leu | Leu | Val | Glu | Gly | Leu | Tyr | Leu | Tyr | Thr | Leu | Leu | Ala | Val | Ser | Phe |
| 1265 |     |     |     |     | 1270 |     |     |     |     | 1275 |     |     |     |     | 1280 |
| Phe | Ser | Glu | Arg | Lys | Thr | Pro | Ile | Asp | Gly | Ile | Asp | Ala | Asn | Phe | Asp |
|     |     |     |     | 1285 |     |     |     |     | 1290 |     |     |     |     | 1295 |     |
| Ala | Ala | Glu | Asp | Glu | Cys | Arg | Glu | Phe | Thr | Trp | Asp | Ser | Ile | Asp | Ser |
|     |     |     | 1300 |     |     |     |     | 1305 |     |     |     |     | 1310 |     |     |
| Ile | Cys | Phe | Met | Trp | Asp | Met | Ser | Trp | Asp | Trp | Asp |     |     |     |     |
|     |     | 1315 |     |     |     |     | 1320 |     |     |     |     |     |     |     |     |